US011718658B2

(12) United States Patent
van Dijk et al.

(10) Patent No.: US 11,718,658 B2
(45) Date of Patent: Aug. 8, 2023

(54) T CELL RECEPTORS THAT BIND TO MIXED LINEAGE LEUKEMIA (MLL)-SPECIFIC PHOSPHOPEPTIDES AND METHODS OF USE THEREOF

(71) Applicant: MiNK Therapeutics, Inc., New York, NY (US)

(72) Inventors: Marc van Dijk, Bosch en Duin (NL); Ekaterina Vladimirovna Breous-Nystrom, Basel (CH); Alessandra Franchino, Basel (CH); Sébastien Lalevée, Saint Louis (FR); Arthur Andrew Hurwitz, Bedford, MA (US); Mark Adrian Exley, Chestnut Hill, MA (US); Benjamin Jacob Wolf, Boston, MA (US)

(73) Assignee: MiNK Therapeutics, Inc., New York, NY (US)

( * ) Notice: Subject to any disclaimer, the term of this patent is extended or adjusted under 35 U.S.C. 154(b) by 445 days.

(21) Appl. No.: 16/807,742

(22) Filed: Mar. 3, 2020

(65) Prior Publication Data

US 2020/0308246 A1 Oct. 1, 2020

Related U.S. Application Data

(63) Continuation of application No. PCT/US2018/049397, filed on Sep. 4, 2018.

(60) Provisional application No. 62/553,957, filed on Sep. 4, 2017.

(51) Int. Cl.
*C07K 14/725* (2006.01)
*C12N 15/63* (2006.01)
*A61K 38/00* (2006.01)
*A61K 45/06* (2006.01)

(52) U.S. Cl.
CPC .......... *C07K 14/7051* (2013.01); *C12N 15/63* (2013.01); *A61K 38/00* (2013.01); *A61K 45/06* (2013.01); *C07K 2317/565* (2013.01)

(58) Field of Classification Search
CPC .................. C07K 14/7051; C07K 2317/565
See application file for complete search history.

(56) References Cited

FOREIGN PATENT DOCUMENTS

| WO | WO 2011/149909 A2 | 12/2011 |
|----|-------------------|---------|
| WO | WO 2017/044672 A1 | 3/2017  |

OTHER PUBLICATIONS

Song et al. Broad TCR repertoire and diverse structural solutions for recognition of an immunodominant CD8+ T cell epitope.Nature structural & molecular biology vol. 24 No. 4 Apr. 2017 (Year: 2017).*
RossJohn et al. Cell Antigen Receptor Recognition of Antigen-Presenting MoleculesAnnu. Rev. Immunol. 2015. 33:169-200. (Year: 2015).*
International Search Report and Written Opinion for Application No. PCT/US2018/049397, dated Jan. 15, 2019.
International Preliminary Report on Patentability for Application No. PCT/US2018/049397, dated Mar. 19, 2020.
Cobbold et al., MHC class I-associated phosphopeptides are the targets of memory-like immunity in leukemia. Sci Transl Med. Sep. 18, 2013;5(203):203ra125. doi:10.1126/scitranslmed.3006061.
Plewa et al., Discovery of phospho-peptide neoantigen tumor targets (PTTs) and identification of novel T cell receptors (TCRs) targeting phospho-MLL for adoptive cell therapy AgenTus Therapeutics: differentiated cell therapy. Aug. 31, 2018. http://www.agentustherapeutics.com/wpcontent/uploads/2018/09/AgenTus-PTT_MLL-Poster-2O18_0831-FINAL.pdf [retrieved on Dec. 11, 2018].

* cited by examiner

*Primary Examiner* — Amy E Juedes
*Assistant Examiner* — Brian Hartnett
(74) *Attorney, Agent, or Firm* — Wolf, Greenfield & Sacks, P.C.

(57) ABSTRACT

Provided are TCRs (e.g., TCRs that bind to MLL, e.g., TCRs that bind to an MLL phosphopeptide, e.g., TCRs that bind to an MLL phosphopeptide/MHC complex), cells and pharmaceutical compositions comprising these TCRs, nucleic acids encoding these TCRs, expression vectors and host cells for making these TCRs, and methods of treating a subject using these TCRs.

21 Claims, 24 Drawing Sheets

Figure 1:
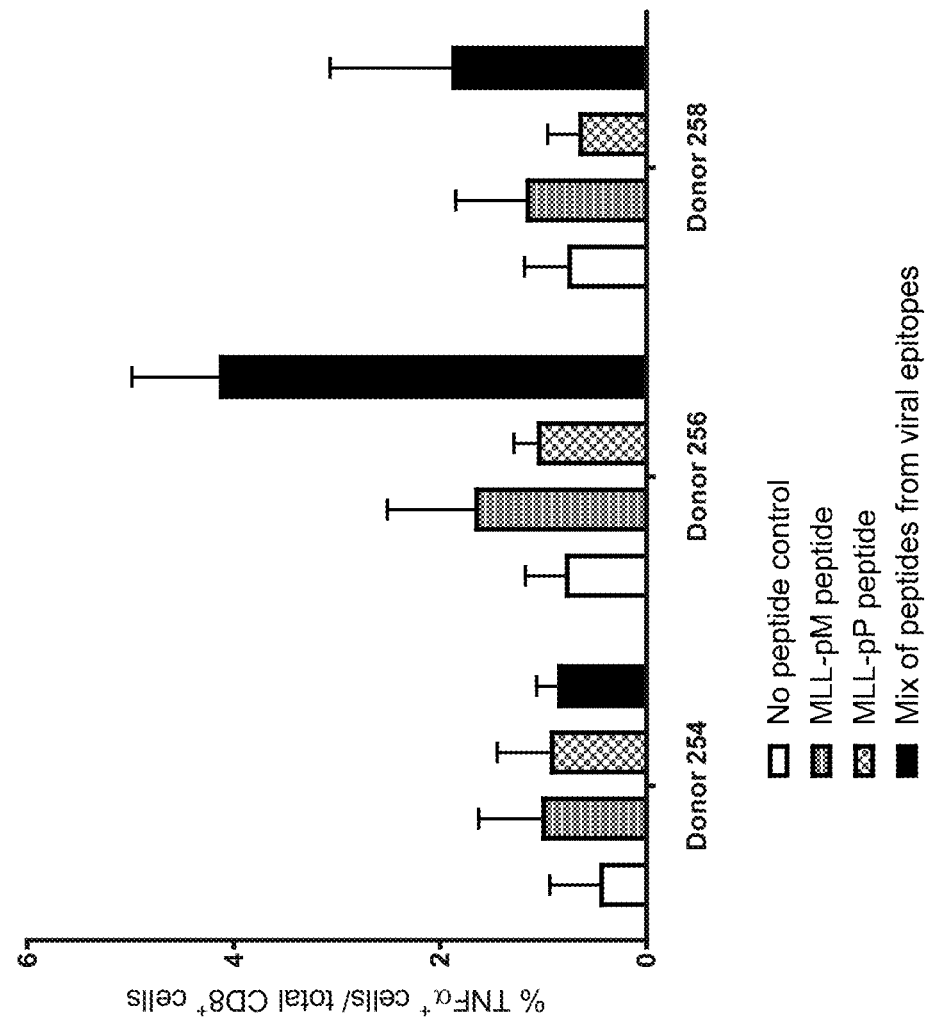

Specification includes a Sequence Listing.

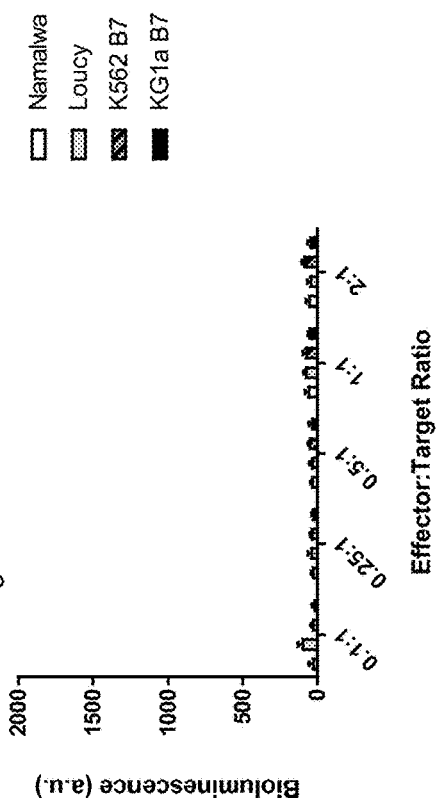
FIG. 12B Effector: non-transduced Jurkat reporter cells
Target: Various tumor cells
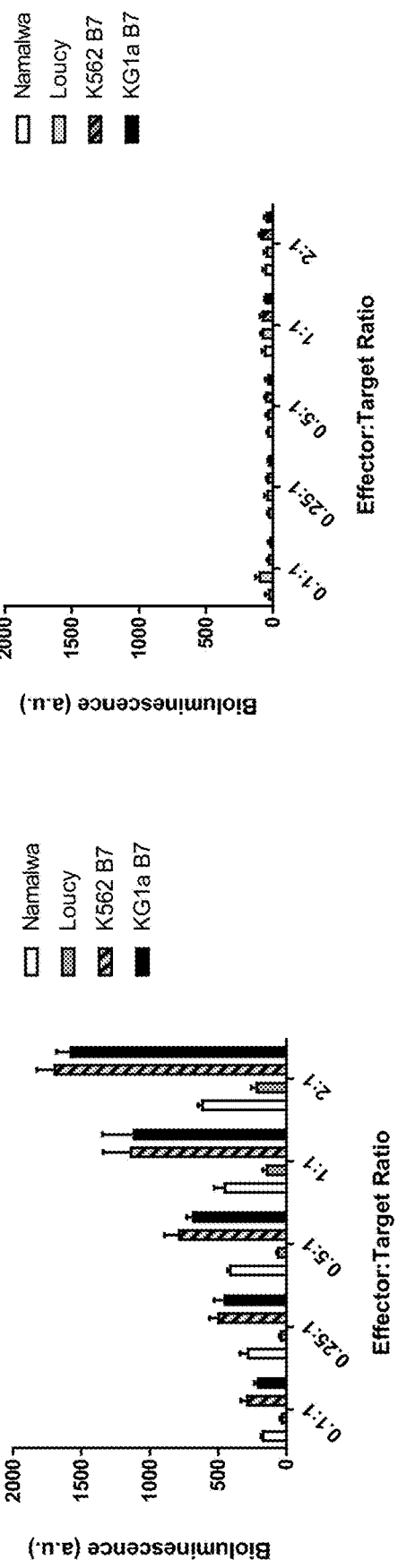
FIG. 12A Effector: Jurkat reporter cells expressing TCR0078
Target: Various tumor cells
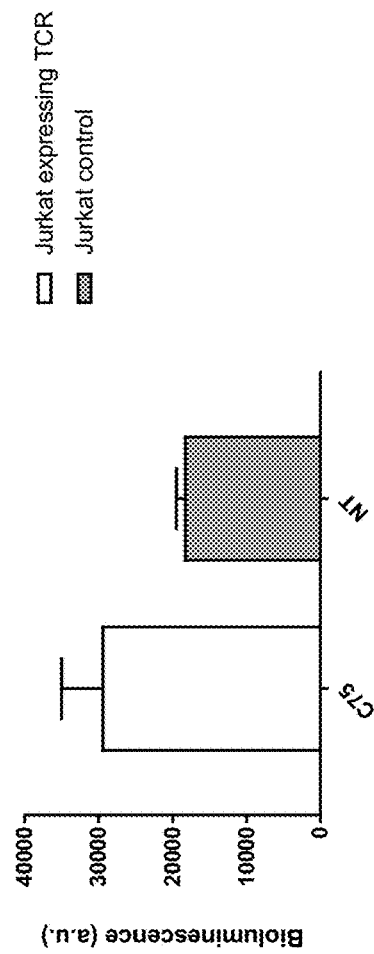
FIG. 12C PMA/Ionomycin Treatment

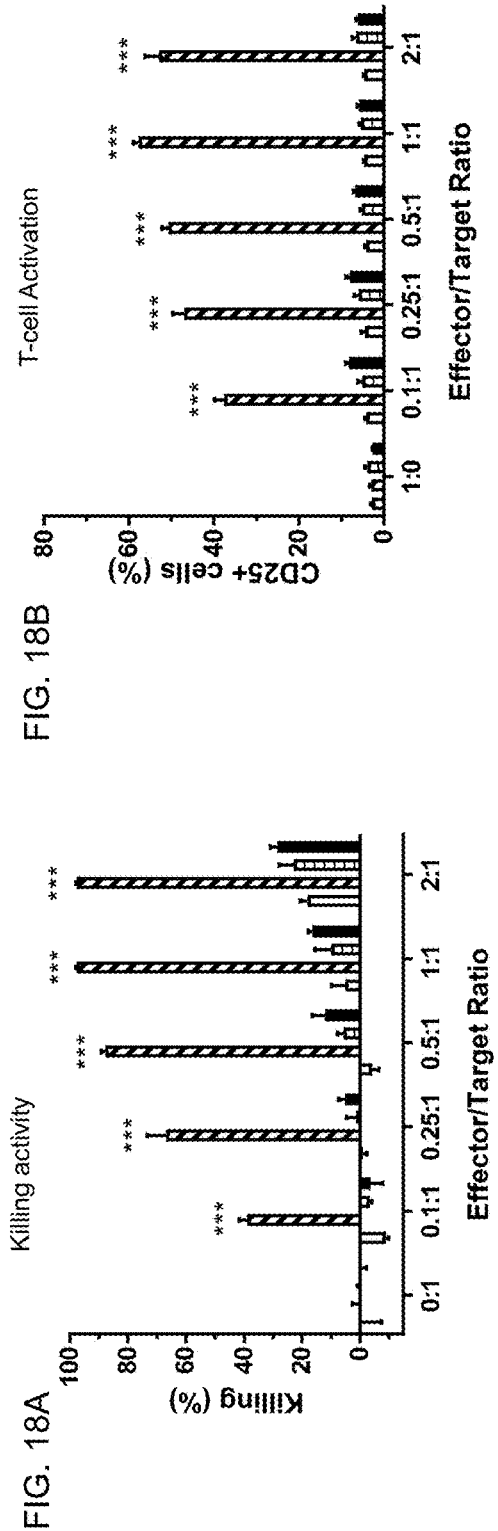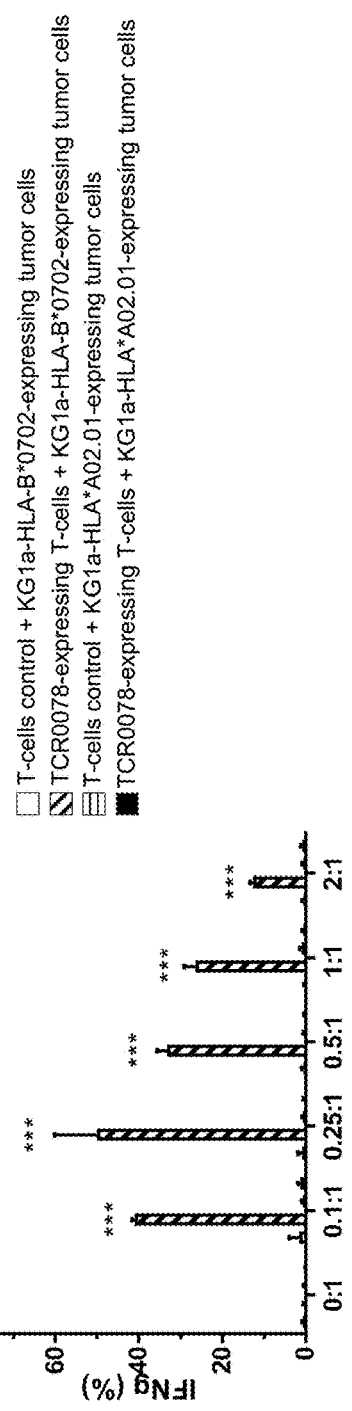
FIG. 18A
FIG. 18B
FIG. 18C

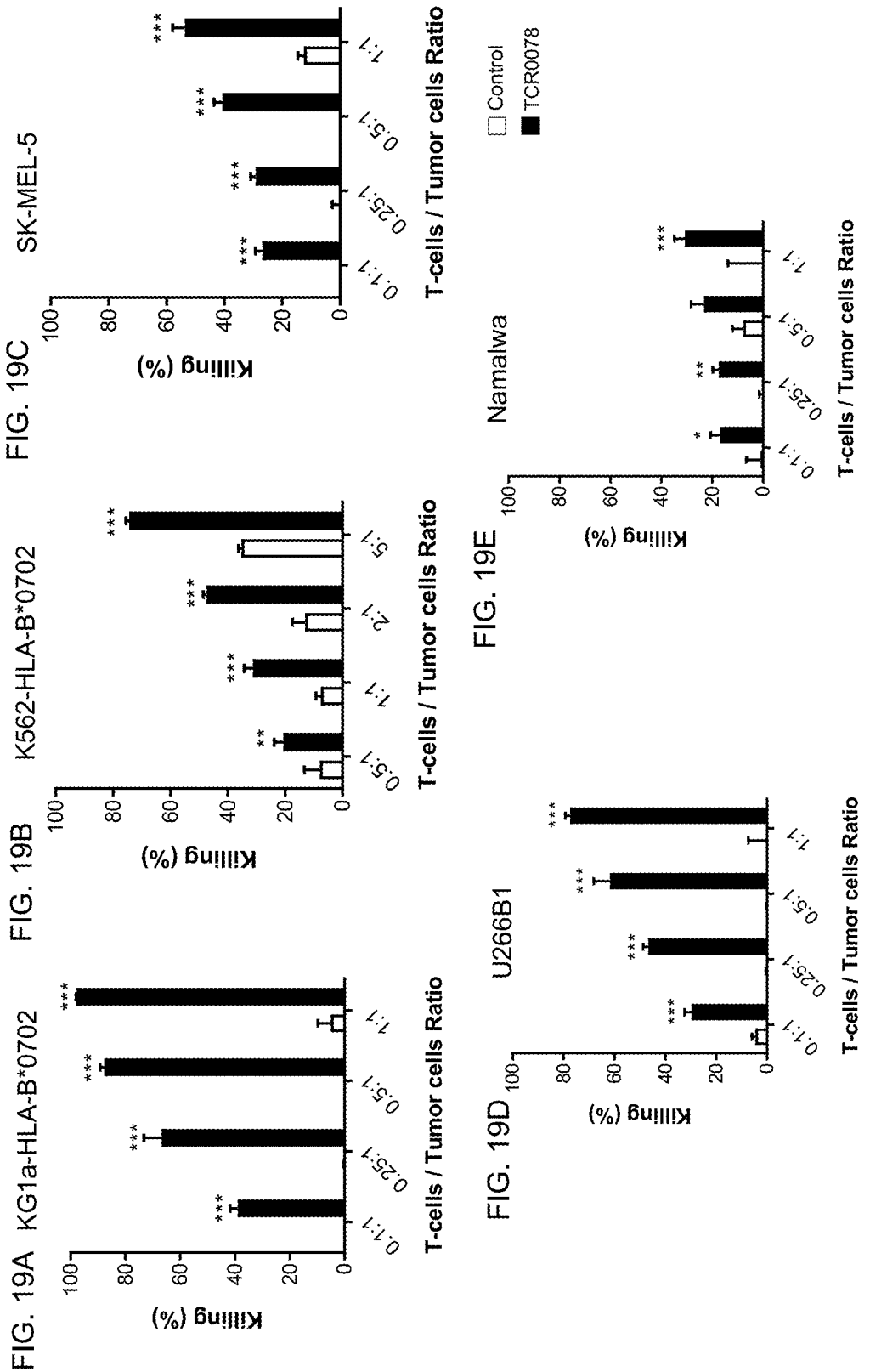

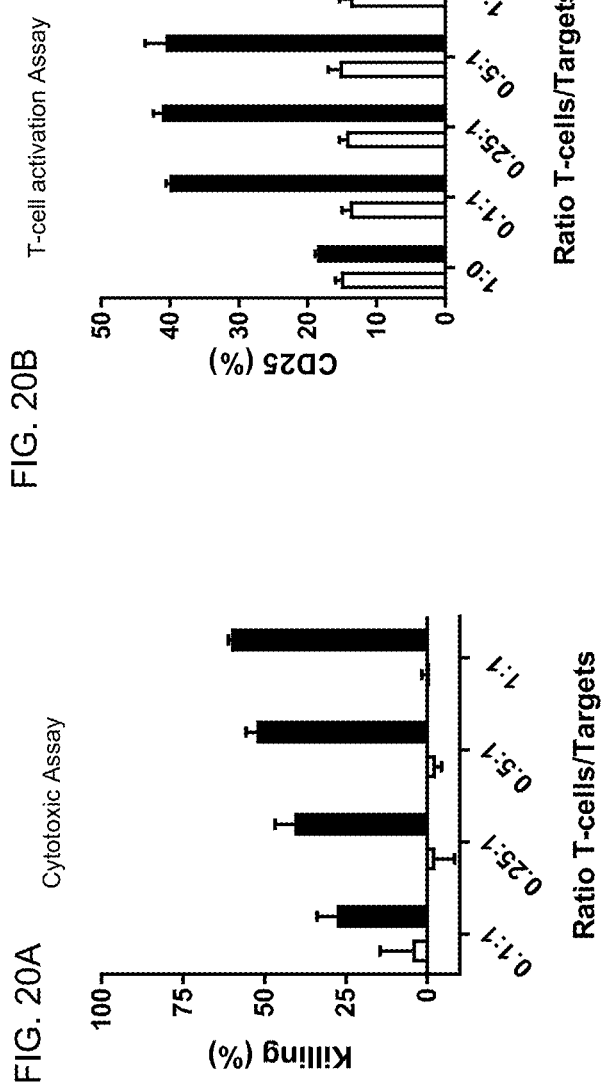

SEQUENCE LISTING

```
<160> NUMBER OF SEQ ID NOS: 273

<210> SEQ ID NO 1
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Tyr Gly Gly Gly Ser
                85                  90                  95

Asn Tyr Lys Leu Thr Phe Gly Ala Gly Thr Arg Leu Thr Val Lys Pro
            100                 105                 110

<210> SEQ ID NO 2
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 2

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Arg Leu Thr
                85                  90                  95

Gly Arg Val His Gly Tyr Thr Phe Gly Pro Gly Thr Arg Leu Thr Val
            100                 105                 110

Leu

<210> SEQ ID NO 3
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Lys Asn Gln Val Glu Gln Ser Pro Gln Ser Leu Ile Ile Leu Glu Gly
1               5                   10                  15

Lys Asn Cys Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Met Thr Phe Ser Glu Asn Thr Lys Ser Asn Gly Arg Tyr Thr Ala
    50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Arg Gly Gly Ala
                85                  90                  95

Ala Gly Asn Lys Leu Thr Phe Gly Ala Gly Thr Arg Leu Thr Val Lys
            100                 105                 110

Pro

<210> SEQ ID NO 4
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asn Ser Leu
            20                  25                  30

Phe Trp Tyr Arg Gln Thr Met Met Arg Gly Leu Glu Leu Leu Ile Tyr
        35                  40                  45

```
Phe Asn Asn Val Pro Ile Asp Asp Ser Gly Met Pro Glu Asp Arg
     50                  55                  60

Phe Ser Ala Lys Met Pro Asn Ala Ser Phe Ser Thr Leu Lys Ile Gln
 65                  70                  75                  80

Pro Ser Glu Pro Arg Asp Ser Ala Val Tyr Phe Cys Ala Ser Ser
                 85                  90                  95

Gly Gly Ala Asn Thr Glu Ala Phe Phe Gly Pro Gly Thr Arg Leu Thr
                100                 105                 110

Val Leu

<210> SEQ ID NO 5
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Gln Ser Val Thr Gln Leu Gly Ser His Val Ser Val Ser Glu Gly
 1               5                  10                  15

Ala Leu Ile Leu Leu Arg Cys Asn Tyr Ser Ser Ser Val Pro Pro Tyr
                 20                  25                  30

Leu Phe Trp Tyr Val Gln Tyr Pro Asn Gln Gly Leu Gln Leu Leu Leu
             35                  40                  45

Lys Tyr Thr Thr Gly Ala Thr Leu Val Lys Gly Ile Asn Gly Phe Glu
 50                  55                  60

Ala Glu Phe Lys Lys Ser Glu Thr Ser Phe His Leu Thr Lys Pro Ser
 65                  70                  75                  80

Ala His Met Ser Asp Ala Ala Glu Tyr Phe Cys Ala Val Ser Ala Arg
                 85                  90                  95

Tyr Asn Phe Asn Lys Phe Tyr Phe Gly Ser Gly Thr Lys Leu Ser Val
                100                 105                 110

Ile Pro

<210> SEQ ID NO 6
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ser Gly Val Thr Gln Thr Pro Lys His Leu Ile Thr Ala Thr Gly
 1               5                  10                  15

Gln Arg Val Thr Leu Arg Cys Ser Pro Arg Ser Gly Asp Leu Ser Val
                 20                  25                  30

Tyr Trp Tyr Gln Gln Ser Leu Asp Gln Gly Leu Gln Phe Leu Ile Gln
             35                  40                  45

Tyr Tyr Asn Gly Glu Glu Arg Ala Lys Gly Asn Ile Leu Glu Arg Phe
 50                  55                  60

Ser Ala Gln Gln Phe Pro Asp Leu His Ser Glu Leu Asn Leu Ser Ser
 65                  70                  75                  80

Leu Glu Leu Gly Asp Ser Ala Leu Tyr Phe Cys Ala Ser Ser Ala Ser
                 85                  90                  95

Gly Gly Arg Ser Tyr Glu Gln Tyr Phe Gly Pro Gly Thr Arg Leu Thr
```

```
                    100                 105                 110
Val Val

<210> SEQ ID NO 7
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Asp Gln Val Thr Gln Ser Pro Glu Ala Leu Arg Leu Gln Glu Gly
1               5                   10                  15

Glu Ser Ser Ser Leu Asn Cys Ser Tyr Thr Val Ser Gly Leu Arg Gly
            20                  25                  30

Leu Phe Trp Tyr Arg Gln Asp Pro Gly Lys Gly Pro Glu Phe Leu Phe
        35                  40                  45

Thr Leu Tyr Ser Ala Gly Glu Glu Lys Glu Lys Glu Arg Leu Lys Ala
    50                  55                  60

Thr Leu Thr Lys Lys Glu Ser Phe Leu His Ile Thr Ala Pro Lys Pro
65                  70                  75                  80

Glu Asp Ser Ala Thr Tyr Leu Cys Ala Val Arg Asn Thr Gly Phe Gln
                85                  90                  95

Lys Leu Val Phe Gly Thr Gly Thr Arg Leu Leu Val Ser Pro
            100                 105                 110

<210> SEQ ID NO 8
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Thr Gly Val Ser Gln Asp Pro Arg His Lys Ile Thr Lys Arg Gly
1               5                   10                  15

Gln Asn Val Thr Phe Arg Cys Asp Pro Ile Ser Glu His Asn Arg Leu
            20                  25                  30

Tyr Trp Tyr Arg Gln Thr Leu Gly Gln Gly Pro Glu Phe Leu Thr Tyr
        35                  40                  45

Phe Gln Asn Glu Ala Gln Leu Glu Lys Ser Arg Leu Leu Ser Asp Arg
    50                  55                  60

Phe Ser Ala Glu Arg Pro Lys Gly Ser Phe Ser Thr Leu Glu Ile Gln
65                  70                  75                  80

Arg Thr Glu Gln Gly Asp Ser Ala Met Tyr Leu Cys Ala Ser Ser Trp
                85                  90                  95

Arg Thr Gly Arg Glu Glu Thr Gln Tyr Phe Gly Pro Gly Thr Arg Leu
            100                 105                 110

Leu Val Leu
        115

<210> SEQ ID NO 9
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 9

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Met Leu Trp Asn
                85                  90                  95

Gln Gly Gly Lys Leu Ile Phe Gly Gln Gly Thr Glu Leu Ser Val Lys
            100                 105                 110

Pro

<210> SEQ ID NO 10
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Lys Ala Gly Val Thr Gln Thr Pro Arg Tyr Leu Ile Lys Thr Arg Gly
1               5                   10                  15

Gln Gln Val Thr Leu Ser Cys Ser Pro Ile Ser Gly His Arg Ser Val
            20                  25                  30

Ser Trp Tyr Gln Gln Thr Pro Gly Gln Gly Leu Gln Phe Leu Phe Glu
        35                  40                  45

Tyr Phe Ser Glu Thr Gln Arg Asn Lys Gly Asn Phe Pro Gly Arg Phe
    50                  55                  60

Ser Gly Arg Gln Phe Ser Asn Ser Arg Ser Glu Met Asn Val Ser Thr
65                  70                  75                  80

Leu Glu Leu Gly Asp Ser Ala Leu Tyr Leu Cys Ala Ser Ser Leu Gly
                85                  90                  95

Arg Gly Tyr Glu Gln Tyr Phe Gly Pro Gly Thr Arg Leu Thr Val Thr
            100                 105                 110

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Val Phe Ser Ser
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Val Ser Pro Phe Ser Asn
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ser Ser Val Pro Pro Tyr
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Ser Gly Leu Arg Gly
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Ser Ala Ile Tyr Asn
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Val Val Thr Gly Gly Glu Val
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Met Thr Phe Ser Glu Asn Thr
1               5

<210> SEQ ID NO 18

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Thr Thr Gly Ala Thr Leu Val
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Tyr Ser Ala Gly Glu Glu
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ile Gln Ser Ser Gln Arg Glu
1               5

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Gly Tyr Gly Gly Gly Ser Asn Tyr Lys Leu Thr
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Val Val Arg Gly Gly Ala Ala Gly Asn Lys Leu Thr
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23
```

```
Ala Val Ser Ala Arg Tyr Asn Phe Asn Lys Phe Tyr
1               5                   10
```

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Ala Val Arg Asn Thr Gly Phe Gln Lys Leu Val
1               5                   10
```

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Ala Val Met Leu Trp Asn Gln Gly Gly Lys Leu Ile
1               5                   10
```

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Met Asn His Glu Tyr
1               5
```

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Ser Gly His Asn Ser
1               5
```

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Ser Gly Asp Leu Ser
1               5
```

<210> SEQ ID NO 29
<211> LENGTH: 5
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 29

Ser Glu His Asn Arg
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ser Gly His Arg Ser
1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ser Met Asn Val Glu Val
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Asn Asn Asn Val Pro
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Tyr Tyr Asn Gly Glu Glu
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Phe Gln Asn Glu Ala Gln
1               5

```
<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Phe Ser Glu Thr Gln
1               5

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Ser Arg Leu Thr Gly Arg Val His Gly Tyr Thr
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Ala Ser Ser Ser Gly Gly Ala Asn Thr Glu Ala Phe
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Ser Ser Ala Ser Gly Gly Arg Ser Tyr Glu Gln Tyr
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Ser Ser Trp Arg Thr Gly Arg Glu Glu Thr Gln Tyr
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40
```

Ala Ser Ser Leu Gly Arg Gly Tyr Glu Gln Tyr
1               5                   10

<210> SEQ ID NO 41
<211> LENGTH: 141
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Asn, Tyr, His or Asp

<400> SEQUENCE: 41

Xaa Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 42
<211> LENGTH: 141
<212> TYPE: PRT
<213> ORGANISM: Homo sapiens

<400> SEQUENCE: 42

Tyr Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser

<210> SEQ ID NO 43
<211> LENGTH: 177
<212> TYPE: PRT
<213> ORGANISM: Homo sapiens

<400> SEQUENCE: 43

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 44
<211> LENGTH: 179
<212> TYPE: PRT
<213> ORGANISM: Homo sapiens

<400> SEQUENCE: 44

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

```
Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 45
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphoserine

<400> SEQUENCE: 45

Glu Pro Arg Ser Pro Ser His Ser Met
1               5

<210> SEQ ID NO 46
<211> LENGTH: 9
<212> TYPE: PRT
<213> ORGANISM: Homo sapiens

<400> SEQUENCE: 46

Glu Pro Arg Ser Pro Ser His Ser Met
1               5

<210> SEQ ID NO 47
<211> LENGTH: 9
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: Phosphoserine

<400> SEQUENCE: 47

Arg Val Arg Ser Pro Thr Arg Ser Pro
1               5

<210> SEQ ID NO 48
<211> LENGTH: 9
<212> TYPE: PRT
<213> ORGANISM: Homo sapiens

<400> SEQUENCE: 48

Arg Val Arg Ser Pro Thr Arg Ser Pro
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 49

Ala Pro Arg Ser Pro Ser His Ser Met
1               5
```

```
<210> SEQ ID NO 50
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 50

Glu Ala Arg Ser Pro Ser His Ser Met
1               5

<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 51

Glu Pro Ala Ser Pro Ser His Ser Met
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Glu Pro Arg Ala Pro Ser His Ser Met
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 53

Glu Pro Arg Ser Ala Ser His Ser Met
1               5

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
```

```
<223> OTHER INFORMATION: Phosphoserine

<400> SEQUENCE: 54

Glu Pro Arg Ser Pro Ala His Ser Met
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 55

Glu Pro Arg Ser Pro Ser Ala Ser Met
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 56

Glu Pro Arg Ser Pro Ser His Ala Met
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 57

Glu Pro Arg Ser Pro Ser His Ser Ala
1               5

<210> SEQ ID NO 58
<211> LENGTH: 253
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
                20                  25                  30

Gln Trp Tyr Arg Gln Glu Pro Gly Glu Gly Pro Val Leu Leu Val Thr
```

```
                35                  40                  45
Val Val Thr Gly Gly Glu Val Lys Lys Leu Lys Arg Leu Thr Phe Gln
 50                  55                  60

Phe Gly Asp Ala Arg Lys Asp Ser Ser Leu His Ile Thr Ala Ala Gln
 65                  70                  75                  80

Pro Gly Asp Thr Gly Leu Tyr Leu Cys Ala Gly Tyr Gly Gly Gly Ser
                 85                  90                  95

Asn Tyr Lys Leu Thr Phe Gly Lys Gly Thr Leu Leu Thr Val Asn Pro
            100                 105                 110

Tyr Ile Gln Asn Pro Asp Pro Ala Val Tyr Gln Leu Arg Asp Ser Lys
        115                 120                 125

Ser Ser Asp Lys Ser Val Cys Leu Phe Thr Asp Phe Asp Ser Gln Thr
130                 135                 140

Asn Val Ser Gln Ser Lys Asp Ser Asp Val Tyr Ile Thr Asp Lys Thr
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser Cys Asp
        195                 200                 205

Val Lys Leu Val Glu Lys Ser Phe Glu Thr Asp Thr Asn Leu Asn Phe
    210                 215                 220

Gln Asn Leu Ser Val Ile Gly Phe Arg Ile Leu Leu Leu Lys Val Ala
225                 230                 235                 240

Gly Phe Asn Leu Leu Met Thr Leu Arg Leu Trp Ser Ser
                245                 250

<210> SEQ ID NO 59
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Ala Gln Val Thr Gln Asn Pro Arg Tyr Leu Ile Thr Val Thr Gly
 1               5                  10                  15

Lys Lys Leu Thr Val Thr Cys Ser Gln Asn Met Asn His Glu Tyr Met
                20                  25                  30

Ser Trp Tyr Arg Gln Asp Pro Gly Leu Gly Leu Arg Gln Ile Tyr Tyr
             35                  40                  45

Ser Met Asn Val Glu Val Thr Asp Lys Gly Asp Val Pro Glu Gly Tyr
 50                  55                  60

Lys Val Ser Arg Lys Glu Lys Arg Asn Phe Pro Leu Ile Leu Glu Ser
 65                  70                  75                  80

Pro Ser Pro Asn Gln Thr Ser Leu Tyr Phe Cys Ala Ser Arg Leu Thr
                 85                  90                  95

Gly Arg Val His Gly Tyr Thr Phe Gly Ser Gly Thr Arg Leu Thr Val
            100                 105                 110

Val Glu Asp Leu Asn Lys Val Phe Pro Pro Glu Val Ala Val Phe Glu
        115                 120                 125

Pro Ser Glu Ala Glu Ile Ser His Thr Gln Lys Ala Thr Leu Val Cys
130                 135                 140
```

-continued

Leu Ala Thr Gly Phe Phe Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
210                 215                 220

Asp Arg Ala Lys Pro Val Thr Gln Ile Val Ser Ala Glu Ala Trp Gly
225                 230                 235                 240

Arg Ala Asp Cys Gly Phe Thr Ser Val Ser Tyr Gln Gln Gly Val Leu
                245                 250                 255

Ser Ala Thr Ile Leu Tyr Glu Ile Leu Leu Gly Lys Ala Thr Leu Tyr
            260                 265                 270

Ala Val Leu Val Ser Ala Leu Val Leu Met Ala Met Val Lys Arg Lys
        275                 280                 285

Asp Phe
    290

<210> SEQ ID NO 60
<211> LENGTH: 292
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
                20                  25                  30

Ser Trp Tyr Arg Gln Asp Pro Gly Leu Gly Leu Arg Gln Ile Tyr Tyr
            35                  40                  45

Ser Met Asn Val Glu Val Thr Asp Lys Gly Asp Val Pro Glu Gly Tyr
50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Arg Leu Thr
                85                  90                  95

Gly Arg Val His Gly Tyr Thr Phe Gly Ser Gly Thr Arg Leu Thr Val
            100                 105                 110

Val Glu Asp Leu Lys Asn Val Phe Pro Pro Glu Val Ala Val Phe Glu
        115                 120                 125

Pro Ser Glu Ala Glu Ile Ser His Thr Gln Lys Ala Thr Leu Val Cys
130                 135                 140

Leu Ala Thr Gly Phe Tyr Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
        195                 200                 205

```
Cys Gln Val Gln Phe Tyr Gly Leu Ser Glu Asn Asp Glu Trp Thr Gln
        210                 215                 220

Asp Arg Ala Lys Pro Val Thr Gln Ile Val Ser Ala Glu Ala Trp Gly
225                 230                 235                 240

Arg Ala Asp Cys Gly Phe Thr Ser Glu Ser Tyr Gln Gln Gly Val Leu
                245                 250                 255

Ser Ala Thr Ile Leu Tyr Glu Ile Leu Leu Gly Lys Ala Thr Leu Tyr
                260                 265                 270

Ala Val Leu Val Ser Ala Leu Val Leu Met Ala Met Val Lys Arg Lys
        275                 280                 285

Asp Ser Arg Gly
    290

<210> SEQ ID NO 61
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Lys Asn Gln Val Glu Gln Ser Pro Gln Ser Leu Ile Ile Leu Glu Gly
1               5                   10                  15

Lys Asn Cys Thr Leu Gln Cys Asn Tyr Thr Val Ser Pro Phe Ser Asn
                20                  25                  30

Leu Arg Trp Tyr Lys Gln Asp Thr Gly Arg Gly Pro Val Ser Leu Thr
            35                  40                  45

Ile Met Thr Phe Ser Glu Asn Thr Lys Ser Asn Gly Arg Tyr Thr Ala
        50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Arg Gly Gly Ala
                85                  90                  95

Ala Gly Asn Lys Leu Thr Phe Gly Gly Gly Thr Arg Val Leu Val Lys
                100                 105                 110

Pro Tyr Ile Gln Asn Pro Asp Pro Ala Val Tyr Gln Leu Arg Asp Ser
            115                 120                 125

Lys Ser Ser Asp Lys Ser Val Cys Leu Phe Thr Asp Phe Asp Ser Gln
130                 135                 140

Thr Asn Val Ser Gln Ser Lys Asp Ser Asp Val Tyr Ile Thr Asp Lys
145                 150                 155                 160

Thr Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Pro Ser Pro Glu Ser Ser Cys
        195                 200                 205

Asp Val Lys Leu Val Glu Lys Ser Phe Glu Thr Asp Thr Asn Leu Asn
    210                 215                 220

Phe Gln Asn Leu Ser Val Ile Gly Phe Arg Ile Leu Leu Leu Lys Val
225                 230                 235                 240

Ala Gly Phe Asn Leu Leu Met Thr Leu Arg Leu Trp Ser Ser
                245                 250
```

```
<210> SEQ ID NO 62
<211> LENGTH: 291
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62
```

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asn Ser Leu
            20                  25                  30

Phe Trp Tyr Arg Gln Thr Met Met Arg Gly Leu Glu Leu Leu Ile Tyr
        35                  40                  45

Phe Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Ser Ser
                85                  90                  95

Gly Gly Ala Asn Thr Glu Ala Phe Phe Gly Gln Gly Thr Arg Leu Thr
            100                 105                 110

Val Val Glu Asp Leu Asn Lys Val Phe Pro Pro Glu Val Ala Val Phe
        115                 120                 125

Glu Pro Ser Glu Ala Glu Ile Ser His Thr Gln Lys Ala Thr Leu Val
130                 135                 140

Cys Leu Ala Thr Gly Phe Phe Pro Asp His Val Glu Leu Ser Trp Trp
145                 150                 155                 160

Val Asn Gly Lys Glu Val His Ser Gly Val Ser Thr Asp Pro Gln Pro
                165                 170                 175

Leu Lys Glu Gln Pro Ala Leu Asn Asp Ser Arg Tyr Cys Leu Ser Ser
            180                 185                 190

Arg Leu Arg Val Ser Ala Thr Phe Trp Gln Asn Pro Arg Asn His Phe
        195                 200                 205

Arg Cys Gln Val Gln Phe Tyr Gly Leu Ser Glu Asn Asp Glu Trp Thr
    210                 215                 220

Gln Asp Arg Ala Lys Pro Val Thr Gln Ile Val Ser Ala Glu Ala Trp
225                 230                 235                 240

Gly Arg Ala Asp Cys Gly Phe Thr Ser Val Ser Tyr Gln Gln Gly Val
                245                 250                 255

Leu Ser Ala Thr Ile Leu Tyr Glu Ile Leu Leu Gly Lys Ala Thr Leu
            260                 265                 270

Tyr Ala Val Leu Val Ser Ala Leu Val Leu Met Ala Met Val Lys Arg
        275                 280                 285

Lys Asp Phe
    290

```
<210> SEQ ID NO 63
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63
```

Asp Ala Gly Val Ile Gln Ser Pro Arg His Glu Val Thr Glu Met Gly

```
                1               5                   10                  15
            Gln Glu Val Thr Leu Arg Cys Lys Pro Ile Ser Gly His Asn Ser Leu
                            20                  25                  30
            Phe Trp Tyr Arg Gln Thr Met Met Arg Gly Leu Glu Leu Leu Ile Tyr
                            35                  40                  45
            Phe Asn Asn Val Pro Ile Asp Asp Ser Gly Met Pro Glu Asp Arg
                50                  55                  60
            Phe Ser Ala Lys Met Pro Asn Ala Ser Phe Ser Thr Leu Lys Ile Gln
            65                  70                  75                  80
            Pro Ser Glu Pro Arg Asp Ser Ala Val Tyr Phe Cys Ala Ser Ser
                            85                  90                  95
            Gly Gly Ala Asn Thr Glu Ala Phe Phe Gly Gln Gly Thr Arg Leu Thr
                            100                 105                 110
            Val Val Glu Asp Leu Lys Asn Val Phe Pro Pro Glu Val Ala Val Phe
                            115                 120                 125
            Glu Pro Ser Glu Ala Glu Ile Ser His Thr Gln Lys Ala Thr Leu Val
                            130                 135                 140
            Cys Leu Ala Thr Gly Phe Tyr Pro Asp His Val Glu Leu Ser Trp Trp
            145                 150                 155                 160
            Val Asn Gly Lys Glu Val His Ser Gly Val Ser Thr Asp Pro Gln Pro
                            165                 170                 175
            Leu Lys Glu Gln Pro Ala Leu Asn Asp Ser Arg Tyr Cys Leu Ser Ser
                            180                 185                 190
            Arg Leu Arg Val Ser Ala Thr Phe Trp Gln Asn Pro Arg Asn His Phe
                            195                 200                 205
            Arg Cys Gln Val Gln Phe Tyr Gly Leu Ser Glu Asn Asp Glu Trp Thr
                            210                 215                 220
            Gln Asp Arg Ala Lys Pro Val Thr Gln Ile Val Ser Ala Glu Ala Trp
            225                 230                 235                 240
            Gly Arg Ala Asp Cys Gly Phe Thr Ser Glu Ser Tyr Gln Gln Gly Val
                            245                 250                 255
            Leu Ser Ala Thr Ile Leu Tyr Glu Ile Leu Leu Gly Lys Ala Thr Leu
                            260                 265                 270
            Tyr Ala Val Leu Val Ser Ala Leu Val Leu Met Ala Met Val Lys Arg
                            275                 280                 285
            Lys Asp Ser Arg Gly
                            290

<210> SEQ ID NO 64
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ala Gln Ser Val Thr Gln Leu Gly Ser His Val Ser Val Ser Glu Gly
1               5                   10                  15
Ala Leu Val Leu Leu Arg Cys Asn Tyr Ser Ser Ser Val Pro Pro Tyr
                20                  25                  30
Leu Phe Trp Tyr Val Gln Tyr Pro Asn Gln Gly Leu Gln Leu Leu Leu
                35                  40                  45
Lys Tyr Thr Ser Ala Ala Thr Leu Val Lys Gly Ile Asn Gly Phe Glu
                50                  55                  60
```

```
Ala Glu Phe Lys Lys Ser Glu Thr Ser Phe His Leu Thr Lys Pro Ser
 65                  70                  75                  80

Ala His Met Ser Asp Ala Ala Glu Tyr Phe Cys Ala Val Ser Ala Arg
                 85                  90                  95

Tyr Asn Phe Asn Lys Phe Tyr Phe Gly Ser Gly Thr Lys Leu Asn Val
            100                 105                 110

Lys Pro Tyr Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
130                 135                 140

Gln Thr Asn Val Ser Gln Ser Lys Asp Ser Asp Val Tyr Ile Thr Asp
145                 150                 155                 160

Lys Thr Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205

Cys Asp Val Lys Leu Val Glu Lys Ser Phe Glu Thr Asp Thr Asn Leu
210                 215                 220

Asn Phe Gln Asn Leu Ser Val Ile Gly Phe Arg Ile Leu Leu Leu Lys
225                 230                 235                 240

Val Ala Gly Phe Asn Leu Leu Met Thr Leu Arg Leu Trp Ser Ser
                245                 250                 255

<210> SEQ ID NO 65
<211> LENGTH: 291
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Asp Ser Gly Val Thr Gln Thr Pro Lys His Leu Ile Thr Ala Thr Gly
 1               5                  10                  15

Gln Arg Val Thr Leu Arg Cys Ser Pro Arg Ser Gly Asp Leu Ser Val
                 20                  25                  30

Tyr Trp Tyr Gln Gln Ser Leu Asp Gln Gly Leu Gln Phe Leu Ile His
             35                  40                  45

Tyr Tyr Asn Gly Glu Glu Arg Ala Lys Gly Asn Ile Leu Glu Arg Phe
         50                  55                  60

Ser Ala Gln Gln Phe Pro Asp Leu His Ser Glu Leu Asn Leu Ser Ser
 65                  70                  75                  80

Leu Glu Leu Gly Asp Ser Ala Leu Tyr Phe Cys Ala Ser Ser Ala Ser
                 85                  90                  95

Gly Gly Arg Ser Tyr Glu Gln Tyr Phe Gly Pro Gly Thr Arg Leu Thr
            100                 105                 110

Val Thr Glu Asp Leu Asn Lys Val Phe Pro Pro Glu Val Ala Val Phe
        115                 120                 125

Glu Pro Ser Glu Ala Glu Ile Ser His Thr Gln Lys Ala Thr Leu Val
130                 135                 140

Cys Leu Ala Thr Gly Phe Phe Pro Asp His Val Glu Leu Ser Trp Trp
145                 150                 155                 160

Val Asn Gly Lys Glu Val His Ser Gly Val Ser Thr Asp Pro Gln Pro
                165                 170                 175
```

Leu Lys Glu Gln Pro Ala Leu Asn Asp Ser Arg Tyr Cys Leu Ser Ser
            180                 185                 190

Arg Leu Arg Val Ser Ala Thr Phe Trp Gln Asn Pro Arg Asn His Phe
        195                 200                 205

Arg Cys Gln Val Gln Phe Tyr Gly Leu Ser Glu Asn Asp Glu Trp Thr
    210                 215                 220

Gln Asp Arg Ala Lys Pro Val Thr Gln Ile Val Ser Ala Glu Ala Trp
225                 230                 235                 240

Gly Arg Ala Asp Cys Gly Phe Thr Ser Val Ser Tyr Gln Gln Gly Val
                245                 250                 255

Leu Ser Ala Thr Ile Leu Tyr Glu Ile Leu Leu Gly Lys Ala Thr Leu
            260                 265                 270

Tyr Ala Val Leu Val Ser Ala Leu Val Leu Met Ala Met Val Lys Arg
        275                 280                 285

Lys Asp Phe
    290

<210> SEQ ID NO 66
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asp Ser Gly Val Thr Gln Thr Pro Lys His Leu Ile Thr Ala Thr Gly
1               5                   10                  15

Gln Arg Val Thr Leu Arg Cys Ser Pro Arg Ser Gly Asp Leu Ser Val
            20                  25                  30

Tyr Trp Tyr Gln Gln Ser Leu Asp Gln Gly Leu Gln Phe Leu Ile His
        35                  40                  45

Tyr Tyr Asn Gly Glu Glu Arg Ala Lys Gly Asn Ile Leu Glu Arg Phe
    50                  55                  60

Ser Ala Gln Gln Phe Pro Asp Leu His Ser Glu Leu Asn Leu Ser Ser
65                  70                  75                  80

Leu Glu Leu Gly Asp Ser Ala Leu Tyr Phe Cys Ala Ser Ser Ala Ser
                85                  90                  95

Gly Gly Arg Ser Tyr Glu Gln Tyr Phe Gly Pro Gly Thr Arg Leu Thr
            100                 105                 110

Val Thr Glu Asp Leu Lys Asn Val Phe Pro Pro Glu Val Ala Val Phe
        115                 120                 125

Glu Pro Ser Glu Ala Glu Ile Ser His Thr Gln Lys Ala Thr Leu Val
130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val Ser Thr Asp Pro Gln Pro
                165                 170                 175

Leu Lys Glu Gln Pro Ala Leu Asn Asp Ser Arg Tyr Cys Leu Ser Ser
            180                 185                 190

Arg Leu Arg Val Ser Ala Thr Phe Trp Gln Asn Pro Arg Asn His Phe
        195                 200                 205

Arg Cys Gln Val Gln Phe Tyr Gly Leu Ser Glu Asn Asp Glu Trp Thr
    210                 215                 220

Gln Asp Arg Ala Lys Pro Val Thr Gln Ile Val Ser Ala Glu Ala Trp

```
225                 230                 235                 240

Gly Arg Ala Asp Cys Gly Phe Thr Ser Glu Ser Tyr Gln Gln Gly Val
                245                 250                 255

Leu Ser Ala Thr Ile Leu Tyr Glu Ile Leu Leu Gly Lys Ala Thr Leu
                260                 265                 270

Tyr Ala Val Leu Val Ser Ala Leu Val Leu Met Ala Met Val Lys Arg
                275                 280                 285

Lys Asp Ser Arg Gly
            290

<210> SEQ ID NO 67
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Glu Asp Gln Val Thr Gln Ser Pro Glu Ala Leu Arg Leu Gln Glu Gly
1               5                   10                  15

Glu Ser Ser Ser Leu Asn Cys Ser Tyr Thr Val Ser Gly Leu Arg Gly
            20                  25                  30

Leu Phe Trp Tyr Arg Gln Asp Pro Gly Lys Gly Pro Glu Phe Leu Phe
        35                  40                  45

Thr Leu Tyr Ser Ala Gly Glu Glu Lys Glu Lys Glu Arg Leu Lys Ala
    50                  55                  60

Thr Leu Thr Lys Lys Glu Ser Phe Leu His Ile Thr Ala Pro Lys Pro
65                  70                  75                  80

Glu Asp Ser Ala Thr Tyr Leu Cys Ala Val Arg Asn Thr Gly Phe Gln
                85                  90                  95

Lys Leu Val Phe Gly Thr Gly Thr Arg Leu Leu Val Ser Pro Tyr Ile
            100                 105                 110

Gln Asn Pro Asp Pro Ala Val Tyr Gln Leu Arg Asp Ser Lys Ser Ser
        115                 120                 125

Asp Lys Ser Val Cys Leu Phe Thr Asp Phe Asp Ser Gln Thr Asn Val
    130                 135                 140

Ser Gln Ser Lys Asp Ser Asp Val Tyr Ile Thr Asp Lys Thr Val Leu
145                 150                 155                 160

Asp Met Arg Ser Met Asp Phe Lys Ser Asn Ser Ala Val Ala Trp Ser
                165                 170                 175

Asn Lys Ser Asp Phe Ala Cys Ala Asn Ala Phe Asn Asn Ser Ile Ile
            180                 185                 190

Pro Glu Asp Thr Phe Phe Pro Ser Pro Glu Ser Ser Cys Asp Val Lys
        195                 200                 205

Leu Val Glu Lys Ser Phe Glu Thr Asp Thr Asn Leu Asn Phe Gln Asn
    210                 215                 220

Leu Ser Val Ile Gly Phe Arg Ile Leu Leu Leu Lys Val Ala Gly Phe
225                 230                 235                 240

Asn Leu Leu Met Thr Leu Arg Leu Trp Ser Ser
                245                 250

<210> SEQ ID NO 68
<211> LENGTH: 292
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 68

Asp Thr Gly Val Ser Gln Asn Pro Arg His Lys Ile Thr Lys Arg Gly
1               5                   10                  15

Gln Asn Val Thr Phe Arg Cys Asp Pro Ile Ser Glu His Asn Arg Leu
            20                  25                  30

Tyr Trp Tyr Arg Gln Thr Leu Gly Gln Gly Pro Glu Phe Leu Thr Tyr
        35                  40                  45

Phe Gln Asn Glu Ala Gln Leu Glu Lys Ser Arg Leu Leu Ser Asp Arg
    50                  55                  60

Phe Ser Ala Glu Arg Pro Lys Gly Ser Phe Ser Thr Leu Glu Ile Gln
65                  70                  75                  80

Arg Thr Glu Gln Gly Asp Ser Ala Met Tyr Leu Cys Ala Ser Ser Trp
                85                  90                  95

Arg Thr Gly Arg Glu Glu Thr Gln Tyr Phe Gly Pro Gly Thr Arg Leu
            100                 105                 110

Leu Val Leu Glu Asp Leu Asn Lys Val Phe Pro Pro Glu Val Ala Val
        115                 120                 125

Phe Glu Pro Ser Glu Ala Glu Ile Ser His Thr Gln Lys Ala Thr Leu
    130                 135                 140

Val Cys Leu Ala Thr Gly Phe Phe Pro Asp His Val Glu Leu Ser Trp
145                 150                 155                 160

Trp Val Asn Gly Lys Glu Val His Ser Gly Val Ser Thr Asp Pro Gln
                165                 170                 175

Pro Leu Lys Glu Gln Pro Ala Leu Asn Asp Ser Arg Tyr Cys Leu Ser
            180                 185                 190

Ser Arg Leu Arg Val Ser Ala Thr Phe Trp Gln Asn Pro Arg Asn His
        195                 200                 205

Phe Arg Cys Gln Val Gln Phe Tyr Gly Leu Ser Glu Asn Asp Glu Trp
    210                 215                 220

Thr Gln Asp Arg Ala Lys Pro Val Thr Gln Ile Val Ser Ala Glu Ala
225                 230                 235                 240

Trp Gly Arg Ala Asp Cys Gly Phe Thr Ser Val Ser Tyr Gln Gln Gly
                245                 250                 255

Val Leu Ser Ala Thr Ile Leu Tyr Glu Ile Leu Leu Gly Lys Ala Thr
            260                 265                 270

Leu Tyr Ala Val Leu Val Ser Ala Leu Val Leu Met Ala Met Val Lys
        275                 280                 285

Arg Lys Asp Phe
    290

<210> SEQ ID NO 69
<211> LENGTH: 294
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Thr Gly Val Ser Gln Asn Pro Arg His Lys Ile Thr Lys Arg Gly
1               5                   10                  15

Gln Asn Val Thr Phe Arg Cys Asp Pro Ile Ser Glu His Asn Arg Leu
            20                  25                  30

Tyr Trp Tyr Arg Gln Thr Leu Gly Gln Gly Pro Glu Phe Leu Thr Tyr
                35                  40                  45

Phe Gln Asn Glu Ala Gln Leu Glu Lys Ser Arg Leu Leu Ser Asp Arg
 50                  55                  60

Phe Ser Ala Glu Arg Pro Lys Gly Ser Phe Ser Thr Leu Glu Ile Gln
65                  70                  75                  80

Arg Thr Glu Gln Gly Asp Ser Ala Met Tyr Leu Cys Ala Ser Ser Trp
                85                  90                  95

Arg Thr Gly Arg Glu Glu Thr Gln Tyr Phe Gly Pro Gly Thr Arg Leu
            100                 105                 110

Leu Val Leu Glu Asp Leu Lys Asn Val Phe Pro Pro Glu Val Ala Val
            115                 120                 125

Phe Glu Pro Ser Glu Ala Glu Ile Ser His Thr Gln Lys Ala Thr Leu
130                 135                 140

Val Cys Leu Ala Thr Gly Phe Tyr Pro Asp His Val Glu Leu Ser Trp
145                 150                 155                 160

Trp Val Asn Gly Lys Glu Val His Ser Gly Val Ser Thr Asp Pro Gln
                165                 170                 175

Pro Leu Lys Glu Gln Pro Ala Leu Asn Asp Ser Arg Tyr Cys Leu Ser
            180                 185                 190

Ser Arg Leu Arg Val Ser Ala Thr Phe Trp Gln Asn Pro Arg Asn His
        195                 200                 205

Phe Arg Cys Gln Val Gln Phe Tyr Gly Leu Ser Glu Asn Asp Glu Trp
    210                 215                 220

Thr Gln Asp Arg Ala Lys Pro Val Thr Gln Ile Val Ser Ala Glu Ala
225                 230                 235                 240

Trp Gly Arg Ala Asp Cys Gly Phe Thr Ser Glu Ser Tyr Gln Gln Gly
                245                 250                 255

Val Leu Ser Ala Thr Ile Leu Tyr Glu Ile Leu Leu Gly Lys Ala Thr
            260                 265                 270

Leu Tyr Ala Val Leu Val Ser Ala Leu Val Leu Met Ala Met Val Lys
        275                 280                 285

Arg Lys Asp Ser Arg Gly
    290

<210> SEQ ID NO 70
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Met Leu Trp Asn
                85                  90                  95

```
Gln Gly Gly Lys Leu Ile Phe Gly Gln Gly Thr Glu Leu Ser Val Lys
                100                 105                 110

Pro Tyr Ile Gln Asn Pro Asp Pro Ala Val Tyr Gln Leu Arg Asp Ser
            115                 120                 125

Lys Ser Ser Asp Lys Ser Val Cys Leu Phe Thr Asp Phe Asp Ser Gln
130                 135                 140

Thr Asn Val Ser Gln Ser Lys Asp Ser Asp Val Tyr Ile Thr Asp Lys
145                 150                 155                 160

Thr Val Leu Asp Met Arg Ser Met Asp Phe Lys Ser Asn Ser Ala Val
                165                 170                 175

Ala Trp Ser Asn Lys Ser Asp Phe Ala Cys Ala Asn Ala Phe Asn Asn
            180                 185                 190

Ser Ile Ile Pro Glu Asp Thr Phe Phe Pro Ser Pro Glu Ser Ser Cys
        195                 200                 205

Asp Val Lys Leu Val Glu Lys Ser Phe Glu Thr Asp Thr Asn Leu Asn
    210                 215                 220

Phe Gln Asn Leu Ser Val Ile Gly Phe Arg Ile Leu Leu Leu Lys Val
225                 230                 235                 240

Ala Gly Phe Asn Leu Leu Met Thr Leu Arg Leu Trp Ser Ser
                245                 250

<210> SEQ ID NO 71
<211> LENGTH: 289
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Lys Ala Gly Val Thr Gln Thr Pro Arg Tyr Leu Ile Lys Thr Arg Gly
1               5                   10                  15

Gln Gln Val Thr Leu Ser Cys Ser Pro Ile Ser Gly His Arg Ser Val
            20                  25                  30

Ser Trp Tyr Gln Gln Thr Pro Gly Gln Gly Leu Gln Phe Leu Phe Glu
        35                  40                  45

Tyr Phe Ser Glu Thr Gln Arg Asn Lys Gly Asn Phe Pro Gly Arg Phe
    50                  55                  60

Ser Gly Arg Gln Phe Ser Asn Ser Arg Ser Glu Met Asn Val Ser Thr
65                  70                  75                  80

Leu Glu Leu Gly Asp Ser Ala Leu Tyr Leu Cys Ala Ser Ser Leu Gly
                85                  90                  95

Arg Gly Tyr Glu Gln Tyr Phe Gly Pro Gly Thr Arg Leu Thr Val Thr
            100                 105                 110

Glu Asp Leu Asn Lys Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Phe Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Cys Leu Ser Ser Arg Leu
            180                 185                 190

Arg Val Ser Ala Thr Phe Trp Gln Asn Pro Arg Asn His Phe Arg Cys
```

```
            195                 200                 205
Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp Cys Gly Phe Thr Ser Val Ser Tyr Gln Gln Gly Val Leu Ser
                245                 250                 255

Ala Thr Ile Leu Tyr Glu Ile Leu Leu Gly Lys Ala Thr Leu Tyr Ala
                260                 265                 270

Val Leu Val Ser Ala Leu Val Leu Met Ala Met Val Lys Arg Lys Asp
            275                 280                 285

Phe

<210> SEQ ID NO 72
<211> LENGTH: 291
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Lys Ala Gly Val Thr Gln Thr Pro Arg Tyr Leu Ile Lys Thr Arg Gly
1               5                   10                  15

Gln Gln Val Thr Leu Ser Cys Ser Pro Ile Ser Gly His Arg Ser Val
                20                  25                  30

Ser Trp Tyr Gln Gln Thr Pro Gly Gln Gly Leu Gln Phe Leu Phe Glu
            35                  40                  45

Tyr Phe Ser Glu Thr Gln Arg Asn Lys Gly Asn Phe Pro Gly Arg Phe
        50                  55                  60

Ser Gly Arg Gln Phe Ser Asn Ser Arg Ser Glu Met Asn Val Ser Thr
65                  70                  75                  80

Leu Glu Leu Gly Asp Ser Ala Leu Tyr Leu Cys Ala Ser Ser Leu Gly
                85                  90                  95

Arg Gly Tyr Glu Gln Tyr Phe Gly Pro Gly Thr Arg Leu Thr Val Thr
                100                 105                 110

Glu Asp Leu Lys Asn Val Phe Pro Pro Glu Val Ala Val Phe Glu Pro
            115                 120                 125

Ser Glu Ala Glu Ile Ser His Thr Gln Lys Ala Thr Leu Val Cys Leu
    130                 135                 140

Ala Thr Gly Phe Tyr Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Cys Leu Ser Ser Arg Leu
            180                 185                 190

Arg Val Ser Ala Thr Phe Trp Gln Asn Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp Cys Gly Phe Thr Ser Glu Ser Tyr Gln Gln Gly Val Leu Ser
                245                 250                 255

Ala Thr Ile Leu Tyr Glu Ile Leu Leu Gly Lys Ala Thr Leu Tyr Ala
```

```
                    260                 265                 270
        Val Leu Val Ser Ala Leu Val Leu Met Ala Met Val Lys Arg Lys Asp
                275                 280                 285

Ser Arg Gly
                290

<210> SEQ ID NO 73
<211> LENGTH: 91
<212> TYPE: PRT
<213> ORGANISM: Homo sapiens

<400> SEQUENCE: 73

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly
                85                  90

<210> SEQ ID NO 74
<211> LENGTH: 93
<212> TYPE: PRT
<213> ORGANISM: Homo sapiens

<400> SEQUENCE: 74

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser
                85                  90

<210> SEQ ID NO 75
<211> LENGTH: 92
<212> TYPE: PRT
<213> ORGANISM: Homo sapiens

<400> SEQUENCE: 75

Lys Asn Gln Val Glu Gln Ser Pro Gln Ser Leu Ile Ile Leu Glu Gly
1               5                   10                  15

Lys Asn Cys Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Met Thr Phe Ser Glu Asn Thr Lys Ser Asn Gly Arg Tyr Thr Ala
    50                  55                  60
```

```
Thr Leu Asp Ala Asp Thr Lys Gln Ser Ser Leu His Ile Thr Ala Ser
 65                  70                  75                  80

Gln Leu Ser Asp Ser Ala Ser Tyr Ile Cys Val Val
                 85                  90

<210> SEQ ID NO 76
<211> LENGTH: 95
<212> TYPE: PRT
<213> ORGANISM: Homo sapiens

<400> SEQUENCE: 76

Asp Ala Gly Val Ile Gln Ser Pro Arg His Glu Val Thr Glu Met Gly
  1               5                  10                  15

Gln Glu Val Thr Leu Arg Cys Lys Pro Ile Ser Gly His Asn Ser Leu
                 20                  25                  30

Phe Trp Tyr Arg Gln Thr Met Met Arg Gly Leu Glu Leu Leu Ile Tyr
             35                  40                  45

Phe Asn Asn Asn Val Pro Ile Asp Asp Ser Gly Met Pro Glu Asp Arg
 50                  55                  60

Phe Ser Ala Lys Met Pro Asn Ala Ser Phe Ser Thr Leu Lys Ile Gln
 65                  70                  75                  80

Pro Ser Glu Pro Arg Asp Ser Ala Val Tyr Phe Cys Ala Ser Ser
                 85                  90                  95

<210> SEQ ID NO 77
<211> LENGTH: 94
<212> TYPE: PRT
<213> ORGANISM: Homo sapiens

<400> SEQUENCE: 77

Ala Gln Ser Val Thr Gln Leu Gly Ser His Val Ser Val Ser Glu Gly
  1               5                  10                  15

Ala Leu Val Leu Leu Arg Cys Asn Tyr Ser Ser Ser Val Pro Pro Tyr
                 20                  25                  30

Leu Phe Trp Tyr Val Gln Tyr Pro Asn Gln Gly Leu Gln Leu Leu Leu
             35                  40                  45

Lys Tyr Thr Ser Ala Ala Thr Leu Val Lys Gly Ile Asn Gly Phe Glu
 50                  55                  60

Ala Glu Phe Lys Lys Ser Glu Thr Ser Phe His Leu Thr Lys Pro Ser
 65                  70                  75                  80

Ala His Met Ser Asp Ala Ala Glu Tyr Phe Cys Ala Val Ser
                 85                  90

<210> SEQ ID NO 78
<211> LENGTH: 94
<212> TYPE: PRT
<213> ORGANISM: Homo sapiens

<400> SEQUENCE: 78

Asp Ser Gly Val Thr Gln Thr Pro Lys His Leu Ile Thr Ala Thr Gly
  1               5                  10                  15

Gln Arg Val Thr Leu Arg Cys Ser Pro Arg Ser Gly Asp Leu Ser Val
                 20                  25                  30

Tyr Trp Tyr Gln Gln Ser Leu Asp Gln Gly Leu Gln Phe Leu Ile His
             35                  40                  45

Tyr Tyr Asn Gly Glu Glu Arg Ala Lys Gly Asn Ile Leu Glu Arg Phe
 50                  55                  60
```

```
Ser Ala Gln Gln Phe Pro Asp Leu His Ser Glu Leu Asn Leu Ser Ser
 65                  70                  75                  80

Leu Glu Leu Gly Asp Ser Ala Leu Tyr Phe Cys Ala Ser Ser
                85                  90
```

<210> SEQ ID NO 79
<211> LENGTH: 90
<212> TYPE: PRT
<213> ORGANISM: Homo sapiens

<400> SEQUENCE: 79

```
Glu Asp Gln Val Thr Gln Ser Pro Glu Ala Leu Arg Leu Gln Glu Gly
  1               5                  10                  15

Glu Ser Ser Ser Leu Asn Cys Ser Tyr Thr Val Ser Gly Leu Arg Gly
                 20                  25                  30

Leu Phe Trp Tyr Arg Gln Asp Pro Gly Lys Gly Pro Glu Phe Leu Phe
             35                  40                  45

Thr Leu Tyr Ser Ala Gly Glu Glu Lys Glu Lys Glu Arg Leu Lys Ala
 50                  55                  60

Thr Leu Thr Lys Lys Glu Ser Phe Leu His Ile Thr Ala Pro Lys Pro
 65                  70                  75                  80

Glu Asp Ser Ala Thr Tyr Leu Cys Ala Val
                85                  90
```

<210> SEQ ID NO 80
<211> LENGTH: 95
<212> TYPE: PRT
<213> ORGANISM: Homo sapiens

<400> SEQUENCE: 80

```
Asp Thr Gly Val Ser Gln Asn Pro Arg His Lys Ile Thr Lys Arg Gly
  1               5                  10                  15

Gln Asn Val Thr Phe Arg Cys Asp Pro Ile Ser Glu His Asn Arg Leu
                 20                  25                  30

Tyr Trp Tyr Arg Gln Thr Leu Gly Gln Gly Pro Glu Phe Leu Thr Tyr
             35                  40                  45

Phe Gln Asn Glu Ala Gln Leu Glu Lys Ser Arg Leu Leu Ser Asp Arg
 50                  55                  60

Phe Ser Ala Glu Arg Pro Lys Gly Ser Phe Ser Thr Leu Glu Ile Gln
 65                  70                  75                  80

Arg Thr Glu Gln Gly Asp Ser Ala Met Tyr Leu Cys Ala Ser Ser
                85                  90                  95
```

<210> SEQ ID NO 81
<211> LENGTH: 92
<212> TYPE: PRT
<213> ORGANISM: Homo sapiens

<400> SEQUENCE: 81

```
Lys Gln Glu Val Thr Gln Ile Pro Ala Ala Leu Ser Val Pro Glu Gly
  1               5                  10                  15

Glu Asn Leu Val Leu Asn Cys Ser Phe Thr Asp Ser Ala Ile Tyr Asn
                 20                  25                  30

Leu Gln Trp Phe Arg Gln Asp Pro Gly Lys Gly Leu Thr Ser Leu Leu
             35                  40                  45

Leu Ile Gln Ser Ser Gln Arg Glu Gln Thr Ser Gly Arg Leu Asn Ala
 50                  55                  60

Ser Leu Asp Lys Ser Ser Gly Arg Ser Thr Leu Tyr Ile Ala Ala Ser
```

```
65                  70                  75                  80

Gln Pro Gly Asp Ser Ala Thr Tyr Leu Cys Ala Val
                85                  90

<210> SEQ ID NO 82
<211> LENGTH: 95
<212> TYPE: PRT
<213> ORGANISM: Homo sapiens

<400> SEQUENCE: 82

Lys Ala Gly Val Thr Gln Thr Pro Arg Tyr Leu Ile Lys Thr Arg Gly
1               5                   10                  15

Gln Gln Val Thr Leu Ser Cys Ser Pro Ile Ser Gly His Arg Ser Val
            20                  25                  30

Ser Trp Tyr Gln Gln Thr Pro Gly Gln Gly Leu Gln Phe Leu Phe Glu
        35                  40                  45

Tyr Phe Ser Glu Thr Gln Arg Asn Lys Gly Asn Phe Pro Gly Arg Phe
    50                  55                  60

Ser Gly Arg Gln Phe Ser Asn Ser Arg Ser Glu Met Asn Val Ser Thr
65                  70                  75                  80

Leu Glu Leu Gly Asp Ser Ala Leu Tyr Leu Cys Ala Ser Ser Leu
                85                  90                  95

<210> SEQ ID NO 83
<211> LENGTH: 604
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Arg Leu Thr Gly Arg Val His Gly Tyr Thr Phe Gly Ser Gly Thr Arg
        115                 120                 125

Leu Thr Val Val Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
```

```
              195                 200                 205
Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
                260                 265                 270

Gly Val Leu Ser Ala Thr Ile Leu Tyr Glu Ile Leu Leu Gly Lys Ala
                275                 280                 285

Thr Leu Tyr Ala Val Leu Val Ser Ala Leu Val Leu Met Ala Met Val
290                 295                 300

Lys Arg Lys Asp Phe Gly Ser Gly Ala Thr Asn Phe Ser Leu Leu Lys
305                 310                 315                 320

Gln Ala Gly Asp Val Glu Glu Asn Pro Gly Pro Met Val Leu Lys Phe
                325                 330                 335

Ser Val Ser Ile Leu Trp Ile Gln Leu Ala Trp Val Ser Thr Gln Leu
                340                 345                 350

Leu Glu Gln Ser Pro Gln Phe Leu Ser Ile Gln Gly Glu Asn Leu
                355                 360                 365

Thr Val Tyr Cys Asn Ser Ser Ser Val Phe Ser Ser Leu Gln Trp Tyr
                370                 375                 380

Arg Gln Glu Pro Gly Glu Gly Pro Val Leu Leu Val Thr Val Val Thr
385                 390                 395                 400

Gly Gly Glu Val Lys Lys Leu Lys Arg Leu Thr Phe Gln Phe Gly Asp
                405                 410                 415

Ala Arg Lys Asp Ser Ser Leu His Ile Thr Ala Ala Gln Pro Gly Asp
                420                 425                 430

Thr Gly Leu Tyr Leu Cys Ala Gly Tyr Gly Gly Ser Asn Tyr Lys
                435                 440                 445

Leu Thr Phe Gly Lys Gly Thr Leu Leu Thr Val Asn Pro Tyr Ile Gln
                450                 455                 460

Asn Pro Asp Pro Ala Val Tyr Gln Leu Arg Asp Ser Lys Ser Ser Asp
465                 470                 475                 480

Lys Ser Val Cys Leu Phe Thr Asp Phe Asp Ser Gln Thr Asn Val Ser
                485                 490                 495

Gln Ser Lys Asp Ser Asp Val Tyr Ile Thr Asp Lys Thr Val Leu Asp
                500                 505                 510

Met Arg Ser Met Asp Phe Lys Ser Asn Ser Ala Val Ala Trp Ser Asn
                515                 520                 525

Lys Ser Asp Phe Ala Cys Ala Asn Ala Phe Asn Asn Ser Ile Ile Pro
                530                 535                 540

Glu Asp Thr Phe Phe Pro Ser Pro Glu Ser Ser Cys Asp Val Lys Leu
545                 550                 555                 560

Val Glu Lys Ser Phe Glu Thr Asp Thr Asn Leu Asn Phe Gln Asn Leu
                565                 570                 575

Ser Val Ile Gly Phe Arg Ile Leu Leu Leu Lys Val Ala Gly Phe Asn
                580                 585                 590

Leu Leu Met Thr Leu Arg Leu Trp Ser Ser Gly Ser
                595                 600

<210> SEQ ID NO 84
```

```
<211> LENGTH: 9
<212> TYPE: PRT
<213> ORGANISM: Influenza A virus

<400> SEQUENCE: 84

Gln Pro Glu Trp Phe Arg Asn Val Leu
1               5

<210> SEQ ID NO 85
<211> LENGTH: 10
<212> TYPE: PRT
<213> ORGANISM: Human cytomegalovirus

<400> SEQUENCE: 85

Thr Pro Arg Val Thr Gly Gly Gly Ala Met
1               5                   10

<210> SEQ ID NO 86
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Val Phe Ser Ser Leu
                20                  25                  30

Gln Trp Tyr Arg Gln Glu Pro Gly Glu Gly Pro Val Leu Leu Val Thr
            35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Tyr Gly Gly Gly Ser
                85                  90                  95

Asn Tyr Lys Leu Thr Phe Gly Lys Gly Thr Leu Leu Thr Val Asn Pro
            100                 105                 110

<210> SEQ ID NO 87
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
                20                  25                  30

Ser Trp Tyr Arg Gln Asp Pro Gly Leu Gly Leu Arg Gln Ile Tyr Tyr
            35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Arg Leu Thr
```

```
                     85                  90                  95

Gly Arg Val His Gly Tyr Thr Phe Gly Ser Gly Thr Arg Leu Thr Val
                100                 105                 110

Val

<210> SEQ ID NO 88
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Lys Asn Gln Val Glu Gln Ser Pro Gln Ser Leu Ile Ile Leu Glu Gly
1               5                   10                  15

Lys Asn Cys Thr Leu Gln Cys Asn Tyr Thr Val Ser Pro Phe Ser Asn
                20                  25                  30

Leu Arg Trp Tyr Lys Gln Asp Thr Gly Arg Gly Pro Val Ser Leu Thr
            35                  40                  45

Ile Met Thr Phe Ser Glu Asn Thr Lys Ser Asn Gly Arg Tyr Thr Ala
50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Arg Gly Gly Ala
                85                  90                  95

Ala Gly Asn Lys Leu Thr Phe Gly Gly Gly Thr Arg Val Leu Val Lys
                100                 105                 110

Pro

<210> SEQ ID NO 89
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asn Ser Leu
                20                  25                  30

Phe Trp Tyr Arg Gln Thr Met Met Arg Gly Leu Glu Leu Leu Ile Tyr
            35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Ser Ser
                85                  90                  95

Gly Gly Ala Asn Thr Glu Ala Phe Phe Gly Gln Gly Thr Arg Leu Thr
                100                 105                 110

Val Val

<210> SEQ ID NO 90
<211> LENGTH: 1821
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 90

| | | | | | |
|---|---|---|---|---|---|
| gccaccatgg | gacctcagct | gctgggatac | gttgtgctgt | gtctgcttgg | agccggacct | 60 |
| ctggaagccc | aagtgacaca | gaaccccaga | tacctgatca | ccgtgaccgg | caagaaactg | 120 |
| accgtgacct | gcagccagaa | catgaaccac | gagtacatga | gctggtacag | acaggaccct | 180 |
| ggcctgggcc | tgagacagat | ctactacagc | atgaacgtgg | aagtgaccga | caagggcgac | 240 |
| gtgcccgagg | gctacaaggt | gtccagaaaa | gagaagcgga | acttcccact | gatcctggaa | 300 |
| agcccatctc | ctaaccagac | cagcctgtac | ttctgcgcca | gcagactgac | aggcagagtg | 360 |
| cacggctaca | catttggcag | cggcaccaga | ctgactgtgg | tggaagatct | gaacaaggtg | 420 |
| ttccctccag | aggtggccgt | gttcgagcct | tctgaggccg | agatcagcca | cacacagaaa | 480 |
| gccacactcg | tgtgcctggc | caccggcttt | tttcccgatc | acgtggaact | gtcttggtgg | 540 |
| gtcaacggca | agaggtgca | cagcggcgtc | agcacagatc | cccagcctct | gaaagaacag | 600 |
| cccgctctga | cgacagccg | gtactgcctg | tcctccagac | tgagagtgtc | cgccaccttc | 660 |
| tggcagaacc | ctcggaacca | cttcagatgc | caggtgcagt | tctacggcct | gagcgagaac | 720 |
| gatgagtgga | cccaggatag | agccaagcct | gtgactcaga | tcgtgtctgc | cgaagcctgg | 780 |
| ggcagagccg | attgtggctt | taccagcgtg | tcctatcagc | agggcgtgct | gtctgccacc | 840 |
| atcctgtatg | agatcctgct | gggcaaagcc | actctgtacg | ccgtgctggt | ttctgccctg | 900 |
| gtgctgatgg | ccatggtcaa | gagaaaggac | tttggctccg | gcgccaccaa | cttcagcctg | 960 |
| ctgaaacagg | ctggcgacgt | ggaagagaac | cccggaccta | tggtgctgaa | gttctccgtg | 1020 |
| tccatcctgt | ggattcagct | ggcttgggtg | tccacacagc | tgctcgaaca | gagccctcag | 1080 |
| ttcctgagca | tccaagaggg | cgagaacctg | acagtgtact | gcaacagcag | cagcgtgttc | 1140 |
| agcagcctgc | agtggtacag | gcaagagcct | ggcgaaggac | ctgtgctgct | ggtcacagtt | 1200 |
| gtgacaggcg | gcgaagtgaa | gaagctgaag | cggctgacct | tccagttcgg | cgacgccaga | 1260 |
| aaggatagct | ccctgcacat | taccgctgct | cagccaggcg | ataccggcct | gtatctgtgt | 1320 |
| gctggatatg | gcggcggaag | caactacaag | ctgacctttg | gcaagggcac | cctgctgaca | 1380 |
| gtgaacccct | acattcagaa | ccccgatcca | gccgtgtatc | agctgagaga | cagcaagagc | 1440 |
| agcgacaaga | gcgtgtgtct | gttcaccgac | ttcgacagcc | agaccaacgt | gtcccagagc | 1500 |
| aaggacagcg | acgtgtacat | caccgacaag | accgtgctgg | acatgcggag | catggacttc | 1560 |
| aagagcaaca | gcgccgtggc | ctggtccaac | aagagcgatt | tcgcctgcgc | caacgccttc | 1620 |
| aacaacagca | ttatccccga | ggacacattc | ttcccaagtc | tgagagcag | ctgcgacgtg | 1680 |
| aagctggtgg | aaaagagctt | cgagacagac | accaacctga | acttccagaa | cctgagcgtg | 1740 |
| atcggcttca | gaatcctgct | gctgaaggtg | gccggcttca | atctgctgat | gaccctgaga | 1800 |
| ctgtggtcca | gcggatcctg | a | | | | 1821 |

<210> SEQ ID NO 91
<211> LENGTH: 609
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 91

```
Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
            35                  40                  45

Asn Ser Leu Phe Trp Tyr Arg Gln Thr Met Met Arg Gly Leu Glu Leu
50                  55                  60

Leu Ile Tyr Phe Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
                85                  90                  95

Lys Ile Gln Pro Ser Glu Pro Arg Asp Ser Ala Val Tyr Phe Cys Ala
            100                 105                 110

Ser Ser Ser Gly Gly Ala Asn Thr Glu Ala Phe Phe Gly Gln Gly Thr
            115                 120                 125

Arg Leu Thr Val Val Glu Asp Leu Asn Lys Val Phe Pro Pro Glu Val
            130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
                180                 185                 190

Pro Gln Pro Leu Lys Glu Gln Pro Ala Leu Asn Asp Ser Arg Tyr Cys
            195                 200                 205

Leu Ser Ser Arg Leu Arg Val Ser Ala Thr Phe Trp Gln Asn Pro Arg
210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
            245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
            275                 280                 285

Ala Thr Leu Tyr Ala Val Leu Val Ser Ala Leu Val Leu Met Ala Met
            290                 295                 300

Val Lys Arg Lys Asp Phe Gly Ser Gly Ala Thr Asn Phe Ser Leu Leu
305                 310                 315                 320

Lys Gln Ala Gly Asp Val Glu Glu Asn Pro Gly Pro Met Lys Lys His
            325                 330                 335

Leu Thr Thr Phe Leu Val Ile Leu Trp Leu Tyr Phe Tyr Arg Gly Asn
                340                 345                 350

Gly Lys Asn Gln Val Glu Gln Ser Pro Gln Ser Leu Ile Ile Leu Glu
            355                 360                 365

Gly Lys Asn Cys Thr Leu Gln Cys Asn Tyr Thr Val Ser Pro Phe Ser
            370                 375                 380

Asn Leu Arg Trp Tyr Lys Gln Asp Thr Gly Arg Gly Pro Val Ser Leu
385                 390                 395                 400

Thr Ile Met Thr Phe Ser Glu Asn Thr Lys Ser Asn Gly Arg Tyr Thr
                405                 410                 415
```

Ala Thr Leu Asp Ala Asp Thr Lys Gln Ser Ser Leu His Ile Thr Ala
            420                 425                 430

Ser Gln Leu Ser Asp Ser Ala Ser Tyr Ile Cys Val Val Arg Gly Gly
            435                 440                 445

Ala Ala Gly Asn Lys Leu Thr Phe Gly Gly Gly Thr Arg Val Leu Val
450                 455                 460

Lys Pro Tyr Ile Gln Asn Pro Asp Pro Ala Val Tyr Gln Leu Arg Asp
465                 470                 475                 480

Ser Lys Ser Ser Asp Lys Ser Val Cys Leu Phe Thr Asp Phe Asp Ser
            485                 490                 495

Gln Thr Asn Val Ser Gln Ser Lys Asp Ser Asp Val Tyr Ile Thr Asp
            500                 505                 510

Lys Thr Val Leu Asp Met Arg Ser Met Asp Phe Lys Ser Asn Ser Ala
            515                 520                 525

Val Ala Trp Ser Asn Lys Ser Asp Phe Ala Cys Ala Asn Ala Phe Asn
            530                 535                 540

Asn Ser Ile Ile Pro Glu Asp Thr Phe Phe Pro Ser Pro Glu Ser Ser
545                 550                 555                 560

Cys Asp Val Lys Leu Val Glu Lys Ser Phe Glu Thr Asp Thr Asn Leu
                565                 570                 575

Asn Phe Gln Asn Leu Ser Val Ile Gly Phe Arg Ile Leu Leu Leu Lys
            580                 585                 590

Val Ala Gly Phe Asn Leu Leu Met Thr Leu Arg Leu Trp Ser Ser Gly
            595                 600                 605

Ser

<210> SEQ ID NO 92
<211> LENGTH: 605
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Met Gly Ser Arg Leu Leu Cys Trp Val Leu Leu Cys Leu Leu Gly Ala
1               5                   10                  15

Gly Pro Val Lys Ala Gly Val Thr Gln Thr Pro Arg Tyr Leu Ile Lys
            20                  25                  30

Thr Arg Gly Gln Gln Val Thr Leu Ser Cys Ser Pro Ile Ser Gly His
        35                  40                  45

Arg Ser Val Ser Trp Tyr Gln Gln Thr Pro Gly Gln Gly Leu Gln Phe
50                  55                  60

Leu Phe Glu Tyr Phe Ser Glu Thr Gln Arg Asn Lys Gly Asn Phe Pro
65                  70                  75                  80

Gly Arg Phe Ser Gly Arg Gln Phe Ser Asn Ser Arg Ser Glu Met Asn
            85                  90                  95

Val Ser Thr Leu Glu Leu Gly Asp Ser Ala Leu Tyr Leu Cys Ala Ser
            100                 105                 110

Ser Leu Gly Arg Gly Tyr Glu Gln Tyr Phe Gly Pro Gly Thr Arg Leu
            115                 120                 125

Thr Val Thr Glu Asp Leu Asn Lys Val Phe Pro Pro Glu Val Ala Val
        130                 135                 140

Phe Glu Pro Ser Glu Ala Glu Ile Ser His Thr Gln Lys Ala Thr Leu
145                 150                 155                 160

-continued

```
Val Cys Leu Ala Thr Gly Phe Phe Pro Asp His Val Glu Leu Ser Trp
            165                 170                 175

Trp Val Asn Gly Lys Glu Val His Ser Gly Val Ser Thr Asp Pro Gln
        180                 185                 190

Pro Leu Lys Glu Gln Pro Ala Leu Asn Asp Ser Arg Tyr Cys Leu Ser
    195                 200                 205

Ser Arg Leu Arg Val Ser Ala Thr Phe Trp Gln Asn Pro Arg Asn His
210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Val Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Phe Gly Ser Gly Ala Thr Asn Phe Ser Leu Leu Lys Gln
305                 310                 315                 320

Ala Gly Asp Val Glu Glu Asn Pro Gly Pro Met Glu Thr Leu Leu Gly
                325                 330                 335

Leu Leu Ile Leu Trp Leu Gln Leu Gln Trp Val Ser Ser Lys Gln Glu
            340                 345                 350

Val Thr Gln Ile Pro Ala Ala Leu Ser Val Pro Glu Gly Glu Asn Leu
        355                 360                 365

Val Leu Asn Cys Ser Phe Thr Asp Ser Ala Ile Tyr Asn Leu Gln Trp
    370                 375                 380

Phe Arg Gln Asp Pro Gly Lys Gly Leu Thr Ser Leu Leu Leu Ile Gln
385                 390                 395                 400

Ser Ser Gln Arg Glu Gln Thr Ser Gly Arg Leu Asn Ala Ser Leu Asp
                405                 410                 415

Lys Ser Ser Gly Arg Ser Thr Leu Tyr Ile Ala Ala Ser Gln Pro Gly
            420                 425                 430

Asp Ser Ala Thr Tyr Leu Cys Ala Val Met Leu Trp Asn Gln Gly Gly
        435                 440                 445

Lys Leu Ile Phe Gly Gln Gly Thr Glu Leu Ser Val Lys Pro Tyr Ile
    450                 455                 460

Gln Asn Pro Asp Pro Ala Val Tyr Gln Leu Arg Asp Ser Lys Ser Ser
465                 470                 475                 480

Asp Lys Ser Val Cys Leu Phe Thr Asp Phe Asp Ser Gln Thr Asn Val
                485                 490                 495

Ser Gln Ser Lys Asp Ser Asp Val Tyr Ile Thr Asp Lys Thr Val Leu
            500                 505                 510

Asp Met Arg Ser Met Asp Phe Lys Ser Asn Ser Ala Val Ala Trp Ser
        515                 520                 525

Asn Lys Ser Asp Phe Ala Cys Ala Asn Ala Phe Asn Asn Ser Ile Ile
    530                 535                 540

Pro Glu Asp Thr Phe Phe Pro Ser Pro Glu Ser Ser Cys Asp Val Lys
545                 550                 555                 560

Leu Val Glu Lys Ser Phe Glu Thr Asp Thr Asn Leu Asn Phe Gln Asn
                565                 570                 575

Leu Ser Val Ile Gly Phe Arg Ile Leu Leu Leu Lys Val Ala Gly Phe
```

```
                580                 585                 590
Asn Leu Leu Met Thr Leu Arg Leu Trp Ser Ser Gly Ser
        595                 600                 605

<210> SEQ ID NO 93
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Ser Gly Ala Thr Asn Phe Ser Leu Leu Lys Gln Ala Gly Asp Val
1               5                   10                  15

Glu Glu Asn Pro Gly
            20

<210> SEQ ID NO 94
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105

<210> SEQ ID NO 95
<211> LENGTH: 282
<212> TYPE: PRT
<213> ORGANISM: Homo sapiens

<400> SEQUENCE: 95

Gly Phe Gly Asp Val Gly Ala Leu Glu Ser Leu Arg Gly Asn Ala Asp
1               5                   10                  15

Leu Ala Tyr Ile Leu Ser Met Glu Pro Cys Gly His Cys Leu Ile Ile
            20                  25                  30

Asn Asn Val Asn Phe Cys Arg Glu Ser Gly Leu Arg Thr Arg Thr Gly
        35                  40                  45

Ser Asn Ile Asp Cys Glu Lys Leu Arg Arg Arg Phe Ser Ser Leu His
    50                  55                  60

Phe Met Val Glu Val Lys Gly Asp Leu Thr Ala Lys Lys Met Val Leu
65                  70                  75                  80

Ala Leu Leu Glu Leu Ala Gln Gln Asp His Gly Ala Leu Asp Cys Cys
                85                  90                  95
```

```
Val Val Val Ile Leu Ser His Gly Cys Gln Ala Ser His Leu Gln Phe
            100                 105                 110

Pro Gly Ala Val Tyr Gly Thr Asp Gly Cys Pro Val Ser Val Glu Lys
            115                 120                 125

Ile Val Asn Ile Phe Asn Gly Thr Ser Cys Pro Ser Leu Gly Gly Lys
130                 135                 140

Pro Lys Leu Phe Phe Ile Gln Ala Cys Gly Gly Glu Gln Lys Asp His
145                 150                 155                 160

Gly Phe Glu Val Ala Ser Thr Ser Pro Glu Asp Ser Pro Gly Ser
            165                 170                 175

Asn Pro Glu Pro Asp Ala Thr Pro Phe Gln Glu Gly Leu Arg Thr Phe
            180                 185                 190

Asp Gln Leu Asp Ala Ile Ser Ser Leu Pro Thr Pro Ser Asp Ile Phe
            195                 200                 205

Val Ser Tyr Ser Thr Phe Pro Gly Phe Val Ser Trp Arg Asp Pro Lys
210                 215                 220

Ser Gly Ser Trp Tyr Val Glu Thr Leu Asp Asp Ile Phe Glu Gln Trp
225                 230                 235                 240

Ala His Ser Glu Asp Leu Gln Ser Leu Leu Leu Arg Val Ala Asn Ala
            245                 250                 255

Val Ser Val Lys Gly Ile Tyr Lys Gln Met Pro Gly Cys Phe Asn Phe
            260                 265                 270

Leu Arg Lys Lys Leu Phe Phe Lys Thr Ser
            275                 280

<210> SEQ ID NO 96
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: Lys or Arg

<400> SEQUENCE: 96

Arg Xaa Xaa Arg
1

<210> SEQ ID NO 97
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Ala Lys Arg
1

<210> SEQ ID NO 98
<211> LENGTH: 4
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Lys or Arg

<400> SEQUENCE: 98

Arg Xaa Xaa Arg
1

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Asp or Gly
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (4)..(4)
<223> OTHER INFORMATION: Any amino acid

<400> SEQUENCE: 99

Xaa Xaa Glu Xaa Asn Pro Gly Pro
1               5

<210> SEQ ID NO 100
<211> LENGTH: 19
<212> TYPE: PRT
<213> ORGANISM: Porcine teschovirus 1

<400> SEQUENCE: 100

Ala Thr Asn Phe Ser Leu Leu Lys Gln Ala Gly Asp Val Glu Glu Asn
1               5                   10                  15

Pro Gly Pro

<210> SEQ ID NO 101
<211> LENGTH: 18
<212> TYPE: PRT
<213> ORGANISM: Thosea asigna virus

<400> SEQUENCE: 101

Glu Gly Arg Gly Ser Leu Leu Thr Cys Gly Asp Val Glu Glu Asn Pro
1               5                   10                  15

Gly Pro

<210> SEQ ID NO 102
<211> LENGTH: 20
<212> TYPE: PRT
<213> ORGANISM: Equine rhinitis A virus

<400> SEQUENCE: 102

Gln Cys Thr Asn Tyr Ala Leu Leu Lys Leu Ala Gly Asp Val Glu Ser
1               5                   10                  15

Asn Pro Gly Pro
            20
```

```
<210> SEQ ID NO 103
<211> LENGTH: 22
<212> TYPE: PRT
<213> ORGANISM: Foot-and-mouth disease virus

<400> SEQUENCE: 103

Val Lys Gln Thr Leu Asn Phe Asp Leu Leu Lys Leu Ala Gly Asp Val
1               5                   10                  15

Glu Ser Asn Pro Gly Pro
            20

<210> SEQ ID NO 104
<211> LENGTH: 22
<212> TYPE: PRT
<213> ORGANISM: Cytoplasmic polyhedrosis virus

<400> SEQUENCE: 104

Asp Val Phe Arg Ser Asn Tyr Asp Leu Leu Lys Leu Cys Gly Asp Ile
1               5                   10                  15

Glu Ser Asn Pro Gly Pro
            20

<210> SEQ ID NO 105
<211> LENGTH: 22
<212> TYPE: PRT
<213> ORGANISM: Infectious flacherie virus

<400> SEQUENCE: 105

Thr Leu Thr Arg Ala Lys Ile Glu Asp Glu Leu Ile Arg Ala Gly Ile
1               5                   10                  15

Glu Ser Asn Pro Gly Pro
            20

<210> SEQ ID NO 106
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Ala Gln Ser Val Thr Gln Leu Gly Ser His Val Ser Val Ser Glu Gly
1               5                   10                  15

Ala Leu Val Leu Leu Arg Cys Asn Tyr Ser Ser Ser Val Pro Pro Tyr
            20                  25                  30

Leu Phe Trp Tyr Val Gln Tyr Pro Asn Gln Gly Leu Gln Leu Leu Leu
        35                  40                  45

Lys Tyr Thr Ser Ala Ala Thr Leu Val Lys Gly Ile Asn Gly Phe Glu
    50                  55                  60

Ala Glu Phe Lys Lys Ser Glu Thr Ser Phe His Leu Thr Lys Pro Ser
65                  70                  75                  80

Ala His Met Ser Asp Ala Ala Glu Tyr Phe Cys Ala Val Ser Ala Arg
                85                  90                  95

Tyr Asn Phe Asn Lys Phe Tyr Phe Gly Ser Gly Thr Lys Leu Asn Val
            100                 105                 110

Lys Pro

<210> SEQ ID NO 107
<211> LENGTH: 114
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 107

Asp Ser Gly Val Thr Gln Thr Pro Lys His Leu Ile Thr Ala Thr Gly
1               5                   10                  15

Gln Arg Val Thr Leu Arg Cys Ser Pro Arg Ser Gly Asp Leu Ser Val
            20                  25                  30

Tyr Trp Tyr Gln Gln Ser Leu Asp Gln Gly Leu Gln Phe Leu Ile His
        35                  40                  45

Tyr Tyr Asn Gly Glu Glu Arg Ala Lys Gly Asn Ile Leu Glu Arg Phe
    50                  55                  60

Ser Ala Gln Gln Phe Pro Asp Leu His Ser Glu Leu Asn Leu Ser Ser
65                  70                  75                  80

Leu Glu Leu Gly Asp Ser Ala Leu Tyr Phe Cys Ala Ser Ser Ala Ser
                85                  90                  95

Gly Gly Arg Ser Tyr Glu Gln Tyr Phe Gly Pro Gly Thr Arg Leu Thr
            100                 105                 110

Val Thr

<210> SEQ ID NO 108
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Thr Gly Val Ser Gln Asn Pro Arg His Lys Ile Thr Lys Arg Gly
1               5                   10                  15

Gln Asn Val Thr Phe Arg Cys Asp Pro Ile Ser Glu His Asn Arg Leu
            20                  25                  30

Tyr Trp Tyr Arg Gln Thr Leu Gly Gln Gly Pro Glu Phe Leu Thr Tyr
        35                  40                  45

Phe Gln Asn Glu Ala Gln Leu Glu Lys Ser Arg Leu Leu Ser Asp Arg
    50                  55                  60

Phe Ser Ala Glu Arg Pro Lys Gly Ser Phe Ser Thr Leu Glu Ile Gln
65                  70                  75                  80

Arg Thr Glu Gln Gly Asp Ser Ala Met Tyr Leu Cys Ala Ser Ser Trp
                85                  90                  95

Arg Thr Gly Arg Glu Glu Thr Gln Tyr Phe Gly Pro Gly Thr Arg Leu
            100                 105                 110

Leu Val Leu
        115

<210> SEQ ID NO 109
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Tyr Thr Ser Ala Ala Thr Leu Val
1               5
```

```
<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 110

Cys Pro Arg Ser Pro Ser His Ser Met
1               5

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 111

Asp Pro Arg Ser Pro Ser His Ser Met
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 112

Phe Pro Arg Ser Pro Ser His Ser Met
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 113

Gly Pro Arg Ser Pro Ser His Ser Met
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                         peptide
<220> FEATURE:
<221> NAME/KEY: MOD_RES
<222> LOCATION: (4)..(4)
<223> OTHER INFORMATION: Phosphoserine

<400> SEQUENCE: 114

His Pro Arg Ser Pro Ser His Ser Met
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 115

Ile Pro Arg Ser Pro Ser His Ser Met
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 116

Lys Pro Arg Ser Pro Ser His Ser Met
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 117

Leu Pro Arg Ser Pro Ser His Ser Met
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 118
```

```
Met Pro Arg Ser Pro Ser His Ser Met
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 119

Asn Pro Arg Ser Pro Ser His Ser Met
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 120

Pro Pro Arg Ser Pro Ser His Ser Met
1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 121

Gln Pro Arg Ser Pro Ser His Ser Met
1               5

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 122

Arg Pro Arg Ser Pro Ser His Ser Met
1               5

<210> SEQ ID NO 123
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 123

Ser Pro Arg Ser Pro Ser His Ser Met
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 124

Thr Pro Arg Ser Pro Ser His Ser Met
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 125

Val Pro Arg Ser Pro Ser His Ser Met
1               5

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 126

Trp Pro Arg Ser Pro Ser His Ser Met
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (4)..(4)
<223> OTHER INFORMATION: Phosphoserine

<400> SEQUENCE: 127

Tyr Pro Arg Ser Pro Ser His Ser Met
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 128

Glu Pro Cys Ser Pro Ser His Ser Met
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 129

Glu Pro Asp Ser Pro Ser His Ser Met
1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 130

Glu Pro Glu Ser Pro Ser His Ser Met
1               5

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 131

Glu Pro Phe Ser Pro Ser His Ser Met
1               5
```

```
<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 132

Glu Pro Gly Ser Pro Ser His Ser Met
1               5

<210> SEQ ID NO 133
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 133

Glu Pro His Ser Pro Ser His Ser Met
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 134

Glu Pro Ile Ser Pro Ser His Ser Met
1               5

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 135

Glu Pro Lys Ser Pro Ser His Ser Met
1               5

<210> SEQ ID NO 136
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 136

Glu Pro Leu Ser Pro Ser His Ser Met
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 137

Glu Pro Met Ser Pro Ser His Ser Met
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 138

Glu Pro Asn Ser Pro Ser His Ser Met
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 139

Glu Pro Pro Ser Pro Ser His Ser Met
1               5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine
```

```
<400> SEQUENCE: 140

Glu Pro Gln Ser Pro Ser His Ser Met
1               5

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 141

Glu Pro Ser Ser Pro Ser His Ser Met
1               5

<210> SEQ ID NO 142
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 142

Glu Pro Thr Ser Pro Ser His Ser Met
1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 143

Glu Pro Val Ser Pro Ser His Ser Met
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 144

Glu Pro Trp Ser Pro Ser His Ser Met
1               5

<210> SEQ ID NO 145
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 145

Glu Pro Tyr Ser Pro Ser His Ser Met
1               5

<210> SEQ ID NO 146
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Glu Pro Arg Cys Pro Ser His Ser Met
1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Glu Pro Arg Asp Pro Ser His Ser Met
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Glu Pro Arg Glu Pro Ser His Ser Met
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Glu Pro Arg Phe Pro Ser His Ser Met
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 150

Glu Pro Arg Gly Pro Ser His Ser Met
1               5

<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Glu Pro Arg His Pro Ser His Ser Met
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Glu Pro Arg Ile Pro Ser His Ser Met
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Glu Pro Arg Lys Pro Ser His Ser Met
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Glu Pro Arg Leu Pro Ser His Ser Met
1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Glu Pro Arg Met Pro Ser His Ser Met
1               5

<210> SEQ ID NO 156
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Glu Pro Arg Asn Pro Ser His Ser Met
1               5

<210> SEQ ID NO 157
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Glu Pro Arg Pro Pro Ser His Ser Met
1               5

<210> SEQ ID NO 158
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Glu Pro Arg Gln Pro Ser His Ser Met
1               5

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Glu Pro Arg Arg Pro Ser His Ser Met
1               5

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Glu Pro Arg Thr Pro Ser His Ser Met
1               5

<210> SEQ ID NO 161
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161
```

```
Glu Pro Arg Val Pro Ser His Ser Met
1               5
```

<210> SEQ ID NO 162
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

```
Glu Pro Arg Trp Pro Ser His Ser Met
1               5
```

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

```
Glu Pro Arg Tyr Pro Ser His Ser Met
1               5
```

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 164

```
Glu Pro Arg Ser Cys Ser His Ser Met
1               5
```

<210> SEQ ID NO 165
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 165

```
Glu Pro Arg Ser Asp Ser His Ser Met
1               5
```

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 166

Glu Pro Arg Ser Glu Ser His Ser Met
1               5

<210> SEQ ID NO 167
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 167

Glu Pro Arg Ser Phe Ser His Ser Met
1               5

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 168

Glu Pro Arg Ser Gly Ser His Ser Met
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 169

Glu Pro Arg Ser His Ser His Ser Met
1               5

<210> SEQ ID NO 170
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 170

Glu Pro Arg Ser Ile Ser His Ser Met
1               5

```
<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 171

Glu Pro Arg Ser Lys Ser His Ser Met
1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 172

Glu Pro Arg Ser Leu Ser His Ser Met
1               5

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 173

Glu Pro Arg Ser Met Ser His Ser Met
1               5

<210> SEQ ID NO 174
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 174

Glu Pro Arg Ser Asn Ser His Ser Met
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (4)..(4)
<223> OTHER INFORMATION: Phosphoserine

<400> SEQUENCE: 175

Glu Pro Arg Ser Gln Ser His Ser Met
1               5

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 176

Glu Pro Arg Ser Arg Ser His Ser Met
1               5

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 177

Glu Pro Arg Ser Ser Ser His Ser Met
1               5

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 178

Glu Pro Arg Ser Thr Ser His Ser Met
1               5

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 179
```

```
Glu Pro Arg Ser Val Ser His Ser Met
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 180

Glu Pro Arg Ser Trp Ser His Ser Met
1               5

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 181

Glu Pro Arg Ser Tyr Ser His Ser Met
1               5

<210> SEQ ID NO 182
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 182

Glu Pro Arg Ser Pro Cys His Ser Met
1               5

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 183

Glu Pro Arg Ser Pro Asp His Ser Met
1               5

<210> SEQ ID NO 184
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 184

Glu Pro Arg Ser Pro Glu His Ser Met
1               5

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 185

Glu Pro Arg Ser Pro Phe His Ser Met
1               5

<210> SEQ ID NO 186
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 186

Glu Pro Arg Ser Pro Gly His Ser Met
1               5

<210> SEQ ID NO 187
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 187

Glu Pro Arg Ser Pro His His Ser Met
1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
```

<223> OTHER INFORMATION: Phosphoserine

<400> SEQUENCE: 188

Glu Pro Arg Ser Pro Ile His Ser Met
1               5

<210> SEQ ID NO 189
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 189

Glu Pro Arg Ser Pro Lys His Ser Met
1               5

<210> SEQ ID NO 190
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 190

Glu Pro Arg Ser Pro Leu His Ser Met
1               5

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 191

Glu Pro Arg Ser Pro Met His Ser Met
1               5

<210> SEQ ID NO 192
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 192

Glu Pro Arg Ser Pro Asn His Ser Met
1               5

```
<210> SEQ ID NO 193
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 193

Glu Pro Arg Ser Pro Pro His Ser Met
1               5

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 194

Glu Pro Arg Ser Pro Gln His Ser Met
1               5

<210> SEQ ID NO 195
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 195

Glu Pro Arg Ser Pro Arg His Ser Met
1               5

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 196

Glu Pro Arg Ser Pro Thr His Ser Met
1               5

<210> SEQ ID NO 197
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (4)..(4)
<223> OTHER INFORMATION: Phosphoserine

<400> SEQUENCE: 197

Glu Pro Arg Ser Pro Val His Ser Met
1               5

<210> SEQ ID NO 198
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 198

Glu Pro Arg Ser Pro Trp His Ser Met
1               5

<210> SEQ ID NO 199
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 199

Glu Pro Arg Ser Pro Tyr His Ser Met
1               5

<210> SEQ ID NO 200
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 200

Glu Pro Arg Ser Pro Ser Cys Ser Met
1               5

<210> SEQ ID NO 201
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 201
```

```
Glu Pro Arg Ser Pro Ser Asp Ser Met
1               5

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 202

Glu Pro Arg Ser Pro Ser Glu Ser Met
1               5

<210> SEQ ID NO 203
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 203

Glu Pro Arg Ser Pro Ser Phe Ser Met
1               5

<210> SEQ ID NO 204
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 204

Glu Pro Arg Ser Pro Ser Gly Ser Met
1               5

<210> SEQ ID NO 205
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 205

Glu Pro Arg Ser Pro Ser Ile Ser Met
1               5

<210> SEQ ID NO 206
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 206

Glu Pro Arg Ser Pro Ser Lys Ser Met
1               5

<210> SEQ ID NO 207
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 207

Glu Pro Arg Ser Pro Ser Leu Ser Met
1               5

<210> SEQ ID NO 208
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 208

Glu Pro Arg Ser Pro Ser Met Ser Met
1               5

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 209

Glu Pro Arg Ser Pro Ser Asn Ser Met
1               5

<210> SEQ ID NO 210
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (4)..(4)
<223> OTHER INFORMATION: Phosphoserine

<400> SEQUENCE: 210

Glu Pro Arg Ser Pro Ser Pro Ser Met
1               5

<210> SEQ ID NO 211
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 211

Glu Pro Arg Ser Pro Ser Gln Ser Met
1               5

<210> SEQ ID NO 212
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 212

Glu Pro Arg Ser Pro Ser Arg Ser Met
1               5

<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 213

Glu Pro Arg Ser Pro Ser Ser Ser Met
1               5

<210> SEQ ID NO 214
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 214

Glu Pro Arg Ser Pro Ser Thr Ser Met
1               5
```

```
<210> SEQ ID NO 215
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 215

Glu Pro Arg Ser Pro Ser Val Ser Met
1               5

<210> SEQ ID NO 216
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 216

Glu Pro Arg Ser Pro Ser Trp Ser Met
1               5

<210> SEQ ID NO 217
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 217

Glu Pro Arg Ser Pro Ser Tyr Ser Met
1               5

<210> SEQ ID NO 218
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 218

Glu Pro Arg Ser Pro Ser His Cys Met
1               5

<210> SEQ ID NO 219
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 219

Glu Pro Arg Ser Pro Ser His Asp Met
1               5

<210> SEQ ID NO 220
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 220

Glu Pro Arg Ser Pro Ser His Glu Met
1               5

<210> SEQ ID NO 221
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 221

Glu Pro Arg Ser Pro Ser His Phe Met
1               5

<210> SEQ ID NO 222
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 222

Glu Pro Arg Ser Pro Ser His Gly Met
1               5

<210> SEQ ID NO 223
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine
```

```
<400> SEQUENCE: 223

Glu Pro Arg Ser Pro Ser His His Met
1               5

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 224

Glu Pro Arg Ser Pro Ser His Ile Met
1               5

<210> SEQ ID NO 225
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 225

Glu Pro Arg Ser Pro Ser His Lys Met
1               5

<210> SEQ ID NO 226
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 226

Glu Pro Arg Ser Pro Ser His Leu Met
1               5

<210> SEQ ID NO 227
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 227

Glu Pro Arg Ser Pro Ser His Met Met
1               5

<210> SEQ ID NO 228
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 228

Glu Pro Arg Ser Pro Ser His Asn Met
1               5

<210> SEQ ID NO 229
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 229

Glu Pro Arg Ser Pro Ser His Pro Met
1               5

<210> SEQ ID NO 230
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 230

Glu Pro Arg Ser Pro Ser His Gln Met
1               5

<210> SEQ ID NO 231
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 231

Glu Pro Arg Ser Pro Ser His Arg Met
1               5

<210> SEQ ID NO 232
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (4)..(4)
<223> OTHER INFORMATION: Phosphoserine

<400> SEQUENCE: 232

Glu Pro Arg Ser Pro Ser His Thr Met
1               5

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 233

Glu Pro Arg Ser Pro Ser His Val Met
1               5

<210> SEQ ID NO 234
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 234

Glu Pro Arg Ser Pro Ser His Trp Met
1               5

<210> SEQ ID NO 235
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phosphoserine

<400> SEQUENCE: 235

Glu Pro Arg Ser Pro Ser His Tyr Met
1               5

<210> SEQ ID NO 236
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
                20                  25                  30
```

Gln Trp Tyr Arg Gln Glu Pro Gly Glu Gly Pro Val Leu Leu Val Thr
            35                  40                  45

Val Val Thr Gly Gly Glu Val Lys Lys Leu Lys Arg Leu Thr Phe Gln
 50                  55                  60

Phe Gly Asp Ala Arg Lys Asp Ser Ser Leu His Ile Thr Ala Ala Gln
 65                  70                  75                  80

Pro Gly Asp Thr Gly Leu Tyr Leu Cys Ala Gly Tyr Gly Gly Ser
                85                  90                  95

Asn Tyr Lys Leu Thr Phe Gly Lys Gly Thr Leu Leu Thr Val Asn Pro
            100                 105                 110

Tyr Ile Gln Asn Pro Asp Pro Ala Val Tyr Gln Leu Arg Asp Ser Lys
            115                 120                 125

Ser Ser Asp Lys Ser Val Cys Leu Phe Thr Asp Phe Asp Ser Gln Thr
130                 135                 140

Asn Val Ser Gln Ser Lys Asp Ser Asp Val Tyr Ile Thr Asp Lys Thr
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser Cys Asp
            195                 200                 205

Val Lys Leu Val Glu Lys Ser Phe Glu Thr Asp Thr Asn Leu Asn Phe
210                 215                 220

Gln Asn Leu Ser Val Ile Gly Phe Arg Ile Leu Leu Leu Lys Val Ala
225                 230                 235                 240

Gly Phe Asn Leu Leu Met Thr Leu Arg Leu Trp Ser Ser Gly Ser
                245                 250                 255

<210> SEQ ID NO 237
<211> LENGTH: 311
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Glu Ala Gln Val Thr Gln Asn Pro Arg Tyr Leu Ile Thr Val Thr Gly
 1               5                  10                  15

Lys Lys Leu Thr Val Thr Cys Ser Gln Asn Met Asn His Glu Tyr Met
                20                  25                  30

Ser Trp Tyr Arg Gln Asp Pro Gly Leu Gly Leu Arg Gln Ile Tyr Tyr
            35                  40                  45

Ser Met Asn Val Glu Val Thr Asp Lys Gly Asp Val Pro Glu Gly Tyr
 50                  55                  60

Lys Val Ser Arg Lys Glu Lys Arg Asn Phe Pro Leu Ile Leu Glu Ser
 65                  70                  75                  80

Pro Ser Pro Asn Gln Thr Ser Leu Tyr Phe Cys Ala Ser Arg Leu Thr
                85                  90                  95

Gly Arg Val His Gly Tyr Thr Phe Gly Ser Gly Thr Arg Leu Thr Val
            100                 105                 110

Val Glu Asp Leu Asn Lys Val Phe Pro Pro Glu Val Ala Val Phe Glu
            115                 120                 125

Pro Ser Glu Ala Glu Ile Ser His Thr Gln Lys Ala Thr Leu Val Cys

```
                 130                 135                 140
Leu Ala Thr Gly Phe Phe Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Cys Gly Phe Thr Ser Val Ser Tyr Gln Gln Gly Val Leu
                245                 250                 255

Ser Ala Thr Ile Leu Tyr Glu Ile Leu Leu Gly Lys Ala Thr Leu Tyr
            260                 265                 270

Ala Val Leu Val Ser Ala Leu Val Leu Met Ala Met Val Lys Arg Lys
        275                 280                 285

Asp Phe Gly Ser Gly Ala Thr Asn Phe Ser Leu Leu Lys Gln Ala Gly
    290                 295                 300

Asp Val Glu Glu Asn Pro Gly
305                 310

<210> SEQ ID NO 238
<211> LENGTH: 1821
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 238
gccaccatgg gacctcagct gctgggatac gttgtgctgt gtctgcttgg agccggacct      60
ctggaagccc aagtgacaca gaaccccaga tacctgatca ccgtgaccgg caagaaactg     120
accgtgacct gcagccagaa catgaaccac gagtacatga gctggtacag acaggaccct     180
ggcctgggcc tgagacagat ctactacagc atgaacgtgg aagtgaccga caagggcgac     240
gtgcccgagg gctacaaggt gtccagaaaa gagaagcgga acttcccact gatcctggaa     300
agccatctct ctaaccagac cagcctgtac ttctgcgcca gcagactgac aggcagagtg     360
cacggctaca catttggcag cggcaccaga ctgactgtgg tggaagatct gaacaaggtg     420
ttcccgccgg aagtggccgt gttcgagcct tctgaggccg agatcagcca cacacagaaa     480
gccacactcg tgtgcctggc caccggcttt tttcccgatc acgtggaact gtcttggtgg     540
gtcaacggca agaggtgcag cggcgtc agcacagatc cccagcctct gaaagaacag     600
cccgctctga cgacagccg gtactgcctg tcctcccgac tgagagtgtc cgccaccttc     660
tggcagaacc ctcggaacca cttcagatgc aggtgcagt tctacggcct gagcgagaac     720
gatgagtgga cccaggatag agccaagcct gtgactcaga tcgtgtctgc cgaagcctgg     780
ggcagagccg attgtggctt taccagcgtg tcctatcagc agggcgtgct gtctgccacc     840
atcctgtatg agatcctgct gggcaaagcc actctgtacg ccgtgctggt ttctgccctg     900
gtgctgatgg ccatggtcaa gagaaaggac tttggctccg gcgccaccaa cttcagcctg     960
ctgaaacagg ctggcgacgt ggaagagaac cccggaccta tggtgctgaa gttctccgtg    1020
```

```
tccatcctgt ggattcagct ggcttgggtg tccacacagc tgctcgaaca gagccctcag    1080
ttcctgagca tccaagaggg cgagaacctg acagtgtact gcaacagcag cagcgtgttc    1140
agcagcctgc agtggtacag gcaagagcct ggcgaaggac ctgtgctgct ggtcacagtt    1200
gtgacaggcg cgaagtgaa gaagctgaag cggctgacct tccagttcgg cgacgccaga    1260
aaggatagct ccctgcacat taccgctgct cagccaggcg ataccggcct gtatctgtgt    1320
gctggatatg gcggcggaag caactacaag ctgacctttg gcaagggcac cctgctgaca    1380
gtgaacccct acattcagaa ccccgatcca gccgtgtatc agctgagaga cagcaagagc    1440
agcgacaaga gcgtgtgtct gttcaccgac ttcgacagcc agaccaacgt gtcccagagc    1500
aaggacagcg acgtgtacat caccgacaag accgtgctgg acatgcggag catggacttc    1560
aagagcaaca cgccgtggc ctggtccaac aagagcgatt cgcctgcgc caacgccttc    1620 aacaacagca ttatccccga ggacacattc ttcccaagtc ctgagagcag ctgcgacgtg    1680
aagctggtgg aaaagagctt cgagacagac accaacctga acttccagaa cctgagcgtg    1740
atcggcttca gaatcctgct gctgaaggtg gccggcttca atctgctgat gaccctgaga    1800
ctgtggtcca gcggatcctg a                                              1821
```

<210> SEQ ID NO 239
<211> LENGTH: 22
<212> TYPE: PRT
<213> ORGANISM: Porcine teschovirus 1

<400> SEQUENCE: 239

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 240
<211> LENGTH: 21
<212> TYPE: PRT
<213> ORGANISM: Thosea asigna virus

<400> SEQUENCE: 240

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 241
<211> LENGTH: 23
<212> TYPE: PRT
<213> ORGANISM: Equine rhinitis A virus

<400> SEQUENCE: 241

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 242
<211> LENGTH: 25
<212> TYPE: PRT
<213> ORGANISM: Foot-and-mouth disease virus

<400> SEQUENCE: 242

```
Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 243
<211> LENGTH: 25
<212> TYPE: PRT
<213> ORGANISM: Cytoplasmic polyhedrosis virus

<400> SEQUENCE: 243

Gly Ser Gly Asp Val Phe Arg Ser Asn Tyr Asp Leu Leu Lys Leu Cys
1               5                   10                  15

Gly Asp Ile Glu Ser Asn Pro Gly Pro
            20                  25

<210> SEQ ID NO 244
<211> LENGTH: 25
<212> TYPE: PRT
<213> ORGANISM: Infectious flacherie virus

<400> SEQUENCE: 244

Gly Ser Gly Thr Leu Thr Arg Ala Lys Ile Glu Asp Glu Leu Ile Arg
1               5                   10                  15

Ala Gly Ile Glu Ser Asn Pro Gly Pro
            20                  25

<210> SEQ ID NO 245
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Ala Thr Asn Phe Ser Leu Leu Lys Gln Ala Gly Asp Val Glu Glu Asn
1               5                   10                  15

Pro Gly Pro Glu Gly Arg Gly Ser Leu Leu Thr Cys Gly Asp Val Glu
            20                  25                  30

Glu Asn Pro Gly Pro
        35

<210> SEQ ID NO 246
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 246

Gly Ser Gly Ala Thr Asn Phe Ser Leu Leu Lys Gln Ala Gly Asp Val
1               5                   10                  15

Glu Glu Asn Pro Gly Pro Glu Gly Arg Gly Ser Leu Leu Thr Cys Gly
            20                  25                  30

Asp Val Glu Glu Asn Pro Gly Pro
        35                  40

<210> SEQ ID NO 247
<211> LENGTH: 137
<212> TYPE: PRT
<213> ORGANISM: Mus musculus
```

<400> SEQUENCE: 247

Tyr Ile Gln Asn Pro Glu Pro Ala Val Tyr Gln Leu Lys Asp Pro Arg
1               5                   10                  15

Ser Gln Asp Ser Thr Leu Cys Leu Phe Thr Asp Phe Asp Ser Gln Ile
            20                  25                  30

Asn Val Pro Lys Thr Met Glu Ser Gly Thr Phe Ile Thr Asp Lys Thr
        35                  40                  45

Val Leu Asp Met Lys Ala Met Asp Ser Lys Ser Asn Gly Ala Ile Ala
    50                  55                  60

Trp Ser Asn Gln Thr Ser Phe Thr Cys Gln Asp Ile Phe Lys Glu Thr
65                  70                  75                  80

Asn Ala Thr Tyr Pro Ser Ser Asp Val Pro Cys Asp Ala Thr Leu Thr
                85                  90                  95

Glu Lys Ser Phe Glu Thr Asp Met Asn Leu Asn Phe Gln Asn Leu Ser
            100                 105                 110

Val Met Gly Leu Arg Ile Leu Leu Leu Lys Val Ala Gly Phe Asn Leu
        115                 120                 125

Leu Met Thr Leu Arg Leu Trp Ser Ser
    130                 135

<210> SEQ ID NO 248
<211> LENGTH: 173
<212> TYPE: PRT
<213> ORGANISM: Mus musculus

<400> SEQUENCE: 248

Glu Asp Leu Arg Asn Val Thr Pro Pro Lys Val Ser Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
        115                 120                 125

Ile Thr Ser Ala Ser Tyr His Gln Gly Val Leu Ser Ala Thr Ile Leu
    130                 135                 140

Tyr Glu Ile Leu Leu Gly Lys Ala Thr Leu Tyr Ala Val Leu Val Ser
145                 150                 155                 160

Gly Leu Val Leu Met Ala Met Val Lys Lys Lys Asn Ser
                165                 170

<210> SEQ ID NO 249
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 249

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Tyr Gly Gly Ser
                85                  90                  95

Asn Tyr Lys Leu Thr Phe Gly Ala Gly Thr Arg Leu Thr Val Lys Pro
            100                 105                 110

Tyr Ile Gln Asn Pro Glu Pro Ala Val Tyr Gln Leu Lys Asp Pro Arg
        115                 120                 125

Ser Gln Asp Ser Thr Leu Cys Leu Phe Thr Asp Phe Asp Ser Gln Ile
130                 135                 140

Asn Val Pro Lys Thr Met Glu Ser Gly Thr Phe Ile Thr Asp Lys Thr
145                 150                 155                 160

Val Leu Asp Met Lys Ala Met Asp Ser Lys Ser Asn Gly Ala Ile Ala
                165                 170                 175

Trp Ser Asn Gln Thr Ser Phe Thr Cys Gln Asp Ile Phe Lys Glu Thr
            180                 185                 190

Asn Ala Thr Tyr Pro Ser Ser Asp Val Pro Cys Asp Ala Thr Leu Thr
        195                 200                 205

Glu Lys Ser Phe Glu Thr Asp Met Asn Leu Asn Phe Gln Asn Leu Ser
210                 215                 220

Val Met Gly Leu Arg Ile Leu Leu Leu Lys Val Ala Gly Phe Asn Leu
225                 230                 235                 240

Leu Met Thr Leu Arg Leu Trp Ser Ser
                245

<210> SEQ ID NO 250
<211> LENGTH: 286
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 250

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Arg Leu Thr
                85                  90                  95

```
Gly Arg Val His Gly Tyr Thr Phe Gly Pro Gly Thr Arg Leu Thr Val
            100                 105                 110

Leu Glu Asp Leu Arg Asn Val Thr Pro Pro Lys Val Ser Leu Phe Glu
        115                 120                 125

Pro Ser Lys Ala Glu Ile Ala Asn Lys Gln Lys Ala Thr Leu Val Cys
130                 135                 140

Leu Ala Arg Gly Phe Phe Pro Asp His Val Glu Leu Ser Trp Trp Val
145                 150                 155                 160

Asn Gly Lys Glu Val His Ser Gly Val Ser Thr Asp Pro Gln Ala Tyr
                165                 170                 175

Lys Glu Ser Asn Tyr Ser Tyr Cys Leu Ser Ser Arg Leu Arg Val Ser
            180                 185                 190

Ala Thr Phe Trp His Asn Pro Arg Asn His Phe Arg Cys Gln Val Gln
        195                 200                 205

Phe His Gly Leu Ser Glu Glu Asp Lys Trp Pro Glu Gly Ser Pro Lys
    210                 215                 220

Pro Val Thr Gln Asn Ile Ser Ala Glu Ala Trp Gly Arg Ala Asp Cys
225                 230                 235                 240

Gly Ile Thr Ser Ala Ser Tyr His Gln Gly Val Leu Ser Ala Thr Ile
                245                 250                 255

Leu Tyr Glu Ile Leu Leu Gly Lys Ala Thr Leu Tyr Ala Val Leu Val
            260                 265                 270

Ser Gly Leu Val Leu Met Ala Met Val Lys Lys Asn Ser
        275                 280                 285

<210> SEQ ID NO 251
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Lys Asn Gln Val Glu Gln Ser Pro Gln Ser Leu Ile Ile Leu Glu Gly
1               5                   10                  15

Lys Asn Cys Thr Leu Gln Cys Asn Tyr Thr Val Ser Pro Phe Ser Asn
            20                  25                  30

Leu Arg Trp Tyr Lys Gln Asp Thr Gly Arg Gly Pro Val Ser Leu Thr
        35                  40                  45

Ile Met Thr Phe Ser Glu Asn Thr Lys Ser Asn Gly Arg Tyr Thr Ala
50                  55                  60

Thr Leu Asp Ala Asp Thr Lys Gln Ser Ser Leu His Ile Thr Ala Ser
65                  70                  75                  80

Gln Leu Ser Asp Ser Ala Ser Tyr Ile Cys Val Val Arg Gly Gly Ala
                85                  90                  95

Ala Gly Asn Lys Leu Thr Phe Gly Ala Gly Thr Arg Leu Thr Val Lys
            100                 105                 110

Pro Tyr Ile Gln Asn Pro Glu Pro Ala Val Tyr Gln Leu Lys Asp Pro
        115                 120                 125

Arg Ser Gln Asp Ser Thr Leu Cys Leu Phe Thr Asp Phe Asp Ser Gln
    130                 135                 140

Ile Asn Val Pro Lys Thr Met Glu Ser Gly Thr Phe Ile Thr Asp Lys
145                 150                 155                 160

Thr Val Leu Asp Met Lys Ala Met Asp Ser Lys Ser Asn Gly Ala Ile
```

```
                       165                 170                 175

Ala Trp Ser Asn Gln Thr Ser Phe Thr Cys Gln Asp Ile Phe Lys Glu
            180                 185                 190

Thr Asn Ala Thr Tyr Pro Ser Ser Asp Val Pro Cys Asp Ala Thr Leu
        195                 200                 205

Thr Glu Lys Ser Phe Glu Thr Asp Met Asn Leu Asn Phe Gln Asn Leu
    210                 215                 220

Ser Val Met Gly Leu Arg Ile Leu Leu Leu Lys Val Ala Gly Phe Asn
225                 230                 235                 240

Leu Leu Met Thr Leu Arg Leu Trp Ser Ser
                245                 250

<210> SEQ ID NO 252
<211> LENGTH: 287
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Asp Ala Gly Val Ile Gln Ser Pro Arg His Glu Val Thr Glu Met Gly
1               5                   10                  15

Gln Glu Val Thr Leu Arg Cys Lys Pro Ile Ser Gly His Asn Ser Leu
            20                  25                  30

Phe Trp Tyr Arg Gln Thr Met Met Arg Gly Leu Glu Leu Leu Ile Tyr
        35                  40                  45

Phe Asn Asn Asn Val Pro Ile Asp Asp Ser Gly Met Pro Glu Asp Arg
    50                  55                  60

Phe Ser Ala Lys Met Pro Asn Ala Ser Phe Ser Thr Leu Lys Ile Gln
65                  70                  75                  80

Pro Ser Glu Pro Arg Asp Ser Ala Val Tyr Phe Cys Ala Ser Ser Ser
                85                  90                  95

Gly Gly Ala Asn Thr Glu Ala Phe Phe Gly Pro Gly Thr Arg Leu Thr
            100                 105                 110

Val Leu Glu Asp Leu Arg Asn Val Thr Pro Pro Lys Val Ser Leu Phe
        115                 120                 125

Glu Pro Ser Lys Ala Glu Ile Ala Asn Lys Gln Lys Ala Thr Leu Val
    130                 135                 140

Cys Leu Ala Arg Gly Phe Phe Pro Asp His Val Glu Leu Ser Trp Trp
145                 150                 155                 160

Val Asn Gly Lys Glu Val His Ser Gly Val Ser Thr Asp Pro Gln Ala
                165                 170                 175

Tyr Lys Glu Ser Asn Tyr Ser Tyr Cys Leu Ser Ser Arg Leu Arg Val
            180                 185                 190

Ser Ala Thr Phe Trp His Asn Pro Arg Asn His Phe Arg Cys Gln Val
        195                 200                 205

Gln Phe His Gly Leu Ser Glu Glu Asp Lys Trp Pro Glu Gly Ser Pro
    210                 215                 220

Lys Pro Val Thr Gln Asn Ile Ser Ala Glu Ala Trp Gly Arg Ala Asp
225                 230                 235                 240

Cys Gly Ile Thr Ser Ala Ser Tyr His Gln Gly Val Leu Ser Ala Thr
                245                 250                 255

Ile Leu Tyr Glu Ile Leu Leu Gly Lys Ala Thr Leu Tyr Ala Val Leu
            260                 265                 270
```

```
Val Ser Gly Leu Val Leu Met Ala Met Val Lys Lys Lys Asn Ser
            275                 280                 285
```

<210> SEQ ID NO 253
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 253

```
Ala Gln Ser Val Thr Gln Leu Gly Ser His Val Ser Val Ser Glu Gly
1               5                   10                  15

Ala Leu Ile Leu Leu Arg Cys Asn Tyr Ser Ser Ser Val Pro Pro Tyr
            20                  25                  30

Leu Phe Trp Tyr Val Gln Tyr Pro Asn Gln Gly Leu Gln Leu Leu Leu
        35                  40                  45

Lys Tyr Thr Thr Gly Ala Thr Leu Val Lys Gly Ile Asn Gly Phe Glu
    50                  55                  60

Ala Glu Phe Lys Lys Ser Glu Thr Ser Phe His Leu Thr Lys Pro Ser
65                  70                  75                  80

Ala His Met Ser Asp Ala Ala Glu Tyr Phe Cys Ala Val Ser Ala Arg
                85                  90                  95

Tyr Asn Phe Asn Lys Phe Tyr Phe Gly Ser Gly Thr Lys Leu Ser Val
            100                 105                 110

Ile Pro Tyr Ile Gln Asn Pro Glu Pro Ala Val Tyr Gln Leu Lys Asp
        115                 120                 125

Pro Arg Ser Gln Asp Ser Thr Leu Cys Leu Phe Thr Asp Phe Asp Ser
    130                 135                 140

Gln Ile Asn Val Pro Lys Thr Met Glu Ser Gly Thr Phe Ile Thr Asp
145                 150                 155                 160

Lys Thr Val Leu Asp Met Lys Ala Met Asp Ser Lys Ser Asn Gly Ala
                165                 170                 175

Ile Ala Trp Ser Asn Gln Thr Ser Phe Thr Cys Gln Asp Ile Phe Lys
            180                 185                 190

Glu Thr Asn Ala Thr Tyr Pro Ser Ser Asp Val Pro Cys Asp Ala Thr
        195                 200                 205

Leu Thr Glu Lys Ser Phe Glu Thr Asp Met Asn Leu Asn Phe Gln Asn
    210                 215                 220

Leu Ser Val Met Gly Leu Arg Ile Leu Leu Lys Val Ala Gly Phe
225                 230                 235                 240

Asn Leu Leu Met Thr Leu Arg Leu Trp Ser Ser
                245                 250
```

<210> SEQ ID NO 254
<211> LENGTH: 287
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 254

```
Asp Ser Gly Val Thr Gln Thr Pro Lys His Leu Ile Thr Ala Thr Gly
1               5                   10                  15

Gln Arg Val Thr Leu Arg Cys Ser Pro Arg Ser Gly Asp Leu Ser Val
            20                  25                  30
```

```
Tyr Trp Tyr Gln Gln Ser Leu Asp Gln Gly Leu Gln Phe Leu Ile Gln
             35                  40                  45

Tyr Tyr Asn Gly Glu Glu Arg Ala Lys Gly Asn Ile Leu Glu Arg Phe
 50                  55                  60

Ser Ala Gln Gln Phe Pro Asp Leu His Ser Glu Leu Asn Leu Ser Ser
 65                  70                  75                  80

Leu Glu Leu Gly Asp Ser Ala Leu Tyr Phe Cys Ala Ser Ser Ala Ser
                 85                  90                  95

Gly Gly Arg Ser Tyr Gln Tyr Phe Gly Pro Gly Thr Arg Leu Thr
                100                 105                 110

Val Val Glu Asp Leu Arg Asn Val Thr Pro Pro Lys Val Ser Leu Phe
            115                 120                 125

Glu Pro Ser Lys Ala Glu Ile Ala Asn Lys Gln Lys Ala Thr Leu Val
130                 135                 140

Cys Leu Ala Arg Gly Phe Phe Pro Asp His Val Glu Leu Ser Trp Trp
145                 150                 155                 160

Val Asn Gly Lys Glu Val His Ser Gly Val Ser Thr Asp Pro Gln Ala
                165                 170                 175

Tyr Lys Glu Ser Asn Tyr Ser Tyr Cys Leu Ser Ser Arg Leu Arg Val
            180                 185                 190

Ser Ala Thr Phe Trp His Asn Pro Arg Asn His Phe Arg Cys Gln Val
        195                 200                 205

Gln Phe His Gly Leu Ser Glu Asp Lys Trp Pro Glu Gly Ser Pro
    210                 215                 220

Lys Pro Val Thr Gln Asn Ile Ser Ala Glu Ala Trp Gly Arg Ala Asp
225                 230                 235                 240

Cys Gly Ile Thr Ser Ala Ser Tyr His Gln Gly Val Leu Ser Ala Thr
                245                 250                 255

Ile Leu Tyr Glu Ile Leu Leu Gly Lys Ala Thr Leu Tyr Ala Val Leu
            260                 265                 270

Val Ser Gly Leu Val Leu Met Ala Met Val Lys Lys Lys Asn Ser
        275                 280                 285

<210> SEQ ID NO 255
<211> LENGTH: 247
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Glu Asp Gln Val Thr Gln Ser Pro Glu Ala Leu Arg Leu Gln Glu Gly
1               5                   10                  15

Glu Ser Ser Ser Leu Asn Cys Ser Tyr Thr Val Ser Gly Leu Arg Gly
            20                  25                  30

Leu Phe Trp Tyr Arg Gln Asp Pro Gly Lys Gly Pro Glu Phe Leu Phe
        35                  40                  45

Thr Leu Tyr Ser Ala Gly Glu Glu Lys Glu Lys Glu Arg Leu Lys Ala
 50                  55                  60

Thr Leu Thr Lys Lys Glu Ser Phe Leu His Ile Thr Ala Pro Lys Pro
65                  70                  75                  80

Glu Asp Ser Ala Thr Tyr Leu Cys Ala Val Arg Asn Thr Gly Phe Gln
                85                  90                  95

Lys Leu Val Phe Gly Thr Gly Thr Arg Leu Leu Val Ser Pro Tyr Ile
            100                 105                 110
```

```
Gln Asn Pro Glu Pro Ala Val Tyr Gln Leu Lys Asp Pro Arg Ser Gln
            115                 120                 125

Asp Ser Thr Leu Cys Leu Phe Thr Asp Phe Asp Ser Gln Ile Asn Val
        130                 135                 140

Pro Lys Thr Met Glu Ser Gly Thr Phe Ile Thr Asp Lys Thr Val Leu
145                 150                 155                 160

Asp Met Lys Ala Met Asp Ser Lys Ser Asn Gly Ala Ile Ala Trp Ser
                165                 170                 175

Asn Gln Thr Ser Phe Thr Cys Gln Asp Ile Phe Lys Glu Thr Asn Ala
            180                 185                 190

Thr Tyr Pro Ser Ser Asp Val Pro Cys Asp Ala Thr Leu Thr Glu Lys
        195                 200                 205

Ser Phe Glu Thr Asp Met Asn Leu Asn Phe Gln Asn Leu Ser Val Met
        210                 215                 220

Gly Leu Arg Ile Leu Leu Leu Lys Val Ala Gly Phe Asn Leu Leu Met
225                 230                 235                 240

Thr Leu Arg Leu Trp Ser Ser
            245

<210> SEQ ID NO 256
<211> LENGTH: 288
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Asp Thr Gly Val Ser Gln Asp Pro Arg His Lys Ile Thr Lys Arg Gly
1               5                   10                  15

Gln Asn Val Thr Phe Arg Cys Asp Pro Ile Ser Glu His Asn Arg Leu
            20                  25                  30

Tyr Trp Tyr Arg Gln Thr Leu Gly Gln Gly Pro Glu Phe Leu Thr Tyr
        35                  40                  45

Phe Gln Asn Glu Ala Gln Leu Glu Lys Ser Arg Leu Leu Ser Asp Arg
    50                  55                  60

Phe Ser Ala Glu Arg Pro Lys Gly Ser Phe Ser Thr Leu Glu Ile Gln
65                  70                  75                  80

Arg Thr Glu Gln Gly Asp Ser Ala Met Tyr Leu Cys Ala Ser Ser Trp
                85                  90                  95

Arg Thr Gly Arg Glu Glu Thr Gln Tyr Phe Gly Pro Gly Thr Arg Leu
            100                 105                 110

Leu Val Leu Glu Asp Leu Arg Asn Val Thr Pro Pro Lys Val Ser Leu
        115                 120                 125

Phe Glu Pro Ser Lys Ala Glu Ile Ala Asn Lys Gln Lys Ala Thr Leu
    130                 135                 140

Val Cys Leu Ala Arg Gly Phe Phe Pro Asp His Val Glu Leu Ser Trp
145                 150                 155                 160

Trp Val Asn Gly Lys Glu Val His Ser Gly Val Ser Thr Asp Pro Gln
                165                 170                 175

Ala Tyr Lys Glu Ser Asn Tyr Ser Tyr Cys Leu Ser Ser Arg Leu Arg
            180                 185                 190

Val Ser Ala Thr Phe Trp His Asn Pro Arg Asn His Phe Arg Cys Gln
        195                 200                 205

Val Gln Phe His Gly Leu Ser Glu Glu Asp Lys Trp Pro Glu Gly Ser
```

```
                    210                 215                 220

Pro Lys Pro Val Thr Gln Asn Ile Ser Ala Glu Ala Trp Gly Arg Ala
225                 230                 235                 240

Asp Cys Gly Ile Thr Ser Ala Ser Tyr His Gln Gly Val Leu Ser Ala
                    245                 250                 255

Thr Ile Leu Tyr Glu Ile Leu Gly Lys Ala Thr Leu Tyr Ala Val
                260                 265                 270

Leu Val Ser Gly Leu Val Leu Met Ala Met Val Lys Lys Lys Asn Ser
            275                 280                 285

<210> SEQ ID NO 257
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 257

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Met Leu Trp Asn
                85                  90                  95

Gln Gly Gly Lys Leu Ile Phe Gly Gln Gly Thr Glu Leu Ser Val Lys
            100                 105                 110

Pro Tyr Ile Gln Asn Pro Glu Pro Ala Val Tyr Gln Leu Lys Asp Pro
        115                 120                 125

Arg Ser Gln Asp Ser Thr Leu Cys Leu Phe Thr Asp Phe Asp Ser Gln
    130                 135                 140

Ile Asn Val Pro Lys Thr Met Glu Ser Gly Thr Phe Ile Thr Asp Lys
145                 150                 155                 160

Thr Val Leu Asp Met Lys Ala Met Asp Ser Lys Ser Asn Gly Ala Ile
                165                 170                 175

Ala Trp Ser Asn Gln Thr Ser Phe Thr Cys Gln Asp Ile Phe Lys Glu
            180                 185                 190

Thr Asn Ala Thr Tyr Pro Ser Ser Asp Val Pro Cys Asp Ala Thr Leu
        195                 200                 205

Thr Glu Lys Ser Phe Glu Thr Asp Met Asn Leu Asn Phe Gln Asn Leu
    210                 215                 220

Ser Val Met Gly Leu Arg Ile Leu Leu Leu Lys Val Ala Gly Phe Asn
225                 230                 235                 240

Leu Leu Met Thr Leu Arg Leu Trp Ser Ser
                245                 250

<210> SEQ ID NO 258
<211> LENGTH: 285
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 258

Lys Ala Gly Val Thr Gln Thr Pro Arg Tyr Leu Ile Lys Thr Arg Gly
1               5                   10                  15

Gln Gln Val Thr Leu Ser Cys Ser Pro Ile Ser Gly His Arg Ser Val
            20                  25                  30

Ser Trp Tyr Gln Gln Thr Pro Gly Gln Gly Leu Gln Phe Leu Phe Glu
        35                  40                  45

Tyr Phe Ser Glu Thr Gln Arg Asn Lys Gly Asn Phe Pro Gly Arg Phe
    50                  55                  60

Ser Gly Arg Gln Phe Ser Asn Ser Arg Ser Glu Met Asn Val Ser Thr
65                  70                  75                  80

Leu Glu Leu Gly Asp Ser Ala Leu Tyr Leu Cys Ala Ser Ser Leu Gly
                85                  90                  95

Arg Gly Tyr Glu Gln Tyr Phe Gly Pro Gly Thr Arg Leu Thr Val Thr
            100                 105                 110

Glu Asp Leu Arg Asn Val Thr Pro Pro Lys Val Ser Leu Phe Glu Pro
        115                 120                 125

Ser Lys Ala Glu Ile Ala Asn Lys Gln Lys Ala Thr Leu Val Cys Leu
    130                 135                 140

Ala Arg Gly Phe Phe Pro Asp His Val Glu Leu Ser Trp Trp Val Asn
145                 150                 155                 160

Gly Lys Glu Val His Ser Gly Val Ser Thr Asp Pro Gln Ala Tyr Lys
                165                 170                 175

Glu Ser Asn Tyr Ser Tyr Cys Leu Ser Ser Arg Leu Arg Val Ser Ala
            180                 185                 190

Thr Phe Trp His Asn Pro Arg Asn His Phe Arg Cys Gln Val Gln Phe
        195                 200                 205

His Gly Leu Ser Glu Glu Asp Lys Trp Pro Glu Gly Ser Pro Lys Pro
    210                 215                 220

Val Thr Gln Asn Ile Ser Ala Glu Ala Trp Gly Arg Ala Asp Cys Gly
225                 230                 235                 240

Ile Thr Ser Ala Ser Tyr His Gln Gly Val Leu Ser Ala Thr Ile Leu
                245                 250                 255

Tyr Glu Ile Leu Leu Gly Lys Ala Thr Leu Tyr Ala Val Leu Val Ser
            260                 265                 270

Gly Leu Val Leu Met Ala Met Val Lys Lys Lys Asn Ser
        275                 280                 285

<210> SEQ ID NO 259
<211> LENGTH: 257
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 259

Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
            20                  25                  30

Gln Trp Tyr Arg Gln Glu Pro Gly Glu Gly Pro Val Leu Leu Val Thr
        35                  40                  45

Val Val Thr Gly Gly Glu Val Lys Lys Leu Lys Arg Leu Thr Phe Gln
 50                  55                  60

Phe Gly Asp Ala Arg Lys Asp Ser Ser Leu His Ile Thr Ala Ala Gln
 65                  70                  75                  80

Pro Gly Asp Thr Gly Leu Tyr Leu Cys Ala Gly Tyr Gly Gly Ser
                 85                  90                  95

Asn Tyr Lys Leu Thr Phe Gly Lys Gly Thr Leu Leu Thr Val Asn Pro
                100                 105                 110

Tyr Ile Gln Asn Pro Asp Pro Ala Val Tyr Gln Leu Arg Asp Ser Lys
                115                 120                 125

Ser Ser Asp Lys Ser Val Cys Leu Phe Thr Asp Phe Asp Ser Gln Thr
130                 135                 140

Asn Val Ser Gln Ser Lys Asp Ser Asp Val Tyr Ile Thr Asp Lys Thr
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
                180                 185                 190

Ile Ile Pro Glu Asp Thr Phe Phe Pro Ser Pro Glu Ser Ser Cys Asp
                195                 200                 205

Val Lys Leu Val Glu Lys Ser Phe Glu Thr Asp Thr Asn Leu Asn Phe
210                 215                 220

Gln Asn Leu Ser Val Ile Gly Phe Arg Ile Leu Leu Leu Lys Val Ala
225                 230                 235                 240

Gly Phe Asn Leu Leu Met Thr Leu Arg Leu Trp Ser Ser Arg Ala Lys
                245                 250                 255

Arg

<210> SEQ ID NO 260
<211> LENGTH: 255
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 260

Thr Gln Leu Leu Glu Gln Ser Pro Gln Phe Leu Ser Ile Gln Glu Gly
 1               5                  10                  15

Glu Asn Leu Thr Val Tyr Cys Asn Ser Ser Ser Val Phe Ser Ser Leu
                 20                  25                  30

Gln Trp Tyr Arg Gln Glu Pro Gly Glu Gly Pro Val Leu Leu Val Thr
                 35                  40                  45

Val Val Thr Gly Gly Glu Val Lys Lys Leu Lys Arg Leu Thr Phe Gln
 50                  55                  60

Phe Gly Asp Ala Arg Lys Asp Ser Ser Leu His Ile Thr Ala Ala Gln
 65                  70                  75                  80

Pro Gly Asp Thr Gly Leu Tyr Leu Cys Ala Gly Tyr Gly Gly Ser
                 85                  90                  95

Asn Tyr Lys Leu Thr Phe Gly Lys Gly Thr Leu Leu Thr Val Asn Pro
                100                 105                 110

Tyr Ile Gln Asn Pro Asp Pro Ala Val Tyr Gln Leu Arg Asp Ser Lys
                115                 120                 125

Ser Ser Asp Lys Ser Val Cys Leu Phe Thr Asp Phe Asp Ser Gln Thr
130                 135                 140

```
Asn Val Ser Gln Ser Lys Asp Ser Asp Val Tyr Ile Thr Asp Lys Thr
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser Cys Asp
        195                 200                 205

Val Lys Leu Val Glu Lys Ser Phe Glu Thr Asp Thr Asn Leu Asn Phe
    210                 215                 220

Gln Asn Leu Ser Val Ile Gly Phe Arg Ile Leu Leu Lys Val Ala
225                 230                 235                 240

Gly Phe Asn Leu Leu Met Thr Leu Arg Leu Trp Ser Ser Arg Ala
                245                 250                 255
```

<210> SEQ ID NO 261
<211> LENGTH: 274
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 261

```
Thr Gln Leu Leu Glu Gln Ser Pro Gln Phe Leu Ser Ile Gln Glu Gly
1               5                   10                  15

Glu Asn Leu Thr Val Tyr Cys Asn Ser Ser Ser Val Phe Ser Ser Leu
                20                  25                  30

Gln Trp Tyr Arg Gln Glu Pro Gly Glu Gly Pro Val Leu Leu Val Thr
            35                  40                  45

Val Val Thr Gly Gly Glu Val Lys Lys Leu Lys Arg Leu Thr Phe Gln
    50                  55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Tyr Gly Gly Ser
                85                  90                  95

Asn Tyr Lys Leu Thr Phe Gly Lys Gly Thr Leu Leu Thr Val Asn Pro
                100                 105                 110

Tyr Ile Gln Asn Pro Asp Pro Ala Val Tyr Gln Leu Arg Asp Ser Lys
            115                 120                 125

Ser Ser Asp Lys Ser Val Cys Leu Phe Thr Asp Phe Asp Ser Gln Thr
130                 135                 140

Asn Val Ser Gln Ser Lys Asp Ser Asp Val Tyr Ile Thr Asp Lys Thr
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
            180                 185                 190

Ile Ile Pro Glu Asp Thr Phe Phe Pro Ser Pro Glu Ser Ser Cys Asp
        195                 200                 205

Val Lys Leu Val Glu Lys Ser Phe Glu Thr Asp Thr Asn Leu Asn Phe
    210                 215                 220

Gln Asn Leu Ser Val Ile Gly Phe Arg Ile Leu Leu Lys Val Ala
225                 230                 235                 240

Gly Phe Asn Leu Leu Met Thr Leu Arg Leu Trp Ser Ser Gly Ser Gly
                245                 250                 255
```

Ala Thr Asn Phe Ser Leu Leu Lys Gln Ala Gly Asp Val Glu Glu Asn
            260                 265                 270

Pro Gly

<210> SEQ ID NO 262
<211> LENGTH: 292
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 262

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Arg Leu Thr
                85                  90                  95

Gly Arg Val His Gly Tyr Thr Phe Gly Ser Gly Thr Arg Leu Thr Val
            100                 105                 110

Val Glu Asp Leu Asn Lys Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Phe Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Cys Gly Phe Thr Ser Val Ser Tyr Gln Gln Gly Val Leu
                245                 250                 255

Ser Ala Thr Ile Leu Tyr Glu Ile Leu Leu Gly Lys Ala Thr Leu Tyr
            260                 265                 270

Ala Val Leu Val Ser Ala Leu Val Leu Met Ala Met Val Lys Arg Lys
        275                 280                 285

Asp Phe Gly Ser
    290

<210> SEQ ID NO 263
<211> LENGTH: 294
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 263

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Arg Leu Thr
                85                  90                  95

Gly Arg Val His Gly Tyr Thr Phe Gly Ser Gly Thr Arg Leu Thr Val
            100                 105                 110

Val Glu Asp Leu Asn Lys Val Phe Pro Pro Glu Val Ala Val Phe Glu
        115                 120                 125

Pro Ser Glu Ala Glu Ile Ser His Thr Gln Lys Ala Thr Leu Val Cys
    130                 135                 140

Leu Ala Thr Gly Phe Phe Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
    210                 215                 220

Asp Arg Ala Lys Pro Val Thr Gln Ile Val Ser Ala Glu Ala Trp Gly
225                 230                 235                 240

Arg Ala Asp Cys Gly Phe Thr Ser Val Ser Tyr Gln Gln Gly Val Leu
                245                 250                 255

Ser Ala Thr Ile Leu Tyr Glu Ile Leu Leu Gly Lys Ala Thr Leu Tyr
            260                 265                 270

Ala Val Leu Val Ser Ala Leu Val Leu Met Ala Met Val Lys Arg Lys
        275                 280                 285

Asp Phe Arg Ala Lys Arg
    290

<210> SEQ ID NO 264
<211> LENGTH: 292
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 264

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30
```

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
 50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Arg Leu Thr
                85                  90                  95

Gly Arg Val His Gly Tyr Thr Phe Gly Ser Gly Thr Arg Leu Thr Val
            100                 105                 110

Val Glu Asp Leu Asn Lys Val Phe Pro Pro Glu Val Ala Val Phe Glu
        115                 120                 125

Pro Ser Glu Ala Glu Ile Ser His Thr Gln Lys Ala Thr Leu Val Cys
130                 135                 140

Leu Ala Thr Gly Phe Phe Pro Asp His Val Glu Leu Ser Trp Trp Val
145                 150                 155                 160

Asn Gly Lys Glu Val His Ser Gly Val Ser Thr Asp Pro Gln Pro Leu
                165                 170                 175

Lys Glu Gln Pro Ala Leu Asn Asp Ser Arg Tyr Cys Leu Ser Ser Arg
            180                 185                 190

Leu Arg Val Ser Ala Thr Phe Trp Gln Asn Pro Arg Asn His Phe Arg
        195                 200                 205

Cys Gln Val Gln Phe Tyr Gly Leu Ser Glu Asn Asp Glu Trp Thr Gln
210                 215                 220

Asp Arg Ala Lys Pro Val Thr Gln Ile Val Ser Ala Glu Ala Trp Gly
225                 230                 235                 240

Arg Ala Asp Cys Gly Phe Thr Ser Val Ser Tyr Gln Gln Gly Val Leu
                245                 250                 255

Ser Ala Thr Ile Leu Tyr Glu Ile Leu Leu Gly Lys Ala Thr Leu Tyr
            260                 265                 270

Ala Val Leu Val Ser Ala Leu Val Leu Met Ala Met Val Lys Arg Lys
        275                 280                 285

Asp Phe Arg Ala
    290

<210> SEQ ID NO 265
<211> LENGTH: 612
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 265

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu

```
                     85                  90                  95
Lys Ile Gln Pro Ser Glu Pro Arg Asp Ser Ala Val Tyr Phe Cys Ala
                100                 105                 110

Ser Ser Ser Gly Gly Ala Asn Thr Glu Ala Phe Phe Gly Gln Gly Thr
            115                 120                 125

Arg Leu Thr Val Val Glu Asp Leu Asn Lys Val Phe Pro Pro Glu Val
        130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Val Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Phe Arg Ala Lys Arg Ser Gly Ser Gly Ala Thr
305                 310                 315                 320

Asn Phe Ser Leu Leu Lys Gln Ala Gly Asp Val Glu Glu Asn Pro Gly
                325                 330                 335

Pro Met Lys Lys His Leu Thr Thr Phe Leu Val Ile Leu Trp Leu Tyr
            340                 345                 350

Phe Tyr Arg Gly Asn Gly Lys Asn Gln Val Glu Gln Ser Pro Gln Ser
        355                 360                 365

Leu Ile Ile Leu Glu Gly Lys Asn Cys Thr Leu Gln Cys Asn Tyr Thr
    370                 375                 380

Val Ser Pro Phe Ser Asn Leu Arg Trp Tyr Lys Gln Asp Thr Gly Arg
385                 390                 395                 400

Gly Pro Val Ser Leu Thr Ile Met Thr Phe Ser Glu Asn Thr Lys Ser
                405                 410                 415

Asn Gly Arg Tyr Thr Ala Thr Leu Asp Ala Asp Thr Lys Gln Ser Ser
            420                 425                 430

Leu His Ile Thr Ala Ser Gln Leu Ser Asp Ser Ala Ser Tyr Ile Cys
        435                 440                 445

Val Val Arg Gly Gly Ala Ala Gly Asn Lys Leu Thr Phe Gly Gly Gly
    450                 455                 460

Thr Arg Val Leu Val Lys Pro Asn Ile Gln Asn Pro Asp Pro Ala Val
465                 470                 475                 480

Tyr Gln Leu Arg Asp Ser Lys Ser Ser Asp Lys Ser Val Cys Leu Phe
                485                 490                 495

Thr Asp Phe Asp Ser Gln Thr Asn Val Ser Gln Ser Lys Asp Ser Asp
            500                 505                 510
```

```
Val Tyr Ile Thr Asp Lys Thr Val Leu Asp Met Arg Ser Met Asp Phe
            515                 520                 525

Lys Ser Asn Ser Ala Val Ala Trp Ser Asn Lys Ser Asp Phe Ala Cys
        530                 535                 540

Ala Asn Ala Phe Asn Asn Ser Ile Ile Pro Glu Asp Thr Phe Pro
545                 550                 555                 560

Ser Pro Glu Ser Ser Cys Asp Val Lys Leu Val Glu Lys Ser Phe Glu
                565                 570                 575

Thr Asp Thr Asn Leu Asn Phe Gln Asn Leu Ser Val Ile Gly Phe Arg
            580                 585                 590

Ile Leu Leu Leu Lys Val Ala Gly Phe Asn Leu Leu Met Thr Leu Arg
            595                 600                 605

Leu Trp Ser Ser
            610

<210> SEQ ID NO 266
<211> LENGTH: 607
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 266

Met Gly Pro Gln Leu Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
            20                  25                  30

Val Thr Gly Lys Lys Leu Thr Val Thr Cys Ser Gln Asn Met Asn His
        35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
            100                 105                 110

Arg Leu Thr Gly Arg Val His Gly Tyr Thr Phe Gly Ser Gly Thr Arg
        115                 120                 125

Leu Thr Val Val Glu Asp Leu Asn Lys Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
```

245                 250                 255

Ala Trp Gly Arg Ala Asp Cys Gly Phe Thr Ser Val Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp Phe Arg Ala Lys Arg Ser Gly Ser Ala Thr Asn
305                 310                 315                 320

Phe Ser Leu Leu Lys Gln Ala Gly Asp Val Glu Glu Asn Pro Gly Pro
                325                 330                 335

Met Val Leu Lys Phe Ser Val Ser Ile Leu Trp Ile Gln Leu Ala Trp
                340                 345                 350

Val Ser Thr Gln Leu Leu Glu Gln Ser Pro Gln Phe Leu Ser Ile Gln
            355                 360                 365

Glu Gly Glu Asn Leu Thr Val Tyr Cys Asn Ser Ser Ser Val Phe Ser
        370                 375                 380

Ser Leu Gln Trp Tyr Arg Gln Glu Pro Gly Glu Gly Pro Val Leu Leu
385                 390                 395                 400

Val Thr Val Val Thr Gly Gly Glu Val Lys Lys Leu Lys Arg Leu Thr
                405                 410                 415

Phe Gln Phe Gly Asp Ala Arg Lys Asp Ser Ser Leu His Ile Thr Ala
                420                 425                 430

Ala Gln Pro Gly Asp Thr Gly Leu Tyr Leu Cys Ala Gly Tyr Gly Gly
            435                 440                 445

Gly Ser Asn Tyr Lys Leu Thr Phe Gly Lys Gly Thr Leu Leu Thr Val
        450                 455                 460

Asn Pro Tyr Ile Gln Asn Pro Asp Pro Ala Val Tyr Gln Leu Arg Asp
465                 470                 475                 480

Ser Lys Ser Ser Asp Lys Ser Val Cys Leu Phe Thr Asp Phe Asp Ser
                485                 490                 495

Gln Thr Asn Val Ser Gln Ser Lys Asp Ser Asp Val Tyr Ile Thr Asp
            500                 505                 510

Lys Thr Val Leu Asp Met Arg Ser Met Asp Phe Lys Ser Asn Ser Ala
        515                 520                 525

Val Ala Trp Ser Asn Lys Ser Asp Phe Ala Cys Ala Asn Ala Phe Asn
        530                 535                 540

Asn Ser Ile Ile Pro Glu Asp Thr Phe Phe Pro Ser Pro Glu Ser Ser
545                 550                 555                 560

Cys Asp Val Lys Leu Val Glu Lys Ser Phe Glu Thr Asp Thr Asn Leu
                565                 570                 575

Asn Phe Gln Asn Leu Ser Val Ile Gly Phe Arg Ile Leu Leu Leu Lys
            580                 585                 590

Val Ala Gly Phe Asn Leu Leu Met Thr Leu Arg Leu Trp Ser Ser
        595                 600                 605

<210> SEQ ID NO 267
<211> LENGTH: 609
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 267

-continued

```
Met Gly Pro Gln Leu Gly Tyr Val Val Leu Cys Leu Leu Gly Ala
1               5                   10                  15

Gly Pro Leu Glu Ala Gln Val Thr Gln Asn Pro Arg Tyr Leu Ile Thr
                20                  25                  30

Val Thr Gly Lys Lys Leu Thr Val Thr Cys Ser Gln Asn Met Asn His
            35                  40                  45

Glu Tyr Met Ser Trp Tyr Arg Gln Asp Pro Gly Leu Gly Leu Arg Gln
    50                  55                  60

Ile Tyr Tyr Ser Met Asn Val Glu Val Thr Asp Lys Gly Asp Val Pro
65                  70                  75                  80

Glu Gly Tyr Lys Val Ser Arg Lys Glu Lys Arg Asn Phe Pro Leu Ile
                85                  90                  95

Leu Glu Ser Pro Ser Pro Asn Gln Thr Ser Leu Tyr Phe Cys Ala Ser
                100                 105                 110

Arg Leu Thr Gly Arg Val His Gly Tyr Thr Phe Gly Ser Gly Thr Arg
            115                 120                 125

Leu Thr Val Val Glu Asp Leu Asn Lys Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Phe Pro Asp His Val Glu Leu Ser
                165                 170                 175

Trp Trp Val Asn Gly Lys Glu Val His Ser Gly Val Ser Thr Asp Pro
                180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
        210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Val Ser Tyr Gln Gln
                260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
        290                 295                 300

Lys Arg Lys Asp Phe Arg Ala Lys Arg Ser Gly Ser Gly Ala Thr Asn
305                 310                 315                 320

Phe Ser Leu Leu Lys Gln Ala Gly Asp Val Glu Glu Asn Pro Gly Pro
                325                 330                 335

Met Val Leu Lys Phe Ser Val Ser Ile Leu Trp Ile Gln Leu Ala Trp
                340                 345                 350

Val Ser Thr Gln Leu Leu Glu Gln Ser Pro Gln Phe Leu Ser Ile Gln
            355                 360                 365

Glu Gly Glu Asn Leu Thr Val Tyr Cys Asn Ser Ser Ser Val Phe Ser
        370                 375                 380

Ser Leu Gln Trp Tyr Arg Gln Glu Pro Gly Glu Gly Pro Val Leu Leu
385                 390                 395                 400

Val Thr Val Val Thr Gly Gly Glu Val Lys Lys Leu Lys Arg Leu Thr
                405                 410                 415

Phe Gln Phe Gly Asp Ala Arg Lys Asp Ser Ser Leu His Ile Thr Ala
```

```
              420                 425                 430
Ala Gln Pro Gly Asp Thr Gly Leu Tyr Leu Cys Ala Gly Tyr Gly Gly
            435                 440                 445

Gly Ser Asn Tyr Lys Leu Thr Phe Gly Lys Gly Thr Leu Leu Thr Val
            450                 455                 460

Asn Pro Tyr Ile Gln Asn Pro Asp Pro Ala Val Tyr Gln Leu Arg Asp
465                 470                 475                 480

Ser Lys Ser Ser Asp Lys Ser Val Cys Leu Phe Thr Asp Phe Asp Ser
                485                 490                 495

Gln Thr Asn Val Ser Gln Ser Lys Asp Ser Asp Val Tyr Ile Thr Asp
            500                 505                 510

Lys Thr Val Leu Asp Met Arg Ser Met Asp Phe Lys Ser Asn Ser Ala
            515                 520                 525

Val Ala Trp Ser Asn Lys Ser Asp Phe Ala Cys Ala Asn Ala Phe Asn
            530                 535                 540

Asn Ser Ile Ile Pro Glu Asp Thr Phe Phe Pro Ser Pro Glu Ser Ser
545                 550                 555                 560

Cys Asp Val Lys Leu Val Glu Lys Ser Phe Glu Thr Asp Thr Asn Leu
                565                 570                 575

Asn Phe Gln Asn Leu Ser Val Ile Gly Phe Arg Ile Leu Leu Leu Lys
            580                 585                 590

Val Ala Gly Phe Asn Leu Leu Met Thr Leu Arg Leu Trp Ser Ser Gly
            595                 600                 605

Ser

<210> SEQ ID NO 268
<211> LENGTH: 607
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 268

Met Val Leu Lys Phe Ser Val Ser Ile Leu Trp Ile Gln Leu Ala Trp
1               5                   10                  15

Val Ser Thr Gln Leu Leu Glu Gln Ser Pro Gln Phe Leu Ser Ile Gln
            20                  25                  30

Glu Gly Glu Asn Leu Thr Val Tyr Cys Asn Ser Ser Ser Val Phe Ser
            35                  40                  45

Ser Leu Gln Trp Tyr Arg Gln Glu Pro Gly Glu Gly Pro Val Leu Leu
        50                  55                  60

Val Thr Val Val Thr Gly Gly Glu Val Lys Lys Leu Lys Arg Leu Thr
65                  70                  75                  80

Phe Gln Phe Gly Asp Ala Arg Lys Asp Ser Ser Leu His Ile Thr Ala
                85                  90                  95

Ala Gln Pro Gly Asp Thr Gly Leu Tyr Leu Cys Ala Gly Tyr Gly Gly
            100                 105                 110

Gly Ser Asn Tyr Lys Leu Thr Phe Gly Lys Gly Thr Leu Leu Thr Val
            115                 120                 125

Asn Pro Tyr Ile Gln Asn Pro Asp Pro Ala Val Tyr Gln Leu Arg Asp
            130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
```

```
            165                 170                 175
Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
            195                 200                 205

Asn Ser Ile Ile Pro Glu Asp Thr Phe Phe Pro Ser Pro Glu Ser Ser
210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
            245                 250                 255

Val Ala Gly Phe Asn Leu Leu Met Thr Leu Arg Leu Trp Ser Ser Arg
            260                 265                 270

Ala Lys Arg Ser Gly Ser Gly Ala Thr Asn Phe Ser Leu Leu Lys Gln
            275                 280                 285

Ala Gly Asp Val Glu Glu Asn Pro Gly Pro Met Gly Pro Gln Leu Leu
            290                 295                 300

Gly Tyr Val Val Leu Cys Leu Leu Gly Ala Gly Pro Leu Glu Ala Gln
305                 310                 315                 320

Val Thr Gln Asn Pro Arg Tyr Leu Ile Thr Val Thr Gly Lys Lys Leu
            325                 330                 335

Thr Val Thr Cys Ser Gln Asn Met Asn His Glu Tyr Met Ser Trp Tyr
            340                 345                 350

Arg Gln Asp Pro Gly Leu Gly Leu Arg Gln Ile Tyr Tyr Ser Met Asn
            355                 360                 365

Val Glu Val Thr Asp Lys Gly Asp Val Pro Glu Gly Tyr Lys Val Ser
            370                 375                 380

Arg Lys Glu Lys Arg Asn Phe Pro Leu Ile Leu Glu Ser Pro Ser Pro
385                 390                 395                 400

Asn Gln Thr Ser Leu Tyr Phe Cys Ala Ser Arg Leu Thr Gly Arg Val
            405                 410                 415

His Gly Tyr Thr Phe Gly Ser Gly Thr Arg Leu Thr Val Val Glu Asp
            420                 425                 430

Leu Asn Lys Val Phe Pro Pro Glu Val Ala Val Phe Glu Pro Ser Glu
            435                 440                 445

Ala Glu Ile Ser His Thr Gln Lys Ala Thr Leu Val Cys Leu Ala Thr
            450                 455                 460

Gly Phe Phe Pro Asp His Val Glu Leu Ser Trp Trp Val Asn Gly Lys
465                 470                 475                 480

Glu Val His Ser Gly Val Ser Thr Asp Pro Gln Pro Leu Lys Glu Gln
            485                 490                 495

Pro Ala Leu Asn Asp Ser Arg Tyr Cys Leu Ser Ser Arg Leu Arg Val
            500                 505                 510

Ser Ala Thr Phe Trp Gln Asn Pro Arg Asn His Phe Arg Cys Gln Val
            515                 520                 525

Gln Phe Tyr Gly Leu Ser Glu Asn Asp Glu Trp Thr Gln Asp Arg Ala
            530                 535                 540

Lys Pro Val Thr Gln Ile Val Ser Ala Glu Ala Trp Gly Arg Ala Asp
545                 550                 555                 560

Cys Gly Phe Thr Ser Val Ser Tyr Gln Gln Gly Val Leu Ser Ala Thr
            565                 570                 575

Ile Leu Tyr Glu Ile Leu Leu Gly Lys Ala Thr Leu Tyr Ala Val Leu
            580                 585                 590
```

```
Val Ser Ala Leu Val Leu Met Ala Met Val Lys Arg Lys Asp Phe
        595                 600                 605

<210> SEQ ID NO 269
<211> LENGTH: 609
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 269

Met Val Leu Lys Phe Ser Val Ser Ile Leu Trp Ile Gln Leu Ala Trp
1               5                   10                  15

Val Ser Thr Gln Leu Leu Glu Gln Ser Pro Gln Phe Leu Ser Ile Gln
            20                  25                  30

Glu Gly Glu Asn Leu Thr Val Tyr Cys Asn Ser Ser Ser Val Phe Ser
        35                  40                  45

Ser Leu Gln Trp Tyr Arg Gln Glu Pro Gly Gly Pro Val Leu Leu
    50                  55                  60

Val Thr Val Val Thr Gly Gly Glu Val Lys Lys Leu Lys Arg Leu Thr
65                  70                  75                  80

Phe Gln Phe Gly Asp Ala Arg Lys Asp Ser Ser Leu His Ile Thr Ala
                85                  90                  95

Ala Gln Pro Gly Asp Thr Gly Leu Tyr Leu Cys Ala Gly Tyr Gly Gly
            100                 105                 110

Gly Ser Asn Tyr Lys Leu Thr Phe Gly Lys Gly Thr Leu Leu Thr Val
        115                 120                 125

Asn Pro Tyr Ile Gln Asn Pro Asp Pro Ala Val Tyr Gln Leu Arg Asp
130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser Arg
            260                 265                 270

Ala Lys Arg Ser Gly Ser Gly Ala Thr Asn Phe Ser Leu Leu Lys Gln
        275                 280                 285

Ala Gly Asp Val Glu Glu Asn Pro Gly Pro Met Gly Pro Gln Leu Leu
    290                 295                 300

Gly Tyr Val Val Leu Cys Leu Leu Gly Ala Gly Pro Leu Glu Ala Gln
305                 310                 315                 320

Val Thr Gln Asn Pro Arg Tyr Leu Ile Thr Val Thr Gly Lys Lys Leu
                325                 330                 335

Thr Val Thr Cys Ser Gln Asn Met Asn His Glu Tyr Met Ser Trp Tyr
```

```
            340                 345                 350
Arg Gln Asp Pro Gly Leu Gly Leu Arg Gln Ile Tyr Tyr Ser Met Asn
            355                 360                 365

Val Glu Val Thr Asp Lys Gly Asp Val Pro Glu Gly Tyr Lys Val Ser
        370                 375                 380

Arg Lys Glu Lys Arg Asn Phe Pro Leu Ile Leu Glu Ser Pro Ser Pro
385                 390                 395                 400

Asn Gln Thr Ser Leu Tyr Phe Cys Ala Ser Arg Leu Thr Gly Arg Val
                405                 410                 415

His Gly Tyr Thr Phe Gly Ser Gly Thr Arg Leu Thr Val Val Glu Asp
            420                 425                 430

Leu Asn Lys Val Phe Pro Pro Glu Val Ala Val Phe Glu Pro Ser Glu
        435                 440                 445

Ala Glu Ile Ser His Thr Gln Lys Ala Thr Leu Val Cys Leu Ala Thr
    450                 455                 460

Gly Phe Phe Pro Asp His Val Glu Leu Ser Trp Trp Val Asn Gly Lys
465                 470                 475                 480

Glu Val His Ser Gly Val Ser Thr Asp Pro Gln Pro Leu Lys Glu Gln
                485                 490                 495

Pro Ala Leu Asn Asp Ser Arg Tyr Cys Leu Ser Ser Arg Leu Arg Val
            500                 505                 510

Ser Ala Thr Phe Trp Gln Asn Pro Arg Asn His Phe Arg Cys Gln Val
        515                 520                 525

Gln Phe Tyr Gly Leu Ser Glu Asn Asp Glu Trp Thr Gln Asp Arg Ala
    530                 535                 540

Lys Pro Val Thr Gln Ile Val Ser Ala Glu Ala Trp Gly Arg Ala Asp
545                 550                 555                 560

Cys Gly Phe Thr Ser Val Ser Tyr Gln Gln Gly Val Leu Ser Ala Thr
                565                 570                 575

Ile Leu Tyr Glu Ile Leu Leu Gly Lys Ala Thr Leu Tyr Ala Val Leu
            580                 585                 590

Val Ser Ala Leu Val Leu Met Ala Met Val Lys Arg Lys Asp Phe Gly
        595                 600                 605

Ser

<210> SEQ ID NO 270
<211> LENGTH: 602
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 270

Met Val Leu Lys Phe Ser Val Ser Ile Leu Trp Ile Gln Leu Ala Trp
1               5                   10                  15

Val Ser Thr Gln Leu Leu Glu Gln Ser Pro Gln Phe Leu Ser Ile Gln
            20                  25                  30

Glu Gly Glu Asn Leu Thr Val Tyr Cys Asn Ser Ser Ser Val Phe Ser
        35                  40                  45

Ser Leu Gln Trp Tyr Arg Gln Glu Pro Gly Glu Gly Pro Val Leu Leu
    50                  55                  60

Val Thr Val Val Thr Gly Gly Glu Val Lys Lys Leu Lys Arg Leu Thr
65                  70                  75                  80

Phe Gln Phe Gly Asp Ala Arg Lys Asp Ser Ser Leu His Ile Thr Ala
```

```
                    85                  90                  95
Ala Gln Pro Gly Asp Thr Gly Leu Tyr Leu Cys Ala Gly Tyr Gly Gly
            100                 105                 110

Gly Ser Asn Tyr Lys Leu Thr Phe Gly Lys Gly Thr Leu Leu Thr Val
            115                 120                 125

Asn Pro Tyr Ile Gln Asn Pro Asp Pro Ala Val Tyr Gln Leu Arg Asp
            130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
            195                 200                 205

Asn Ser Ile Ile Pro Glu Asp Thr Phe Phe Pro Ser Pro Glu Ser Ser
210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser Gly
            260                 265                 270

Ser Gly Ala Thr Asn Phe Ser Leu Leu Lys Gln Ala Gly Asp Val Glu
            275                 280                 285

Glu Asn Pro Gly Pro Met Gly Pro Gln Leu Leu Gly Tyr Val Val Leu
            290                 295                 300

Cys Leu Leu Gly Ala Gly Pro Leu Glu Ala Gln Val Thr Gln Asn Pro
305                 310                 315                 320

Arg Tyr Leu Ile Thr Val Thr Gly Lys Lys Leu Thr Val Thr Cys Ser
                325                 330                 335

Gln Asn Met Asn His Glu Tyr Met Ser Trp Tyr Arg Gln Asp Pro Gly
            340                 345                 350

Leu Gly Leu Arg Gln Ile Tyr Tyr Ser Met Asn Val Glu Val Thr Asp
            355                 360                 365

Lys Gly Asp Val Pro Glu Gly Tyr Lys Val Ser Arg Lys Glu Lys Arg
            370                 375                 380

Asn Phe Pro Leu Ile Leu Glu Ser Pro Ser Pro Asn Gln Thr Ser Leu
385                 390                 395                 400

Tyr Phe Cys Ala Ser Arg Leu Thr Gly Arg Val His Gly Tyr Thr Phe
                405                 410                 415

Gly Ser Gly Thr Arg Leu Thr Val Val Glu Asp Leu Asn Lys Val Phe
            420                 425                 430

Pro Pro Glu Val Ala Val Phe Glu Pro Ser Glu Ala Glu Ile Ser His
            435                 440                 445

Thr Gln Lys Ala Thr Leu Val Cys Leu Ala Thr Gly Phe Phe Pro Asp
            450                 455                 460

His Val Glu Leu Ser Trp Trp Val Asn Gly Lys Glu Val His Ser Gly
465                 470                 475                 480

Val Ser Thr Asp Pro Gln Pro Leu Lys Glu Gln Pro Ala Leu Asn Asp
                485                 490                 495

Ser Arg Tyr Cys Leu Ser Ser Arg Leu Arg Val Ser Ala Thr Phe Trp
            500                 505                 510
```

-continued

```
Gln Asn Pro Arg Asn His Phe Arg Cys Gln Val Gln Phe Tyr Gly Leu
            515                 520                 525

Ser Glu Asn Asp Glu Trp Thr Gln Asp Arg Ala Lys Pro Val Thr Gln
    530                 535                 540

Ile Val Ser Ala Glu Ala Trp Gly Arg Ala Asp Cys Gly Phe Thr Ser
545                 550                 555                 560

Val Ser Tyr Gln Gln Gly Val Leu Ser Ala Thr Ile Leu Tyr Glu Ile
                565                 570                 575

Leu Leu Gly Lys Ala Thr Leu Tyr Ala Val Leu Val Ser Ala Leu Val
                580                 585                 590

Leu Met Ala Met Val Lys Arg Lys Asp Phe
            595                 600

<210> SEQ ID NO 271
<211> LENGTH: 604
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 271

Met Val Leu Lys Phe Ser Val Ser Ile Leu Trp Ile Gln Leu Ala Trp
1               5                   10                  15

Val Ser Thr Gln Leu Leu Glu Gln Ser Pro Gln Phe Leu Ser Ile Gln
            20                  25                  30

Glu Gly Glu Asn Leu Thr Val Tyr Cys Asn Ser Ser Ser Val Phe Ser
        35                  40                  45

Ser Leu Gln Trp Tyr Arg Gln Glu Pro Gly Glu Gly Pro Val Leu Leu
    50                  55                  60

Val Thr Val Val Thr Gly Gly Glu Val Lys Lys Leu Lys Arg Leu Thr
65                  70                  75                  80

Phe Gln Phe Gly Asp Ala Arg Lys Asp Ser Ser Leu His Ile Thr Ala
                85                  90                  95

Ala Gln Pro Gly Asp Thr Gly Leu Tyr Leu Cys Ala Gly Tyr Gly Gly
            100                 105                 110

Gly Ser Asn Tyr Lys Leu Thr Phe Gly Lys Gly Thr Leu Leu Thr Val
        115                 120                 125

Asn Pro Tyr Ile Gln Asn Pro Asp Pro Ala Val Tyr Gln Leu Arg Asp
    130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser Gly
```

```
            260                 265                 270
Ser Gly Ala Thr Asn Phe Ser Leu Leu Lys Gln Ala Gly Asp Val Glu
        275                 280                 285

Glu Asn Pro Gly Pro Met Gly Pro Gln Leu Leu Gly Tyr Val Val Leu
    290                 295                 300

Cys Leu Leu Gly Ala Gly Pro Leu Glu Ala Gln Val Thr Gln Asn Pro
305                 310                 315                 320

Arg Tyr Leu Ile Thr Val Thr Gly Lys Lys Leu Thr Val Thr Cys Ser
                325                 330                 335

Gln Asn Met Asn His Glu Tyr Met Ser Trp Tyr Arg Gln Asp Pro Gly
            340                 345                 350

Leu Gly Leu Arg Gln Ile Tyr Tyr Ser Met Asn Val Glu Val Thr Asp
        355                 360                 365

Lys Gly Asp Val Pro Glu Gly Tyr Lys Val Ser Arg Lys Glu Lys Arg
    370                 375                 380

Asn Phe Pro Leu Ile Leu Glu Ser Pro Ser Pro Asn Gln Thr Ser Leu
385                 390                 395                 400

Tyr Phe Cys Ala Ser Arg Leu Thr Gly Arg Val His Gly Tyr Thr Phe
                405                 410                 415

Gly Ser Gly Thr Arg Leu Thr Val Val Glu Asp Leu Asn Lys Val Phe
            420                 425                 430

Pro Pro Glu Val Ala Val Phe Glu Pro Ser Glu Ala Glu Ile Ser His
        435                 440                 445

Thr Gln Lys Ala Thr Leu Val Cys Leu Ala Thr Gly Phe Phe Pro Asp
    450                 455                 460

His Val Glu Leu Ser Trp Trp Val Asn Gly Lys Glu Val His Ser Gly
465                 470                 475                 480

Val Ser Thr Asp Pro Gln Pro Leu Lys Glu Gln Pro Ala Leu Asn Asp
                485                 490                 495

Ser Arg Tyr Cys Leu Ser Ser Arg Leu Arg Val Ser Ala Thr Phe Trp
            500                 505                 510

Gln Asn Pro Arg Asn His Phe Arg Cys Gln Val Gln Phe Tyr Gly Leu
        515                 520                 525

Ser Glu Asn Asp Glu Trp Thr Gln Asp Arg Ala Lys Pro Val Thr Gln
    530                 535                 540

Ile Val Ser Ala Glu Ala Trp Gly Arg Ala Asp Cys Gly Phe Thr Ser
545                 550                 555                 560

Val Ser Tyr Gln Gln Gly Val Leu Ser Ala Thr Ile Leu Tyr Glu Ile
                565                 570                 575

Leu Leu Gly Lys Ala Thr Leu Tyr Ala Val Leu Val Ser Ala Leu Val
            580                 585                 590

Leu Met Ala Met Val Lys Arg Lys Asp Phe Gly Ser
        595                 600

<210> SEQ ID NO 272
<211> LENGTH: 256
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 272

Thr Gln Leu Leu Glu Gln Ser Pro Gln Phe Leu Ser Ile Gln Glu Gly
1               5                   10                  15
```

```
Glu Asn Leu Thr Val Tyr Cys Asn Ser Ser Val Phe Ser Ser Leu
                20                  25                  30

Gln Trp Tyr Arg Gln Glu Pro Gly Gly Pro Val Leu Leu Val Thr
            35                  40                  45

Val Val Thr Gly Gly Glu Val Lys Lys Leu Lys Arg Leu Thr Phe Gln
50                      55                  60

Phe Gly Asp Ala Arg Lys Asp Ser Ser Leu His Ile Thr Ala Ala Gln
65                  70                  75                  80

Pro Gly Asp Thr Gly Leu Tyr Leu Cys Ala Gly Tyr Gly Gly Ser
                85                  90                  95

Asn Tyr Lys Leu Thr Phe Gly Lys Gly Thr Leu Leu Thr Val Asn Pro
                100                 105                 110

Tyr Ile Gln Asn Pro Asp Pro Ala Val Tyr Gln Leu Arg Asp Ser Lys
            115                 120                 125

Ser Ser Asp Lys Ser Val Cys Leu Phe Thr Asp Phe Asp Ser Gln Thr
130                 135                 140

Asn Val Ser Gln Ser Lys Asp Ser Asp Val Tyr Ile Thr Asp Lys Thr
145                 150                 155                 160

Val Leu Asp Met Arg Ser Met Asp Phe Lys Ser Asn Ser Ala Val Ala
                165                 170                 175

Trp Ser Asn Lys Ser Asp Phe Ala Cys Ala Asn Ala Phe Asn Asn Ser
                180                 185                 190

Ile Ile Pro Glu Asp Thr Phe Phe Pro Ser Pro Glu Ser Ser Cys Asp
            195                 200                 205

Val Lys Leu Val Glu Lys Ser Phe Glu Thr Asp Thr Asn Leu Asn Phe
210                 215                 220

Gln Asn Leu Ser Val Ile Gly Phe Arg Ile Leu Leu Leu Lys Val Ala
225                 230                 235                 240

Gly Phe Asn Leu Leu Met Thr Leu Arg Leu Trp Ser Ser Arg Ala Lys
                245                 250                 255

<210> SEQ ID NO 273
<211> LENGTH: 293
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 273

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
                20                  25                  30

Ser Trp Tyr Arg Gln Asp Pro Gly Leu Gly Leu Arg Gln Ile Tyr Tyr
            35                  40                  45

Ser Met Asn Val Glu Val Thr Asp Lys Gly Asp Val Pro Glu Gly Tyr
50                  55                  60

Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Arg Leu Thr
                85                  90                  95

Gly Arg Val His Gly Tyr Thr Phe Gly Ser Gly Thr Arg Leu Thr Val
                100                 105                 110

Val Glu Asp Leu Asn Lys Val Phe Pro Pro Glu Val Ala Val Phe Glu
            115                 120                 125
```

```
Pro Ser Glu Ala Glu Ile Ser His Thr Gln Lys Ala Thr Leu Val Cys
    130             135                 140

Leu Ala Thr Gly Phe Phe Pro Asp His Val Glu Leu Ser Trp Trp Val
145             150                 155                 160

Asn Gly Lys Glu Val His Ser Gly Val Ser Thr Asp Pro Gln Pro Leu
                165             170                 175

Lys Glu Gln Pro Ala Leu Asn Asp Ser Arg Tyr Cys Leu Ser Ser Arg
            180             185                 190

Leu Arg Val Ser Ala Thr Phe Trp Gln Asn Pro Arg Asn His Phe Arg
        195             200                 205

Cys Gln Val Gln Phe Tyr Gly Leu Ser Glu Asn Asp Glu Trp Thr Gln
    210             215                 220

Asp Arg Ala Lys Pro Val Thr Gln Ile Val Ser Ala Glu Ala Trp Gly
225             230                 235                 240

Arg Ala Asp Cys Gly Phe Thr Ser Val Ser Tyr Gln Gln Gly Val Leu
            245                 250                 255

Ser Ala Thr Ile Leu Tyr Glu Ile Leu Leu Gly Lys Ala Thr Leu Tyr
                260             265                 270

Ala Val Leu Val Ser Ala Leu Val Leu Met Ala Met Val Lys Arg Lys
            275             280                 285

Asp Phe Arg Ala Lys
    290
```

T CELL RECEPTORS THAT BIND TO MIXED LINEAGE LEUKEMIA (MLL)-SPECIFIC PHOSPHOPEPTIDES AND METHODS OF USE THEREOF

RELATED APPLICATIONS

This application is a continuation of International Patent Application No. PCT/US2018/049397, filed Sep. 4, 2018, which claims the benefit of U.S. Provisional Application No. 62/553,957, filed Sep. 4, 2017, both of which are incorporated by reference herein in their entirety.

1. FIELD

The instant disclosure relates to T cell receptors (TCRs) that bind to mixed lineage leukemia (MLL) phosphopeptides and methods of using the same.

2. BACKGROUND

Phosphoproteins arising from deregulated post-translational modifications are critical determinants for cancerous cell transformation. Degradation of these phosphoproteins can generate phosphopeptides that are presented by MHC molecules and mediate cancer-specific T cell responses. Mixed lineage leukemia (MLL, also known as Histone-lysine N-methyltransferase 2A (KMT2A)) is a histone-modifying enzyme regulating genome accessibility and transcription. A number of phosphopeptides that are derived from MLL have been reported, see, e.g., Cobbold et al., Sci Transl Med. 2013 Sep. 18; 5(203): 203ra125, incorporated herein by reference in its entirety. In view of their tumor expression profiles, MLL phosphopeptides hold great promise as targets for cancer therapies.

Accordingly, there is a need in the art for novel compositions that can recognize cancer cells presenting MLL phosphopeptides on their surface and direct an immune response against these cells.

3. SUMMARY

The instant disclosure provides TCRs (e.g., TCRs that bind to a MLL phosphopeptide, e.g., the phosphopeptide MLL-pM EPR[pS]PSHSM (SEQ ID NO: 45) or MLL-pP RVR[pS]PTRSP (SEQ ID NO: 47)), cells and pharmaceutical compositions comprising these TCRs, nucleic acids encoding these TCRs, expression vectors and host cells for making these TCRs, and methods of treating a subject using these TCRs. The TCRs disclosed herein are particularly useful for directing an immune response against cancer cells expressing MLL (e.g., cancer cells displaying a MLL phosphopeptide, e.g., the phosphopeptide MLL-pM EPR[pS] PSHSM (SEQ ID NO: 45) or MLL-pP RVR[pS]PTRSP (SEQ ID NO: 47)), and hence for treating a MLL-expressing cancer in a subject.

Accordingly, in one aspect, the instant disclosure provides an isolated T cell receptor (TCR) that binds to a peptide consisting of the amino acid sequence set forth in SEQ ID NO: 45, the TCR comprising an α chain variable region (Vα) comprising complementarity determining region CDR3α, wherein the CDR3α comprises the amino acid sequence set forth in SEQ ID NO: 21. In certain embodiments, the Vα comprises CDR1α and CDR2α comprising the amino acid sequences set forth in SEQ ID NOs: 11 and 16, respectively. In certain embodiments, the Vα comprises the amino acid sequence set forth in SEQ ID NO: 86. In certain embodiments, the Vα comprises the amino acid sequence set forth in SEQ ID NO: 1. In certain embodiments, the TCR comprises an α chain comprising the amino acid sequence set forth in SEQ ID NO: 58. In certain embodiments, the α chain further comprises the amino acid sequence of GS at the C-terminus. In certain embodiments, the TCR comprises an α chain comprising the amino acid sequence set forth in SEQ ID NO: 236. In certain embodiments, the TCR comprises an α chain comprising an amino acid sequence selected from the group consisting of SEQ ID NOs: 58, 236, 259, 260, 272, 261, and 249. In certain embodiments, the TCR comprises a β chain variable region (Vβ) comprising CDR3β, wherein the CDR3β comprises the amino acid sequence set forth in SEQ ID NO: 36. In certain embodiments, the Vβ comprises CDR1β and CDR2β comprising the amino acid sequences set forth in SEQ ID NOs: 26 and 31, respectively. In certain embodiments, the Vβ comprises the amino acid sequence set forth in SEQ ID NO: 87. In certain embodiments, the Vβ comprises the amino acid sequence set forth in SEQ ID NO: 2. In certain embodiments, the TCR comprises a β chain comprising the amino acid sequence set forth in SEQ ID NO: 59. In certain embodiments, the TCR comprises a β chain comprising the amino acid sequence set forth in SEQ ID NO: 60. In certain embodiments, the β chain further comprises the amino acid sequence of GSGATNFSLLKQAGDVEENPG (SEQ ID NO: 93) at the C-terminus. In certain embodiments, the TCR comprises a β chain comprising the amino acid sequence set forth in SEQ ID NO: 237. In certain embodiments, the TCR comprises a β chain comprising an amino acid sequence selected from the group consisting of SEQ ID NOs: 59, 237, 262, 263, 264, 273, 60, and 250.

In another aspect, provided herein is an isolated TCR that binds to a peptide consisting of the amino acid sequence set forth in SEQ ID NO: 45, the TCR comprising a β chain variable region (Vβ) comprising complementarity determining region CDR3β, wherein the CDR3β comprises the amino acid sequence set forth in SEQ ID NO: 36. In certain embodiments, the Vβ comprises CDR1β and CDR2β comprising the amino acid sequences set forth in SEQ ID NOs: 26 and 31, respectively. In certain embodiments, the Vβ comprises the amino acid sequence set forth in SEQ ID NO: 87. In certain embodiments, the Vβ comprises the amino acid sequence set forth in SEQ ID NO: 2. In certain embodiments, the TCR comprises a β chain comprising the amino acid sequence set forth in SEQ ID NO: 59. In certain embodiments, the TCR comprises a β chain comprising the amino acid sequence set forth in SEQ ID NO: 60. In certain embodiments, the β chain further comprises the amino acid sequence of GSGATNFSLLKQAGDVEENPG (SEQ ID NO: 93) at the C-terminus. In certain embodiments, the TCR comprises a β chain comprising the amino acid sequence set forth in SEQ ID NO: 237. In certain embodiments, the TCR comprises a β chain comprising an amino acid sequence selected from the group consisting of SEQ ID NOs: 59, 237, 262, 263, 264, 273, 60, and 250.

In another aspect, provided herein is an isolated TCR that binds to a peptide consisting of the amino acid sequence set forth in SEQ ID NO: 45, the TCR comprising an α chain variable region (Vα) comprising an amino acid sequence at least 75%, 80%, 85%, 90%, 95%, 99%, or 100% identical to the amino acid sequence set forth in SEQ ID NO: 73. In certain embodiments, the Vα comprises the amino acid sequence set forth in SEQ ID NO: 73. In certain embodiments, the TCR comprises a β chain variable region (Vβ) comprising an amino acid sequence at least 75%, 80%, 85%, 90%, 95%, 99%, or 100% identical to the amino acid sequence set forth in SEQ ID NO: 74. In certain embodiments, the Vβ comprises the amino acid sequence set forth in SEQ ID NO: 74.

In another aspect, provided herein is an isolated TCR that binds to a peptide consisting of the amino acid sequence set forth in SEQ ID NO: 45, the TCR comprising a β chain variable region (Vβ) comprising an amino acid sequence at least 75%, 80%, 85%, 90%, 95%, 99%, or 100% identical to the amino acid sequence set forth in SEQ ID NO: 74. In certain embodiments, the Vβ comprises the amino acid sequence set forth in SEQ ID NO: 74.

In certain embodiments of the foregoing aspects, the TCR comprises an α chain variable region (Vα) comprising CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 11, 16, 21, 26, 31, and 36, respectively.

In another aspect, disclosed herein is an isolated TCR comprising an α chain variable region (Vα) comprising complementarity determining regions CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 11, 16, 21, 26, 31, and 36, respectively. In certain embodiments, the Vα and Vβ comprise the amino acid sequences set forth in SEQ ID NOs: 86 and 87, respectively. In certain embodiments, the Vα and Vβ comprise the amino acid sequences set forth in SEQ ID NOs: 1 and 2, respectively.

In another aspect, disclosed herein is an isolated TCR comprising an α chain and a β chain, wherein the α chain comprises the amino acid sequence set forth in SEQ ID NO: 58 and/or the β chain comprises the amino acid sequence set forth in SEQ ID NO: 59. In certain embodiments, the α chain further comprises the amino acid sequence of GS at the C-terminus, and/or the β chain further comprises the amino acid sequence of GSGATNFSLLKQAGDVEENPG (SEQ ID NO: 93) at the C-terminus. In certain embodiments, the α chain comprises the amino acid sequence set forth in SEQ ID NO: 236 and/or the β chain comprises the amino acid sequence set forth in SEQ ID NO: 237. In certain embodiments, the isolated TCR disclosed herein comprises an α chain comprising an amino acid sequence selected from the group consisting of SEQ ID NOs: 58, 236, 259, 260, 272, 261, and 249 and a β chain comprising an amino acid sequence selected from the group consisting of SEQ ID NOs: 59, 237, 262, 263, 264, 273, 60, and 250. In certain embodiments, the TCR comprises an α chain comprising the amino acid sequence set forth in SEQ ID NO: 249 and a β chain comprising the amino acid sequence set forth in SEQ ID NO: 250.

In another aspect, disclosed herein is an isolated TCR comprising an α chain and a β chain, wherein the α chain comprises the amino acid sequence set forth in SEQ ID NO: 58 or 236 and/or the β chain comprises the amino acid sequence set forth in SEQ ID NO: 60. In certain embodiments, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, disclosed herein is an isolated TCR that binds to a peptide consisting of the amino acid sequence set forth in SEQ ID NO: 45, the TCR comprising an α chain variable region (Vα) comprising complementarity determining region CDR3α, wherein the CDR3α comprises the amino acid sequence set forth in SEQ ID NO: 22. In certain embodiments, the Vα comprises CDR1α and CDR2α comprising the amino acid sequences set forth in SEQ ID NOs: 12 and 17, respectively. In certain embodiments, the Vα comprises the amino acid sequence set forth in SEQ ID NO: 88. In certain embodiments, the Vα comprises the amino acid sequence set forth in SEQ ID NO: 3. In certain embodiments, the TCR comprises an α chain comprising the amino acid sequence set forth in SEQ ID NO: 61. In certain embodiments, the TCR comprises an α chain comprising the amino acid sequence set forth in SEQ ID NO: 251. In certain embodiments, the α chain further comprises the amino acid sequence of GS at the C-terminus. In certain embodiments, the TCR comprises a β chain variable region (Vβ) comprising CDR3β, wherein the CDR3β comprises the amino acid sequence set forth in SEQ ID NO: 37. In certain embodiments, the Vβ comprises CDR1β and CDR2β comprising the amino acid sequences set forth in SEQ ID NOs: 27 and 32, respectively. In certain embodiments, the Vβ comprises the amino acid sequence set forth in SEQ ID NO: 89. In certain embodiments, the Vβ comprises the amino acid sequence set forth in SEQ ID NO: 4. In certain embodiments, the TCR comprises a β chain comprising the amino acid sequence set forth in SEQ ID NO: 62. In certain embodiments, the TCR comprises a β chain comprising the amino acid sequence set forth in SEQ ID NO: 63. In certain embodiments, the TCR comprises a β chain comprising the amino acid sequence set forth in SEQ ID NO: 252. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising a β chain variable region (Vβ) comprising complementarity determining region CDR3β, wherein the CDR3β comprises the amino acid sequence set forth in SEQ ID NO: 37. In certain embodiments, the Vβ comprises CDR1β and CDR2β comprising the amino acid sequences set forth in SEQ ID NOs: 27 and 32, respectively. In certain embodiments, the Vβ comprises the amino acid sequence set forth in SEQ ID NO: 89. In certain embodiments, the Vβ comprises the amino acid sequence set forth in SEQ ID NO: 4. In certain embodiments, the TCR comprises a β chain comprising the amino acid sequence set forth in SEQ ID NO: 62. In certain embodiments, the TCR comprises a β chain comprising the amino acid sequence set forth in SEQ ID NO: 63. In certain embodiments, the TCR comprises a β chain comprising the amino acid sequence set forth in SEQ ID NO: 252. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising an α chain variable region (Vα) comprising an amino acid sequence at least 75%, 80%, 85%, 90%, 95%, 99%, or 100% identical to the amino acid sequence set forth in SEQ ID NO: 75. In certain embodiments, the Vα comprises the amino acid sequence set forth in SEQ ID NO: 75. In certain embodiments, the TCR comprises a β chain variable region (Vβ) comprising an amino acid sequence at least 75%, 80%, 85%, 90%, 95%, 99%, or 100% identical to the amino acid sequence set forth in SEQ ID NO: 76. In certain embodiments, the Vβ comprises the amino acid sequence set forth in SEQ ID NO: 76.

In another aspect, provided herein is an isolated TCR that binds to a peptide consisting of the amino acid sequence set forth in SEQ ID NO: 45, the TCR comprising a β chain variable region (Vβ) comprising an amino acid sequence at least 75%, 80%, 85%, 90%, 95%, 99%, or 100% identical to the amino acid sequence set forth in SEQ ID NO: 76. In certain embodiments, the Vβ comprises the amino acid sequence set forth in SEQ ID NO: 76.

In certain embodiments of the foregoing aspects, the TCR comprises an α chain variable region (Vα) comprising CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 12, 17, 22, 27, 32, and 37, respectively.

In another aspect, provided herein is an isolated TCR comprising an α chain variable region (Vα) comprising complementarity determining regions CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 12, 17, 22, 27, 32, and 37, respectively. In certain embodiments, the Vα and Vβ comprise the amino acid sequences set forth in SEQ ID NOs: 88 and 89, respectively. In certain embodiments, the Vα and Vβ comprise the amino acid sequences set forth in SEQ ID NOs: 3 and 4, respectively.

In another aspect, provided herein is an isolated TCR comprising an α chain and a β chain, wherein the α chain comprises the amino acid sequence set forth in SEQ ID NO: 61 and the β chain comprises the amino acid sequence set forth in SEQ ID NO: 62. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR comprising an α chain and a β chain, wherein the α chain comprises the amino acid sequence set forth in SEQ ID NO: 61 and the β chain comprises the amino acid sequence set forth in SEQ ID NO: 63. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR comprising an α chain and a β chain, wherein the α chain comprises the amino acid sequence set forth in SEQ ID NO: 251 and/or the β chain comprises the amino acid sequence set forth in SEQ ID NO: 252. In certain embodiment, the α chain further comprises the amino acid sequence of GS at the C-terminus, and/or the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising an α chain variable region (Vα) comprising complementarity determining region CDR3α, wherein the CDR3α comprises the amino acid sequence set forth in SEQ ID NO: 23. In certain embodiments, the Vα comprises CDR1α and CDR2α comprising the amino acid sequences set forth in SEQ ID NOs: 13 and 109, respectively. In certain embodiments, the Vα comprises the amino acid sequence set forth in SEQ ID NO: 106. In certain embodiments, the TCR comprises an α chain comprising the amino acid sequence set forth in SEQ ID NO: 64. In certain embodiments, the α chain further comprises the amino acid sequence of GS at the C-terminus. In certain embodiments, the TCR comprises a β chain variable region (Vβ) comprising CDR3β, wherein the CDR3β comprises the amino acid sequence set forth in SEQ ID NO: 38. In certain embodiments, the Vβ comprises CDR1β and CDR2β comprising the amino acid sequences set forth in SEQ ID NOs: 28 and 33, respectively. In certain embodiments, the Vβ comprises the amino acid sequence set forth in SEQ ID NO: 107. In certain embodiments, the TCR comprises a β chain comprising the amino acid sequence set forth in SEQ ID NO: 65. In certain embodiments, the TCR comprises a β chain comprising the amino acid sequence set forth in SEQ ID NO: 66. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising an α chain variable region (Vα) comprising complementarity determining region CDR3α, wherein the CDR3α comprises the amino acid sequence set forth in SEQ ID NO: 23. In certain embodiments, the Vα comprises CDR1α and CDR2α comprising the amino acid sequences set forth in SEQ ID NOs: 13 and 18, respectively. In certain embodiments, the Vα comprises the amino acid sequence set forth in SEQ ID NO: 5. In certain embodiments, the TCR comprises an α chain comprising the amino acid sequence set forth in SEQ ID NO: 253. In certain embodiments, the α chain further comprises the amino acid sequence of GS at the C-terminus. In certain embodiments, the TCR comprises a β chain variable region (Vβ) comprising CDR3β, wherein the CDR3β comprises the amino acid sequence set forth in SEQ ID NO: 38. In certain embodiments, the Vβ comprises CDR1β and CDR2β comprising the amino acid sequences set forth in SEQ ID NOs: 28 and 33, respectively. In certain embodiments, the Vβ comprises the amino acid sequence set forth in SEQ ID NO: 6. In certain embodiments, the TCR comprises a β chain comprising the amino acid sequence set forth in SEQ ID NO: 254. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising a β chain variable region (Vβ) comprising complementarity determining region CDR3β, wherein the CDR3β comprises the amino acid sequence set forth in SEQ ID NO: 38. In certain embodiments, the Vβ comprises CDR1β and CDR2β comprising the amino acid sequences set forth in SEQ ID NOs: 28 and 33, respectively. In certain embodiments, the Vβ comprises the amino acid sequence set forth in SEQ ID NO: 107. In certain embodiments, the Vβ comprises the amino acid sequence set forth in SEQ ID NO: 6. In certain embodiments, the TCR comprises a β chain comprising the amino acid sequence set forth in SEQ ID NO: 65. In certain embodiments, the TCR comprises a β chain comprising the amino acid sequence set forth in SEQ ID NO: 66. In certain embodiments, the TCR comprises a β chain comprising the amino acid sequence set forth in SEQ ID NO: 254. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising an α chain variable region (Vα) comprising an amino acid sequence at least 75%, 80%, 85%, 90%, 95%, 99%, or 100% identical to the amino acid sequence set forth in SEQ ID NO: 77. In certain embodiments, the Vα comprises the amino acid sequence set forth in SEQ ID NO: 77. In certain embodiments, the TCR comprises a β chain variable region (Vβ) comprising an amino acid sequence at least 75%, 80%, 85%, 90%, 95%, 99%, or 100% identical to the amino acid sequence set forth in SEQ ID NO: 78. In certain embodiments, the Vβ comprises the amino acid sequence set forth in SEQ ID NO: 78.

In another aspect, provided herein is an isolated TCR that binds to a peptide consisting of the amino acid sequence set forth in SEQ ID NO: 45, the TCR comprising a β chain variable region (Vβ) comprising an amino acid sequence at least 75%, 80%, 85%, 90%, 95%, 99%, or 100% identical to the amino acid sequence set forth in SEQ ID NO: 78. In certain embodiments, the Vβ comprises the amino acid sequence set forth in SEQ ID NO: 78.

In certain embodiments of the foregoing aspects, the TCR comprises an α chain variable region (Vα) comprising CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 13, 109, 23, 28, 33, and 38, respectively.

In certain embodiments of the foregoing aspects, the TCR comprises an α chain variable region (Vα) comprising CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 13, 18, 23, 28, 33, and 38, respectively.

In another aspect, provided herein is an isolated TCR comprising an α chain variable region (Vα) comprising complementarity determining regions CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 13, 109, 23, 28, 33, and 38, respectively. In certain embodiments, the Vα and Vβ comprise the amino acid sequences set forth in SEQ ID NOs: 106 and 107, respectively.

In another aspect, provided herein is an isolated TCR comprising an α chain variable region (Vα) comprising complementarity determining regions CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 13, 18, 23, 28, 33, and 38, respectively. In certain embodiments, the Vα and Vβ comprise the amino acid sequences set forth in SEQ ID NOs: 5 and 6, respectively.

In another aspect, provided herein is an isolated TCR comprising an α chain and a β chain, wherein the α chain comprises the amino acid sequence set forth in SEQ ID NO: 64 and the β chain comprises the amino acid sequence set forth in SEQ ID NO: 65. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR comprising an α chain and a β chain, wherein the α chain comprises the amino acid sequence set forth in SEQ ID NO: 64 and the β chain comprises the amino acid sequence set forth in SEQ ID NO: 66. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR comprising an α chain and a β chain, wherein the α chain comprises the amino acid sequence set forth in SEQ ID NO: 253 and the β chain comprises the amino acid sequence set forth in SEQ ID NO: 254. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising an α chain variable region (Vα) comprising complementarity determining region CDR3α, wherein the CDR3α comprises the amino acid sequence set forth in SEQ ID NO: 24. In certain embodiment, the Vα comprises CDR1α and CDR2α comprising the amino acid sequences set forth in SEQ ID NOs: 14 and 19, respectively. In certain embodiments, the Vα comprises the amino acid sequence set forth in SEQ ID NO: 7. In certain embodiments, the TCR comprises an α chain comprising the amino acid sequence set forth in SEQ ID NO: 67. In certain embodiments, the TCR comprises an α chain comprising the amino acid sequence set forth in SEQ ID NO: 255. In certain embodiment, the α chain further comprises the amino acid sequence of GS at the C-terminus. In certain embodiments, the TCR comprises a β chain variable region (Vβ) comprising CDR3β, wherein the CDR3β comprises the amino acid sequence set forth in SEQ ID NO: 39. In certain embodiments, the Vβ comprises CDR1β and CDR2β comprising the amino acid sequences set forth in SEQ ID NOs: 29 and 34, respectively. In certain embodiments, the Vβ comprises the amino acid sequence set forth in SEQ ID NO: 108. In certain embodiments, the Vβ comprises the amino acid sequence set forth in SEQ ID NO: 8. In certain embodiments, the TCR comprises a β chain comprising the amino acid sequence set forth in SEQ ID NO: 68. In certain embodiments, the TCR comprises a β chain comprising the amino acid sequence set forth in SEQ ID NO: 69. In certain embodiments, the TCR comprises a β chain comprising the amino acid sequence set forth in SEQ ID NO: 256. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising a β chain variable region (Vβ) comprising complementarity determining region CDR3β, wherein the CDR3β comprises the amino acid sequence set forth in SEQ ID NO: 39. In certain embodiments, the Vβ comprises CDR1β and CDR2β comprising the amino acid sequences set forth in SEQ ID NOs: 29 and 34, respectively. In certain embodiments, the Vβ comprises the amino acid sequence set forth in SEQ ID NO: 108. In certain embodiments, the Vβ comprises the amino acid sequence set forth in SEQ ID NO: 8. In certain embodiments, the TCR comprises a β chain comprising the amino acid sequence set forth in SEQ ID NO: 68. In certain embodiments, the TCR comprises a β chain comprising the amino acid sequence set forth in SEQ ID NO: 69. In certain embodiments, the TCR comprises a β chain comprising the amino acid sequence set forth in SEQ ID NO: 256. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 45, the TCR comprising an α chain variable region (Vα) comprising an amino acid sequence at least 75%, 80%, 85%, 90%, 95%, 99%, or 100% identical to the amino acid sequence set forth in SEQ ID NO: 79. In certain embodiments, the Vα comprises the amino acid sequence set forth in SEQ ID NO: 79. In certain embodiments, the TCR comprises a β chain variable region (Vβ) comprising an amino acid sequence at least 75%, 80%, 85%, 90%, 95%, 99%, or 100% identical to the amino acid sequence set forth in SEQ ID NO: 80. In certain embodiments, the Vβ comprises the amino acid sequence set forth in SEQ ID NO: 80.

In another aspect, provided herein is an isolated TCR that binds to a peptide consisting of the amino acid sequence set forth in SEQ ID NO: 45, the TCR comprising a β chain variable region (Vβ) comprising an amino acid sequence at least 75%, 80%, 85%, 90%, 95%, 99%, or 100% identical to the amino acid sequence set forth in SEQ ID NO: 80. In certain embodiments, the Vβ comprises the amino acid sequence set forth in SEQ ID NO: 80.

In certain embodiments of the foregoing aspects, the TCR comprises an α chain variable region (Vα) comprising CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 14, 19, 24, 29, 34, and 39, respectively.

In another aspect, provided herein is an isolated TCR comprising an α chain variable region (Vα) comprising complementarity determining regions CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 14, 19, 24, 29, 34, and 39, respectively. In certain embodiments, the Vα and Vβ comprise the amino acid sequences set forth in SEQ ID NOs: 7 and 108, respectively. In certain embodiments, the Vα and Vβ comprise the amino acid sequences set forth in SEQ ID NOs: 7 and 8, respectively.

In another aspect, provided herein is an isolated TCR comprising an α chain and a β chain, wherein the α chain comprises the amino acid sequence set forth in SEQ ID NO: 67 and the β chain comprises the amino acid sequence set forth in SEQ ID NO: 68. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR comprising an α chain and a β chain, wherein the α chain comprises the amino acid sequence set forth in SEQ ID NO: 67 and the β chain comprises the amino acid sequence set forth in SEQ ID NO: 69. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR comprising an α chain and a β chain, wherein the α chain comprises the amino acid sequence set forth in SEQ ID NO: 255 and the β chain comprises the amino acid sequence set forth in SEQ ID NO: 256. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 47, the TCR comprising an α chain variable region (Vα) comprising complementarity determining region CDR3α, wherein the CDR3α comprises the amino acid sequence set forth in SEQ ID NO: 25. In certain embodiments, the Vα comprises CDR1α and CDR2α comprising the amino acid sequences set forth in SEQ ID NOs: 15 and 20, respectively. In certain embodiments, the Vα comprises the amino acid sequence set forth in SEQ ID NO: 9. In certain embodiments, the TCR comprises an α chain comprising the amino acid sequence set forth in SEQ ID NO: 70. In certain embodiments, the TCR comprises an α chain comprising the amino acid sequence set forth in SEQ ID NO: 257. In certain embodiments, the α chain further comprises the amino acid sequence of GS at the C-terminus. In certain embodiments, the TCR comprises a β chain variable region (Vβ) comprising CDR3β, wherein the CDR3β comprises the amino acid sequence set forth in SEQ ID NO: 40. In certain embodiments, the Vβ comprises CDR1β and CDR2β comprising the amino acid sequences set forth in SEQ ID NOs: 30 and 35, respectively. In certain embodiments, the Vβ comprises the amino acid sequence set forth in SEQ ID NO: 10. In certain embodiments, the TCR comprises a β chain comprising the amino acid sequence set forth in SEQ ID NO: 71. In certain embodiments, the TCR comprises a β chain comprising the amino acid sequence set forth in SEQ ID NO: 72. In certain embodiments, the TCR comprises a β chain comprising the amino acid sequence set forth in SEQ ID NO: 258. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 47, the TCR comprising a β chain variable region (Vβ) comprising complementarity determining region CDR3β, wherein the CDR3β comprises the amino acid sequence set forth in SEQ ID NO: 40. In certain embodiments, the Vβ comprises CDR1β and CDR2β comprising the amino acid sequences set forth in SEQ ID NOs: 30 and 35, respectively. In certain embodiments, the Vβ comprises the amino acid sequence set forth in SEQ ID NO: 10. In certain embodiments, the TCR comprises a β chain comprising the amino acid sequence set forth in SEQ ID NO: 71. In certain embodiments, the TCR comprises a β chain comprising the amino acid sequence set forth in SEQ ID NO: 72. In certain embodiments, the TCR comprises a β chain comprising the amino acid sequence set forth in SEQ ID NO: 258. In certain embodiments, the β chain further comprises the amino acid sequence of GSGATNFSLLKQAGDVEENPG (SEQ ID NO: 93) at the C-terminus.

In another aspect, provided herein is an isolated TCR that binds to a peptide consisting of the amino acid sequence set forth in SEQ ID NO: 47, the TCR comprising an α chain variable region (Vα) comprising an amino acid sequence at least 75%, 80%, 85%, 90%, 95%, 99%, or 100% identical to the amino acid sequence set forth in SEQ ID NO: 81. In certain embodiments, the Vα comprises the amino acid sequence set forth in SEQ ID NO: 81. In certain embodiments, the TCR comprises a β chain variable region (Vβ) comprising an amino acid sequence at least 75%, 80%, 85%, 90%, 95%, 99%, or 100% identical to the amino acid sequence set forth in SEQ ID NO: 82. In certain embodiments, the Vβ comprises the amino acid sequence set forth in SEQ ID NO: 82.

In another aspect, provided herein is an isolated TCR that binds to a peptide consisting of the amino acid sequence set forth in SEQ ID NO: 47, the TCR comprising a β chain variable region (Vβ) comprising an amino acid sequence at least 75%, 80%, 85%, 90%, 95%, 99%, or 100% identical to the amino acid sequence set forth in SEQ ID NO: 82. In certain embodiments, the Vβ comprises the amino acid sequence set forth in SEQ ID NO: 82.

In certain embodiments of the foregoing aspects, the TCR comprises an α chain variable region (Vα) comprising CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 15, 20, 25, 30, 35, and 40, respectively.

In another aspect, provided herein is an isolated TCR comprising an α chain variable region (Vα) comprising complementarity determining regions CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 15, 20, 25, 30, 35, and 40, respectively. In certain embodiments, the Vα and Vβ comprise the amino acid sequences set forth in SEQ ID NOs: 9 and 10, respectively.

In another aspect, provided herein is an isolated TCR comprising an α chain and a β chain, wherein the α chain comprises the amino acid sequence set forth in SEQ ID NO: 70 and the β chain comprises the amino acid sequence set forth in SEQ ID NO: 71. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR comprising an α chain and a β chain, wherein the α chain comprises the amino acid sequence set forth in SEQ ID NO: 70 and the β chain comprises the amino acid sequence set forth in SEQ ID NO: 72. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR comprising an α chain and a β chain, wherein the α chain comprises the amino acid sequence set forth in SEQ ID NO: 257 and the β chain comprises the amino acid sequence set forth in SEQ ID NO: 258. In certain embodiment, the α chain further comprises the amino acid sequence of GS at the C-terminus, and the β chain further comprises the amino acid sequence of GSGATNFSLLKQAGDVEENPG (SEQ ID NO: 93) at the C-terminus.

In another aspect, provided herein is an isolated TCR that binds to the same epitope as a TCR disclosed herein.

In another aspect, provided herein is an isolated T cell receptor (TCR) that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, or viii) a peptide consisting of the amino acid sequence set forth in SEQ ID NO: 233, or ix) any combination thereof.

In another aspect, provided herein is an isolated T cell receptor (TCR) that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, and viii) a peptide consisting of the amino acid sequence set forth in SEQ ID NO: 233.

In some embodiments, the isolated TCR described herein does not bind to, or does not substantially bind to: i) a peptide consisting of the amino acid sequence set forth in SEQ ID NO: 46, ii) a peptide consisting of the amino acid sequence set forth in SEQ ID NO: 49, 50, 52, 53, 54, 55, or 57, or iii) a peptide consisting of the amino acid sequence set forth in SEQ ID NO: 47, or iv) any combination thereof. In some embodiments, the isolated TCR described herein does not bind to, or does not substantially bind to: i) a peptide consisting of the amino acid sequence set forth in SEQ ID NO: 46, ii) a peptide consisting of the amino acid sequence set forth in SEQ ID NO: 49, 50, 52, 53, 54, 55, or 57, and iii) a peptide consisting of the amino acid sequence set forth in SEQ ID NO: 47.

In another aspect, provided herein is an isolated T cell receptor (TCR) that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, or viii) a peptide consisting of the amino acid sequence set forth in SEQ ID NO: 233, or ix) any combination thereof, wherein the isolated TCR does not bind to, or does not substantially bind to: a) a peptide consisting of the amino acid sequence set forth in SEQ ID NO: 46, b) a peptide consisting of the amino acid sequence set forth in SEQ ID NO: 49, 50, 52, 53, 54, 55, or 57, or c) a peptide consisting of the amino acid sequence set forth in SEQ ID NO: 47, or d) any combination thereof.

In another aspect, provided herein is an isolated T cell receptor (TCR) that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, and viii) a peptide consisting of the amino acid sequence set forth in SEQ ID NO: 233, wherein the isolated TCR does not bind to, or does not substantially bind to: a) a peptide consisting of the amino acid sequence set forth in SEQ ID NO: 46, b) a peptide consisting of the amino acid sequence set forth in SEQ ID NO: 49, 50, 52, 53, 54, 55, or 57, and c) a peptide consisting of the amino acid sequence set forth in SEQ ID NO: 47.

In another aspect, provided herein is an isolated T cell receptor (TCR) that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, viii) a peptide consisting of the amino acid sequence set forth in SEQ ID NO: 219, ix) a peptide consisting of the amino acid sequence set forth in SEQ ID NO: 220, x) a peptide consisting of the amino acid sequence set forth in SEQ ID NO: 226, or xi) a peptide consisting of the amino acid sequence set forth in SEQ ID NO: 233, or xii) any combination thereof.

In another aspect, provided herein is an isolated T cell receptor (TCR) that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, viii) a peptide consisting of the amino acid sequence set forth in SEQ ID NO: 219, ix) a peptide consisting of the amino acid sequence set forth in SEQ ID NO: 220, x) a peptide consisting of the amino acid sequence set forth in SEQ ID NO: 226, and xi) a peptide consisting of the amino acid sequence set forth in SEQ ID NO: 233.

In another aspect, provided herein is an isolated T cell receptor (TCR) that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, viii) a peptide consisting of the amino acid sequence set forth in SEQ ID NO: 219, ix) a peptide consisting of the amino acid sequence set forth in SEQ ID NO: 220, x) a peptide consisting of the amino acid sequence set forth in SEQ ID NO: 226, or xi) a peptide consisting of the amino acid sequence set forth in SEQ ID NO: 233, or xii) any combination thereof, wherein the isolated TCR does not bind to, or does not substantially bind to: a) a peptide consisting of the amino acid sequence set forth in SEQ ID NO: 46, b) a peptide consisting of the amino acid sequence set forth in SEQ ID NO: 49, 50, 52, 53, 54, 55, or 57, or c) a peptide consisting of the amino acid sequence set forth in SEQ ID NO: 47, or d) any combination thereof.

In another aspect, provided herein is an isolated T cell receptor (TCR) that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, viii) a peptide consisting of the amino acid sequence set forth in SEQ ID NO: 219, ix) a peptide consisting of the amino acid sequence set forth in SEQ ID NO: 220, x) a peptide consisting of the amino acid sequence set forth in SEQ ID NO: 226, and xi) a peptide consisting of the amino acid sequence set forth in SEQ ID NO: 233, wherein the isolated TCR does not bind to, or does not substantially bind to: a) a peptide consisting of the amino acid sequence set forth in SEQ ID NO: 46, b) a peptide consisting of the amino acid sequence set forth in SEQ ID NO: 49, 50, 52, 53, 54, 55, or 57, and c) a peptide consisting of the amino acid sequence set forth in SEQ ID NO: 47.

In another aspect, provided herein is an isolated TCR that binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, or viii) a peptide consisting of the amino acid sequence set forth in SEQ ID NO: 233, or ix) any combination thereof. In certain embodiments, the TCR binds to i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, and viii) a peptide consisting of the amino acid sequence set forth in SEQ ID NO: 233. In certain embodiments, the TCR does not bind to, or does not substantially bind to: i) a peptide consisting of the amino acid sequence set forth in SEQ ID NO: 46, ii) a peptide consisting of the amino acid sequence set forth in SEQ ID NO: 49, 50, 52, 53, 54, 55, or 57, or iii) a peptide consisting of the amino acid sequence set forth in SEQ ID NO: 47, or iv) any combination thereof. In certain embodiments, the TCR does not bind to, or does not substantially bind to, any of: i) a peptide consisting of the amino acid sequence set forth in SEQ ID NO: 46, ii) a peptide consisting of the amino acid sequence set forth in SEQ ID NO: 49, iii) a peptide consisting of the amino acid sequence set forth in SEQ ID NO: 50, iv) a peptide consisting of the amino acid sequence set forth in SEQ ID NO: 52, v) a peptide consisting of the amino acid sequence set forth in SEQ ID NO: 53, vi) a peptide consisting of the amino acid sequence set forth in SEQ ID NO: 54, vii) a peptide consisting of the amino acid sequence set forth in SEQ ID NO: 55, viii) a peptide consisting of the amino acid sequence set forth in SEQ ID NO: 57, and ix) a peptide consisting of the amino acid sequence set forth in SEQ ID NO: 47. In certain embodiments, the binding between the TCR and a peptide consisting of the amino acid sequence set forth in SEQ ID NO: 46, 49, 50, 52, 53, 54, 55, 57, or 47 is substantially weakened relative to the binding between the TCR and a peptide consisting of the amino acid sequence set forth in SEQ ID NO: 45, 51, 56, 117, 128, 135, 192, or 233. In certain embodiments, the binding between the TCR and any of: i) a peptide consisting of the amino acid sequence set forth in SEQ ID NO: 46, ii) a peptide consisting of the amino acid sequence set forth in SEQ ID NO: 49, iii) a peptide consisting of the amino acid sequence set forth in SEQ ID NO: 50, iv) a peptide consisting of the amino acid sequence set forth in SEQ ID NO: 52, v) a peptide consisting of the amino acid sequence set forth in SEQ ID NO: 53, vi) a peptide consisting of the amino acid sequence set forth in SEQ ID NO: 54, vii) a peptide consisting of the amino acid sequence set forth in SEQ ID NO: 55, viii) a peptide consisting of the amino acid sequence set forth in SEQ ID NO: 57, and ix) a peptide consisting of the amino acid sequence set forth in SEQ ID NO: 47 is substantially weakened relative to the binding between the TCR and any of: a) a peptide consisting of the amino acid sequence set forth in SEQ ID NO: 45, b) a peptide consisting of the amino acid sequence set forth in SEQ ID NO: 51, c) a peptide consisting of the amino acid sequence set forth in SEQ ID NO: 56, d) a peptide consisting of the amino acid sequence set forth in SEQ ID NO: 117, e) a peptide consisting of the amino acid sequence set forth in SEQ ID NO: 128, f) a peptide consisting of the amino acid sequence set forth in SEQ ID NO: 135, g) a peptide consisting of the amino acid sequence set forth in SEQ ID NO: 192, and h) a peptide consisting of the amino acid sequence set forth in SEQ ID NO: 233.

In another aspect, provided herein is an isolated TCR that binds to at least one of peptide selected from the group consisting of:

i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, and viii) a peptide consisting of the amino acid sequence set forth in SEQ ID NO: 233, wherein the isolated TCR does not bind to, or does not substantially bind to at least one of peptide selected from the group consisting of:

a) a peptide consisting of the amino acid sequence set forth in SEQ ID NO: 46, b) a peptide consisting of the amino acid sequence set forth in SEQ ID NO: 49, 50, 52, 53, 54, 55, or 57, and c) a peptide consisting of the amino acid sequence set forth in SEQ ID NO: 47.

In another aspect, provided herein is an isolated TCR that:

a) binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, or viii) a peptide consisting of the amino acid sequence set forth in SEQ ID NO: 233, or ix) any combination thereof; and b) comprises an α chain variable region (Vα) comprising CDR3α, wherein the CDR3α comprises the amino acid sequence set forth in SEQ ID NO: 21. In certain embodiments, the Vα comprises CDR1α and CDR2α comprising the amino acid sequences set forth in SEQ ID NOs: 11 and 16, respectively. In certain embodiments, the Vα comprises the amino acid sequence set forth in SEQ ID NO: 86. In certain embodiments, the Vα comprises the amino acid sequence set forth in SEQ ID NO: 1. In certain embodiments, the TCR comprises an α chain comprising the amino acid sequence set forth in SEQ ID NO: 58. In certain embodiments, the α chain further comprises the amino acid sequence of GS at the C-terminus. In certain embodiments, the TCR comprises an α chain comprising the amino acid sequence set forth in SEQ ID NO: 236. In certain embodiments, the TCR comprises an α chain comprising the amino acid sequence set forth in SEQ ID NO: 259, 260, 272, 261, or 249. In certain embodiments, the TCR comprises a β chain variable region (Vβ) comprising CDR3β, wherein the CDR3β comprises the amino acid sequence set forth in SEQ ID NO: 36. In certain embodiments, the Vβ comprises CDR1β and CDR2β comprising the amino acid sequences set forth in SEQ ID NOs: 26 and 31, respectively. In certain embodiments, the Vβ comprises the amino acid sequence set forth in SEQ ID NO: 87. In certain embodiments, the Vβ comprises the amino acid sequence set forth in SEQ ID NO: 2. In certain embodiments, the TCR comprises a β chain comprising the amino acid sequence set forth in SEQ ID NO: 59. In certain embodiments, the TCR comprises a β chain comprising the amino acid sequence set forth in SEQ ID NO: 60. In certain embodiments, the β chain further comprises the amino acid sequence of GSGATNFSLLKQAGDVEENPG (SEQ ID NO: 93) at the C-terminus. In certain embodiments, the TCR comprises a β chain comprising the amino acid sequence set forth in SEQ ID NO: 237. In certain embodiments, the TCR comprises a β chain comprising the amino acid sequence set forth in SEQ ID NO: 262, 263, 264, 273, or 250.

In another aspect, provided herein is an isolated TCR that:

a) binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, or viii) a peptide consisting of the amino acid sequence set forth in SEQ ID NO: 233, or ix) any combination thereof; and b) comprises a β chain variable region (Vβ) comprising CDR3β, wherein the CDR3β comprises the amino acid sequence set forth in SEQ ID NO: 36. In certain embodiments, the Vβ comprises CDR1β and CDR2β comprising the amino acid sequences set forth in SEQ ID NOs: 26 and 31, respectively. In certain embodiments, the Vβ comprises the amino acid sequence set forth in SEQ ID NO: 87. In certain embodiments, the Vβ comprises the amino acid sequence set forth in SEQ ID NO: 2. In certain embodiments, the TCR comprises a β chain comprising the amino acid sequence set forth in SEQ ID NO: 59. In certain embodiments, the TCR comprises a β chain comprising the amino acid sequence set forth in SEQ ID NO: 60. In certain embodiments, the β chain further comprises the amino acid sequence of GSGATNFSLLKQAGDVEENPG (SEQ ID NO: 93) at the C-terminus. In certain embodiments, the TCR comprises a β chain comprising the amino acid sequence set forth in SEQ ID NO: 237. In certain embodiments, the TCR comprises a β chain comprising the amino acid sequence selected from the group consisting of SEQ ID NOs: 262, 263, 264, 273, and 250.

In another aspect, provided herein is an isolated TCR that:
a) binds to: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, iv) a peptide consisting of the amino acid sequence set forth in SEQ ID NO: 117, v) a peptide consisting of the amino acid sequence set forth in SEQ ID NO: 128, vi) a peptide consisting of the amino acid sequence set forth in SEQ ID NO: 135, vii) a peptide consisting of the amino acid sequence set forth in SEQ ID NO: 192, or viii) a peptide consisting of the amino acid sequence set forth in SEQ ID NO: 233, or ix) any combination thereof and
b) comprises an α chain variable region (Vα) comprising CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 11, 16, 21, 26, 31, and 36, respectively. In certain embodiments, the Vα and Vβ comprise the amino acid sequences set forth in SEQ ID NOs: 86 and 87, respectively. In certain embodiments, the Vα and Vβ comprise the amino acid sequences set forth in SEQ ID NOs: 1 and 2, respectively.

In another aspect, provided herein is an isolated TCR, wherein when the TCR is expressed on the surface of a T cell, the T cell is activated: i) when co-cultured with a second cell displaying a peptide consisting of the amino acid sequence set forth in SEQ ID NO: 45 (e.g., a second cell displaying a peptide consisting of the amino acid sequence set forth in SEQ ID NO: 45 in the context of HLA-B*0702), ii) when co-cultured with a second cell displaying a peptide consisting of the amino acid sequence set forth in SEQ ID NO: 51 (e.g., a second cell displaying a peptide consisting of the amino acid sequence set forth in SEQ ID NO: 51 in the context of HLA-B*0702); iii) when co-cultured with a second cell displaying a peptide consisting of the amino acid sequence set forth in SEQ ID NO: 56 (e.g., a second cell displaying a peptide consisting of the amino acid sequence set forth in SEQ ID NO: 56 in the context of HLA-B*0702), or iv) when co-cultured with a second cell displaying a peptide consisting of an amino acid sequence selected from the group consisting of SEQ ID NOs: 117, 128, 135, 192, and 233 (e.g., a second cell displaying a peptide consisting of an amino acid sequence selected from the group consisting of SEQ ID NOs: 117, 128, 135, 192, and 233 in the context of HLA-B*0702), or v) any combination thereof. In certain embodiments, when the TCR is expressed on the surface of a T cell, the T cell is activated: i) when co-cultured with a second cell displaying a peptide consisting of the amino acid sequence set forth in SEQ ID NO: 45 (e.g., a second cell displaying a peptide consisting of the amino acid sequence set forth in SEQ ID NO: 45 in the context of HLA-B*0702), ii) when co-cultured with a second cell displaying a peptide consisting of the amino acid sequence set forth in SEQ ID NO: 51 (e.g., a second cell displaying a peptide consisting of the amino acid sequence set forth in SEQ ID NO: 51 in the context of HLA-B*0702), iii) when co-cultured with a second cell displaying a peptide consisting of the amino acid sequence set forth in SEQ ID NO: 56 (e.g., a second cell displaying a peptide consisting of the amino acid sequence set forth in SEQ ID NO: 56 in the context of HLA-B*0702), and iv) when co-cultured with a second cell displaying a peptide consisting of an amino acid sequence selected from the group consisting of SEQ ID NOs: 117, 128, 135, 192, and 233 (e.g., a second cell displaying a peptide consisting of an amino acid sequence selected from the group consisting of SEQ ID NOs: 117, 128, 135, 192, and 233 in the context of HLA-B*0702). In certain embodiments, when the TCR is expressed on the surface of a T cell, the T cell is not activated, or is not substantially activated: i) when co-cultured with a second cell displaying a peptide consisting of the amino acid sequence set forth in SEQ ID NO: 46 (e.g., a second cell displaying a peptide consisting of the amino acid sequence set forth in SEQ ID NO: 46 in the context of HLA-B*0702), ii) when co-cultured with a second cell displaying a peptide consisting of the amino acid sequence set forth in SEQ ID NO: 49, 50, 52, 53, 54, 55, or 57 (e.g., a second cell displaying a peptide consisting of the amino acid sequence set forth in SEQ ID NO: 49, 50, 52, 53, 54, 55, or 57 in the context of HLA-B*0702), or iii) when co-cultured with a second cell displaying a peptide consisting of the amino acid sequence set forth in SEQ ID NO: 47 (e.g., a second cell displaying a peptide consisting of the amino acid sequence set forth in SEQ ID NO: 47 in the context of HLA-B*0702), or iv) any combination thereof. In certain embodiments, when the TCR is expressed on the surface of a T cell, the T cell is not activated, or is not substantially activated, when co-cultured with a second cell displaying any of the following peptides: i) a peptide consisting of the amino acid sequence set forth in SEQ ID NO: 46 (e.g., in the context of HLA-B*0702), ii) a peptide consisting of the amino acid sequence set forth in SEQ ID NO: 49 (e.g., in the context of HLA-B*0702), iii) a peptide consisting of the amino acid sequence set forth in SEQ ID NO: 50 (e.g., in the context of HLA-B*0702), iv) a peptide consisting of the amino acid sequence set forth in SEQ ID NO: 52 (e.g., in the context of HLA-B*0702), v) a peptide consisting of the amino acid sequence set forth in SEQ ID NO: 53 (e.g., in the context of HLA-B*0702), vi) a peptide consisting of the amino acid sequence set forth in SEQ ID NO: 54 (e.g., in the context of HLA-B*0702), vii) a peptide consisting of the amino acid sequence set forth in SEQ ID NO: 55 (e.g., in the context of HLA-B*0702), viii) a peptide consisting of the amino acid sequence set forth in SEQ ID NO: 57 (e.g., in the context of HLA-B*0702), and ix) a peptide consisting of the amino acid sequence set forth in SEQ ID NO: 47 (e.g., in the context of HLA-B*0702). In certain embodiments, when the TCR is expressed on the surface of a T cell, the activation of the T cell is substantially weakened when the T cell is co-cultured with a second cell displaying a peptide consisting of the amino acid sequence set forth in SEQ ID NO: 46, 49, 50, 52, 53, 54, 55, 57, or 47 (e.g., a second cell displaying a peptide consisting of the amino acid sequence set forth in SEQ ID NO: 46, 49, 50, 52, 53, 54, 55, 57, or 47 in the context of HLA-B*0702) relative to the activation of the T cell when the T cell is co-cultured with a third cell displaying a peptide consisting of the amino acid sequence set forth in SEQ ID NO: 45, 51, 56, 117, 128, 135, 192, or 233 (e.g., a third cell displaying a peptide consisting of the amino acid sequence set forth in SEQ ID NO: 45, 51, 56, 117, 128, 135, 192, or 233 in the context of HLA-B*0702). In certain embodiments, when the TCR is expressed on the surface of a T cell, the activation of the T cell is substantially weakened when the T cell is co-cultured with a second cell displaying any of the following peptides: i) a peptide consisting of the amino acid sequence set forth in SEQ ID NO: 46 (e.g., in the context of HLA-B*0702), ii) a peptide consisting of the amino acid sequence set forth in SEQ ID NO: 49 (e.g., in the context of HLA-B*0702), iii) a peptide consisting of the amino acid sequence set forth in SEQ ID NO: 50 (e.g., in the context of HLA-B*0702), iv) a peptide consisting of the amino acid sequence set forth in SEQ ID NO: 52 (e.g., in the context of HLA-B*0702), v) a peptide consisting of the amino acid sequence set forth in SEQ ID NO: 53 (e.g., in the context of HLA-B*0702), vi) a peptide consisting of the amino acid sequence set forth in SEQ ID NO: 54 (e.g., in the context of HLA-B*0702), vii) a peptide consisting of the amino acid sequence set forth in SEQ ID NO: 55 (e.g., in the context of HLA-B*0702), viii) a peptide consisting of the amino acid sequence set forth in SEQ ID NO: 57 (e.g., in the context of HLA-B*0702), and ix) a peptide consisting of the amino acid sequence set forth in SEQ ID NO: 47 (e.g., in the context of HLA-B*0702), relative to the activation of the T cell when the T cell is co-cultured with a third cell displaying any of the following peptides: a) a peptide consisting of the amino acid sequence set forth in SEQ ID NO: 45 (e.g., in the context of HLA-B*0702), b) a peptide consisting of the amino acid sequence set forth in SEQ ID NO: 51 (e.g., in the context of HLA-B*0702), c) a peptide consisting of the amino acid sequence set forth in SEQ ID NO: 56 (e.g., in the context of HLA-B*0702), and d) a peptide consisting of an amino acid sequence selected from the group consisting of SEQ ID NOs: 117, 128, 135, 192, and 233 (e.g., in the context of HLA-B*0702).

In another aspect, provided herein is an isolated TCR, wherein when the TCR is expressed on the surface of a T cell, the activation of the T cell is substantially weakened when the T cell is separately co-cultured with each of: i) a second cell displaying a peptide consisting of the amino acid sequence set forth in SEQ ID NO: 46, ii) a second cell displaying a peptide consisting of the amino acid sequence set forth in SEQ ID NO: 49, iii) a second cell displaying a peptide consisting of the amino acid sequence set forth in SEQ ID NO: 50, iv) a second cell displaying a peptide consisting of the amino acid sequence set forth in SEQ ID NO: 52, v) a second cell displaying a peptide consisting of the amino acid sequence set forth in SEQ ID NO: 53, vi) a second cell displaying a peptide consisting of the amino acid sequence set forth in SEQ ID NO: 54, vii) a second cell displaying a peptide consisting of the amino acid sequence set forth in SEQ ID NO: 55, viii) a second cell displaying a peptide consisting of the amino acid sequence set forth in SEQ ID NO: 57, and ix) a second cell displaying a peptide consisting of the amino acid sequence set forth in SEQ ID NO: 47, relative to the activation of the T cell when the T cell is separately co-cultured with each of: a) a third cell displaying a peptide consisting of the amino acid sequence set forth in SEQ ID NO: 45, b) a third cell displaying a peptide consisting of the amino acid sequence set forth in SEQ ID NO: 51, c) a third cell displaying a peptide consisting of the amino acid sequence set forth in SEQ ID NO: 56, d) a third cell displaying a peptide consisting of the amino acid sequence set forth in SEQ ID NO: 117, e) a third cell displaying a peptide consisting of the amino acid sequence set forth in SEQ ID NO: 128, f) a third cell displaying a peptide consisting of the amino acid sequence set forth in SEQ ID NO: 135, g) a third cell displaying a peptide consisting of the amino acid sequence set forth in SEQ ID NO: 192, and h) a third cell displaying a peptide consisting of the amino acid sequence set forth in SEQ ID NO: 233. In another aspect, provided herein is an isolated TCR compris-ing an α chain variable region (Vα) comprising CDR3α, wherein the CDR3α comprises the amino acid sequence set forth in SEQ ID NO: 21, wherein when the TCR is expressed on the surface of a T cell, the T cell is activated: i) when co-cultured with a second cell displaying a peptide consisting of the amino acid sequence set forth in SEQ ID NO: 45 (e.g., a second cell displaying a peptide consisting of the amino acid sequence set forth in SEQ ID NO: 45 in the context of HLA-B*0702), ii) when co-cultured with a second cell displaying a peptide consisting of the amino acid sequence set forth in SEQ ID NO: 51 (e.g., a second cell displaying a peptide consisting of the amino acid sequence set forth in SEQ ID NO: 51 in the context of HLA-B*0702); iii) when co-cultured with a second cell displaying a peptide consisting of the amino acid sequence set forth in SEQ ID NO: 56 (e.g., a second cell displaying a peptide consisting of the amino acid sequence set forth in SEQ ID NO: 56 in the context of HLA-B*0702), or iv) when co-cultured with a second cell displaying a peptide consisting of an amino acid sequence selected from the group consisting of SEQ ID NOs: 117, 128, 135, 192, and 233 (e.g., a second cell displaying a peptide consisting of an amino acid sequence selected from the group consisting of SEQ ID NOs: 117, 128, 135, 192, and 233 in the context of HLA-B*0702), or v) any combination thereof. In certain embodiments, the Vα comprises CDR1α and CDR2α comprising the amino acid sequences set forth in SEQ ID NOs: 11 and 16, respectively. In certain embodiments, the Vα comprises the amino acid sequence set forth in SEQ ID NO: 86. In certain embodiments, the Vα comprises the amino acid sequence set forth in SEQ ID NO: 1. In certain embodiments, the TCR comprises an α chain comprising the amino acid sequence set forth in SEQ ID NO: 58. In certain embodiments, the α chain further comprises the amino acid sequence of GS at the C-terminus. In certain embodiments, the TCR comprises an α chain comprising the amino acid sequence set forth in SEQ ID NO: 236. In certain embodiments, the TCR comprises an α chain comprising an amino acid sequence selected from the group consisting of SEQ ID NOs: 259, 260, 272, 261, and 249. In certain embodiments, the TCR comprises a β chain variable region (Vβ) comprising CDR3β, wherein the CDR3β comprises the amino acid sequence set forth in SEQ ID NO: 36. In certain embodiments, the Vβ comprises CDR1β and CDR2β comprising the amino acid sequences set forth in SEQ ID NOs: 26 and 31, respectively. In certain embodiments, the Vβ comprises the amino acid sequence set forth in SEQ ID NO: 87. In certain embodiments, the Vβ comprises the amino acid sequence set forth in SEQ ID NO: 2. In certain embodiments, the TCR comprises a β chain comprising the amino acid sequence set forth in SEQ ID NO: 59. In certain embodiments, the TCR comprises a β chain comprising the amino acid sequence set forth in SEQ ID NO: 60. In certain embodiments, the β chain further comprises the amino acid sequence of GSGATNFSLLKQAGDVEENPG (SEQ ID NO: 93) at the C-terminus. In certain embodiments, the TCR comprises a β chain comprising the amino acid sequence set forth in SEQ ID NO: 237. In certain embodiments, the TCR comprises a β chain comprising an amino acid sequence selected from the group consisting of SEQ ID NOs: 262, 263, 264, 273, and 250.

In another aspect, provided herein is an isolated TCR that comprises a β chain variable region (Vβ) comprising CDR3β, wherein the CDR3β comprises the amino acid sequence set forth in SEQ ID NO: 36, wherein when the TCR is expressed on the surface of a T cell, the T cell is activated: i) when co-cultured with a second cell displaying a peptide consisting of the amino acid sequence set forth in SEQ ID NO: 45 (e.g., a second cell displaying a peptide consisting of the amino acid sequence set forth in SEQ ID NO: 45 in the context of HLA-B*0702), ii) when co-cultured with a second cell displaying a peptide consisting of the amino acid sequence set forth in SEQ ID NO: 51 (e.g., a second cell displaying a peptide consisting of the amino acid sequence set forth in SEQ ID NO: 51 in the context of HLA-B*0702); iii) when co-cultured with a second cell displaying a peptide consisting of the amino acid sequence set forth in SEQ ID NO: 56 (e.g., a second cell displaying a peptide consisting of the amino acid sequence set forth in SEQ ID NO: 56 in the context of HLA-B*0702); or iv) when co-cultured with a second cell displaying a peptide consisting of an amino acid sequence selected from the group consisting of SEQ ID NOs: 117, 128, 135, 192, and 233 (e.g., a second cell displaying a peptide consisting of an amino acid sequence selected from the group consisting of SEQ ID NOs: 117, 128, 135, 192, and 233 in the context of HLA-B*0702); or v) any combination thereof. In certain embodiments, the Vβ comprises CDR1β and CDR2β comprising the amino acid sequences set forth in SEQ ID NOs: 26 and 31, respectively. In certain embodiments, the Vβ comprises the amino acid sequence set forth in SEQ ID NO: 87. In certain embodiments, the Vβ comprises the amino acid sequence set forth in SEQ ID NO: 2. In certain embodiments, the TCR comprises a β chain comprising the amino acid sequence set forth in SEQ ID NO: 59. In certain embodiments, the TCR comprises a β chain comprising the amino acid sequence set forth in SEQ ID NO: 60. In certain embodiments, the β chain further comprises the amino acid sequence of GSGATNFSLLKQAGDVEENPG (SEQ ID NO: 93) at the C-terminus. In certain embodiments, the TCR comprises a β chain comprising the amino acid sequence set forth in SEQ ID NO: 237. In certain embodiments, the TCR comprises a β chain comprising an amino acid sequence selected from the group consisting of SEQ ID NOs: 262, 263, 264, 273, and 250.

In another aspect, provided herein is an isolated TCR that comprises an α chain variable region (Vα) comprising CDR1α, CDR2α, and CDR3α and a β chain variable region (Vβ) comprising CDR1β, CDR2β, and CDR3β, wherein the CDR1α, CDR2α, CDR3α, CDR1β, CDR2β, and CDR3β comprise the amino acid sequences set forth in SEQ ID NOs: 11, 16, 21, 26, 31, and 36, respectively, wherein when the TCR is expressed on the surface of a T cell, the T cell is activated: i) when co-cultured with a second cell displaying a peptide consisting of the amino acid sequence set forth in SEQ ID NO: 45 (e.g., a second cell displaying a peptide consisting of the amino acid sequence set forth in SEQ ID NO: 45 in the context of HLA-B*0702), ii) when co-cultured with a second cell displaying a peptide consisting of the amino acid sequence set forth in SEQ ID NO: 51 (e.g., a second cell displaying a peptide consisting of the amino acid sequence set forth in SEQ ID NO: 51 in the context of HLA-B*0702); iii) when co-cultured with a second cell displaying a peptide consisting of the amino acid sequence set forth in SEQ ID NO: 56 (e.g., a second cell displaying a peptide consisting of the amino acid sequence set forth in SEQ ID NO: 56 in the context of HLA-B*0702), or iv) when co-cultured with a second cell displaying a peptide consisting of an amino acid sequence selected from the group consisting of SEQ ID NOs: 117, 128, 135, 192, and 233 (e.g., a second cell displaying a peptide consisting of an amino acid sequence selected from the group consisting of SEQ ID NOs: 117, 128, 135, 192, and 233 in the context of HLA-B*0702), or v) any combination thereof. In certain embodiments, the Vα and Vβ comprise the amino acid sequences set forth in SEQ ID NOs: 86 and 87, respectively. In certain embodiments, the Vα and Vβ comprise the amino acid sequences set forth in SEQ ID NOs: 1 and 2, respectively.

In another aspect, provided herein is an isolated TCR that binds to a peptide consisting of the amino acid sequence set forth in SEQ ID NO: 47. In certain embodiments, the TCR does not bind to, or does not substantially bind to a peptide consisting of an amino acid sequence selected from the group consisting of SEQ ID NOs: 45, 46, and 49-57. In certain embodiments, the binding between the TCR and a peptide consisting of an amino acid sequence selected from the group consisting of SEQ ID NOs: 45, 46, and 49-57 is substantially weakened relative to the binding between the TCR and a peptide consisting of the amino acid sequence set forth in SEQ ID NO: 47.

In another aspect, provided herein is an isolated TCR, wherein when the TCR is expressed on the surface of a T cell, the T cell is activated when co-cultured with a second cell displaying a peptide consisting of the amino acid sequence set forth in SEQ ID NO: 47 (e.g., a second cell displaying a peptide consisting of the amino acid sequence set forth in SEQ ID NO: 47 in the context of HLA-B*0702). In certain embodiments, when the TCR is expressed on the surface of a T cell, the T cell is not activated, or is not substantially activated when co-cultured with a second cell displaying a peptide consisting of an amino acid sequence selected from the group consisting of SEQ ID NOs: 45, 46, and 49-57 (e.g., a second cell displaying a peptide consisting of an amino acid sequence selected from the group consisting of SEQ ID NOs: 45, 46, and 49-57 in the context of HLA-B*0702). In certain embodiments, when the TCR is expressed on the surface of a T cell, the activation of the T cell is substantially weakened when the T cell is co-cultured with a second cell displaying a peptide consisting of an amino acid sequence selected from the group consisting of SEQ ID NOs: 45, 46, and 49-57 (e.g., a second cell displaying a peptide consisting of an amino acid sequence selected from the group consisting of SEQ ID NOs: 45, 46, and 49-57 in the context of HLA-B*0702) relative to the activation of the T cell when the T cell is co-cultured with a third cell displaying a peptide consisting of the amino acid sequence set forth in SEQ ID NO: 47 (e.g., a third cell displaying a peptide consisting of the amino acid sequence set forth in SEQ ID NO: 47 in the context of HLA-B*0702).

In certain embodiments of the foregoing aspects, the TCR comprises an α chain comprising an α chain constant region comprising the amino acid sequence set forth in SEQ ID NO: 41. In certain embodiments, the α chain constant region comprises the amino acid sequence set forth in SEQ ID NO: 42. In certain embodiments of the foregoing aspects, the TCR comprises an α chain comprising an α chain constant region comprising the amino acid sequence set forth in SEQ ID NO: 247.

In certain embodiments of the foregoing aspects, the TCR comprises a β chain comprising a β chain constant region comprising the amino acid sequence set forth in SEQ ID NO: 43, 44, or 248.

The following embodiments apply to each of the foregoing aspects.

In certain embodiment, the TCR is a human TCR (e.g., a full-length human TCR). In certain embodiment, the TCR is a full-length TCR, a soluble TCR, or a single-chain TCR.

In certain embodiment, the peptide is presented in the context of HLA-B*0702. In certain embodiment, when the TCR is expressed on the surface of a T cell, the T cell is activated when co-cultured with a second cell displaying the peptide (e.g., a second cell displaying the peptide in the context of HLA-B*0702). In certain embodiment, the T cell exhibits (a) increased CD69 surface expression, (b) increased CD25 surface expression, (c) increased CD107a expression, (d) increased T cell proliferation, (e) increased IFNγ secretion, or (0 increased nuclear factor of activated T cells (NFAT) promoter activation when co-cultured with the second cell displaying the peptide (e.g., a second cell displaying the peptide in the context of HLA-B*0702). In certain embodiment, the T cell induces apoptosis or death of the second cell displaying the peptide (e.g., a second cell displaying the peptide in the context of HLA-B*0702).

In certain embodiment, the TCR is conjugated to an effector moiety. In certain embodiments, the effector moiety is a cytotoxic agent, cytostatic agent, toxin, radionuclide, detectable label, or binding moiety. In certain embodiments, the binding moiety is an antibody. In certain embodiments, the binding moiety is an antibody Fc region.

In another aspect, the instant disclosure provides an isolated polynucleotide encoding a polypeptide comprising an α chain variable region and/or a β chain variable region, or an α chain and/or a β chain of a TCR disclosed herein. In certain embodiments, the polynucleotide comprises the nucleic acid sequence of SEQ ID NO: 90. In certain embodiments, the polynucleotide comprises the nucleic acid sequence of SEQ ID NO: 238. In certain embodiments, the polynucleotide encodes a polypeptide comprising an amino acid sequence selected from the group consisting of SEQ ID NOs: 83, 266, 267, 268, 269, 270, and 271. In certain embodiments, the polynucleotide encodes a polypeptide comprising the amino acid sequence of SEQ ID NO: 91. In certain embodiments, the polynucleotide encodes a polypeptide comprising the amino acid sequence of SEQ ID NO: 265. In certain embodiments, the polynucleotide encodes a polypeptide comprising the amino acid sequence of SEQ ID NO: 92.

In another aspect, the instant disclosure provides an isolated vector comprising a polynucleotide disclosed herein. In certain embodiments, the vector is a viral vector selected from the group consisting of a lentiviral vector, a retroviral vector, an adenoviral vector, an adeno-associated viral vector, and a baculoviral vector. In certain embodiments, the vector comprises an amino acid sequence selected from the group consisting of SEQ ID NOs: 83, 266, 267, 268, 269, 270, and 271.

In another aspect, the instant disclosure provides an engineered cell comprising a polynucleotide or vector disclosed herein. In certain embodiments, the polynucleotide or vector encodes an amino acid sequence selected from the group consisting of SEQ ID NOs: 83, 266, 267, 268, 269, 270, and 271. In another aspect, the instant disclosure provides a method of producing a TCR that binds to a peptide consisting of the amino acid sequence set forth in SEQ ID NO: 45 or 47, the method comprising culturing the engineered cell so that the polynucleotide is expressed and the TCR is produced. In another aspect, the instant disclosure provides an isolated TCR produced by such methods.

In another aspect, the instant disclosure provides a TCR encoded by a polynucleotide sequence disclosed herein. In another aspect, the instant disclosure provides a TCR that results from expression of a polynucleotide sequence disclosed herein.

In another aspect, the instant disclosure provides a method of producing an engineered cell expressing a TCR that binds to a peptide consisting of the amino acid sequence set forth in SEQ ID NO: 45 or 47, the method comprising contacting a cell with a polynucleotide (or a vector comprising such polynucleotide) encoding an α chain variable region and/or a β chain variable region, or an α chain and/or a β chain of a TCR disclosed herein (e.g., a polynucleotide comprising the nucleic acid sequence of SEQ ID NO: 90 or 238) under conditions that allow introduction of the vector into the cell. In certain embodiments, the polynucleotide is introduced into the cell using a vector (e.g., a viral vector). In certain embodiments, the polynucleotide is introduced into the cell by electroporation. In certain embodiments, the polynucleotide is mRNA and is introduced into the cell by electroporation.

In another aspect, the instant disclosure provides an engineered cell presenting a TCR disclosed herein on the cell surface. In certain embodiments, the cell expresses the TCR. In certain embodiments, the cell is a human lymphocyte. In certain embodiments, the cell is selected from the group consisting of an alpha beta or gamma delta T cell (e.g., a CD8$^+$ T cell, or a CD4$^+$ T cell), a natural killer T (NKT) cell, an invariant natural killer T (iNKT) cell, a mucosal-associated invariant T (MAiT) cell, and a natural killer (NK) cell. In one embodiment, the cell is an iNKT cell.

In another aspect, the instant disclosure provides a pharmaceutical composition comprising a TCR, polynucleotide, vector, or engineered cell disclosed herein, and a pharmaceutically acceptable carrier.

In another aspect, the instant disclosure provides a method of inducing an immune response to a cell displaying a peptide consisting of the amino acid sequence set forth in SEQ ID NO: 45 or 47 in a subject, the method comprising administering to the subject an effective amount of a TCR, polynucleotide, vector, engineered cell, or pharmaceutical composition disclosed herein. In another aspect, the instant disclosure provides a method of treating cancer in a subject, the method comprising administering to the subject an effective amount of a TCR, polynucleotide, vector, engineered cell, or pharmaceutical composition disclosed herein. In certain embodiments, the TCR, polynucleotide, vector, engineered cell, or pharmaceutical composition is administered intravenously. In certain embodiments, the methods further comprise administering an additional therapeutic agent to the subject. In certain embodiments, the additional therapeutic agent is a chemotherapeutic, a radiotherapeutic, or a checkpoint targeting agent. In certain embodiments, the checkpoint targeting agent is selected from the group consisting of an antagonist anti-PD-1 antibody, an antagonist anti-PD-L1 antibody, an antagonist anti-PD-L2 antibody, an antagonist anti-CTLA-4 antibody, an antagonist anti-TIM-3 antibody, an antagonist anti-LAG-3 antibody, an antagonist VISTA antibody, an antagonist CD96 antibody, an antagonist anti-CEACAM1 antibody, an antagonist anti-TIGIT antibody, an agonist anti-CD137 antibody, an agonist anti-GITR antibody, and an agonist anti-OX40 antibody. In certain embodiments, the additional therapeutic agent is an anti-PD-1 antibody, optionally wherein the anti-PD-1 antibody is pembrolizumab or nivolumab. In certain embodiments, the additional therapeutic agent is an inhibitor of indoleamine-2,3-dioxygenase (IDO). In certain embodiments, the inhibitor is selected from the group consisting of epacadostat, F001287, indoximod, and NLG919. In certain embodiments, the inhibitor is epacadostat. In certain embodiments, the additional therapeutic agent is a vaccine. In certain embodiments, the vaccine comprises a heat shock protein peptide complex (HSPPC) comprising a heat shock protein complexed with an antigenic peptide. In certain embodiments, the heat shock protein is hsc70 and is complexed with a tumor-associated antigenic peptide. In certain embodiments, the heat shock protein is gp96 and is complexed with a tumor-associated antigenic peptide, wherein the HSPPC is derived from a tumor obtained from a subject. In certain embodiments, the cancer is leukemia (e.g., mixed lineage leukemia, acute lymphocytic leukemia, acute myeloid leukemia, chronic lymphocytic leukemia, or chronic myeloid leukemia), alveolar rhabdomyosarcoma, bone cancer, brain cancer (e.g., glioblastoma), breast cancer, cancer of the anus, anal canal, or anorectum, cancer of the eye, cancer of the intrahepatic bile duct (e.g., intrahepatic cholangiocellular cancer), cancer of the joints, cancer of the neck, gallbladder, or pleura, cancer of the nose, nasal cavity, or middle ear, cancer of the oral cavity, cancer of the vulva, myeloma (e.g., chronic myeloid cancer), colon cancer, esophageal cancer, cervical cancer, gastrointestinal carcinoid tumor. Hodgkin's lymphoma, hypopharynx cancer, kidney cancer, larynx cancer, liver cancer (e.g., hepatocellular carcinoma), lung cancer (e.g., non-small cell lung cancer), malignant mesothelioma, melanoma, multiple myeloma, nasopharynx cancer, non-Hodgkin's lymphoma, ovarian cancer, pancreatic cancer, peritoneum, omentum, and mesentery cancer, pharynx cancer, prostate cancer, rectal cancer, renal cancer (e.g., renal cell carcinoma (RCC)), gastric cancer, small intestine cancer, soft tissue cancer, stomach cancer, carcinoma, sarcoma (e.g., synovial sarcoma, rhabdomyosarcoma), testicular cancer, thyroid cancer, head and neck cancer, ureter cancer, and urinary bladder cancer. In certain embodiments, the cancer is melanoma, breast cancer, lung cancer, prostate cancer, thyroid cancer, ovarian cancer, or synovial sarcoma. In one embodiment, the cancer is synovial sarcoma or liposarcoma (e.g., myxoid/round cell liposarcoma).

4. BRIEF DESCRIPTION OF THE DRAWINGS

FIG. 1 is a bar graph showing the percentage of TNFα+ cells among the total CD8+ cells from three HLA-B*0702 healthy donors after their PBMCs were stimulated with the MLL-pM peptide (EPR[pS]PSHSM; SEQ ID NO: 45), the MLL-pP peptide (RVR[pS]PTRSP; SEQ ID NO: 47), or a mix of peptides selected from viral T cell epitopes.

Figure 2:
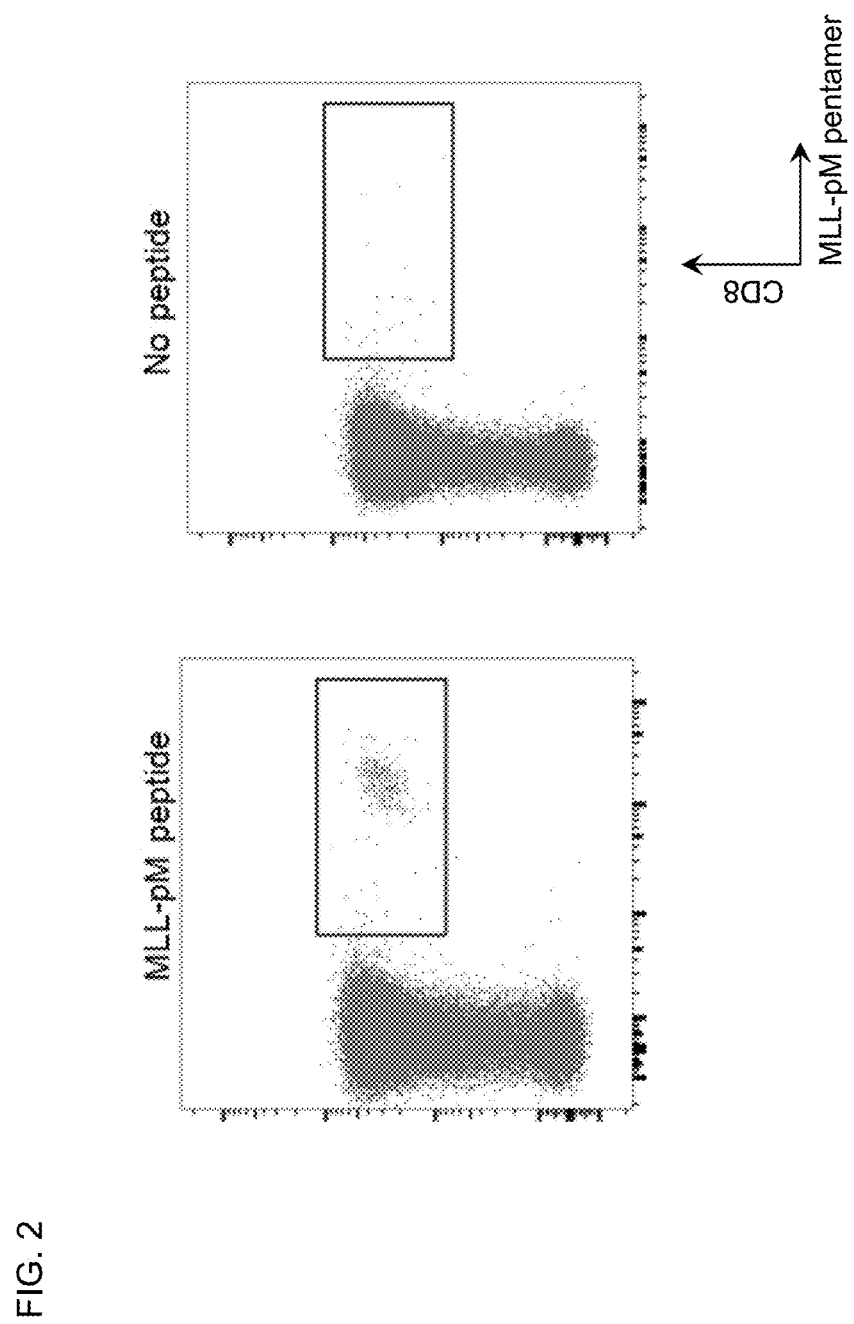

FIG. 2 is a pair of flow cytometry plots showing analysis of memory CD8+ T cells that were co-cultured with non-pulsed DCs ("No peptide") or DCs pulsed with the peptide EPR[pS]PSHSM (SEQ ID NO: 45) ("MLL-pM peptide"). After co-culturing, the cells were stained with the MLL-pM/HLA-B*0702 pentamers and an anti-CD8 antibody.

Figure 3:
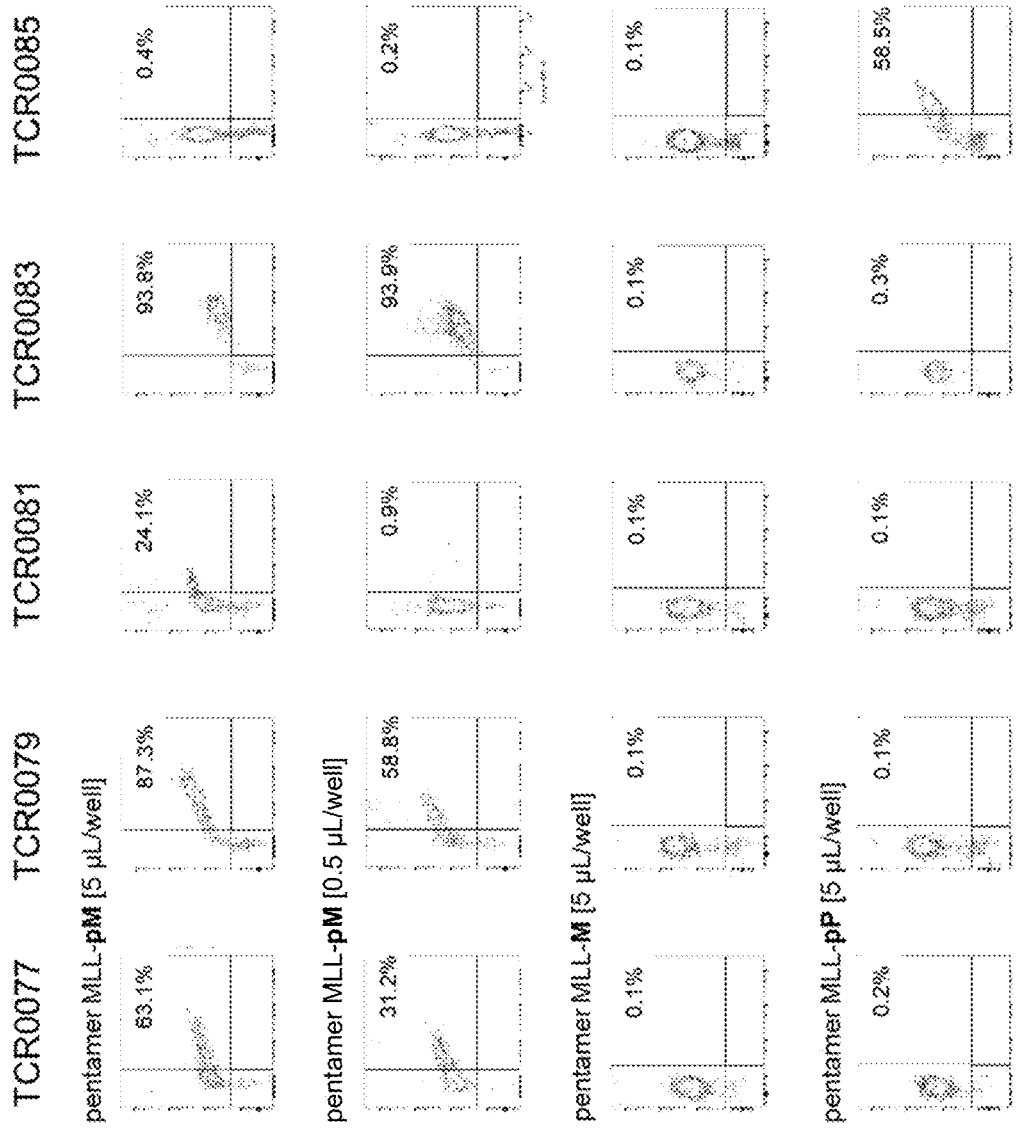

FIG. 3 is a set of flow cytometry plots showing staining of AK-D10R3 cells expressing the chimeric TCRs TCR0077, TCR0079, TCR0081, TCR0083, or TCR0085 with PE-labeled HLA-B*0702 pentamers loaded with the MLL-pM peptide (EPR[pS]PSHSM; SEQ ID NO: 45) (5 µL/well or 0.5 µL/well), the non-phosphorylated MLL-M control peptide (EPRSPSHSM; SEQ ID NO: 46) (5 µL/well) or the MLL-pP peptide (RVR[pS]PTRSP; SEQ ID NO: 47) (5 µL/well). The percentages of pentamer+ TCR+ cells are indicated in the upper right panel of each plot.

Figure 4A:

FIGS. 4A and 4B are flow cytometry plots showing the results of an assay testing activation of AK-D10R3 single cell clones expressing the chimeric TCRs TCR0077, TCR0079, TCR0081, TCR0083, or TCR0085 after co-culture with T2-B7 cells (i.e., T2 cells overexpressing HLA-B*0702) pulsed with 50 µg/ml or 5 µg/mL of the MLL-pM peptide (EPR[pS]PSHSM; SEQ ID NO: 45), 50 µg/mL of the MLL-M control peptide (EPRSPSHSM; SEQ ID NO: 46), or 50 µg/mL of the MLL-pP peptide (RVR[pS]PTRSP; SEQ ID NO: 47) at an effector to target cell ratio of 2:1. TCR-expressing AK-D10R3 cells alone or co-cultures containing TCR-expressing AK-D10R3 cells and non-pulsed T2-B7 cells were included as controls. The percentages of TCR+EGFP+ cells are indicated in the upper right panel of each plot.

Figure 5:
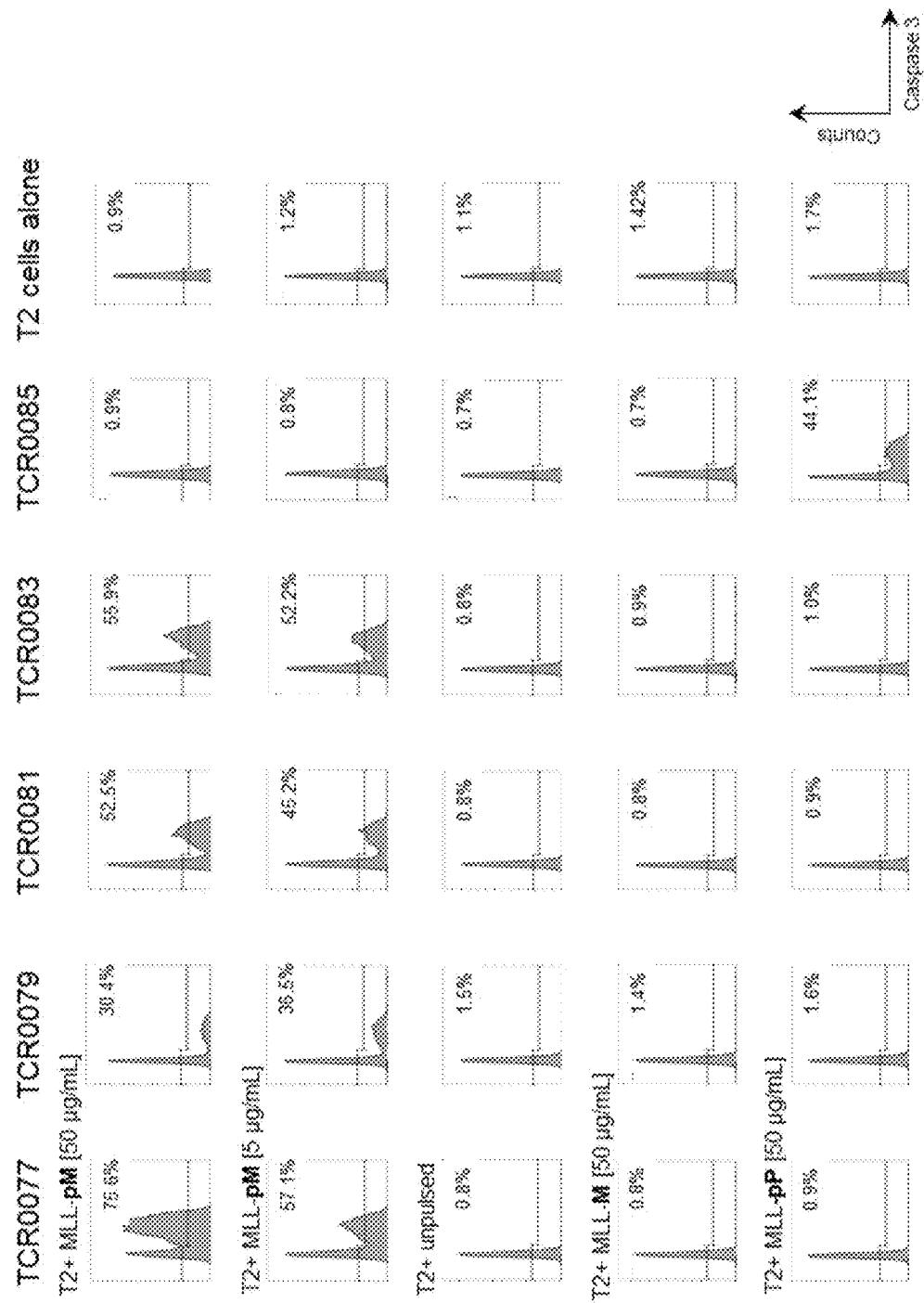

FIG. 5 is a set of histograms showing the results of an assay testing the potential of TCR-expressing AK-D10R3 single cell clones to induce apoptosis in T2-B7 target cells pulsed with 50 µg/ml or 5 µg/mL of the MLL-pM peptide (EPR[pS]PSHSM; SEQ ID NO: 45), 50 µg/mL of the MLL-M control peptide (EPRSPSHSM; SEQ ID NO: 46), or 50 µg/mL of the MLL-pP peptide (RVR[pS]PTRSP; SEQ ID NO: 47). Co-cultures containing non-pulsed T2-B7 cells or T2-B7 cells incubated without TCR-expressing AK-D10R3 cells served as controls. The percentages of caspase+ T2-B7 cells are indicated in the upper right panel of each histogram.

Figures 6A, 6B:
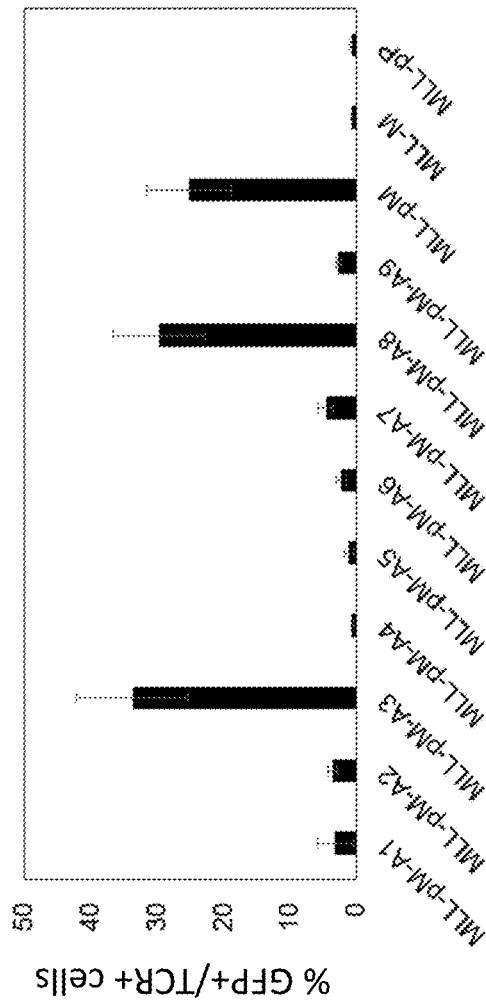

FIGS. 6A and 6B are bar graphs showing activation of TCR0077-expressing or TCR0085-expressing AK-D10R3 cells after co-culturing with T2-B7 target cells pulsed with the MLL-pM peptide (EPR[pS]PSHSM; SEQ ID NO: 45), its alanine-modified variants, the MLL-M peptide, or the MLL-pP peptide. Activation of the AK-D10R3 cells was assessed by measuring EGFP expression resulting from the activation of an IL-2-(NFAT)$_3$-EGFP reporter construct. Assays were performed in triplicate and the y axis shows the percentage of EGFP-positive TCR-positive AK-D10R3 cells.

Figures 7A, 7B:
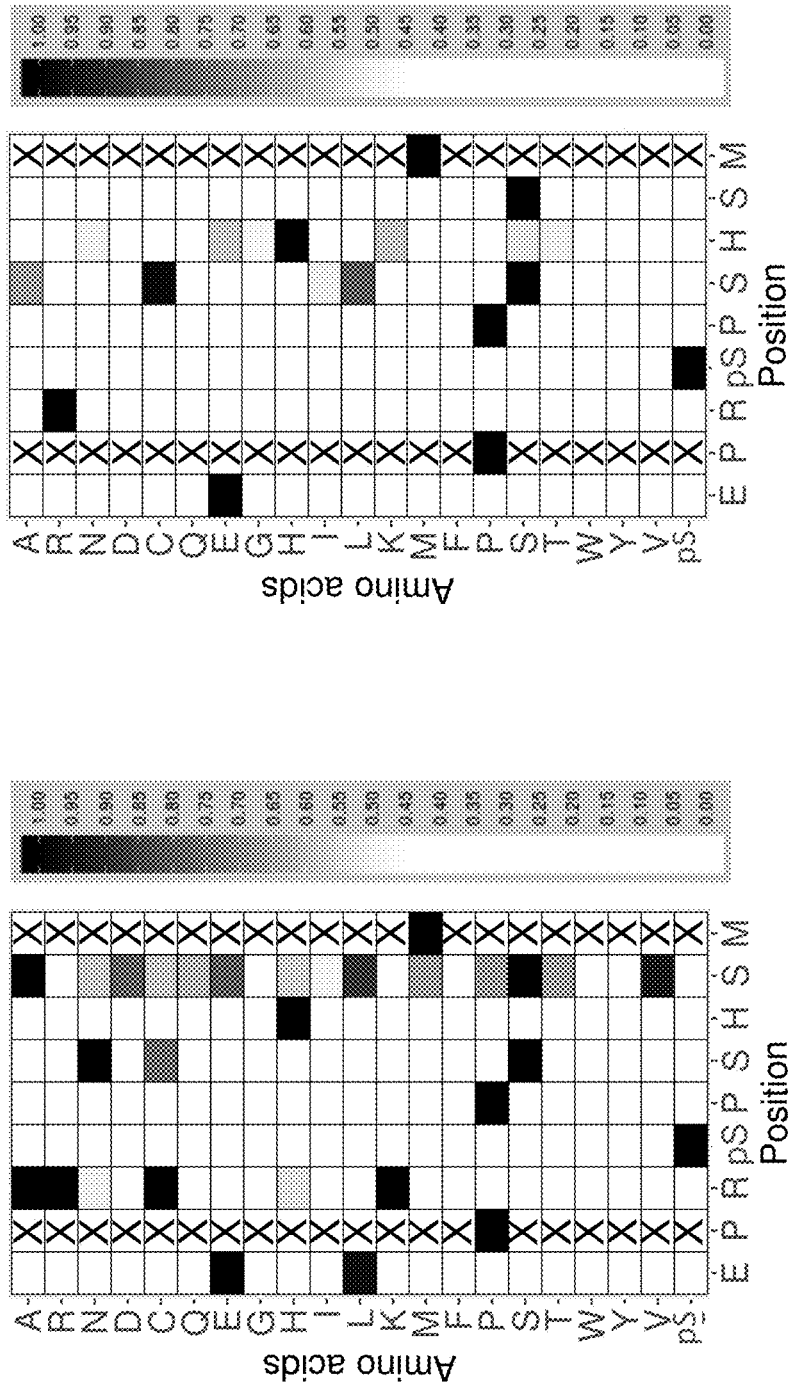

FIGS. 7A and 7B are heat maps comparing specificities of the indicated TCRs (FIG. 7A: TCR0077; FIG. 7B: TCR0081) to a panel of variants of the peptide EPR[pS]PSHSM (SEQ ID NO: 45), where each amino acid position in each peptide, except for the anchor positions P2 (P) and P9 (M), of SEQ ID NO: 45 was individually substituted with each of the 19 other possible naturally occurring amino acids, and position P4 ([pS]) was additionally substituted with non-phosphorylated serine. Each peptide of the panel was separately loaded onto T2 target cells, prior to co-culturing with TCR-expressing AK-D10R3 effector cells. Upon binding of the TCR to a resulting mutant peptide, the AK-D10R3 cells were activated to express an EGFP reporter, which was detected by FACS. The results are shown as heat maps in which each block represents the amino acid residue substitution of the native residue in the MLL-pM peptide EPR[pS]PSHSM (SEQ ID NO: 45). The native residues are shown on the horizontal axis and the substituted residues indicated on the vertical axis. Each block is shaded in scale to the normalized mean activation (with normalized values cropped to a minimum of 0.0 and to a maximum of 1.0). "X" denotes untested mutants. Background activation (no peptide loaded) was subtracted from all peptide-loaded samples (altered and native sequences).

Figure 8A:
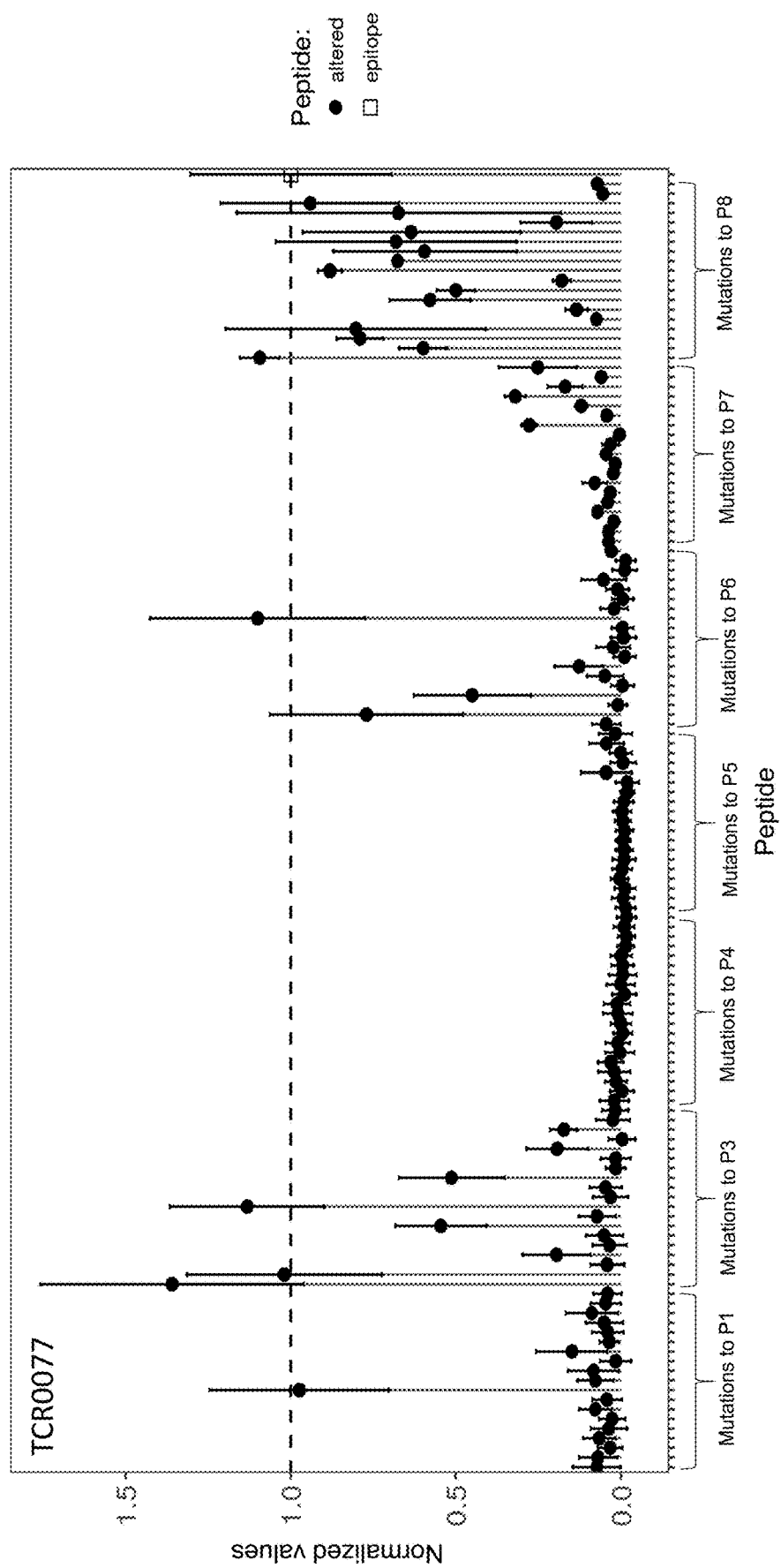
Figure 8B:
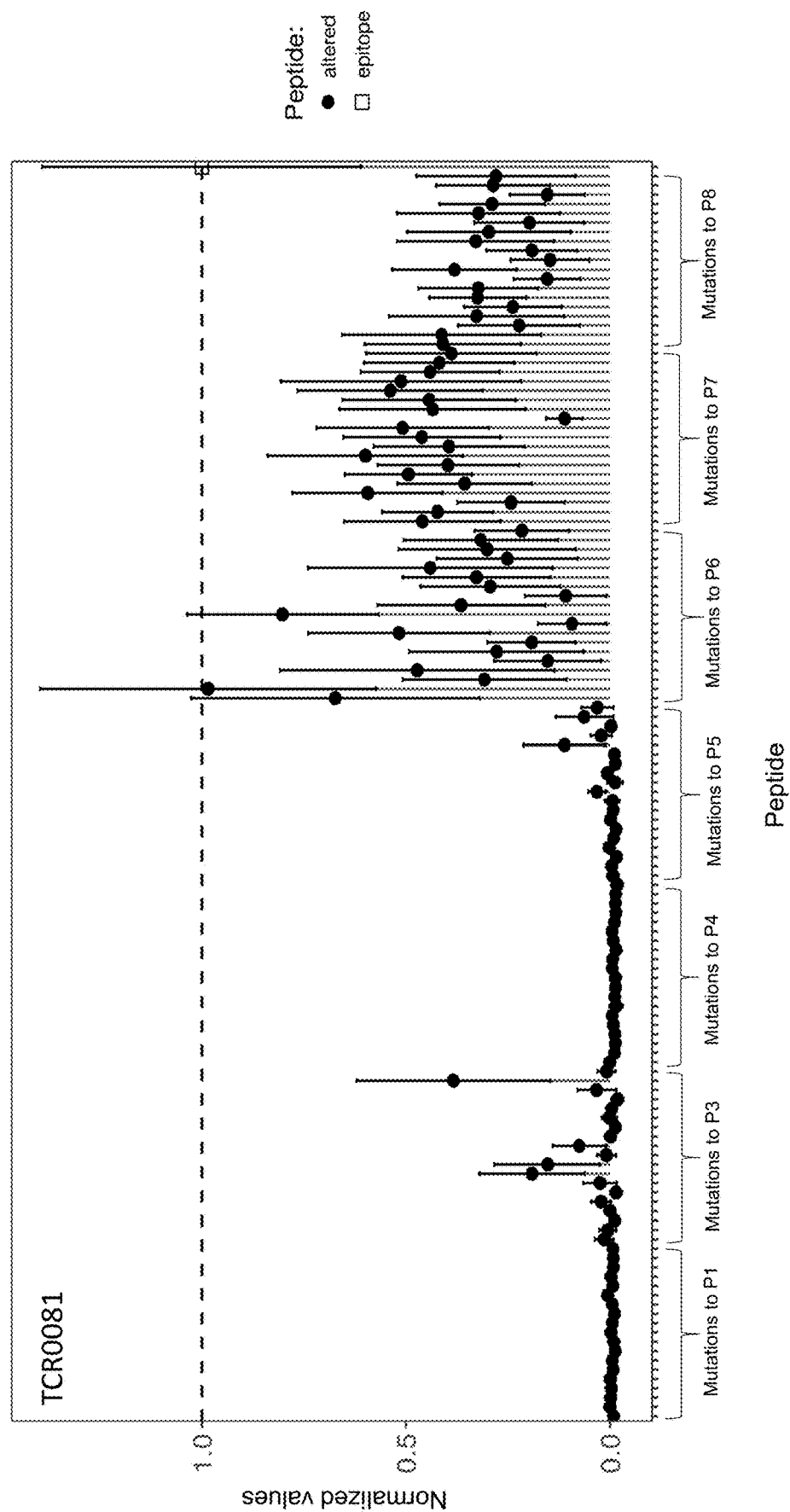

FIGS. 8A and 8B are bar graphs comparing the specificity profiles of the indicated TCRs (FIG. 8A: TCR0077; FIG. 8B: TCR0081), and show normalized mean activation values for each variant MLL-pM peptide (black dot, "altered") described in Table 8, as well as the values for the peptide EPR[pS]PSHSM (SEQ ID NO: 45) (open square, "epitope"). Normalized mean activation values corresponding to the variant MLL-pM peptides in Table 8 are displayed, left to right, according to the peptide sequence in Table 8, i.e., SEQ ID NOs: 49, 110-127, 51, 128-145, 52, 146-159, 46, 160-163, 53, 164-181, 54, 182-199, 55, 200-217, 56, and 218-235. Brackets were used to designate groups of variant MLL-pM peptides according to the position of their variant residue in the MLL-pM peptide sequence. Error bars represent the standard error of the mean (SEM).

Figure 9A:
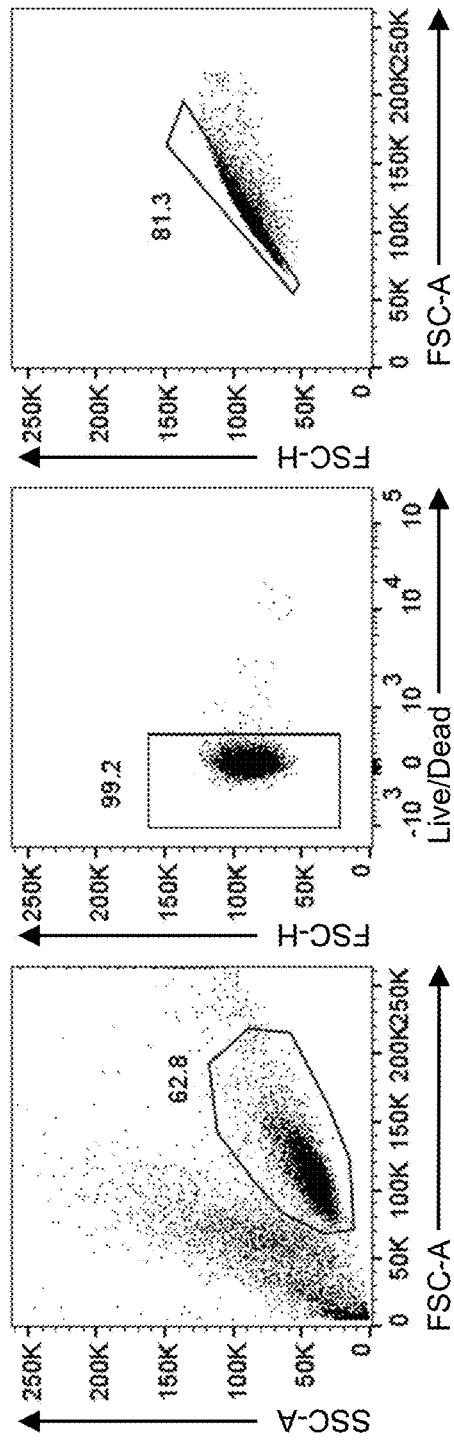
Figure 9B:
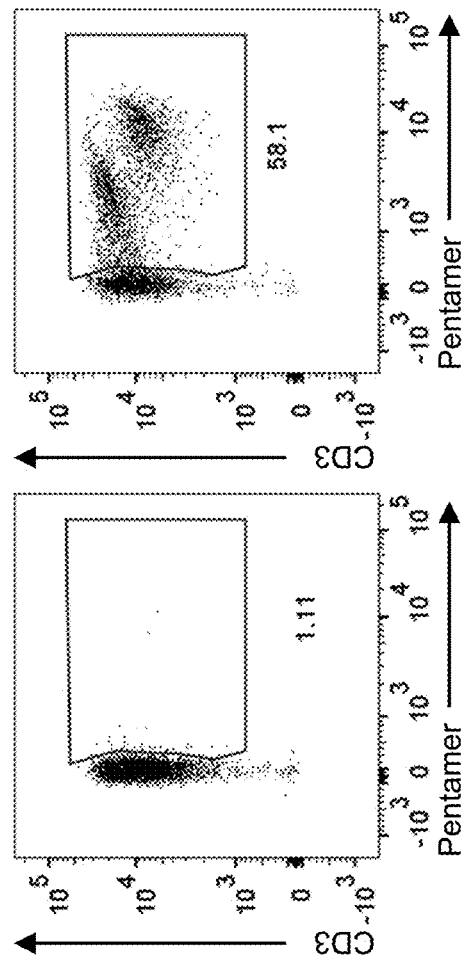
Figures 9C, 9D:
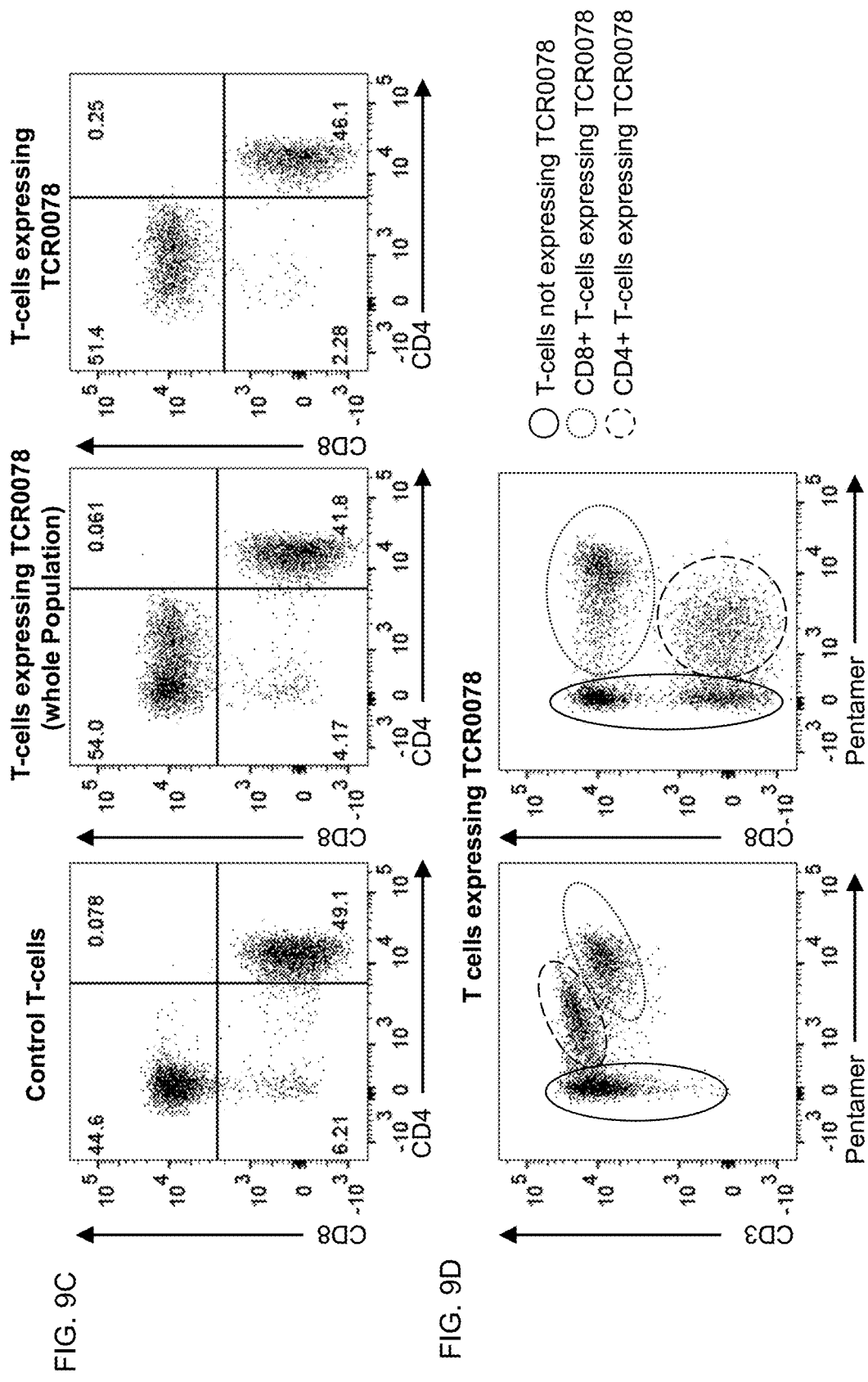

FIGS. 9A-9D are flow cytometry plots showing the phenotype of control T cells and TCR0078-transduced T cells. Specifically, stimulated primary T cells, with or without TCR transduction, were stained with a Zombie NIR™ Live/Dead reagent, anti-CD3-FITC, anti-CD4-PerCp/Cy5.5 and anti-CD8-PE/Cy7 antibodies, and the PE-conjugated HLA-B*0702 pentamer loaded with the MLL-pM peptide EPR[pS]PSHSM (SEQ ID NO:45). FIG. 9A shows the sequence of flow cytometry gates used to identify intact, live, singlet cells. Specifically, the left panel shows the gate used for the selection of intact cells from the whole sample; the middle panel shows the gate used for the selection of live cells from intact cells; and the right panel shows the gate used for the selection of singlet cells from live cells. The data in FIG. 9A are for control T cells. Similar data was obtained for TCR0078-transduced T cells using the same flow cytometry gate parameters. Numbers in each panel show the percentage of cells passing through each gate, with intact, live, singlet cells used for the remainder of the experiment. In FIG. 9B, anti-CD3-FITC antibody staining was used to identify T cells and pentamer staining was used to identify cells expressing TCR0078 in both control (left) and TCR0078-transduced (right) T cells. FIG. 9C shows the expression of CD4 and CD8 in each of three conditions: the left panel shows data from the whole population of control T cells (from left panel, FIG. 9B); the middle panel shows data from the whole population of TCR0078 transduced cells (from right panel, FIG. 9B); and, the right panel shows data from the 58.1% of cells identified as expressing TCR0078 by pentamer staining (from gated cells in right panel of FIG. 9B). CD4 and CD8 were identified by staining with anti-CD4-PerCp/Cy5.5 and anti-CD8-PE/Cy7 antibodies respectively. Two cell populations were identified (CD4+/CD8− and CD4−/CD8+). The two cell populations were also apparent with other staining, such as anti-CD3 or anti-CD8 antibodies with pentamer staining (FIG. 9D).

Figure 10:
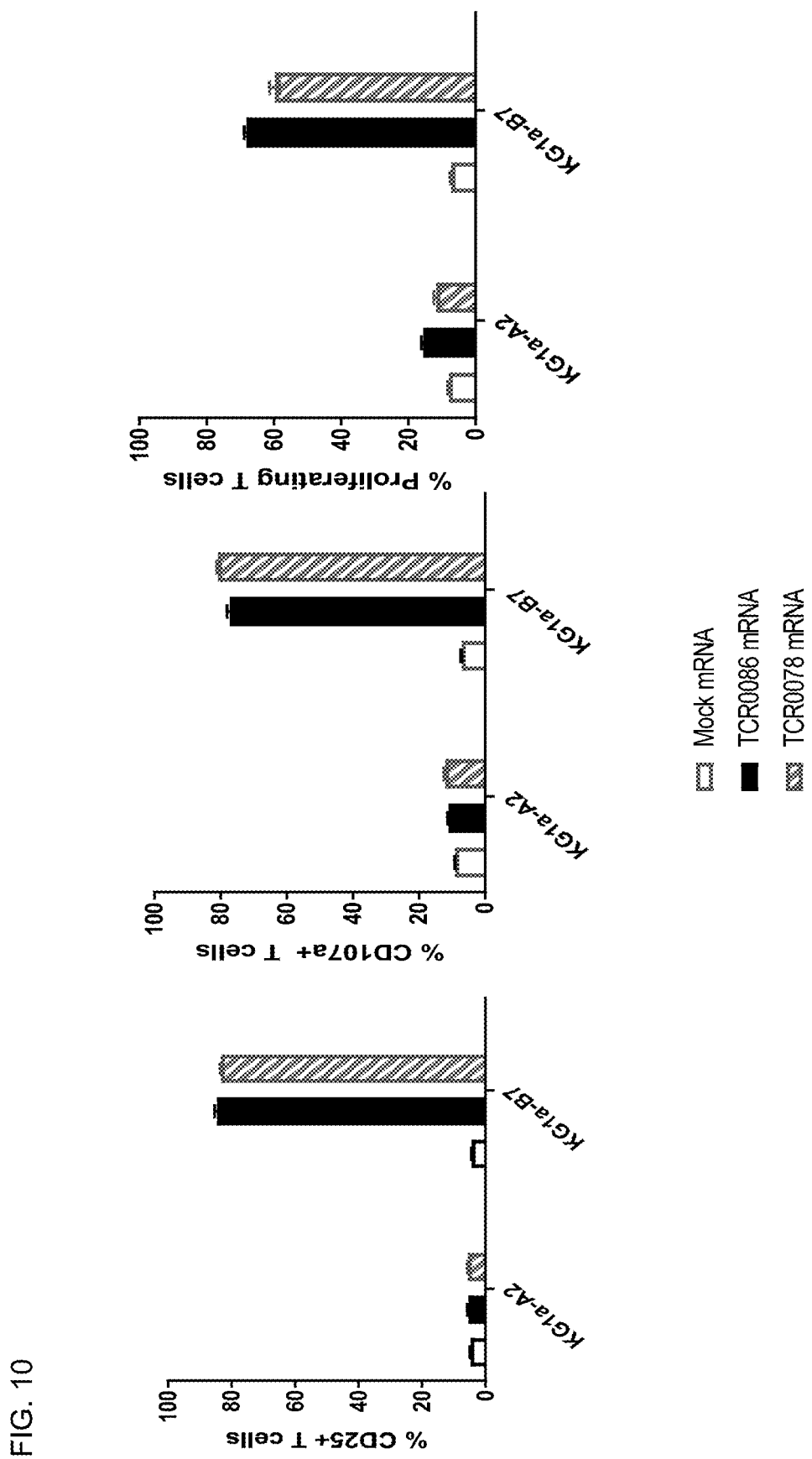

FIG. 10 is a set of bar graphs showing results from an assay testing the activation of T cells that were electroporated with mock mRNA, TCR0086 mRNA, or TCR0078 mRNA and co-cultured with KG1a-A2 cells expressing MLL or KG1a-B7 cells expressing MLL, at an effector:target ratio of 2:1. The left panel shows the percentage of CD25+ T cells. The middle panel shows the percentage of CD107a+ T cells. The right panel shows the percentage of proliferating T cells.

Figure 11:
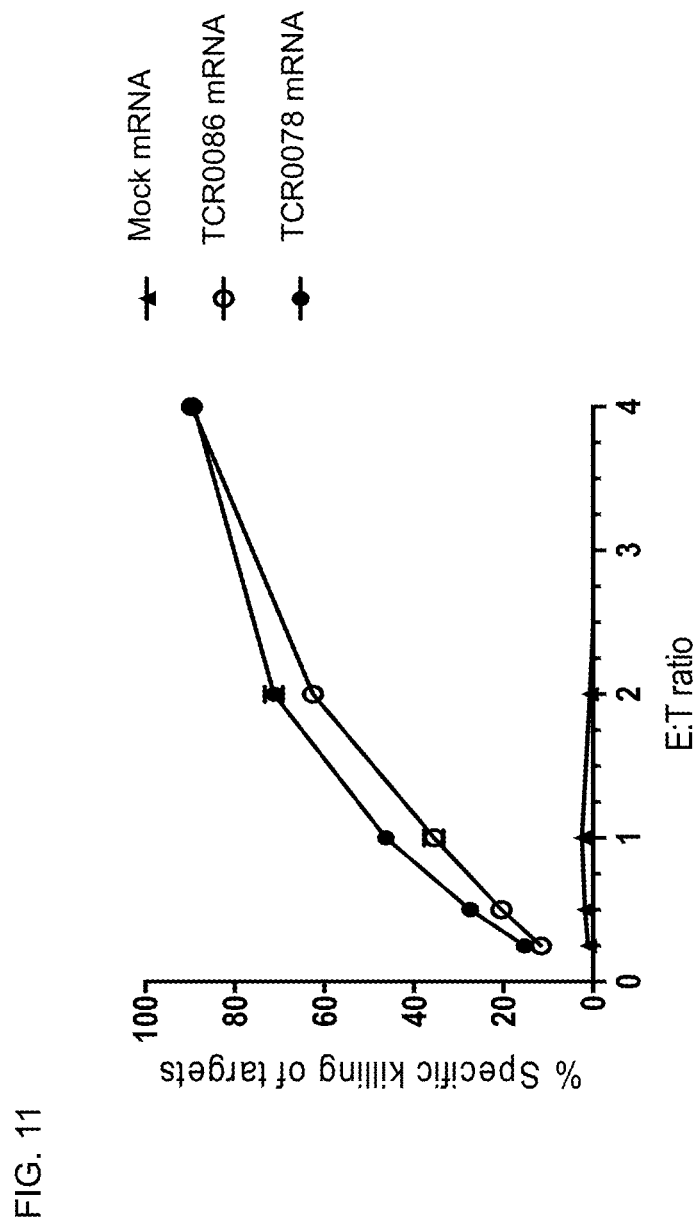

FIG. 11 is a graph showing the percentage of specific killing of KG1a-B7 target cells by T cells electroporated with mock mRNA, TCR0086 mRNA, or TCR0078 mRNA. The x axis shows the effector:target (E:T) ratios used in this study.

FIGS. 12A-12C are a set of bar graphs showing activation of a Jurkat IL-2-NFAT-luciferase reporter cell line expressing TCR0078, upon co-culturing with various tumor cell lines expressing HLA-B*0702. In FIG. 12A, the Jurkat cells (Effector) were co-cultured with KG1a cells overexpressing HLA-B*0702 ("KG1a B7"), K562 cells overexpressing HLA-B*0702 ("K562 B7"), Namalwa cells, or Loucy cells (Target) for 24 hours at various effector:target ratios (as the x-axis). Activation of the Jurkat cells was assessed by measuring luciferase activity (represented on the y-axis by arbitrary units (a.u.)) resulting from the activation of the IL-2-NFAT-luciferase reporter. FIG. 12B represents a negative control in which Jurkat reporter cells not transduced with TCR0078 were co-cultured with the same tumor cells. As a positive control, the luminescence was measured after Jurkat cells, either expressing TCR0078 or not, were stimulated with phorbol 12-myristate 13-acetate (PMA) and Ionomycin (representing maximum NFAT-luciferase expression) (FIG. 12C). For "Jurkat control," the non-transduced Jurkat report cells described for FIG. 12B were used. For "Jurkat expressing TCR," TCR0078-transduced Jurkat reporter cells originating from one cell clone ("c75") with optimal TCR expression were used.

Figure 13A:
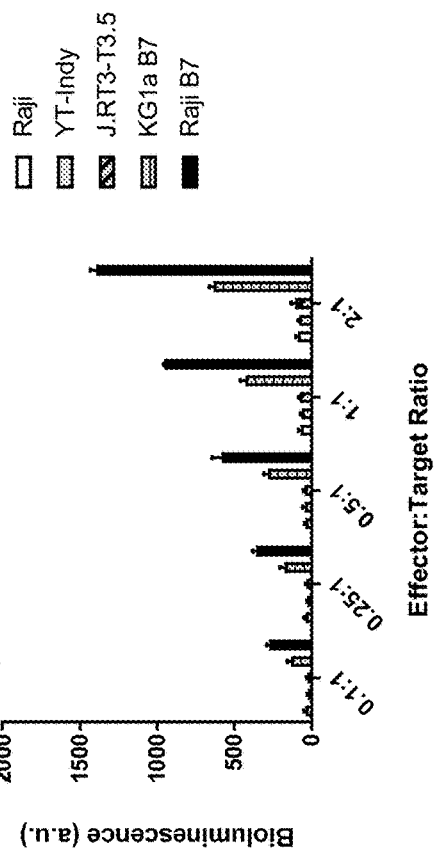
Figure 13B:
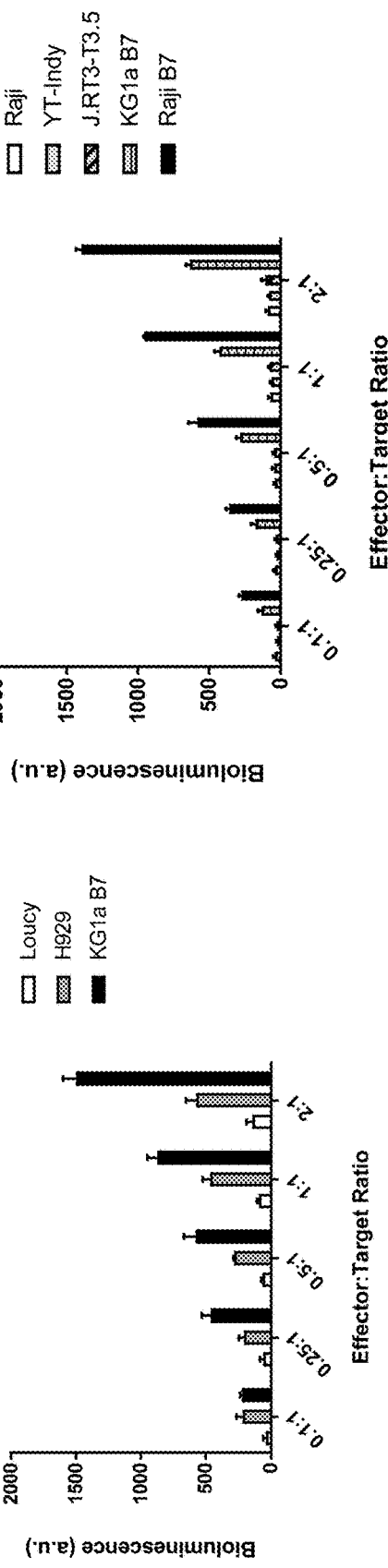
Figure 13C:
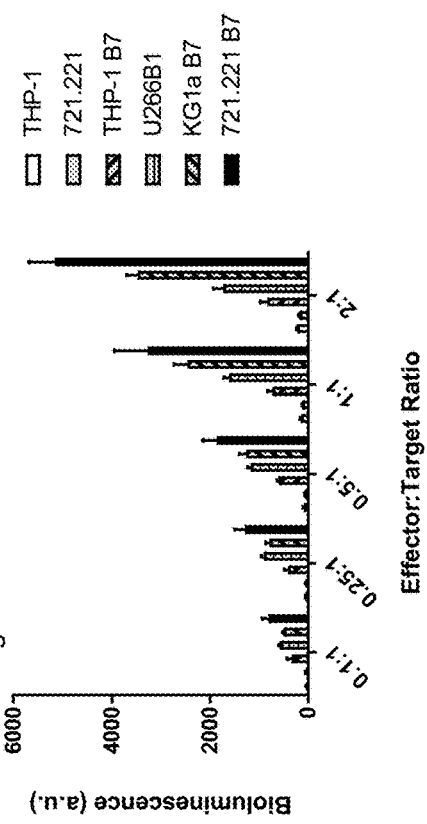

FIGS. 13A-13C are a set of bar graphs showing activation of a Jurkat NFAT-luciferase reporter cell line expressing TCR0078, after co-culturing with various tumor cell lines. TCR0078-transduced Jurkat reporter cells expressing HLA-B*0702 (Effector) were co-cultured for 24 hours at various ratios with tumor cell lines such as Loucy, H929, and KG1a overexpressing HLA-B*0702 ("KG1a B7") (FIG. 13A); Raji, YT-Indy, J.RT3-T3.5, KG1a B7, and Raji overexpressing HLA-B*0702 (FIG. 13B); and THP-1, LCL 721.221, THP-1 overexpressing HLA-B*0702, U266B1, KG1a B7, and LCL 721.221 overexpressing HLA-B*0702 ("721.221 B7") (FIG. 13C). Activation of the Jurkat cells was assessed by measuring luciferase bioluminescence activity (represented on the y-axis by arbitrary units (a.u.)) resulting from the activation of the IL-2-NFAT-Luciferase reporter. KG1a-HLA-B*0702 cell line was used as a reference for other tumor cell lines in each Figure.

Figure 14:
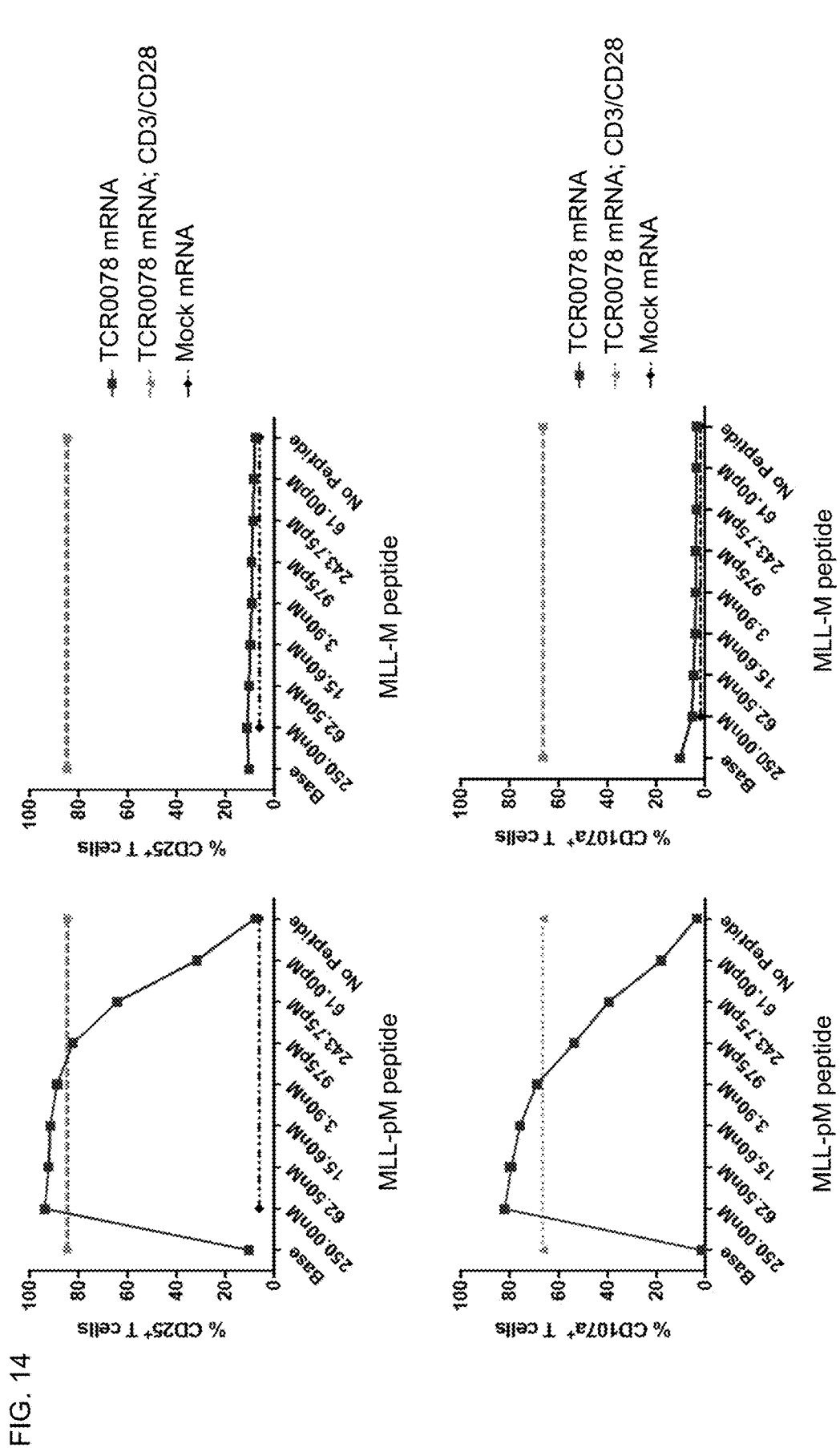

FIG. 14 is a panel of graphs showing results from an assay testing the activation of T cells that were electroporated with mock mRNA or TCR0078-encoding mRNA and co-cultured with T2-B7 target cells pulsed with either the MLL-pM phosphopeptide or the non-phosphorylated MLL-M control peptide. T cells incubated with anti-CD3 and anti-CD28 antibodies were used as positive controls ("TCR0078 mRNA; CD3/CD28"). The upper two panels show the percentage of CD25+ T cells. The lower two panels show the percentage of CD107a+ T cells. In all four panels, the x axis shows the concentrations of the peptides used to pulse the T2-B7 cells.

Figure 15:
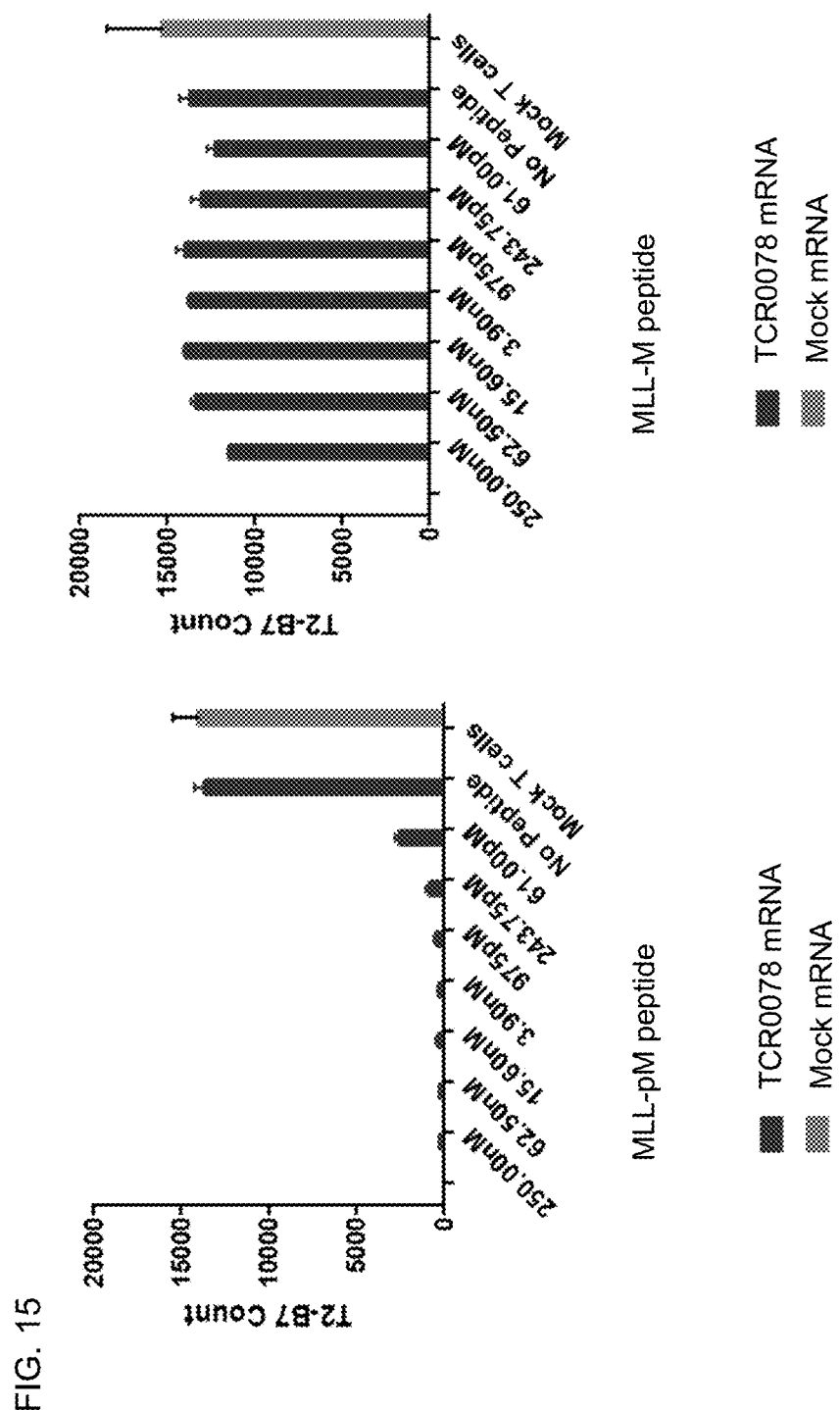

FIG. 15 is a pair of graphs showing the counts of peptide-pulsed T2-B7 cells after being co-cultured with T cells electroporated with mock mRNA or TCR0078 mRNA. The T2-B7 cell had been pulsed with the MLL-pM phosphopeptide or the non-phosphorylated MLL-M control peptide before co-culturing. The x axis shows the concentrations of the peptides used to pulse the T2-B7 cells.

Figure 16A:
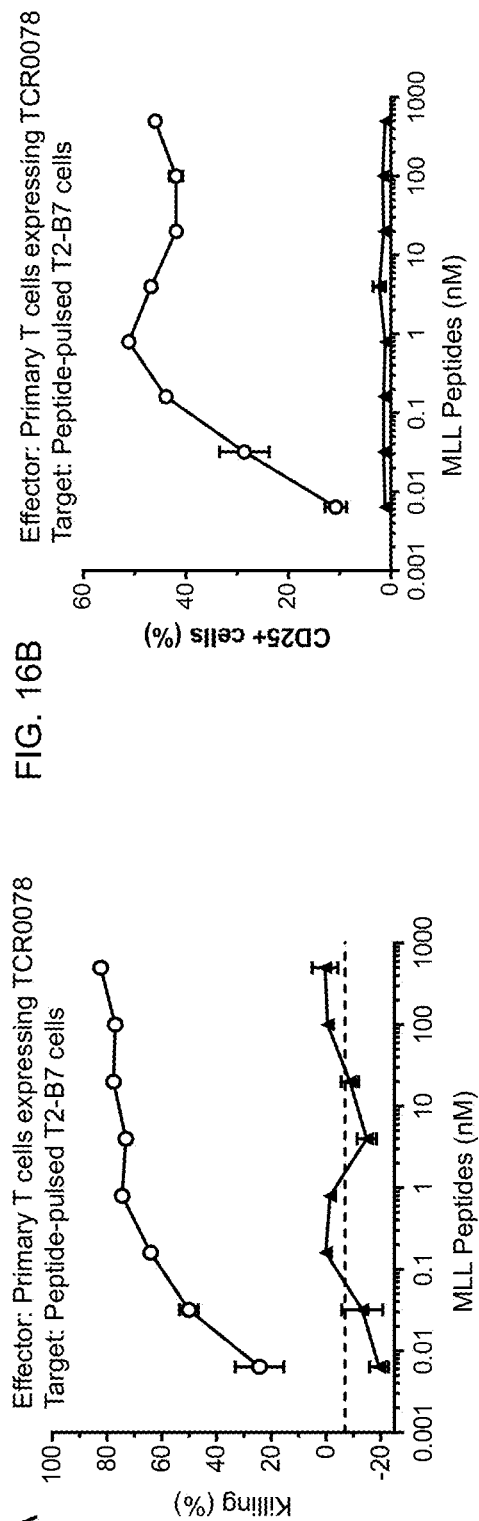
Figure 16B:
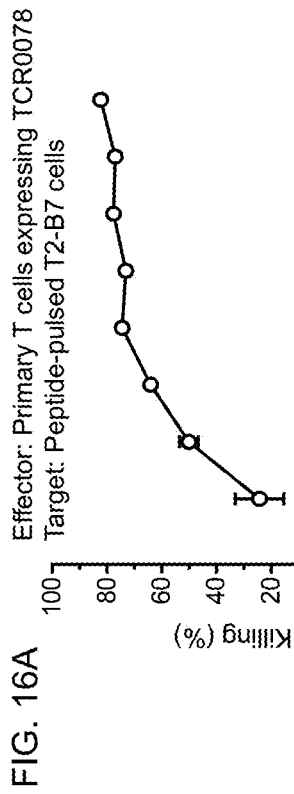
Figure 16C:
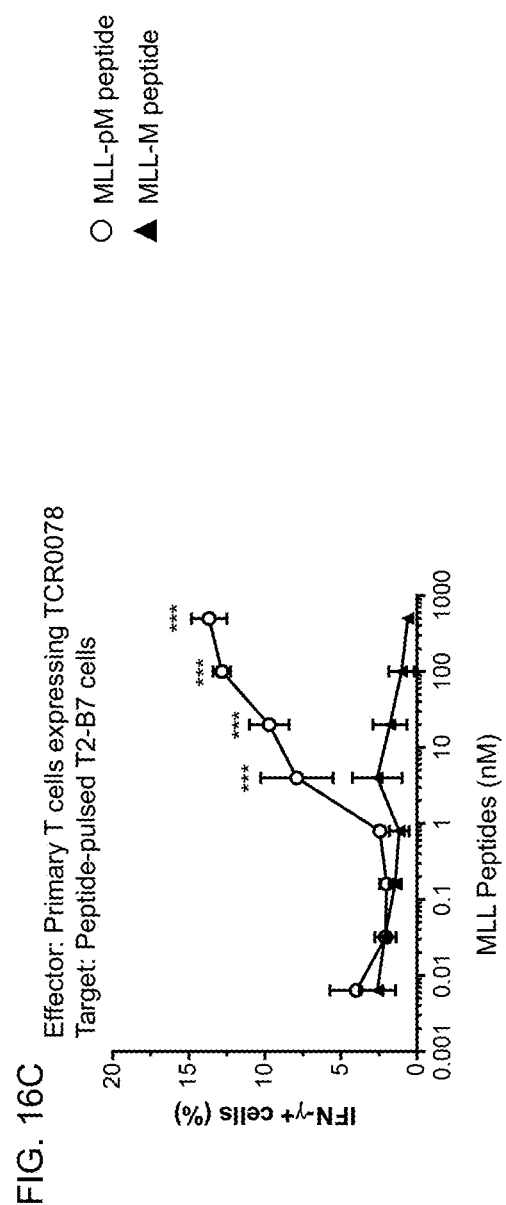

FIGS. 16A-16C are a set of graphs showing an assay testing the activation and cytotoxic activity of TCR0078-transduced T cells co-cultured with T2-HLA-B*0702 ("T2-B7 cells") pulsed with the MLL phosphopeptide EPR[pS]SHSM (SEQ ID NO: 45) or the non-phosphorylated control peptide EPRSPSHSM (SEQ ID NO: 46). T2 cells expressing HLA-B*0702 were labeled with CFSE and then pulsed for 2.5 hours with a dose titration of either peptide, prior to co-culturing with primary T cells stably expressing TCR0078 for 20 hours. FIG. 16A shows the percentage of killing of T2-HLA-B*0702 cells (calculated by subtracting the alive T2-B7 cell number from the total T2-B7 number without co-culturing with the effector primary T cell, then divided by the total T2-B7 number without co-culturing) by TCR0078-transduced T cells after co-culturing. FIGS. 16B and 16C show the percentage of CD25 and IFN-γ positive primary T cells, respectively, in all primary T cells, detected by anti-CD25-PE/Cy7 and anti-IFNγ-FITC antibodies and measured by fluorescence emitted from the corresponding fluorescent-dye. The x-axis shows the concentration of the peptides used to pulse the T2-B7 cells. A two-way ANOVA with Bonferroni test was used. "***" signifies p=0.001.

Figure 17B:
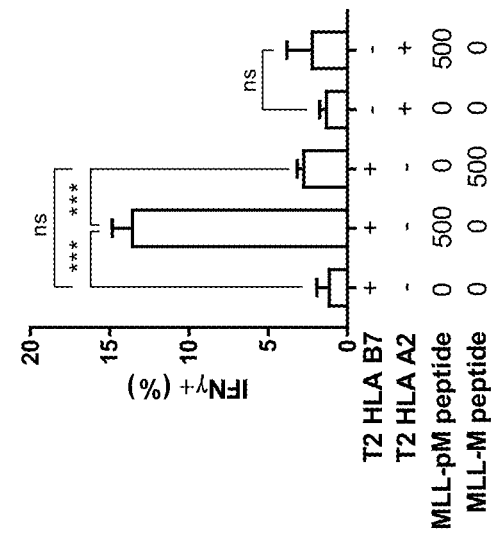
Figure 17A:
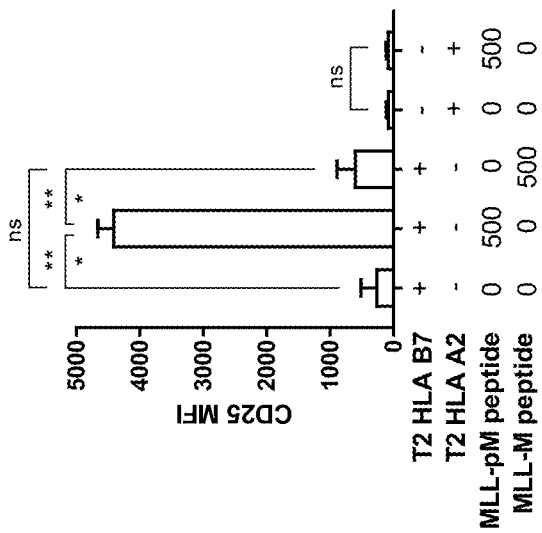

FIGS. 17A and 17B are a pair of bar graphs showing an assay testing the activation of TCR0078-transduced primary T cells co-cultured with T2 cells expressing HLA*A02.01 or T2-HLA-B*0702 and pulsed with either the phosphopeptide EPR[pS]PSHSM (SEQ ID NO: 45) or non-phosphorylated peptide EPRSPSHSM (SEQ ID NO: 46). CD25 and IFNγ expression by the effector primary T cells were measured as in FIG. 16. FIG. 17A compares the surface expression of CD25 on the T cells (MFI=Mean Fluorescent Expression) after co-culturing with T2 target cells pulsed with different peptides. FIG. 17B compares the percentage of IFN-γ positive T cells of the total effector primary T cells after the co-culturing. A two-way ANOVA with Bonferroni test was used. "*" signifies p=0.05. "" signifies p=0.01. "*" signifies p=0.001. "ns" signifies non-significant.

FIGS. 18A-18C are a set of bar graphs showing an assay testing the cytotoxic activity and activation of control or TCR0078-transduced primary T cells, co-cultured with either KG1a-HLA*A02.01 or KG1a-HLA-B*0702. The co-culturing, cell staining, and number counting methods were the same as those in FIG. 16. FIG. 18A shows the percentage of killing of KG1a tumor cells by primary T cells after co-culturing, representing the cytotoxic activity of T cells toward KG1a tumor cells. FIG. 18B and FIG. 18C show the percentage of CD25 and IFN-γ positive primary T cells, respectively, after co-culturing. A two-way ANOVA with Bonferroni test was used. "***" signifies p=0.001.

FIGS. 19A-19E are a set of bar graphs showing assays testing the cytotoxic activity of control and TCR0078-transduced primary T cells co-cultured with KG1a-HLA-B*0702, K562-HLA-B*0702, SK-MEL-5, U266B1, or Namalwa tumor cell lines. The co-culturing, cell staining, and number counting methods were the same as those used in the experiments set forth in FIGS. 18A-18C. The x-axis indicates the ratio of T cell/Tumor cells used. A two-way ANOVA with Bonferroni test was used. "*" signifies p=0.05. "" signifies p=0.01. "*" signifies p=0.001.

FIGS. 20A and 20B are a set of bar graphs showing an in vitro assay of cytotoxic activity and activation of TCR0078-transduced T cells co-cultured with KG1a-HLA-B*0702 before adoptive transfer to NOG mice bearing KG1a-HLA-B*0702 tumor. FIG. 20A and FIG. 20B compare the cytotoxic activity and T cell activation (represented by CD25 expression), respectively, between control and TCR0078-transduced T cells. The x-axis indicates the various T cell/tumor cell ratios.

Figure 21B:
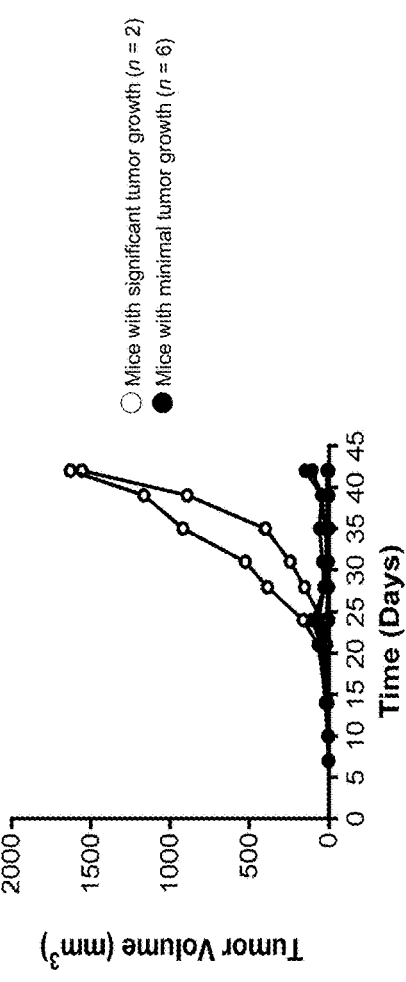
Figure 21C:
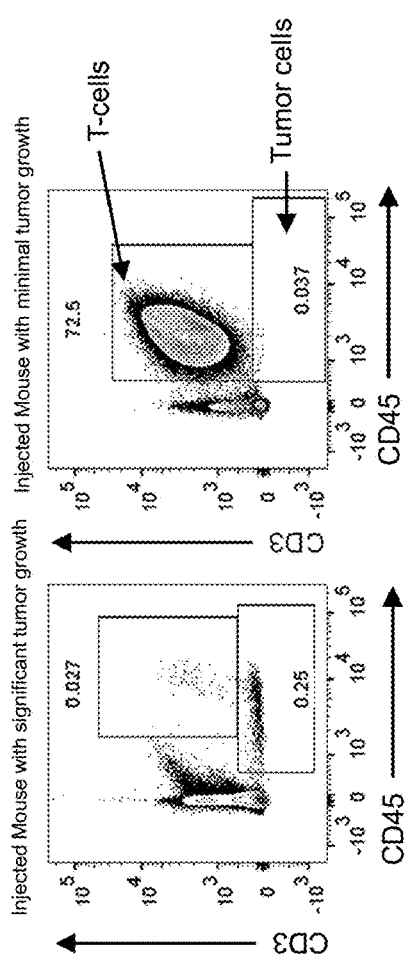
Figure 21A:
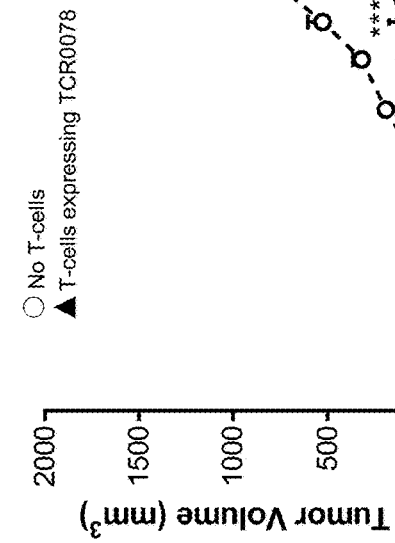

FIGS. 21A-21C are a set of graphs and flow cytometry plots showing the anti-tumor activity of TCR0078-transduced human primary T cells after adoptive transfer to NOG mice bearing a KG1a-HLA-B*0702 tumor. Twenty mice were each injected with one million tumor cells (KG1a-HLA-B*0702) subcutaneously. One day post-injection ten of the twenty mice were injected intravenously with 5 million TCR0078-transduced primary T cells ("T cells expressing TCR0078") and the other ten mice remained un-injected ("no T cells"). FIG. 21A compares tumor volumes (average+/−SEM) in the two groups (n=10 each) of mice measured every 3-5 days from Day 7 to Day 42. A two-way ANOVA with Bonferroni test was used. "*" signifies p=0.001. FIG. 21B compares tumor volumes of the 10 individual mice injected with the T cells expressing TCR0078. After the first measurement at Day 7, two of the ten mice were sacrificed to confirm T cells injection and homing; hence, no data points after Day 7 were available for these two mice. Each line in FIG. 21B represents the tumor volumes of one of the eight remaining mice throughout the 42-day period. Except for two mice with significant tumor growth (white circles), six of the eight mice had minimal tumor growth (black circles). FIG. 21C shows a pair of flow cytometry plots identifying human T-cells and metastatic tumor cells in the spleen of mice injected with TCR0078 transduced T cells. All mice were sacrificed at day 41 post tumor implantation and their spleens were collected, processed and stained with anti-CD3 and anti-CD45 antibodies for subsequent detection by Fluorescence-activated cell sorting (FACS). The left panel of FIG. 21C shows the percentage of T cells (CD3+/CD45+, 0.027% of all cells in the sample) and tumor cells (CD3−/CD45+, 0.25% of all cells in the sample) in an injected mouse with significant tumor growth in FIG. 21B. The right panel of FIG. 21C shows the percentage of T cells (72.5%) and tumor cells (0.037%) in the spleen of an injected mouse with minimal tumor growth in FIG. 21B**. The percentage of cells within each gate is indicated.

5. DETAILED DESCRIPTION

Provided are TCRs (e.g., TCRs that bind to MLL phosphopeptides), cells and pharmaceutical compositions comprising these TCRs, nucleic acids encoding these TCRs, expression vectors and host cells for making these TCRs, and methods of treating a subject using these TCRs. The TCRs disclosed herein are particularly useful for directing an immune response against cancer cells displaying MLL phosphopeptides on the cell surface, and hence for treating a MLL-expressing cancer in a subject.

5.1 Definitions

As used herein, the terms "about" and "approximately," when used to modify a numeric value or numeric range, indicate that deviations of 5% to 10% above (e.g., up to 5% to 10% above) and 5% to 10% below (e.g., up to 5% to 10% below) the value or range remain within the intended meaning of the recited value or range.

As used herein, the term "MLL" refers to mixed lineage leukemia (also known as Histone-lysine N-methyltransferase 2A), that in human is encoded by the KMT2A gene.

As used herein, the terms "T cell receptor" and "TCR" are used interchangeably and refer to molecules comprising CDRs or variable regions from αβ or γδ T cell receptors. Examples of TCRs include, but are not limited to, full-length TCRs, antigen-binding fragments of TCRs, soluble TCRs lacking transmembrane and cytoplasmic regions, single-chain TCRs containing variable regions of TCRs attached by a flexible linker, TCR chains linked by an engineered disulfide bond, single TCR variable domains, single peptide-MHC-specific TCRs, multi-specific TCRs (including bispecific TCRs), TCR fusions, TCRs comprising co-stimulatory regions, human TCRs, humanized TCRs, chimeric TCRs, recombinantly produced TCRs, and synthetic TCRs. In certain embodiments, the TCR is a full-length TCR comprising a full-length α chain and a full-length β chain. In certain embodiments, the TCR is a soluble TCR lacking transmembrane and/or cytoplasmic region(s). In certain embodiments, the TCR is a single-chain TCR (scTCR) comprising Vα and Vβ linked by a peptide linker, such as a scTCR having a structure as described in PCT Publication No.: WO 2003/020763, WO 2004/033685, or WO 2011/044186, each of which is incorporated by reference herein in its entirety. In certain embodiments, the TCR comprises a transmembrane region. In certain embodiment, the TCR comprises a co-stimulatory signaling region.

As used herein, the term "full-length TCR" refers to a TCR comprising a dimer of a first and a second polypeptide chain, each of which comprises a TCR variable region and a TCR constant region comprising a TCR transmembrane region and a TCR cytoplasmic region. In certain embodiments, the full-length TCR comprises one or two unmodified TCR chains, e.g., unmodified α, β, γ, or δ TCR chains. In certain embodiments, the full-length TCR comprises one or two altered TCR chains, such as chimeric TCR chains and/or TCR chains comprising one or more amino acid substitutions, insertions, or deletions relative to an unmodified TCR chain. In certain embodiments, the full-length TCR comprises a mature, full-length TCR α chain and a mature, full-length TCR β chain. In certain embodiments, the full-length TCR comprises a mature, full-length TCR γ chain and a mature, full-length TCR δ chain.

As used herein, the term "TCR variable region" refers to the portion of a mature TCR polypeptide chain (e.g., a TCR α chain or β chain) which is not encoded by the TRAC gene for TCR α chains, either the TRBC1 or TRBC2 genes for TCRβ chains, the TRDC gene for TCR δ chains, or either the TRGC1 or TRGC2 gene for TCR γ chains. In some embodiments, the TCR variable region of a TCR α chain encompasses all amino acids of a mature TCR α chain polypeptide which are encoded by a TRAV and/or TRAJ gene, and the TCR variable region of a TCR β chain encompasses all amino acids of a mature TCR β chain polypeptide which are encoded by a TRBV, TRBD, and/or TRBJ gene (see, e.g., *T cell receptor Factsbook*, (2001) LeFranc and LeFranc, Academic Press, ISBN 0-12-441352-8, which is incorporated by reference herein in its entirety). TCR variable regions generally comprise framework regions (FR) 1, 2, 3 and 4 and complementarity determining regions (CDR) 1, 2 and 3.

As used herein, the terms "α chain variable region" and "Vα" are used interchangeably and refer to the variable region of a TCR α chain.

As used herein, the terms "β chain variable region" and "Vβ" are used interchangeably and refer to the variable region of a TCRβ chain.

As used herein in the context of a TCR, the term "CDR" or "complementarity determining region" means the noncontiguous antigen combining sites found within the variable regions of a TCR chain (e.g., an α chain or a β chain). These regions have been described in Lefranc, (1999) The Immunologist 7: 132-136, Lefranc et al., (1999) Nucleic Acids Res 27: 209-212, LeFranc (2001) *T cell receptor Factsbook*, Academic Press, ISBN 0-12-441352-8, Lefranc et al., (2003) Dev Comp Immunol. 27(1):55-77, and in Kabat et al., (1991) *Sequences of protein of immunological interest*, each of which is herein incorporated by reference in its entirety. In certain embodiments, CDRs are determined according to the IMGT numbering system described in Lefranc (1999) supra. In certain embodiments, CDRs are defined according to the Kabat numbering system described in Kabat supra. In certain embodiments, CDRs are defined empirically, e.g., based upon a structural analysis of the interaction of a TCR with a cognate antigen (e.g., a peptide or a peptide-MHC complex). In certain embodiments, the α chain and β chain CDRs of a TCR are defined according to different conventions (e.g., according to the Kabat or IMGT numbering systems, or empirically based upon structural analysis).

As used herein, the term "framework amino acid residues" refers to those amino acids in the framework region of a TCR chain (e.g., an α chain or a β chain). The term "framework region" or "FR" as used herein includes the amino acid residues that are part of the TCR variable region, but are not part of the CDRs.

As used herein, the term "constant region" with respect to a TCR refers to the portion of a TCR that is encoded by the TRAC gene (for TCR α chains), either the TRBC1 or TRBC2 gene (for TCR β chains), the TRDC gene (for TCR δ chains), or either the TRGC1 or TRGC2 gene (for TCR γ chains), optionally lacking all or a portion of a transmembrane region and/or all or a portion of a cytoplasmic region. In certain embodiments, a TCR constant region lacks a transmembrane region and a cytoplasmic region. A TCR constant region does not include amino acids encoded by a TRAV, TRAJ, TRBV, TRBD, TRBJ, TRDV, TRDD, TRDJ, TRGV, or TRGJ gene (see, e.g., *T cell receptor Factsbook*, (2001) LeFranc and LeFranc, Academic Press, ISBN 0-12-441352-8, which is incorporated by reference herein in its entirety).

As used herein, the terms "major histocompatibility complex" and "MHC" are used interchangeably and refer to an MHC class I molecule and/or an MHC class II molecule.

As used herein, the term "MHC class I" refers to a dimer of an MHC class I a chain and a β2 microglobulin chain and the term "MHC class II" refers to a dimer of an MHC class II α chain and an MHC class II β chain.

As used herein, the term "peptide-MHC complex" refers to an MHC molecule (MHC class I or MHC class II) with a peptide bound in the art-recognized peptide binding pocket of the MHC. In some embodiments, the MHC molecule is a membrane-bound protein expressed on cell surface. In some embodiments, the MHC molecule is a soluble protein lacking transmembrane or cytoplasmic regions.

As used herein, the terms "[pS]" and "(pS)" are used interchangeably and refer to phosphoserine.

As used herein, the term "extracellular" with respect to TCR refers to the portion or portions of a recombinant transmembrane protein that are located outside of a cell.

As used herein, the term "transmembrane" with respect to a TCR chain refers to the portion or portions of a TCR chain that are embedded in the plasma membrane of a cell.

As used herein, the term "cytoplasmic" with respect to a TCR chain refers to the portion or portions of a TCR chain that are located in the cytoplasm of a cell.

As used herein, the term "co-stimulatory signaling region" refers to the intracellular portion of a co-stimulatory molecule that is responsible for mediating intracellular signaling events.

"Binding affinity" generally refers to the strength of the sum total of non-covalent interactions between a single binding site of a molecule (e.g., a TCR) and its binding partner (e.g., a peptide-MHC complex). Unless indicated otherwise, as used herein, "binding affinity" refers to intrinsic binding affinity which reflects a 1:1 interaction between members of a binding pair (e.g., a TCR and a peptide-MHC complex). The affinity of a molecule X for its partner Y can generally be represented by the dissociation constant ($K_D$). Affinity can be measured and/or expressed in a number of ways known in the art, including, but not limited to, equilibrium dissociation constant ($K_D$) and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., a TCR to a peptide-MHC complex, and $k_{off}$ refers to the dissociation rate constant of, e.g., a TCR to a peptide-MHC complex. The $k_{on}$ and $k_{off}$ can be determined by techniques known to one of ordinary skill in the art, such as use of BIAcore® or KinExA. As used herein, a "lower affinity" refers to a larger $K_D$.

As used herein, the term "specifically binds to" refers to the ability of a TCR to preferentially bind to a particular antigen (e.g., a specific peptide or a specific peptide-MHC complex combination) as such binding is understood by one skilled in the art. For example, a TCR that specifically binds to an antigen can bind to other antigens, generally with lower affinity as determined by, e.g., BIAcore®, or other immunoassays known in the art (see, e.g., Savage et al., Immunity. 1999, 10(4):485-92, which is incorporated by reference herein in its entirety). In a specific embodiment, a TCR that specifically binds to an antigen binds to the antigen with an association constant ($K_a$) that is at least 2-fold, 5-fold, 10-fold, 50-fold, 100-fold, 500-fold, 1,000-fold, 5,000-fold, or 10,000-fold greater than the $K_a$ when the TCR binds to another antigen. In certain embodiments, the TCRs disclosed herein specifically bind to a peptide consisting of the amino acid sequence set forth in SEQ ID NO: 45. In certain embodiments, the TCRs disclosed herein specifically bind to a peptide consisting of the amino acid sequence set forth in SEQ ID NO: 47.

In some embodiments, a TCR does not substantially bind to an antigen when the
TCR binds to the antigen with an association constant ($K_a$) that is at least 2-fold, 5-fold, 10-fold, 50-fold, 100-fold, 500-fold, 1,000-fold, 5,000-fold, or 10,000-fold smaller than the $K_a$ when the TCR binds to another antigen. In some embodiments, a TCR does not substantially bind to an antigen when the binding between the TCR and the antigen is at least 2-fold, 5-fold, 10-fold, 50-fold, 100-fold, 500-fold, 1,000-fold, 5,000-fold, or 10,000-fold weaker than the binding between the TCR and another antigen.

As used herein, the binding between a test TCR and a first antigen is "substantially weakened" relative to the binding between the test TCR and a second antigen if the binding between the test TCR and the first antigen is reduced by at least 30%, 40%, 50%, 60%, 70%, or 80%, relative to the binding between the test TCR and the second antigen, e.g., in a given experiment, or using mean values from multiple experiments.

In some embodiments, when a TCR is expressed on the surface of a T cell, the T cell is not substantially activated when the T cell is co-cultured with a second cell displaying a peptide if the activation of the T cell is at least 2-fold, 5-fold, 10-fold, 50-fold, 100-fold, 500-fold, 1,000-fold, 5,000-fold, or 10,000-fold weaker than the activation of the T cell when the T cell is co-cultured with a third cell displaying another peptide.

As used herein, when a test TCR is expressed on the surface of a T cell, the activation of the T cell when the T cell is co-cultured with a second cell displaying a first peptide is "substantially weakened" relative to the activation of the T cell when the T cell is co-cultured with a third cell displaying a second peptide if the activation of the T cell when co-cultured with the second cell displaying the first peptide is reduced by at least 30%, 40%, 50%, 60%, 70%, or 80%, relative to the activation of the T cell when co-cultured with the third cell displaying the second peptide, e.g., in a given experiment, or using mean values from multiple experiments, as assessed by, e.g., an assay comprising the following steps: (a) expressing the test TCR in a T cell comprising an IL-2-(NFAT)$_3$-EGFP reporter construct; (b) pulsing a HLA-B*0702 positive T2 cell ("T2-B7 cell") with the first peptide or the second peptide; (c) co-culturing the TCR-expressing T cell with the peptide-pulsed T2-B7 target cell at a ratio of 1:2 for 16 hours at 37° C. and 10% CO$_2$; (d) analyzing the expression of TCR and EGFP using flow cytometry; (e) determining the percentage of TCR+ EGFP+ cells; and (f) determining the reduction of T cell activation when co-cultured with a T2-B7 target cell displaying the first peptide relative to when co-cultured with a T2-B7 target cell displaying the second peptide based on the respective percentages of TCR+EGFP+ cells.

As used herein, an "epitope" is a term in the art and refers to a localized region of an antigen (e.g., a peptide or a peptide-MHC complex) to which a TCR can bind. In certain embodiments, the epitope to which a TCR binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), flow cytometry analysis, mutagenesis mapping (e.g., site-directed mutagenesis mapping), and/or structural modeling. For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303, each of which is herein incorporated by reference in its entirety). TCR:antigen crystals may be studied using well-known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323), each of which is herein incorporated by reference in its entirety. Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085, each of which is herein incorporated by reference in its entirety, for a description of mutagenesis techniques, including alanine scanning mutagenesis techniques. In a specific embodiment, the epitope of an antigen is determined using alanine scanning mutagenesis studies. In a specific embodiment, the epitope of an antigen is determined using hydrogen/deuterium exchange coupled with mass spectrometry. In certain embodiments, the antigen is a peptide-MHC complex. In certain embodiments, the antigen is a peptide presented by an MHC molecule.

As used herein, the terms "treat," "treating," and "treatment" refer to therapeutic or preventative measures described herein. In some embodiments, the methods of "treatment" employ administration of a TCR or a cell expressing a TCR to a subject having a disease or disorder, or predisposed to having such a disease or disorder, in order to prevent, cure, delay, reduce the severity of, or ameliorate one or more symptoms of the disease or disorder or recurring disease or disorder, or in order to prolong the survival of a subject beyond that expected in the absence of such treatment.

As used herein, the term "effective amount" in the context of the administration of a therapy to a subject refers to the amount of a therapy that achieves a desired prophylactic or therapeutic effect.

As used herein, the term "subject" includes any human or non-human animal. In one embodiment, the subject is a human or non-human mammal. In one embodiment, the subject is a human.

The determination of "percent identity" between two sequences (e.g., amino acid sequences or nucleic acid sequences) can be accomplished using a mathematical algorithm. A specific, non-limiting example of a mathematical algorithm utilized for the comparison of two sequences is the algorithm of Karlin S & Altschul S F (1990) PNAS 87: 2264-2268, modified as in Karlin S & Altschul S F (1993) PNAS 90: 5873-5877, each of which is herein incorporated by reference in its entirety. Such an algorithm is incorporated into the NBLAST and XBLAST programs of Altschul S F et al., (1990) J Mol Biol 215: 403, which is herein incorporated by reference in its entirety. BLAST nucleotide searches can be performed with the NBLAST nucleotide program parameters set, e.g., at score=100, wordlength=12 to obtain nucleotide sequences homologous to a nucleic acid molecule described herein. BLAST protein searches can be performed with the XBLAST program parameters set, e.g., at score=50, wordlength=3 to obtain amino acid sequences homologous to a protein molecule described herein. To obtain gapped alignments for comparison purposes, Gapped BLAST can be utilized as described in Altschul S F et al., (1997) Nuc Acids Res 25: 3389-3402, which is herein incorporated by reference in its entirety. Alternatively, PSI BLAST can be used to perform an iterated search which detects distant relationships between molecules. Id. When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another specific, non-limiting example of a mathematical algorithm utilized for the comparison of sequences is the algorithm of Myers and Miller, 1988, CABIOS 4:11-17, which is herein incorporated by reference in its entirety. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "effector moiety" refers to a component or functional group of a molecule that increases or decreases a natural activity of the molecule, or confers a novel activity upon the molecule. In certain embodiments, the effector moiety is a binding moiety. In an embodiment, the binding moiety binds to a cell surface protein. In certain embodiments, the binding moiety is an antibody.

As used herein, the terms "antibody" and "antibodies" include full-length antibodies, antigen-binding fragments of full-length antibodies, and molecules comprising antibody CDRs, VH regions or VL regions. Examples of antibodies include monoclonal antibodies, recombinantly produced antibodies, monospecific antibodies, multi-specific antibodies (including bispecific antibodies), human antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, antibody-drug conjugates, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), and antigen-binding fragments of any of the above. In certain embodiments, antibodies described herein refer to polyclonal antibody populations. Antibodies can be of any type (e.g., IgG, IgE, IgM, IgD, IgA or IgY), any class (e.g., IgG$_1$, IgG$_2$, IgG$_3$, IgG$_4$, IgA$_1$ or IgA$_2$), or any subclass (e.g., IgG$_{2a}$ or IgG$_{2b}$) of immunoglobulin molecule. In certain embodiments, antibodies described herein are IgG antibodies, or a class (e.g., human IgG$_1$ or IgG$_4$) or subclass thereof. In a specific embodiment, the antibody is a humanized monoclonal antibody. In another specific embodiment, the antibody is a human monoclonal antibody.

5.2 T Cell Receptors

In one aspect, the instant disclosure provides TCRs that bind to a peptide consisting of the amino acid sequence of EPR[pS]PSHSM (SEQ ID NO: 45). In certain embodiments, the TCR specifically binds to a peptide consisting of the amino acid sequence of EPR[pS]PSHSM (SEQ ID NO: 45). In certain embodiments, the TCR binds to a peptide-MHC complex comprising a peptide consisting of the amino acid sequence of EPR[pS]PSHSM (SEQ ID NO: 45). In certain embodiments, the TCR specifically binds to the peptide-MHC complex comprising a peptide consisting of the amino acid sequence set forth in SEQ ID NO: 45. In one aspect, the instant disclosure provides TCRs that bind to EPR[pS]PSHSM (SEQ ID NO: 45) presented by a major histocompatibility complex (MHC) molecule. In one aspect, the instant disclosure provides TCRs that bind to a EPR[pS]PSHSM (SEQ ID NO: 45)-HLA-B*0702 complex. The amino acid sequences of exemplary TCRs are set forth in Table 1, herein.

In one aspect, the instant disclosure provides TCRs that bind to a peptide consisting of the amino acid sequence of RVR[pS]PTRSP (SEQ ID NO: 47). In certain embodiments, the TCR specifically binds to a peptide consisting of the amino acid sequence of RVR[pS]PTRSP (SEQ ID NO: 47). In certain embodiments, the TCR binds to a peptide-MHC complex comprising a peptide consisting of the amino acid sequence of RVR[pS]PTRSP (SEQ ID NO: 47). In certain embodiments, the TCR specifically binds to the peptide-MHC complex comprising a peptide consisting of the amino acid sequence set forth in SEQ ID NO: 47. In one aspect, the instant disclosure provides TCRs that bind to RVR[pS]PTRSP (SEQ ID NO: 47) presented by a major histocompatibility complex (MHC) molecule. In one aspect, the instant disclosure provides TCRs that bind to a RVR[pS]PTRSP (SEQ ID NO: 47)-HLA-B*0702 complex. The amino acid sequences of exemplary TCRs are set forth in Table 1, herein.

TABLE 1

Amino acid sequences of exemplary TCRs.

| SEQ ID NO: | Description | Amino acid sequence |
|---|---|---|
| 1 | TCR0077 Vα | TQLLEQSPQFLSIQEGENLTVYCNSSSVFSSLQWYRQ EPGEGPVLLVTVVTGGEVKKLKRLTFQFGDARKDSSL HITAAQPGDTGLYLCAGYGGGSNYKLTFGAGTRLTVK P |

TABLE 1-continued

Amino acid sequences of exemplary TCRs.

| SEQ ID NO: | Description | Amino acid sequence |
| --- | --- | --- |
| 2 | TCR0077 Vβ | EAQVTQNPRYLITVTGKKLTVTCSQNMNHEYMSWYRQDPGLGLRQIYYSMNVEVTDKGDVPEGYKVSRKEKRNFPLILESPSPNQTSLYFCASRLTGRVHGYTFGPGTRLTVL |
| 3 | TCR0079 Vα | KNQVEQSPQSLIILEGKNCTLQCNYTVSPFSNLRWYKQDTGRGPVSLTIMTFSENTKSNGRYTATLDADTKQSSLHITASQLSDSASYICVVRGGAAGNKLTFGAGTRLTVKP |
| 4 | TCR0079 Vβ | DAGVIQSPRHEVTEMGQEVTLRCKPISGHNSLFWYRQTMMRGLELLIYFNNNVPIDDSGMPEDRFSAKMPNASFSTLKIQPSEPRDSAVYFCASSSGGANTEAFFGPGTRLTVL |
| 5 | TCR0081 Vα | AQSVTQLGSHVSVSEGALILLRCNYSSSVPPYLFWYVQYPNQGLQLLLKYTTGATLVKGINGFEAEFKKSETSFHLTKPSAHMSDAAEYFCAVSARYNFNKFYFGSGTKLSVIP |
| 6 | TCR0081 Vβ | DSGVTQTPKHLITATGQRVTLRCSPRSGDLSVYWYQQSLDQGLQFLIQYYNGEERAKGNILERFSAQQPPDLHSELNLSSLELGDSALYFCASSASGGRSYEQYFGPGTRLTVV |
| 7 | TCR0083 Vα; TCR0084 Vα | EDQVTQSPEALRLQEGESSSLNCSYTVSGLRGLFWYRQDPGKGPEFLFTLYSAGEEKEKERLKATLTKKESFLHITAPKPEDSATYLCAVRNTGFQKLVFGTGTRLLVSP |
| 8 | TCR0083 Vβ | DTGVSQDPRHKITKRGQNVTFRCDPISEHNRLYWYRQTLGQGPEFLTYFQNEAQLEKSRLLSDRFSAERPKGSFSTLEIQRTEQGDSAMYLCASSWRTGREETQYFGPGTRLLVL |
| 9 | TCR0085 Vα, TCR0086 Vα | KQEVTQIPAALSVPEGENLVLNCSFTDSAIYNLQWFRQDPGKGLTSLLLIQSSQREQTSGRLNASLDKSSGRSTLYIAASQPGDSATYLCAVMLWNQGGKLIFGQGTELSVKP |
| 10 | TCR0085 Vβ, TCR0086 Vβ | KAGVTQTPRYLIKTRGQQVTLSCSPISGHRSVSWYQQTPGQGLQFLFEYFSETQRNKGNFPGRFSGRQFSNSRSEMNVSTLELGDSALYLCASSLGRGYEQYFGPGTRLTVT |
| 86 | TCR0078 Vα | TQLLEQSPQFLSIQEGENLTVYCNSSSVFSSLQWYRQEPGEGPVLLVTVVTGGEVKKLKRLTFQFGDARKDSSLHITAAQPGDTGLYLCAGYGGGSNYKLTFGKGTLLTVNP |
| 87 | TCR0078 Vβ | EAQVTQNPRYLITVTGKKLTVTCSQNMNHEYMSWYRQDPGLGLRQIYYSMNVEVTDKGDVPEGYKVSRKEKRNFPLILESPSPNQTSLYFCASRLTGRVHGYTFGSGTRLTVV |
| 88 | TCR0080 Vα | KNQVEQSPQSLIILEGKNCTLQCNYTVSPFSNLRWYKQDTGRGPVSLTIMTFSENTKSNGRYTATLDADTKQSSLHITASQLSDSASYICVVRGGAAGNKLTFGGGTRVLVKP |
| 89 | TCR0080 Vβ | DAGVIQSPRHEVTEMGQEVTLRCKPISGHNSLFWYRQTMMRGLELLIYFNNNVPIDDSGMPEDRFSAKMPNASFSTLKIQPSEPRDSAVYFCASSSGGANTEAFFGQGTRLTVV |
| 106 | TCR0082 Vα | AQSVTQLGSHVSVSEGALVLLRCNYSSSVPPYLFWYVQYPNQGLQLLLKYTSAATLVKGINGFEAEFKKSETSFHLTKPSAHMSDAAEYFCAVSARYNFNKFYFGSGTKLNVKP |
| 107 | TCR0082 Vβ | DSGVTQTPKHLITATGQRVTLRCSPRSGDLSVYWYQQSLDQGLQFLIHYYNGEERAKGNILERFSAQQPPDLHSELNLSSLELGDSALYFCASSASGGRSYEQYFGPGTRLTVT |

TABLE 1-continued

Amino acid sequences of exemplary TCRs.

| SEQ ID NO: | Description | Amino acid sequence |
|---|---|---|
| 108 | TCR0084 Vβ | DTGVSQNPRHKITKRGQNVTFRCDPISEHNRLYWYRQTLGQGPEFLTYFQNEAQLEKSRLLSDRFSAERPKGSFSTLEIQRTEQGDSAMYLCASSWRTGREETQYFGPGTRLLVL |
| 11 | TCR0078 CDR1α | SVFSS |
| 12 | TCR0080 CDR1α | VSPFSN |
| 13 | TCR0082 CDR1α | SSVPPY |
| 14 | TCR0084 CDR1α | VSGLRG |
| 15 | TCR0086 CDR1α | DSAIYN |
| 16 | TCR0078 CDR2α | VVTGGEV |
| 17 | TCR0080 CDR2α | MTFSENT |
| 18 | TCR0081 CDR2α | YTTGATLV |
| 109 | TCR0082 CDR2α | YTSAATLV |
| 19 | TCR0084 CDR2α | LYSAGEE |
| 20 | TCR0086 CDR2α | IQSSQRE |
| 21 | TCR0078 CDR3α | AGYGGGSNYKLT |
| 22 | TCR0080 CDR3α | VVRGGAAGNKLT |
| 23 | TCR0082 CDR3α | AVSARYNFNKFY |
| 24 | TCR0084 CDR3α | AVRNTGFQKLV |
| 25 | TCR0086 CDR3α | AVMLWNQGGKLI |
| 26 | TCR0078 CDR1β | MNHEY |
| 27 | TCR0080 CDR1β | SGHNS |
| 28 | TCR0082 CDR1β | SGDLS |
| 29 | TCR0084 CDR1β | SEHNR |
| 30 | TCR0086 CDR1β | SGHRS |
| 31 | TCR0078 CDR2β | SMNVEV |
| 32 | TCR0080 CDR2β | FNNNVP |
| 33 | TCR0082 CDR2β | YYNGEE |
| 34 | TCR0084 CDR2β | FQNEAQ |
| 35 | TCR0086 CDR2β | YFSETQ |
| 36 | TCR0078 CDR3β | ASRLTGRVHGYT |
| 37 | TCR0080 CDR3β | ASSSGGANTEAF |
| 38 | TCR0082 CDR3β | ASSASGGRSYEQY |
| 39 | TCR0084 CDR3β | ASSWRTGREETQY |
| 40 | TCR0086 CDR3β | ASSLGRGYEQY |
| 41 | TCR α chain human constant region consensus sequence (TRAC*01) | XIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS, wherein X is N, Y, H, or D |

TABLE 1-continued

Amino acid sequences of exemplary TCRs.

| SEQ ID NO: | Description | Amino acid sequence |
|---|---|---|
| 42 | TCR α chain human constant region | YIQNPDPAVYQLRDSKSSDKSVCLFTDFDSQTNVSQS KDSDVYITDKTVLDMRSMDFKSNSAVAWSNKSDFACA NAFNNSIIPEDTFFPSPESSCDVKLVEKSFETDTNLN FQNLSVIGFRILLLKVAGFNLLMTLRLWSS |
| 247 | TCR α chain mouse constant region | YIQNPEPAVYQLKDPRSQDSTLCLFTDFDSQINVPKT MESGTFITDKTVLDMKAMDSKSNGAIAWSNQTSFTCQ DIFKETNATYPSSDVPCDATLTEKSFETDMNLNFQNL SVMGLRILLLKVAGFNLLMTLRLWSS |
| 43 | TCR β chain human constant region variant 1 (TRBC1*01) | EDLNKVFPPEVAVFEPSEAEISHTQKATLVCLATGFF PDHVELSWWVNGKEVHSGVSTDPQPLKEQPALNDSRY CLSSRLRVSATFWQNPRNHFRCQVQFYGLSENDEWTQ DRAKPVTQIVSAEAWGRADCGFTSVSYQQGVLSATIL YEILLGKATLYAVLVSALVLMAMVKRKDF |
| 44 | TCR β chain human constant region variant 2 (TRBC2*01) | EDLKNVFPPEVAVFEPSEAEISHTQKATLVCLATGFY PDHVELSWWVNGKEVHSGVSTDPQPLKEQPALNDSRY CLSSRLRVSATFWQNPRNHFRCQVQFYGLSENDEWTQ DRAKPVTQIVSAEAWGRADCGFTSESYQQGVLSATIL YEILLGKATLYAVLVSALVLMAMVKRKDSRG |
| 248 | TCR β chain mouse constant region | EDLRNVTPPKVSLFEPSKAEIANKQKATLVCLARGFF PDHVELSWWVNGKEVHSGVSTDPQAYKESNYSYCLSS RLRVSATFWHNPRNHFRCQVQFHGLSEEDKWPEGSPK PVTQNISAEAWGRADCGITSASYHQGVLSATILYEIL LGKATLYAVLVSGLVLMAMVKKKNS |
| 249 | TCR0077 full-length α chain | TQLLEQSPQFLSIQEGENLTVYCNSSSVFSSLQWYRQ EPGEGPVLLVTVVTGGEVKKLKRLTFQFGDARKDSSL HITAAQPGDTGLYLCAGYGGGSNYKLTFGAGTRLTVK PYIQNPEPAVYQLKDPRSQDSTLCLFTDFDSQINVPK TMESGTFITDKTVLDMKAMDSKSNGAIAWSNQTSFTC QDIFKETNATYPSSDVPCDATLTEKSFETDMNLNFQN LSVMGLRILLLKVAGFNLLMTLRLWSS |
| 250 | TCR0077 full-length β chain | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCASRLTGRVHGYTFGPGTRLT VLEDLRNVTPPKVSLFEPSKAEIANKQKATLVCLARG FFPDHVELSWWVNGKEVHSGVSTDPQAYKESNYSYCL SSRLRVSATFWHNPRNHFRCQVQFHGLSEEDKWPEGS PKPVTQNISAEAWGRADCGITSASYHQGVLSATILYE ILLGKATLYAVLVSGLVLMAMVKKKNS |
| 251 | TCR0079 full-length α chain | KNQVEQSPQSLIILEGKNCTLQCNYTVSPFSNLRWYK QDTGRGPVSLTIMTFSENTKSNGRYTATLDADTKQSS LHITASQLSDSASYICVVRGGAAGNKLTFGAGTRLTV KPYIQNPEPAVYQLKDPRSQDSTLCLFTDFDSQINVP KTMESGTFITDKTVLDMKAMDSKSNGAIAWSNQTSFT CQDIFKETNATYPSSDVPCDATLTEKSFETDMNLNFQ NLSVMGLRILLLKVAGFNLLMTLRLWSS |
| 252 | TCR0079 full-length β chain | DAGVIQSPRHEVTEMGQEVTLRCKPISGHNSLFWYRQ TMMRGLELLIYFNNNVPIDDSGMPEDRFSAKMPNASF STLKIQPSEPRDSAVYFCASSSGGANTEAFFGPGTRL TVLEDLRNVTPPKVSLFEPSKAEIANKQKATLVCLAR GFFPDHVELSWWVNGKEVHSGVSTDPQAYKESNYSYC LSSRLRVSATFWHNPRNHFRCQVQFHGLSEEDKWPEG SPKPVTQNISAEAWGRADCGITSASYHQGVLSATILY EILLGKATLYAVLVSGLVLMAMVKKKNS |
| 253 | TCR0081 full-length α chain | AQSVTQLGSHVSVSEGALILLRCNYSSSVPPYLFWYV QYPNQGLQLLLKYTTGATLVKGINGFEAEFKKSETSF HLTKPSAHMSDAAEYFCAVSARYNFNKFYFGSGTKLS VIPYIQNPEPAVYQLKDPRSQDSTLCLFTDFDSQINV PKTMESGTFITDKTVLDMKAMDSKSNGAIAWSNQTSF TCQDIFKETNATYPSSDVPCDATLTEKSFETDMNLNF QNLSVMGLRILLLKVAGFNLLMTLRLWSS |
| 254 | TCR0081 full-length β chain | DSGVTQTPKHLITATGQRVTLRCSPRSGDLSVYWYQQ SLDQGLQFLIQYYNGEERAKGNILERFSAQQFPDLHS ELNLSSLELGDSALYFCASSASGGRSYEQYFGPGTRL TVVEDLRNVTPPKVSLFEPSKAEIANKQKATLVCLAR GFFPDHVELSWWVNGKEVHSGVSTDPQAYKESNYSYC LSSRLRVSATFWHNPRNHFRCQVQFHGLSEEDKWPEG |

TABLE 1-continued

Amino acid sequences of exemplary TCRs.

| SEQ ID NO: | Description | Amino acid sequence |
|---|---|---|
| | | SPKPVTQNISAEAWGRADCGITSASYHQGVLSATILY EILLGKATLYAVLVSGLVLMAMVKKKNS |
| 255 | TCR0083 full-length α chain | EDQVTQSPEALRLQEGESSSLNCSYTVSGLRGLFWYR QDPGKGPEFLFTLYSAGEEKEKERLKATLTKKESFLH ITAPKPEDSATYLCAVRNTGFQKLVFGTGTRLLVSPY IQNPEPAVYQLKDPRSQDSTLCLFTDFDSQINVPKTM ESGTFITDKTVLDMKAMDSKSNGAIAWSNQTSFTCQD IFKETNATYPSSDVPCDATLTEKSFETDMNLNFQNLS VMGLRILLLKVAGFNLLMTLRLWSS |
| 256 | TCR0083 full-length β chain | DTGVSQDPRHKITKRGQNVTFRCDPISEHNRLYWYRQ TLGQGPEFLTYFQNEAQLEKSRLLSDRFSAERPKGSF STLEIQRTEQGDSAMYLCASSWRTGREETQYFGPGTR LLVLEDLRNVTPPKVSLFEPSKAEIANKQKATLVCLA RGFFPDHVELSWWVNGKEVHSGVSTDPQAYKESNYSY CLSSRLRVSATFWHNPRNHFRCQVQFHGLSEEDKWPE GSPKPVTQNISAEAWGRADCGITSASYHQGVLSATIL YEILLGKATLYAVLVSGLVLMAMVKKKNS |
| 257 | TCR0085 full-length α chain | KQEVTQIPAALSVPEGENLVLNCSFTDSAIYNLQWFR QDPGKGLTSLLLIQSSQREQTSGRLNASLDKSSGRST LYIAASQPGDSATYLCAVMLWNQGGKLIFGQGTELSV KPYIQNPEPAVYQLKDPRSQDSTLCLFTDFDSQINVP KTMESGTFITDKTVLDMKAMDSKSNGAIAWSNQTSFT CQDIFKETNATYPSSDVPCDATLTEKSFETDMNLNFQ NLSVMGLRILLLKVAGFNLLMTLRLWSS |
| 258 | TCR0085 full-length β chain | KAGVTQTPRYLIKTRGQQVTLSCSPISGHRSVSWYQQ TPGQGLQFLFEYFSETQRNKGNFPGRFSGRQFSNSRS EMNVSTLELGDSALYLCASSLGRGYEQYFGPGTRLTV TEDLRNVTPPKVSLFEPSKAEIANKQKATLVCLARGF FPDHVELSWWVNGKEVHSGVSTDPQAYKESNYSYCLS SRLRVSATFWHNPRNHFRCQVQFHGLSEEDKWPEGSP KPVTQNISAEAWGRADCGITSASYHQGVLSATILYEI LLGKATLYAVLVSGLVLMAMVKKKNS |
| 58 | TCR0078 full-length α chain | TQLLEQSPQFLSIQEGENLTVYCNSSSVFSSLQWYRQ EPGEGPVLLVTVVTGGEVKKLKRLTFQFGDARKDSSL HITAAQPGDTGLYLCAGYGGGSNYKLTFGKGTLLTVN PYIQNPDPAVYQLRDSKSSDKSVCLFTDFDSQTNVSQ SKDSDVYITDKTVLDMRSMDFKSNSAVAWSNKSDFAC ANAFNNSIIPEDTFFPSPESSCDVKLVEKSFETDTNL NFQNLSVIGFRILLLKVAGFNLLMTLRLWSS |
| 236 | TCR0078 full-length α chain, with a GS extension | TQLLEQSPQFLSIQEGENLTVYCNSSSVFSSLQWYRQ EPGEGPVLLVTVVTGGEVKKLKRLTFQFGDARKDSSL HITAAQPGDTGLYLCAGYGGGSNYKLTFGKGTLLTVN PYIQNPDPAVYQLRDSKSSDKSVCLFTDFDSQTNVSQ SKDSDVYITDKTVLDMRSMDFKSNSAVAWSNKSDFAC ANAFNNSIIPEDTFFPSPESSCDVKLVEKSFETDTNL NFQNLSVIGFRILLLKVAGFNLLMTLRLWSSGS |
| 259 | TCR0078 full-length α chain, with Furin residues (cleaved), variant 1 | TQLLEQSPQFLSIQEGENLTVYCNSSSVFSSLQWYRQ EPGEGPVLLVTVVTGGEVKKLKRLTFQFGDARKDSSL HITAAQPGDTGLYLCAGYGGGSNYKLTFGKGTLLTVN PYIQNPDPAVYQLRDSKSSDKSVCLFTDFDSQTNVSQ SKDSDVYITDKTVLDMRSMDFKSNSAVAWSNKSDFAC ANAFNNSIIPEDTFFPSPESSCDVKLVEKSFETDTNL NFQNLSVIGFRILLLKVAGFNLLMTLRLWSSRAKR |
| 260 | TCR0078 full-length α chain, with Furin residues (cleaved), variant 2 | TQLLEQSPQFLSIQEGENLTVYCNSSSVFSSLQWYRQ EPGEGPVLLVTVVTGGEVKKLKRLTFQFGDARKDSSL HITAAQPGDTGLYLCAGYGGGSNYKLTFGKGTLLTVN PYIQNPDPAVYQLRDSKSSDKSVCLFTDFDSQTNVSQ SKDSDVYITDKTVLDMRSMDFKSNSAVAWSNKSDFAC ANAFNNSIIPEDTFFPSPESSCDVKLVEKSFETDTNL NFQNLSVIGFRILLLKVAGFNLLMTLRLWSSRA |
| 272 | TCR0078 full-length α chain, with Furin residues (cleaved), variant 3 | TQLLEQSPQFLSIQEGENLTVYCNSSSVFSSLQWYRQ EPGEGPVLLVTVVTGGEVKKLKRLTFQFGDARKDSSL HITAAQPGDTGLYLCAGYGGGSNYKLTFGKGTLLTVN PYIQNPDPAVYQLRDSKSSDKSVCLFTDFDSQTNVSQ SKDSDVYITDKTVLDMRSMDFKSNSAVAWSNKSDFAC ANAFNNSIIPEDTFFPSPESSCDVKLVEKSFETDTNL NFQNLSVIGFRILLLKVAGFNLLMTLRLWSSRAK |

TABLE 1-continued

Amino acid sequences of exemplary TCRs.

| SEQ ID NO: | Description | Amino acid sequence |
|---|---|---|
| 261 | TCR0078 full-length α chain, with P2A residues (cleaved) | TQLLEQSPQFLSIQEGENLTVYCNSSSVFSSLQWYRQ EPGEGPVLLVTVVTGGEVKKLKRLTFQFGDARKDSSL HITAAQPGDTGLYLCAGYGGGSNYKLTFGKGTLLTVN PYIQNPDPAVYQLRDSKSSDKSVCLFTDFDSQTNVSQ SKDSDVYITDKTVLDMRSMDFKSNSAVAWSNKSDFAC ANAFNNSIIPEDTFFPSPESSCDVKLVEKSFETDTNL NFQNLSVIGFRILLLKVAGFNLLMTLRLWSSGSGATN FSLLKQAGDVEENPG |
| 59 | TCR0078 full-length β chain variant 1 | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCASRLTGRVHGYTFGSGTRLT VVEDLNKVFPPEVAVFEPSEAEISHTQKATLVCLATG FFPDHVELSWWVNGKEVHSGVSTDPQPLKEQPALNDS RYCLSSRLRVSATFWQNPRNHFRCQVQFYGLSENDEW TQDRAKPVTQIVSAEAWGRADCGFTSVSYQQGVLSAT ILYEILLGKATLYAVLVSALVLMAMVKRKDF |
| 237 | TCR0078 full-length β chain variant 1, with P2A residues (cleaved) | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCASRLTGRVHGYTFGSGTRLT VVEDLNKVFPPEVAVFEPSEAEISHTQKATLVCLATG FFPDHVELSWWVNGKEVHSGVSTDPQPLKEQPALNDS RYCLSSRLRVSATFWQNPRNHFRCQVQFYGLSENDEW TQDRAKPVTQIVSAEAWGRADCGFTSVSYQQGVLSAT ILYEILLGKATLYAVLVSALVLMAMVKRKDFGSGATN FSLLKQAGDVEENPG |
| 262 | TCR0078 full-length β chain variant 1, with a GS extension | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCASRLTGRVHGYTFGSGTRLT VVEDLNKVFPPEVAVFEPSEAEISHTQKATLVCLATG FFPDHVELSWWVNGKEVHSGVSTDPQPLKEQPALNDS RYCLSSRLRVSATFWQNPRNHFRCQVQFYGLSENDEW TQDRAKPVTQIVSAEAWGRADCGFTSVSYQQGVLSAT ILYEILLGKATLYAVLVSALVLMAMVKRKDFGS |
| 263 | TCR0078 full-length β chain variant 1, with Furin residues (cleaved), variant 1 | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCASRLTGRVHGYTFGSGTRLT VVEDLNKVFPPEVAVFEPSEAEISHTQKATLVCLATG FFPDHVELSWWVNGKEVHSGVSTDPQPLKEQPALNDS RYCLSSRLRVSATFWQNPRNHFRCQVQFYGLSENDEW TQDRAKPVTQIVSAEAWGRADCGFTSVSYQQGVLSAT ILYEILLGKATLYAVLVSALVLMAMVKRKDFRAKR |
| 264 | TCR0078 full-length β chain variant 1, with Furin residues (cleaved), variant 2 | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCASRLTGRVHGYTFGSGTRLT VVEDLNKVFPPEVAVFEPSEAEISHTQKATLVCLATG FFPDHVELSWWVNGKEVHSGVSTDPQPLKEQPALNDS RYCLSSRLRVSATFWQNPRNHFRCQVQFYGLSENDEW TQDRAKPVTQIVSAEAWGRADCGFTSVSYQQGVLSAT ILYEILLGKATLYAVLVSALVLMAMVKRKDFRA |
| 273 | TCR0078 full-length β chain variant 1, with Furin residues (cleaved), variant 3 | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCASRLTGRVHGYTFGSGTRLT VVEDLNKVFPPEVAVFEPSEAEISHTQKATLVCLATG FFPDHVELSWWVNGKEVHSGVSTDPQPLKEQPALNDS RYCLSSRLRVSATFWQNPRNHFRCQVQFYGLSENDEW TQDRAKPVTQIVSAEAWGRADCGFTSVSYQQGVLSAT ILYEILLGKATLYAVLVSALVLMAMVKRKDFRAK |
| 60 | TCR0078 full-length β chain variant 2 | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCASRLTGRVHGYTFGSGTRLT VVEDLKNVFPPEVAVFEPSEAEISHTQKATLVCLATG FYPDHVELSWWVNGKEVHSGVSTDPQPLKEQPALNDS RYCLSSRLRVSATFWQNPRNHFRCQVQFYGLSENDEW TQDRAKPVTQIVSAEAWGRADCGFTSESYQQGVLSAT ILYEILLGKATLYAVLVSALVLMAMVKRKDSRG |
| 61 | TCR0080 full-length α chain | KNQVEQSPQSLIILEGKNCTLQCNYTVSPFSNLRWYK QDTGRGPVSLTIMTFSENTKSNGRYTATLDADTKQSS LHITASQLSDSASYICVVRGGAAGNKLTFGGGTRVLV |

TABLE 1-continued

Amino acid sequences of exemplary TCRs.

| SEQ ID NO: | Description | Amino acid sequence |
|---|---|---|
| | | KPYIQNPDPAVYQLRDSKSSDKSVCLFTDFDSQTNVS QSKDSDVYITDKTVLDMRSMDFKSNSAVAWSNKSDFA CANAFNNSIIPEDTFFPSPESSCDVKLVEKSFETDTN LNFQNLSVIGFRILLLKVAGFNLLMTLRLWSS |
| 62 | TCR0080 full-length β chain variant 1 | DAGVIQSPRHEVTEMGQEVTLRCKPISGHNSLFWYRQ TMMRGLELLIYFNNNVPIDDSGMPEDRFSAKMPNASF STLKIQPSEPRDSAVYFCASSSGGANTEAFFGQGTRL TVVEDLNKVFPPEVAVFEPSEAEISHTQKATLVCLAT GFFPDHVELSWWVNGKEVHSGVSTDPQPLKEQPALND SRYCLSSRLRVSATFWQNPRNHFRCQVQFYGLSENDE WTQDRAKPVTQIVSAEAWGRADCGFTSVSYQQGVLSA TILYEILLGKATLYAVLVSALVLMAMVKRKDF |
| 63 | TCR0080 full-length β chain variant 2 | DAGVIQSPRHEVTEMGQEVTLRCKPISGHNSLFWYRQ TMMRGLELLIYFNNNVPIDDSGMPEDRFSAKMPNASF STLKIQPSEPRDSAVYFCASSSGGANTEAFFGQGTRL TVVEDLKNVFPPEVAVFEPSEAEISHTQKATLVCLAT GFYPDHVELSWWVNGKEVHSGVSTDPQPLKEQPALND SRYCLSSRLRVSATFWQNPRNHFRCQVQFYGLSENDE WTQDRAKPVTQIVSAEAWGRADCGFTSESYQQGVLSA TILYEILLGKATLYAVLVSALVLMAMVKRKDSRG |
| 64 | TCR0082 full-length α chain | AQSVTQLGSHVSVSEGALVLLRCNYSSSVPPYLFWYV QYPNQGLQLLLKYTSAATLVKGINGFEAEFKKSETSF HLTKPSAHMSDAAEYFCAVSARYNFNKFYFGSGTKLN VKPYIQNPDPAVYQLRDSKSSDKSVCLFTDFDSQTNV SQSKDSDVYITDKTVLDMRSMDFKSNSAVAWSNKSDF ACANAFNNSIIPEDTFFPSPESSCDVKLVEKSFETDT NLNFQNLSVIGFRILLLKVAGFNLLMTLRLWSS |
| 65 | TCR0082 full-length β chain variant 1 | DSGVTQTPKHLITATGQRVTLRCSPRSGDLSVYWYQQ SLDQGLQFLIHYYNGEERAKGNILERFSAQQFPDLHS ELNLSSLELGDSALYFCASSASGGRSYEQYFGPGTRL TVTEDLNKVFPPEVAVFEPSEAEISHTQKATLVCLAT GFFPDHVELSWWVNGKEVHSGVSTDPQPLKEQPALND SRYCLSSRLRVSATFWQNPRNHFRCQVQFYGLSENDE WTQDRAKPVTQIVSAEAWGRADCGFTSVSYQQGVLSA TILYEILLGKATLYAVLVSALVLMAMVKRKDF |
| 66 | TCR0082 full-length β chain variant 2 | DSGVTQTPKHLITATGQRVTLRCSPRSGDLSVYWYQQ SLDQGLQFLIHYYNGEERAKGNILERFSAQQFPDLHS ELNLSSLELGDSALYFCASSASGGRSYEQYFGPGTRL TVTEDLKNVFPPEVAVFEPSEAEISHTQKATLVCLAT GFYPDHVELSWWVNGKEVHSGVSTDPQPLKEQPALND SRYCLSSRLRVSATFWQNPRNHFRCQVQFYGLSENDE WTQDRAKPVTQIVSAEAWGRADCGFTSESYQQGVLSA TILYEILLGKATLYAVLVSALVLMAMVKRKDSRG |
| 67 | TCR0084 full-length α chain | EDQVTQSPEALRLQEGESSSLNCSYTVSGLRGLFWYR QDPGKGPEFLFTLYSAGEEKEKERLKATLTKKESFLH ITAPKPEDSATYLCAVRNTGFQKLVFGTGTRLLVSPY IQNPDPAVYQLRDSKSSDKSVCLFTDFDSQTNVSQSK DSDVYITDKTVLDMRSMDFKSNSAVAWSNKSDFACAN AFNNSIIPEDTFFPSPESSCDVKLVEKSFETDTNLNF QNLSVIGFRILLLKVAGFNLLMTLRLWSS |
| 68 | TCR0084 full-length β chain variant 1 | DTGVSQNPRHKITKRGQNVTFRCDPISEHNRLYWYRQ TLGQGPEFLTYFQNEAQLEKSRLLSDRFSAERPKGSF STLEIQRTEQGDSAMYLCASSWRTGREETQYFGPGTR LLVLEDLNKVFPPEVAVFEPSEAEISHTQKATLVCLA TGFFPDHVELSWWVNGKEVHSGVSTDPQPLKEQPALN DSRYCLSSRLRVSATFWQNPRNHFRCQVQFYGLSEND EWTQDRAKPVTQIVSAEAWGRADCGFTSVSYQQGVLS ATILYEILLGKATLYAVLVSALVLMAMVKRKDF |
| 69 | TCR0084 full-length β chain variant 2 | DTGVSQNPRHKITKRGQNVTFRCDPISEHNRLYWYRQ TLGQGPEFLTYFQNEAQLEKSRLLSDRFSAERPKGSF STLEIQRTEQGDSAMYLCASSWRTGREETQYFGPGTR LLVLEDLKNVFPPEVAVFEPSEAEISHTQKATLVCLA TGFYPDHVELSWWVNGKEVHSGVSTDPQPLKEQPALN DSRYCLSSRLRVSATFWQNPRNHFRCQVQFYGLSEND EWTQDRAKPVTQIVSAEAWGRADCGFTSESYQQGVLS ATILYEILLGKATLYAVLVSALVLMAMVKRKDSRG |

TABLE 1-continued

Amino acid sequences of exemplary TCRs.

| SEQ ID NO: | Description | Amino acid sequence |
|---|---|---|
| 70 | TCR0086 full-length α chain | KQEVTQIPAALSVPEGENLVLNCSFTDSAIYNLQWFR QDPGKGLTSLLLIQSSQREQTSGRLNASLDKSSGRST LYIAASQPGDSATYLCAVMLWNQGGKLIFGQGTELSV KPYIQNPDPAVYQLRDSKSSDKSVCLFTDFDSQTNVS QSKDSDVYITDKTVLDMRSMDFKSNSAVAWSNKSDFA CANAFNNSIIPEDTFFPSPESSCDVKLVEKSFETDTN LNFQNLSVIGFRILLLKVAGFNLLMTLRLWSS |
| 71 | TCR0086 full-length β chain variant 1 | KAGVTQTPRYLIKTRGQQVTLSCSPISGHRSVSWYQQ TPGQGLQFLFEYFSETQRNKGNFPGRFSGRQFSNSRS EMNVSTLELGDSALYLCASSLGRGYEQYFGPGTRLTV TEDLNKVFPPEVAVFEPSEAEISHTQKATLVCLATGF FPDHVELSWWVNGKEVHSGVSIDPQPLKEQPALNDSR YCLSSRLRVSATFWQNPRNHFRCQVQFYGLSENDEWT QDRAKPVTQIVSAEAWGRADCGFTSVSYQQGVLSATI LYEILLGKATLYAVLVSALVLMAMVKRKDF |
| 72 | TCR0086 full-length β chain variant 2 | KAGVTQTPRYLIKTRGQQVTLSCSPISGHRSVSWYQQ TPGQGLQFLFEYFSETQRNKGNFPGRFSGRQFSNSRS EMNVSTLELGDSALYLCASSLGRGYEQYFGPGTRLTV TEDLKNVFPPEVAVFEPSEAEISHTQKATLVCLATGF YPDHVELSWWVNGKEVHSGVSTDPQPLKEQPALNDSR YCLSSRLRVSATFWQNPRNHFRCQVQFYGLSENDEWT QDRAKPVTQIVSAEAWGRADCGFTSESYQQGVLSATI LYEILLGKATLYAVLVSALVLMAMVKRKDSRG |
| 73 | α chain germline sequence TRAV27 | TQLLEQSPQFLSIQEGENLTVYCNSSSVFSSLQWYRQ EPGEGPVLLVTVVTGGEVKKLKRLTFQFGDARKDSSL HITAAQPGDTGLYLCAG |
| 74 | β chain germline sequence TRBV27 | EAQVTQNPRYLITVTGKKLTVTCSQNMNHEYMSWYRQ DPGLGLRQIYYSMNVEVTDKGDVPEGYKVSRKEKRNF PLILESPSPNQTSLYFCAS |
| 75 | α chain germline sequence TRAV10 | KNQVEQSPQSLIILEGKNCTLQCNYTVSPFSNLRWYK QDTGRGPVSLTIMTFSENTKSNGRYTATLDADTKQSS LHITASQLSDSASYICVV |
| 76 | β chain germline sequence TRBV12-3 | DAGVIQSPRHEVTEMGQEVTLRCKPISGHNSLFWYRQ TMMRGLELLIYFNNNVPIDDSGMPEDRFSAKMPNASF STLKIQPSEPRDSAVYFCASS |
| 77 | α chain germline sequence TRAV8-4 | AQSVTQLGSHVSVSEGALVLLRCNYSSSVPPYLFWYV QYPNQGLQLLLKYTSAATLVKGINGFEAEFKKSETSF HLTKPSAHMSDAAEYFCAVS |
| 78 | β chain germline sequence TRBV9 | DSGVTQTPKHLITATGQRVTLRCSPRSGDLSVYWYQQ SLDQGLQFLIHYYNGEERAKGNILERFSAQQFPDLHS ELNLSSLELGDSALYFCASS |
| 79 | α chain germline sequence TRAV20 | EDQVTQSPEALRLQEGESSSLNCSYTVSGLRGLFWYR QDPGKGPEFLFTLYSAGEEKEKERLKATLTKKESFLH ITAPKPEDSATYLCAV |
| 80 | β chain germline sequence TRBV7-9 | DTGVSQNPRHKITKRGQNVTFRCDPISEHNRLYWYRQ TLGQGPEFLTYFQNEAQLEKSRLLSDRFSAERPKGSF STLEIQRTEQGDSAMYLCASS |
| 81 | α chain germline sequence TRAV21 | KQEVTQIPAALSVPEGENLVLNCSFTDSAIYNLQWFR QDPGKGLTSLLLIQSSQREQTSGRLNASLDKSSGRST LYIAASQPGDSATYLCAV |
| 82 | β chain germline sequence TRBV5-1 | KAGVTQTPRYLIKTRGQQVTLSCSPISGHRSVSWYQQ TPGQGLQFLFEYFSETQRNKGNFPGRFSGRQFSNSRS EMNVSTLELGDSALYLCASSL |
| 83 | Immature TCR0078 β chain-P2A cleavage site-TCR0078 α chain sequence | MGPQLLGYVVLCLLGAGPLEAQVTQNPRYLITVTGKK LTVTCSQNMNHEYMSWYRQDPGLGLRQIYYSMNVEVT DKGDVPEGYKVSRKEKRNFPLILESPSPNQTSLYFCA SRLTGRVHGYTFGSGTRLTVVEDLNKVFPPEVAVFEP SEAEISHTQKATLVCLATGFFPDHVELSWWVNGKEVH SGVSTDPQPLKEQPALNDSRYCLSSRLRVSATFWQNP RNHFRCQVQFYGLSENDEWTQDRAKPVTQIVSAEAWG RADCGFTSVSYQQGVLSATILYEILLGKATLYAVLVS ALVLMAMVKRKDFGSGATNFSLLKQAGDVEENPGPMV LKFSVSILWIQLAWVSTQLLEQSPQFLSIQEGENLTV |

TABLE 1-continued

Amino acid sequences of exemplary TCRs.

| SEQ ID NO: | Description | Amino acid sequence |
|---|---|---|
| | | YCNSSSVFSSLQWYRQEPGEGPVLLVTVVTGGEVKKL KRLTFQFGDARKDSSLHITAAQPGDTGLYLCAGYGGG SNYKLTFGKGTLLTVNPYIQNPDPAVYQLRDSKSSDK SVCLFTDFDSQTNVSQSKDSDVYITDKTVLDMRSMDF KSNSAVAWSNKSDFACANAFNNSIIPEDTFFPSPESS CDVKLVEKSFETDTNLNFQNLSVIGFRILLLKVAGFN LLMTLRLWSSGS |
| 266 | Immature TCR0078 β chain-Furin-P2A-TCR0078 α chain sequence | MGPQLLGYVVLCLLGAGPLEAQVTQNPRYLTTVTGKK LTVTCSQNMNHEYMSWYRQDPGLGLRQIYYSMNVEVT DKGDVPEGYKVSRKEKRNFPLILESPSPNQTSLYFCA SRLTGRVHGYTFGSGTRLTVVEDLNKVFPPEVAVFEP SEAEISHTQKATLVCLATGFFPDHVELSWWVNGKEVH SGVSTDPQPLKEQPALNDSRYCLSSRLRVSATFWQNP RNHFRCQVQFYGLSENDEWTQDRAKPVTQIVSAEAWG RADCGFTSVSYQQGVLSATILYEILLGKATLYAVLVS ALVLMAMVKRKDFRAKRSGSGATNFSLLKQAGDVEEN PGPMVLKFSVSILWIQLAWVSTQLLEQSPQFLSIQEG ENLTVYCNSSSVFSSLQWYRQEPGEGPVLLVTVVTGG EVKKLKRLTFQFGDARKDSSLHITAAQPGDTGLYLCA GYGGGSNYKLIFGKGTLLTVNPYIQNPDPAVYQLRDS KSSDKSVCLFTDFDSQTNVSQSKDSDVYITDKTVLDM RSMDFKSNSAVAWSNKSDFACANAFNNSIIPEDTFFP SPESSCDVKLVEKSFETDTNLNFQNLSVIGFRILLLK VAGFNLLMTLRLWSS |
| 267 | Immature TCR0078 β chain-Furin-P2A-TCR0078 α chain sequence, with a GS extension | MGPQLLGYVVLCLLGAGPLEAQVTQNPRYLITVTGKK LTVTCSQNMNHEYMSWYRQDPGLGLRQIYYSMNVEVT DKGDVPEGYKVSRKEKRNFPLILESPSPNQTSLYFCA SRLTGRVHGYTFGSGTRLTVVEDLNKVFPPEVAVFEP SEAEISHTQKATLVCLATGFFPDHVELSWWVNGKEVH SGVSTDPQPLKEQPALNDSRYCLSSRLRVSATFWQNP RNHFRCQVQFYGLSENDEWTQDRAKPVTQIVSAEAWG RADCGFTSVSYQQGVLSATILYEILLGKATLYAVLVS ALVLMAMVKRKDFRAKRSGSGATNFSLLKQAGDVEEN PGPMVLKFSVSILWIQLAWVSTQLLEQSPQFLSIQEG ENLTVYCNSSSVFSSLQWYRQEPGEGPVLLVTVVTGG EVKKLKRLTFQFGDARKDSSLHITAAQPGDTGLYLCA GYGGGSNYKLIFGKGILLTVNPYIQNPDPAVYQLRDS KSSDKSVCLFTDFDSQTNVSQSKDSDVYITDKTVLDM RSMDFKSNSAVAWSNKSDFACANAFNNSIIPEDTFFP SPESSCDVKLVEKSFETDTNLNFQNLSVIGFRILLLK VAGFNLLMTLRLWSSGS |
| 268 | Immature TCR0078 α chain-Furin-P2A-TCR0078 β chain sequence | MVLKFSVSILWIQLAWVSTQLLEQSPQFLSIQEGENL TVYCNSSSVFSSLQWYRQEPGEGPVLLVTVVTGGEVK KLKRLTFQFGDARKDSSLHITAAQPGDTGLYLCAGYG GGSNYKLTFGKGTLLTVNPYIQNPDPAVYQLRDSKSS DKSVCLFTDFDSQTNVSQSKDSDVYITDKTVLDMRSM DFKSNSAVAWSNKSDFACANAFNNSIIPEDTFFPSPE SSCDVKLVEKSFETDTNLNFQNLSVIGFRILLLKVAG FNLLMTLRLWSSRAKRSGSGATNFSLLKQAGDVEENP GPMGPQLLGYVVLCLLGAGPLEAQVTQNPRYLITVTG KKLTVTCSQNMNHEYMSWYRQDPGLGLRQIYYSMNVE VTDKGDVPEGYKVSRKEKRNFPLILESPSPNQTSLYF CASRLTGRVHGYTFGSGTRLTVVEDLNKVFPPEVAVF EPSEAEISHTQKATLVCLATGFFPDHVELSWWVNGKE VHSGVSTDPQPLKEQPALNDSRYCLSSRLRVSATFWQ NPRNHFRCQVQFYGLSENDEWTQDRAKPVTQIVSAEA WGRADCGFTSVSYQQGVLSATILYEILLGKATLYAVL VSALVLMAMVKRKDF |
| 269 | Immature TCR0078 α chain-Furin-P2A-TCR0078 β chain sequence, with a GS extension | MVLKFSVSILWIQLAWVSTQLLEQSPQFLSIQEGENL TVYCNSSSVFSSLQWYRQEPGEGPVLLVTVVTGGEVK KLKRLTFQFGDARKDSSLHITAAQPGDTGLYLCAGYG GGSNYKLTFGKGTLLTVNPYIQNPDPAVYQLRDSKSS DKSVCLFTDFDSQTNVSQSKDSDVYITDKTVLDMRSM DFKSNSAVAWSNKSDFACANAFNNSIIPEDTFFPSPE SSCDVKLVEKSFETDTNLNFQNLSVIGFRILLLKVAG FNLLMTLRLWSSRAKRSGSGATNFSLLKQAGDVEENP GPMGPQLLGYVVLCLLGAGPLEAQVTQNPRYLITVTG KKLTVTCSQNMNHEYMSWYRQDPGLGLRQIYYSMNVE VTDKGDVPEGYKVSRKEKRNFPLILESPSPNQTSLYF CASRLTGRVHGYTFGSGTRLTVVEDLNKVFPPEVAVF EPSEAEISHTQKATLVCLATGFFPDHVELSWWVNGKE VHSGVSTDPQPLKEQPALNDSRYCLSSRLRVSATFWQ |

TABLE 1-continued

Amino acid sequences of exemplary TCRs.

| SEQ ID NO: | Description | Amino acid sequence |
|---|---|---|
|  |  | NPRNHFRCQVQFYGLSENDEWTQDRAKPVTQIVSAEA<br>WGRADCGFTSVSYQQGVLSATILYEILLGKATLYAVL<br>VSALVLMAMVKRKDFGS |
| 270 | Immature TCR0078 α chain-P2A cleavage site-TCR0078 β chain sequence | MVLKFSVSILWIQLAWVSTQLLEQSPQFLSIQEGENL<br>TVYCNSSSVFSSLQWYRQEPGEGPVLLVTVVTGGEVK<br>KLKRLTFQFGDARKDSSLHITAAQPGDTGLYLCAGYG<br>GGSNYKLTFGKGTLLTVNPYIQNPDPAVYQLRDSKSS<br>DKSVCLFTDFDSQTNVSQSKDSDVYITDKTVLDMRSM<br>DFKSNSAVAWSNKSDFACANAFNNSIIPEDTFFPSPE<br>SSCDVKLVEKSFETDTNLNFQNLSVIGFRILLLKVAG<br>FNLLMTLRLWSSGSGATNFSLLKQAGDVEENPGPMGP<br>QLLGYVVLCLLGAGPLEAQVTQNPRYLITVTGKKLTV<br>TCSQNMNHEYMSWYRQDPGLGLRQIYYSMNVEVTDKG<br>DVPEGYKVSRKEKRNFPLILESPSPNQTSLYFCASRL<br>TGRVHGYTFGSGTRLTVVEDLNKVFPPEVAVFEPSEA<br>EISHTQKATLVCLATGFFPDHVELSWWVNGKEVHSGV<br>STDPQPLKEQPALNDSRYCLSSRLRVSATFWQNPRNH<br>FRCQVQFYGLSENDEWTQDRAKPVTQIVSAEAWGRAD<br>CGFTSVSYQQGVLSATILYEILLGKATLYAVLVSALV<br>LMAMVKRKDF |
| 271 | Immature TCR0078 α chain-P2A cleavage site-TCR0078 β chain sequence, with GS extension | MVLKFSVSILWIQLAWVSTQLLEQSPQFLSIQEGENL<br>TVYCNSSSVFSSLQWYRQEPGEGPVLLVTVVTGGEVK<br>KLKRLTFQFGDARKDSSLHITAAQPGDTGLYLCAGYG<br>GGSNYKLTFGKGTLLTVNPYIQNPDPAVYQLRDSKSS<br>DKSVCLFTDFDSQTNVSQSKDSDVYITDKTVLDMRSM<br>DFKSNSAVAWSNKSDFACANAFNNSIIPEDTFFPSPE<br>SSCDVKLVEKSFETDTNLNFQNLSVIGFRILLLKVAG<br>FNLLMTLRLWSSGSGATNFSLLKQAGDVEENPGPMGP<br>QLLGYVVLCLLGAGPLEAQVTQNPRYLITVTGKKLTV<br>TCSQNMNHEYMSWYRQDPGLGLRQIYYSMNVEVTDKG<br>DVPEGYKVSRKEKRNFPLILESPSPNQTSLYFCASRL<br>TGRVHGYTFGSGTRLTVVEDLNKVFPPEVAVFEPSEA<br>EISHTQKATLVCLATGFFPDHVELSWWVNGKEVHSGV<br>STDPQPLKEQPALNDSRYCLSSRLRVSATFWQNPRNH<br>FRCQVQFYGLSENDEWTQDRAKPVTQIVSAEAWGRAD<br>CGFTSVSYQQGVLSATILYEILLGKATLYAVLVSALV<br>LMAMVKRKDFGS |
| 90 | Kozak-TCR0078 β chain-P2A cleavage site-TCR0078 α chain nucleic acid sequence variant 1 | gccaccatgggacctcagctgctgggatacgttgtgc<br>tgtgtctgcttggagccgaacctctggaagcccaagt<br>gacacagaaccccagatacctgatcaccgtgaccggc<br>aagaaactgaccgtgacctgcagccagaacatgaacc<br>acgagtacatgagctggtacagacaggaccctggcct<br>gggcctgagacagatctactacagcatgaacgtggaa<br>gtgaccgacaagggcgacgtgcccgagggctacaagg<br>tgtccagaaaagagaagcggaacttcccactgatcct<br>ggaaagcccatctcctaaccagaccagcctgtacttc<br>tgcgccagcagactgacaggcagagtgcacggctaca<br>catttggcagcggcaccagactgactgtggtggaaga<br>tctgaacaaggtgttccctccagaggtggccgtgttc<br>gagccttctgaggccgagatcagccacacacagaaag<br>ccacactcgtgtgcctggccaccggcttttttcccga<br>tcacgtggaactgtcttggtgggtcaacggcaaagag<br>gtgcacagcggcgtcagcacagatccccagcctctga<br>agaacagcccgctctgaacgacagccggtactgcct<br>gtcctccagactgagagtgtccgccaccttctggcag<br>aaccctcggaaccacttcagatgccaggtgcagttct<br>acggcctgagcgagaacgatgagtggacccaggatag<br>agccaagcctgtgactcagatcgtgtctgccgaagcc<br>tggggcagagccgattgtggctttaccagcgtgtcct<br>atcagcagggcgtgctgtctgccaccatcctgtatga<br>gatcctgctgggcaaagccactctgtacgccgtgctg<br>gtttctgccctggtgctgatggccatggtcaagagaa<br>aggactttggctccggcgccaccaacttcagcctgct<br>gaaacaggctggcgacgtggaagagaaccccggacct<br>atggtgctgaagttctccgtgtccatcctgtggattc<br>agctggcttgggtgtccacacagctgctcgaacagag<br>ccctcagttcctgagcatccaagagggcgagaacctg<br>acagtgtactgcaacagcagcagcgtgttcagcagcc<br>tgcagtggtacaggcaagagcctggcgaaggacctgt<br>gctgctggtcacagttgtgacaggcggcgaagtgaag<br>aagctgaagcggctgaccttccagttcggcgacgcca<br>gaaaggatagctccctgcacattaccgctgctcagcc<br>aggcgataccggcctgtatctgtgtgctggatatggc |

TABLE 1-continued

Amino acid sequences of exemplary TCRs.

| SEQ ID NO: | Description | Amino acid sequence |
|---|---|---|
| | | ggcggaagcaactacaagctgacctttggcaagggca<br>ccctgctgacagtgaaccctacattcagaacccga<br>tccagccgtgtatcagctgagagacagcaagagcagc<br>gacaagagcgtgtgtctgttcaccgacttcgacagcc<br>agaccaacgtgtcccagagcaaggacagcgacgtgta<br>catcaccgacaagaccgtgctggacatgcggagcatg<br>gacttcaagagcaacagcgccgtggcctggtccaaca<br>agagcgatttcgcctgcgccaacgccttcaacaacag<br>cattatccccgaggacacattcttcccaagtcctgag<br>agcagctgcgacgtgaagctggtggaaaagagcttcg<br>agacagacaccaacctgaacttccagaacctgagcgt<br>gatcggcttcagaatcctgctgctgaaggtggccggc<br>ttcaatctgctgatgaccctgagactgtggtccagcg<br>gatcctga |
| 238 | Kozak-TCR0078 β chain-<br>P2A cleavage site-<br>TCR0078 α chain nucleic<br>acid sequence variant 2 | gccaccatgggacctcagctgctgggatacgttgtgc<br>tgtgtctgcttggagccgacctctggaagcccaagt<br>gacacagaaccccagatacctgatcaccgtgaccggc<br>aagaaactgaccgtgacctgcagccagaacatgaacc<br>acgagtacatgagctggtacagacaggaccctggcct<br>gggcctgagacagatctactacagcatgaacgtggaa<br>gtgaccgacaagggcgacgtgcccgagggctacaagg<br>tgtccagaaaagagaagcggaacttcccactgatcct<br>ggaaagcccatctcctaaccagaccagcctgtacttc<br>tgcgccagcagactgacaggcagagtgcacggctaca<br>catttggcagcggcaccagactgactgtggtggaaga<br>tctgaacaaggtgttcccgccggaagtggccgtgttc<br>gagccttctgaggccgagatcagccacacacagaaag<br>ccacactcgtgtgcctggccaccggctttttcccga<br>tcacgtggaactgtcttggtgggtcaacggcaaagag<br>gtgcacagcggcgtcagcacagatccccagcctctga<br>agaacagcccgctctgaacgacagccggtactgcct<br>gtcctcccgactgagagtgtccgccaccttctggcag<br>aaccctcggaaccacttcagatgccaggtgcagttct<br>acggcctgagcgagaacgatgagtggaccaggatag<br>agccaagcctgtgactcagatcgtgtctgccgaagcc<br>tggggcagagccgattgtggctttaccagcgtgtcct<br>atcagcagggcgtgctgtctgccaccatcctgtatga<br>gatcctgctgggcaaagccactctgtacgccgtgctg<br>gttctgccctggtgctgatggccatggtcaagagaa<br>aggactttggctccggcgccaccaacttcagcctgct<br>gaaacaggctggcgacgtggaagagaaccccggacct<br>atggtgctgaagttctccgtgtccatcctgtggattc<br>agctggcttgggtgtccacacagctgctcgaacagag<br>ccctcagttcctgagcatccaagagggcgagaacctg<br>acagtgtactgcaacagcagcagcgtgttcagcagcc<br>tgcagtggtacaggcaagagcctggcgaaggacctgt<br>gctgctggtcacagttgtgacaggcggcgaagtgaag<br>aagctgaagcggctgacctccagttcggcgacgcca<br>gaaaggatagctccctgcacattaccgctgctcagcc<br>aggcgataccggcctgtatctgtgtgctggatatggc<br>ggcggaagcaactacaagctgacctttggcaagggca<br>ccctgctgacagtgaaccctacattcagaacccga<br>tccagccgtgtatcagctgagagacagcaagagcagc<br>gacaagagcgtgtgtctgttcaccgacttcgacagcc<br>agaccaacgtgtcccagagcaaggacagcgacgtgta<br>catcaccgacaagaccgtgctggacatgcggagcatg<br>gacttcaagagcaacagcgccgtggcctggtccaaca<br>agagcgatttcgcctgcgccaacgccttcaacaacag<br>cattatccccgaggacacattcttcccaagtcctgag<br>agcagctgcgacgtgaagctggtggaaaagagcttcg<br>agacagacaccaacctgaacttccagaacctgagcgt<br>gatcggcttcagaatcctgctgctgaaggtggccggc<br>ttcaatctgctgatgaccctgagactgtggtccagcg<br>gatcctga |
| 91 | Immature TCR0080 β<br>chain-P2A cleavage site-<br>TCR0080 α chain<br>sequence | MDSWTFCCVSLCILVAKHTDAGVIQSPRHEVTEMGQE<br>VTLRCKPISGHNSLFWYRQTMMRGLELLIYFNNNVPI<br>DDSGMPEDRFSAKMPNASFSTLKIQPSEPRDSAVYFC<br>ASSSGGANTEAFFGQGTRLTVVEDLNKVFPPEVAVFE<br>PSEAEISHTQKATLVCLATGFFPDHVELSWWVNGKEV<br>HSGVSTDPQPLKEQPALNDSRYCLSSRLRVSATFWQN<br>PRNHFRCQVQFYGLSENDEWTQDRAKPVTQIVSAEAW<br>GRADCGFTSVSYQQGVLSATILYEILLGKATLYAVLV<br>SALVLMAMVKRKDFGSGATNFSLLKQAGDVEENPGPM<br>KKHLTTFLVILWLYFYRGNGKNQVEQSPQSLIILEGK |

TABLE 1-continued

Amino acid sequences of exemplary TCRs.

| SEQ ID NO: | Description | Amino acid sequence |
|---|---|---|
| | | NCTLQCNYTVSPFSNLRWYKQDTGRGPVSLTIMTFSE NTKSNGRYTATLDADTKQSSLHITASQLSDSASYICV VRGGAAGNKLTFGGGTRVLVKPYIQNPDPAVYQLRDS KSSDKSVCLFTDFDSQTNVSQSKDSDVYITDKTVLDM RSMDFKSNSAVAWSNKSDFACANAFNNSIIPEDTFFP SPESSCDVKLVEKSFETDTNLNFQNLSVIGFRILLLK VAGFNLLMTLRLWSSGS |
| 265 | Immature TCR0080 β chain-Furin-P2A-TCR0080 α chain sequence | MDSWTFCCVSLCILVAKHTDAGVIQSPRHEVTEMGQE VTLRCKPISGHNSLFWYRQTMMRGLELLIYFNNNVPI DDSGMPEDRFSAKMPNASFSTLKIQPSEPRDSAVYFC ASSSGGANTEAFFGQGTRLTVVEDLNKVFPPEVAVFE PSEAEISHTQKATLVCLATGFFPDHVELSWWVNGKEV HSGVSTDPQPLKEQPALNDSRYCLSSRLRVSATFWQN PRNHFRCQVQFYGLSENDEWTQDRAKPVTQIVSAEAW GRADCGFTSVSYQQGVLSATILYEILLGKATLYAVLV SALVLMAMVKRKDFRAKRSGSGATNFSLLKQAGDVEE NPGPMKKHLTTFLVILWLYFYRGNGKNQVEQSPQSLI ILEGKNCTLQCNYTVSPFSNLRWYKQDTGRGPVSLTI MTFSENTKSNGRYTATLDADTKQSSLHITASQLSDSA SYICVVRGGAAGNKLTFGGGTRVLVKPNIQNPDPAVY QLRDSKSSDKSVCLFTDFDSQTNVSQSKDSDVYITDK TVLDMRSMDFKSNSAVAWSNKSDFACANAFNNSIIPE DTFFPSPESSCDVKLVEKSFETDTNLNFQNLSVIGFR ILLLKVAGFNLLMTLRLWSS |
| 92 | Immature TCR0086 β chain-P2A cleavage site-TCR0086 α chain sequence | MGSRLLCWVLLCLLGAGPVKAGVTQTPRYLIKTRGQQ VTLSCSPISGHRSVSWYQQTPGQGLQFLFEYFSETQR NKGNFPGRFSGRQFSNSRSEMNVSTLELGDSALYLCA SSLGRGYEQYFGPGTRLTVTEDLNKVFPPEVAVFEPS EAEISHTQKATLVCLATGFFPDHVELSWWVNGKEVHS GVSTDPQPLKEQPALNDSRYCLSSRLRVSATFWQNPR NHFRCQVQFYGLSENDEWTQDRAKPVTQIVSAEAWGR ADCGFTSVSYQQGVLSATILYEILLGKATLYAVLVSA LVLMAMVKRKDFGSGATNFSLLKQAGDVEENPGPMET LLGLLILWLQLQWVSSKQEVTQIPAALSVPEGENLVL NCSFTDSAIYNLQWFRQDPGKGLTSLLLIQSSQREQT SGRLNASLDKSSGRSTLYIAASQPGDSATYLCAVMLW NQGGKLIFGQGTELSVKPYIQNPDPAVYQLRDSKSSD KSVCLFTDFDSQTNVSQSKDSDVYITDKTVLDMRSMD FKSNSAVAWSNKSDFACANAFNNSIIPEDTFFPSPES SCDVKLVEKSFETDTNLNFQNLSVIGFRILLLKVAGF NLLMTLRLWSSGS |

TABLE 2

Alpha chain CDR amino acid sequences of exemplary MLL TCRs. *

| Vα (SEQ ID NO:) | CDR1α (SEQ ID NO:) | CDR2α (SEQ ID NO:) | CDR3α (SEQ ID NO:) |
|---|---|---|---|
| TCR0077 Vα (1)/ TCR0078 Vα (86) | SVFSS (11) | VVTGGEV (16) | AGYGGGSNYKLT (21) |
| TCR0079 Vα (3)/ TCR0080 Vα (88) | VSPFSN (12) | MTFSENT (17) | VVRGGAAGNKLT (22) |
| TCR0081 Vα (5) | SSVPPY (13) | YTTGATLV (18) | AVSARYNFNKFY (23) |
| TCR0082 Vα (106) | SSVPPY (13) | YTSAATLV (109) | AVSARYNFNKFY (23) |
| TCR0083 Vα (7)/ TCR0084 Vα (7) | VSGLRG (14) | LYSAGEE (19) | AVRNTGFQKLV (24) |
| TCR0085 Vα (9)/ TCR0086 Vα (9) | DSAIYN (15) | IQSSQRE (20) | AVMLWNQGGKLI (25) |

*CDRs are defined according to Lefranc et al., Dev Comp Immunol. 2003; 27(1): 55-77.

TABLE 3

Beta chain CDR amino acid sequences of exemplary MLL TCRs.*

| Vβ (SEQ ID NO:) | CDR1β (SEQ ID NO:) | CDR2β (SEQ ID NO:) | CDR3β (SEQ ID NO:) |
|---|---|---|---|
| TCR0077 Vβ (2)/ TCR0078 Vβ (87) | MNHEY (26) | SMNVEV (31) | ASRLTGRVHGYT (36) |
| TCR0079 Vβ (4)/ TCR0080 Vβ (89) | SGHNS (27) | FNNNVP (32) | ASSSGGANTEAF (37) |
| TCR0081 Vβ (6)/ TCR0082 Vβ (107) | SGDLS (28) | YYNGEE (33) | ASSASGGRSYEQY (38) |
| TCR0083 Vβ (8)/ TCR0084 Vβ (108) | SEHNR (29) | FQNEAQ (34) | ASSWRTGREETQY (39) |
| TCR0085 Vβ (10)/ TCR0086 Vβ (10) | SGHRS (30) | YFSETQ (35) | ASSLGRGYEQY (40) |

*CDRs are defined according to Lefranc et al, Dev Comp Immunol. 2003; 27(1): 55-77.

TABLE 4

Variable region amino acid sequences of exemplary MLL TCRs.

| Chimeric TCR name | SEQ ID NO of Vα | SEQ ID NO of Vβ | Human TCR name | SEQ ID NO of Vα | SEQ ID NO of Vβ |
|---|---|---|---|---|---|
| TCR0077 | 1 | 2 | TCR0078 | 86 | 87 |
| TCR0079 | 3 | 4 | TCR0080 | 88 | 89 |
| TCR0081 | 5 | 6 | TCR0082 | 106 | 107 |
| TCR0083 | 7 | 8 | TCR0084 | 7 | 108 |
| TCR0085 | 9 | 10 | TCR0086 | 9 | 10 |

TABLE 5

Exemplary peptide sequences.

| SEQ ID NO: | Description | Amino acid Sequence |
|---|---|---|
| 45 | MLL-pM | EPR[pS]PSHSM |
| 46 | MLL-M | EPRSPSHSM |
| 47 | MLL-pP | RVR[pS]PTRSP |
| 48 | MLL-P | RVRSPTRSP |
| 49 | MLL-pM-A1 | APR[pS]PSHSM |
| 50 | MLL-pM-A2 | EAR[pS]PSHSM |
| 51 | MLL-pM-A3 | EPA[pS]PSHSM |
| 52 | MLL-pM-A4 | EPRAPSHSM |
| 53 | MLL-pM-A5 | EPR[pS]ASHSM |
| 54 | MLL-pM-A6 | EPR[pS]PAHSM |
| 55 | MLL-pM-A7 | EPR[pS]PSASM |
| 56 | MLL-pM-A8 | EPR[pS]PSHAM |
| 57 | MLL-pM-A9 | EPR[pS]PSHSA |
| 84 | Flu peptide | QPEWFRNVL |
| 85 | CMV peptide | TPRVTGGGAM |

The CDRs of a TCR disclosed herein can be defined using any art recognized numbering convention. Additionally or alternatively, the CDRs can be defined empirically, e.g., based upon structural analysis of the interaction of the TCR with a cognate antigen (e.g., a peptide or a peptide-MHC complex).

In certain embodiments, the instant disclosure provides a TCR that binds to a peptide consisting of the amino acid sequence set forth in SEQ ID NO: 45 (e.g., a TCR that binds to a EPR[pS]PSHSM (SEQ ID NO: 45)-HLA-B*0702 complex) or a peptide consisting of the amino acid sequence set forth in SEQ ID NO: 47 (e.g., a TCR that binds to a RVR[pS]PTRSP (SEQ ID NO: 47)-HLA-B*0702 complex), wherein the TCR comprises one, two, or all three of the CDRs of a Vα or Vβ disclosed in Table 1 herein, wherein the CDRs are defined according to the IMGT numbering system, for example, as described in Lefranc M-P (1999) supra and Lefranc M-P et al., (1999) supra.

In certain embodiments, the instant disclosure provides a TCR that binds to a peptide consisting of the amino acid sequence set forth in SEQ ID NO: 45 (e.g., a TCR that binds to a EPR[pS]PSHSM (SEQ ID NO: 45)-HLA-B*0702 complex) or a peptide consisting of the amino acid sequence set forth in SEQ ID NO: 47 (e.g., a TCR that binds to a RVR[pS]PTRSP (SEQ ID NO: 47)-HLA-B*0702 complex), wherein the TCR comprises one, two, or all three of the CDRs of a Vα or Vβ disclosed in Table 1 herein, wherein the CDRs are defined according to the Kabat numbering system described in Kabat supra.

In certain embodiments, the instant disclosure provides a TCR that binds to a peptide consisting of the amino acid sequence set forth in SEQ ID NO: 45 (e.g., a TCR that binds to a EPR[pS]PSHSM (SEQ ID NO: 45)-HLA-B*0702 complex) or a peptide consisting of the amino acid sequence set forth in SEQ ID NO: 47 (e.g., a TCR that binds to a RVR[pS]PTRSP (SEQ ID NO: 47)-HLA-B*0702 complex), wherein the TCR comprises one, two, or all three of the CDRs of a Vα or Vβ disclosed in Table 1 herein, wherein the CDRs are determined empirically, e.g., based upon structural analysis of the interaction of the TCR with a cognate antigen (e.g., a peptide-MHC complex).

In certain embodiments, the instant disclosure provides a TCR that binds to SEQ ID NO: 45 (e.g., a TCR that binds to a EPR[pS]PSHSM (SEQ ID NO: 45)-HLA-B*0702 complex) or a peptide consisting of the amino acid sequence set forth in SEQ ID NO: 47 (e.g., a TCR that binds to a RVR[pS]PTRSP (SEQ ID NO: 47)-HLA-B*0702 complex), wherein the TCR comprises one, two, or all three of the CDRs of a Vα or Vβ disclosed in Table 1 herein, wherein each CDR is defined in accordance with the IMGT or the Kabat numbering system, or is determined empirically, e.g., based upon structural analysis of the interaction of the TCR with a cognate antigen (e.g., a peptide or a peptide-MHC complex).

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences of SEQ ID NO: 1, respectively, and the CDR1β, CDR2β, and CDR3β comprise the CDR1β, CDR2β, and CDR3β amino acid sequences of SEQ ID NO: 2, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences of SEQ ID NO: 86, respectively, and the CDR1β, CDR2β, and CDR3β comprise the CDR1β, CDR2β, and CDR3β amino acid sequences of SEQ ID NO: 87, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences of SEQ ID NO: 3, respectively, and the CDR1β, CDR2β, and CDR3β comprise the CDR1β, CDR2β, and CDR3β amino acid sequences of SEQ ID NO: 4, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences of SEQ ID NO: 88, respectively, and the CDR1β, CDR2β, and CDR3β comprise the CDR1β, CDR2β, and CDR3β amino acid sequences of SEQ ID NO: 89, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences of SEQ ID NO: 5, respectively, and the CDR1β, CDR2β, and CDR3β comprise the CDR1β, CDR2β, and CDR3β amino acid sequences of SEQ ID NO: 6, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences of SEQ ID NO: 106, respectively, and the CDR1β, CDR2β, and CDR3β comprise the CDR1β, CDR2β, and CDR3β amino acid sequences of SEQ ID NO: 107, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences of SEQ ID NO: 7, respectively, and the CDR1β, CDR2β, and CDR3β comprise the CDR1β, CDR2β, and CDR3β amino acid sequences of SEQ ID NO: 8, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences of SEQ ID NO: 7, respectively, and the CDR1β, CDR2β, and CDR3β comprise the CDR1β, CDR2β, and CDR3β amino acid sequences of SEQ ID NO: 108, respectively. In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising a Vα comprising CDR1α, CDR2α, and CDR3α and a Vβ comprising CDR1β, CDR2β, and CDR3β, wherein the CDR1α, CDR2α, and CDR3α comprise the CDR1α, CDR2α, and CDR3α amino acid sequences of SEQ ID NO: 9, respectively, and the CDR1β, CDR2β, and CDR3β comprise the CDR1β, CDR2β, and CDR3β amino acid sequences of SEQ ID NO: 10, respectively. In one embodiment, each CDR is defined in accordance with the IMGT numbering system. In one embodiment, each CDR is defined in accordance with the Kabat numbering system. In one embodiment, each CDR is defined empirically, e.g., based upon structural analysis of the interaction of the TCR with a cognate antigen (e.g., a peptide or a peptide-MHC complex). In one embodiment, each CDR is independently defined in accordance with the IMGT or Kabat numbering system, or is determined empirically, e.g., based upon structural analysis of the interaction of the TCR with a cognate antigen (e.g., a peptide-MHC complex).

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising:
(a) a CDR1α comprising the amino acid sequence of SEQ ID NO: 11, and/or
(b) a CDR2α comprising the amino acid sequence of SEQ ID NO: 16, and/or
(c) a CDR3α comprising the amino acid sequence of SEQ ID NO: 21, and/or
(d) a CDR1β comprising the amino acid sequence of SEQ ID NO: 26, and/or (e) a CDR2β comprising the amino acid sequence of SEQ ID NO: 31, and/or (f) a CDR3β comprising the amino acid sequence of SEQ ID NO: 36.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising:

(a) a CDR1α comprising the amino acid sequence of SEQ ID NO: 12, and/or (b) a CDR2α comprising the amino acid sequence of SEQ ID NO: 17, and/or (c) a CDR3α comprising the amino acid sequence of SEQ ID NO: 22, and/or (d) a CDR1β comprising the amino acid sequence of SEQ ID NO: 27, and/or (e) a CDR2β comprising the amino acid sequence of SEQ ID NO: 32, and/or (f) a CDR3β comprising the amino acid sequence of SEQ ID NO: 37.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising (a) a CDR1α comprising the amino acid sequence of SEQ ID NO: 13, and/or (b) a CDR2α comprising the amino acid sequence of SEQ ID NO: 18, and/or (c) a CDR3α comprising the amino acid sequence of SEQ ID NO: 23, and/or (d) a CDR1β comprising the amino acid sequence of SEQ ID NO: 28, and/or (e) a CDR2β comprising the amino acid sequence of SEQ ID NO: 33, and/or (f) a CDR3β comprising the amino acid sequence of SEQ ID NO: 38.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising (a) a CDR1α comprising the amino acid sequence of SEQ ID NO: 13, and/or (b) a CDR2α comprising the amino acid sequence of SEQ ID NO: 109, and/or (c) a CDR3α comprising the amino acid sequence of SEQ ID NO: 23, and/or (d) a CDR1β comprising the amino acid sequence of SEQ ID NO: 28, and/or (e) a CDR2β comprising the amino acid sequence of SEQ ID NO: 33, and/or (f) a CDR3β comprising the amino acid sequence of SEQ ID NO: 38.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising (a) a CDR1α comprising the amino acid sequence of SEQ ID NO: 14, and/or (b) a CDR2α comprising the amino acid sequence of SEQ ID NO: 19, and/or (c) a CDR3α comprising the amino acid sequence of SEQ ID NO: 24, and/or (d) a CDR1β comprising the amino acid sequence of SEQ ID NO: 29, and/or (e) a CDR2β comprising the amino acid sequence of SEQ ID NO: 34, and/or (f) a CDR3β comprising the amino acid sequence of SEQ ID NO: 39.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising (a) a CDR1α comprising the amino acid sequence of SEQ ID NO: 15, and/or (b) a CDR2α comprising the amino acid sequence of SEQ ID NO: 20, and/or (c) a CDR3α comprising the amino acid sequence of SEQ ID NO: 25, and/or (d) a CDR1β comprising the amino acid sequence of SEQ ID NO: 30, and/or (e) a CDR2β comprising the amino acid sequence of SEQ ID NO: 35, and/or (f) a CDR3β comprising the amino acid sequence of SEQ ID NO: 40.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a CDR3α comprising the amino acid sequence of SEQ ID NO: 21 and/or a CDR3β comprising the amino acid sequence of SEQ ID NO: 36. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a CDR3α comprising the amino acid sequence of SEQ ID NO: 22 and/or a CDR3β comprising the amino acid sequence of SEQ ID NO: 37. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a CDR3α comprising the amino acid sequence of SEQ ID NO: 23 and/or a CDR3β comprising the amino acid sequence of SEQ ID NO: 38. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a CDR3α comprising the amino acid sequence of SEQ ID NO: 24 and/or a CDR3β comprising the amino acid sequence of SEQ ID NO: 39. In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising a CDR3α comprising the amino acid sequence of SEQ ID NO: 25 and/or a CDR3β comprising the amino acid sequence of SEQ ID NO: 40.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), wherein the TCR comprises a Vα having the CDR1α, CDR2α, and CDR3α amino acid sequences set forth in SEQ ID NOs: 11, 16, and 21; 12, 17, and 22; 13, 18, and 23; 13, 109, and 23; or 14, 19, and 24, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), wherein the TCR comprises a Vα having the CDR1α, CDR2α, and CDR3α amino acid sequences set forth in SEQ ID NOs: 11, 16, and 21, respectively.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), wherein the TCR comprises a Vβ having the CDR1β, CDR2β, and CDR3β amino acid sequences set forth in SEQ ID NOs: 26, 31, and 36; 27, 32, and 37; 28, 33, and 38; or 29, 34, and 39, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), wherein the TCR comprises a Vβ having the CDR1β, CDR2β, and CDR3β amino acid sequences set forth in SEQ ID NOs: 26, 31, and 36, respectively.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), wherein the TCR comprises a Vα having the CDR1α, CDR2α, and CDR3α amino acid sequences set forth in SEQ ID NOs: 15, 20, and 25, respectively.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), wherein the TCR comprises a Vβ having the CDR1β, CDR2β, and CDR3β amino acid sequences set forth in SEQ ID NOs: 30, 35, and 40, respectively.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), wherein the TCR comprises a Vα having CDR1α, CDR2α, and CDR3α, and a Vβ having CDR1β, CDR2β, and CDR3β, and wherein the CDR1α, CDR2α, CDR3α, CDR1β, CDR2β, and CDR3β comprise the amino acid sequences set forth in SEQ ID NOs: 11, 16, 21, 26, 31, and 36; 12, 17, 22, 27, 32, and 37; 13, 18, 23, 28, 33, and 38; 13, 109, 23, 28, 33, and 38; or 14, 19, 24, 29, 34, and 39, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS] PSHSM (SEQ ID NO: 45)-HLA-B*0702 complex), wherein the TCR comprises a Vα having CDR1α, CDR2α, and CDR3α, and a Vβ having CDR1β, CDR2β, and CDR3β, and wherein the CDR1α, CDR2α, CDR3α, CDR1β, CDR2β, and CDR3β comprise the amino acid sequences set forth in SEQ ID NOs: 11, 16, 21, 26, 31, and 36, respectively.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), wherein the TCR comprises a Vα having CDR1α, CDR2α, and CDR3α, and a Vβ having CDR1β, CDR2β, and CDR3β, and wherein the CDR1α, CDR2α, CDR3α, CDR1β, CDR2β, and CDR3β comprise the amino acid sequences set forth in SEQ ID NOs: 15, 20, 25, 30, 35, and 40, respectively.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 3, 5, 7, 86, 88, or 106. In certain embodiments, the TCR comprises a Vα having the amino acid sequence set forth in SEQ ID NO: 1, 3, 5, 7, 86, 88, or 106. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS] PSHSM (SEQ ID NO: 45)-HLA-B*0702 complex), the TCR comprising a Vα having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 86. In certain embodiments, the TCR comprises a Vα having the amino acid sequence set forth in SEQ ID NO: 86.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vβ having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 2, 4, 6, 8, 87, 89, 107, or 108. In certain embodiments, the TCR comprises a Vβ having the amino acid sequence set forth in SEQ ID NO: 2, 4, 6, 8, 87, 89, 107, or 108. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vβ having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 87. In certain embodiments, the TCR comprises a Vβ having the amino acid sequence set forth in SEQ ID NO: 87.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising a Vα having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 9. In certain embodiments, the TCR comprises a Vα having the amino acid sequence set forth in SEQ ID NO: 9.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising a Vβ having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 10. In certain embodiments, the TCR comprises a Vβ having the amino acid sequence set forth in SEQ ID NO: 10.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 1, 3, 5, 7, 86, 88, 106, and a Vβ having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 2, 4, 6, 8, 87, 89, 107, or 108. In certain embodiments, the TCR comprises a Vα and a Vβ comprising the amino acid sequences set forth in SEQ ID NOs: 1 and 2, 3 and 4, 5 and 6, 7 and 8, 86 and 87, 88 and 89, 106 and 107, 7 and 108, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 86, and a Vβ having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 87. In certain embodiments, the TCR comprises a Vα and a Vβ comprising the amino acid sequences set forth in SEQ ID NOs: 86 and 87, respectively.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising a Vα having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 9, and a Vβ having an amino acid sequence that is at least 75%, 80%, 85%, 90%, 95%, or 100% (e.g., at least 86, 87, 88, 89, 90, 91, 92, 93, 94, 95, 96, 97, 98 or 99%) identical to the amino acid sequence set forth in SEQ ID NO: 10. In certain embodiments, the TCR comprises a Vα and a Vβ comprising the amino acid sequences set forth in SEQ ID NOs: 9 and 10, respectively.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα having an amino acid sequence derived from a human TRAV27 germline sequence (e.g., comprising the amino acid sequence of SEQ ID NO: 73). One or more regions selected from framework 1, framework 2, framework 3, CDR1α, and CDR2α (e.g., two, three, four, or five of these regions) can be derived from a human TRAV27 germline sequence (e.g., comprising the amino acid sequence of SEQ ID NO: 73). In certain embodiments, framework 1, framework 2, framework 3, CDR1α, and CDR2α are all derived from a human TRAV27 germline sequence (e.g., comprising the amino acid sequence of SEQ ID NO: 73). In certain embodiments, the TCR comprises a Vα having an amino acid sequence derived a human TRAV27 germline sequence (e.g., comprising the amino acid sequence of SEQ ID NO: 73) and a CDR3α having the amino acid sequence set forth in SEQ ID NO: 21.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vβ having an amino acid sequence derived from a human TRBV27 germline sequence (e.g., comprising the amino acid sequence of SEQ ID NO: 74). One or more regions selected from framework 1, framework 2, framework 3, CDR1β, and CDR2β (e.g., two, three, four or five of these regions) can be derived from a human TRBV27 germline sequence (e.g., comprising the amino acid sequence of SEQ ID NO: 74). In certain embodiments, framework 1, framework 2, framework 3, CDR1β, and CDR2β are all derived from a human TRBV27 germline sequence (e.g., comprising the amino acid sequence of SEQ ID NO: 74). In certain embodiments, the TCR comprises a Vβ having an amino acid sequence derived from a human TRBV27 germline sequence (e.g., comprising the amino acid sequence of SEQ ID NO: 74) and a CDR3β having the amino acid sequence set forth in SEQ ID NO: 36.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα having an amino acid sequence derived from a human TRAV10 germline sequence (e.g., comprising the amino acid sequence of SEQ ID NO: 75). One or more regions selected from framework 1, framework 2, framework 3, CDR1α, and CDR2α (e.g., two, three, four, or five of these regions) can be derived from a human TRAV10 germline sequence (e.g., comprising the amino acid sequence of SEQ ID NO: 75). In certain embodiments, framework 1, framework 2, framework 3, CDR1α, and CDR2α are all derived from a human TRAV10 germline sequence (e.g., comprising the amino acid sequence of SEQ ID NO: 75). In certain embodiments, the TCR comprises a Vα having an amino acid sequence derived a human TRAV10 germline sequence (e.g., comprising the amino acid sequence of SEQ ID NO: 75) and a CDR3α having the amino acid sequence set forth in SEQ ID NO: 22.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vβ having an amino acid sequence derived from a human TRBV12-3 germline sequence (e.g., comprising the amino acid sequence of SEQ ID NO: 76). One or more regions selected from framework 1, framework 2, framework 3, CDR1β, and CDR2β (e.g., two, three, four or five of these regions) can be derived from a human TRBV12-3 germline sequence (e.g., comprising the amino acid sequence of SEQ ID NO: 76). In certain embodiments, framework 1, framework 2, framework 3, CDR1β, and CDR2β are all derived from a human TRBV12-3 germline sequence (e.g., comprising the amino acid sequence of SEQ ID NO: 76). In certain embodiments, the TCR comprises a Vβ having an amino acid sequence derived from a human TRBV12-3 germline sequence (e.g., comprising the amino acid sequence of SEQ ID NO: 76) and a CDR3β having the amino acid sequence set forth in SEQ ID NO: 37.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα having an amino acid sequence derived from a human TRAV8-4 germline sequence (e.g., comprising the amino acid sequence of SEQ ID NO: 77). One or more regions selected from framework 1, framework 2, framework 3, CDR1α, and CDR2α (e.g., two, three, four, or five of these regions) can be derived from a human TRAV8-4 germline sequence (e.g., comprising the amino acid sequence of SEQ ID NO: 77). In certain embodiments, framework 1, framework 2, framework 3, CDR1α, and CDR2α are all derived from a human TRAV8-4 germline sequence (e.g., comprising the amino acid sequence of SEQ ID NO: 77). In certain embodiments, the TCR comprises a Vα having an amino acid sequence derived a human TRAV8-4 germline sequence (e.g., comprising the amino acid sequence of SEQ ID NO: 77) and a CDR3α having the amino acid sequence set forth in SEQ ID NO: 23.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vβ having an amino acid sequence derived from a human TRBV9 germline sequence (e.g., comprising the amino acid sequence of SEQ ID NO: 78). One or more regions selected from framework 1, framework 2, framework 3, CDR1β, and CDR2β (e.g., two, three, four or five of these regions) can be derived from a human TRBV9 germline sequence (e.g., comprising the amino acid sequence of SEQ ID NO: 78). In certain embodiments, framework 1, framework 2, framework 3, CDR1β, and CDR2β are all derived from a human TRBV9 germline sequence (e.g., comprising the amino acid sequence of SEQ ID NO: 78). In certain embodiments, the TCR comprises a Vβ having an amino acid sequence derived from a human TRBV9 germline sequence (e.g., comprising the amino acid sequence of SEQ ID NO: 78) and a CDR3β having the amino acid sequence set forth in SEQ ID NO: 38.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vα having an amino acid sequence derived from a human TRAV20 germline sequence (e.g., comprising the amino acid sequence of SEQ ID NO: 79). One or more regions selected from framework 1, framework 2, framework 3, CDR1α, and CDR2α (e.g., two, three, four or five of these regions) can be derived from a human TRAV20 germline sequence (e.g., comprising the amino acid sequence of SEQ ID NO: 79). In certain embodiments, framework 1, framework 2, framework 3, CDR1α, and CDR2α are all derived from a human TRAV20 germline sequence (e.g., comprising the amino acid sequence of SEQ ID NO: 79). In certain embodiments, the TCR comprises a Vα having an amino acid sequence derived a human TRAV20 germline sequence (e.g., comprising the amino acid sequence of SEQ ID NO: 79) and a CDR3α having the amino acid sequence set forth in SEQ ID NO: 24.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising a Vβ having an amino acid sequence derived from a human TRBV7-9 germline sequence (e.g., comprising the amino acid sequence of SEQ ID NO: 80). One or more regions selected from framework 1, framework 2, framework 3, CDR1β, and CDR2β (e.g., two, three, four or five of these regions) can be derived from a human TRBV7-9 germline sequence (e.g., comprising the amino acid sequence of SEQ ID NO: 80). In certain embodiments, framework 1, framework 2, framework 3, CDR1β, and CDR2β are all derived from a human TRBV7-9 germline sequence (e.g., comprising the amino acid sequence of SEQ ID NO: 80). In certain embodiments, the TCR comprises a Vβ having an amino acid sequence derived from a human TRBV7-9 germline sequence (e.g., comprising the amino acid sequence of SEQ ID NO: 80) and a CDR3β having the amino acid sequence set forth in SEQ ID NO: 39.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising a Vα having an amino acid sequence derived from a human TRAV21 germline sequence (e.g., comprising the amino acid sequence of SEQ ID NO: 81). One or more regions selected from framework 1, framework 2, framework 3, CDR1α, and CDR2α (e.g., two, three, four, or five of these regions) can be derived from a human TRAV21 germline sequence (e.g., comprising the amino acid sequence of SEQ ID NO: 81). In certain embodiments, framework 1, framework 2, framework 3, CDR1α, and CDR2α are all derived from a human TRAV21 germline sequence (e.g., comprising the amino acid sequence of SEQ ID NO: 81). In certain embodiments, the TCR comprises a Vα having an amino acid sequence derived a human TRAV21 germline sequence (e.g., comprising the amino acid sequence of SEQ ID NO: 81) and a CDR3α having the amino acid sequence set forth in SEQ ID NO: 25.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising a Vβ having an amino acid sequence derived from a human TRBVS-1 germline sequence (e.g., comprising the amino acid sequence of SEQ ID NO: 82). One or more regions selected from framework 1, framework 2, framework 3, CDR1β, and CDR2β (e.g., two, three, four or five of these regions) can be derived from a human TRBVS-1 germline sequence (e.g., comprising the amino acid sequence of SEQ ID NO: 82). In certain embodiments, framework 1, framework 2, framework 3, CDR1β, and CDR2β are all derived from a human TRBVS-1 germline sequence (e.g., comprising the amino acid sequence of SEQ ID NO: 82). In certain embodiments, the TCR comprises a Vβ having an amino acid sequence derived from a human TRBVS-1 germline sequence (e.g., comprising the amino acid sequence of SEQ ID NO: 82) and a CDR3β having the amino acid sequence set forth in SEQ ID NO: 40.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO:

45)-HLA-B*0702 complex), the TCR comprising an α chain and a β chain comprising the amino acid sequences set forth in SEQ ID NOs: 249 and 250, 251 and 252, 253 and 254, 255 and 256, or 257 and 258, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 249 and 250, 251 and 252, 253 and 254, 255 and 256, or 257 and 258, respectively. In certain embodiments, the α chain further comprises the amino acid sequence of GSGATNFSLLKQAGDVEENPG (SEQ ID NO: 93) at the C-terminus, or the β chain further comprises the amino acid sequence of GSGATNFSLLKQAGDVEENPG (SEQ ID NO: 93) at the C-terminus. In certain embodiments, the α chain further comprises the amino acid sequence of GS at the C-terminus, or the β chain further comprises the amino acid sequence of GS at the C-terminus. In certain embodiment, the α chain further comprises the amino acid sequence of GS at the C-terminus, and the β chain further comprises the amino acid sequence of GSGATNFSLLKQAGD-VEENPG (SEQ ID NO: 93) at the C-terminus.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 58 and 59, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 58 and 60, respectively. In certain embodiments, the α chain further comprises the amino acid sequence of GSGATNFSLLKQAGDVEENPG (SEQ ID NO: 93) at the C-terminus, or the β chain further comprises the amino acid sequence of GSGATNFSLLKQAGDVEENPG (SEQ ID NO: 93) at the C-terminus. In certain embodiments, the α chain further comprises the amino acid sequence of GS at the C-terminus, or the β chain further comprises the amino acid sequence of GS at the C-terminus. In certain embodiment, the α chain further comprises the amino acid sequence of GS at the C-terminus, and the β chain further comprises the amino acid sequence of GSGATNFSLLKQAGD-VEENPG (SEQ ID NO: 93) at the C-terminus. In certain embodiments, the α chain and the β chain comprise the amino acid sequences set forth in SEQ ID NOs: 236 and 237, respectively. In certain embodiments, the α chain comprises an amino acid sequences selected from the group consisting of SEQ ID NOs: 58, 236, 259, 260, 272, and 261, and the β chain further comprises an amino acid sequences selected from the group consisting of SEQ ID NOs: 59, 237, 262, 263, 264, 273, and 60, respectively.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 61 and 62, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 61 and 63, respectively. In certain embodiments, the α chain further comprises the amino acid sequence of GSGATNFSLLKQAGDVEENPG (SEQ ID NO: 93) at the C-terminus, or the β chain further comprises the amino acid sequence of GSGATNFSLLKQAGDVEENPG (SEQ ID NO: 93) at the C-terminus. In certain embodiments, the α chain further comprises the amino acid sequence of GS at the C-terminus, or the β chain further comprises the amino acid sequence of GS at the C-terminus. In certain embodiment, the α chain further comprises the amino acid sequence of GS at the C-terminus, and the β chain further comprises the amino acid sequence of GSGATNFSLLKQAGD-VEENPG (SEQ ID NO: 93) at the C-terminus.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 64 and 65, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 64 and 66, respectively. In certain embodiments, the α chain further comprises the amino acid sequence of GSGATNFSLLKQAGDVEENPG (SEQ ID NO: 93) at the C-terminus, or the β chain further comprises the amino acid sequence of GSGATNFSLLKQAGDVEENPG (SEQ ID NO: 93) at the C-terminus. In certain embodiments, the α chain further comprises the amino acid sequence of GS at the C-terminus, or the β chain further comprises the amino acid sequence of GS at the C-terminus. In certain embodiment, the α chain further comprises the amino acid sequence of GS at the C-terminus, and the β chain further comprises the amino acid sequence of GSGATNFSLLKQAGD-VEENPG (SEQ ID NO: 93) at the C-terminus.

In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 67 and 68, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 67 and 69, respectively. In certain embodiments, the α chain further comprises the amino acid sequence of GSGATNFSLLKQAGDVEENPG (SEQ ID NO: 93) at the C-terminus, or the β chain further comprises the amino acid sequence of GSGATNFSLLKQAGDVEENPG (SEQ ID NO: 93) at the C-terminus. In certain embodiments, the α chain further comprises the amino acid sequence of GS at the C-terminus, or the β chain further comprises the amino acid sequence of GS at the C-terminus. In certain embodiment, the α chain further comprises the amino acid sequence of GS at the C-terminus, and the β chain further comprises the amino acid sequence of GSGATNFSLLKQAGD-VEENPG (SEQ ID NO: 93) at the C-terminus.

In certain embodiments, the instant disclosure provides a TCR (e.g., an isolated TCR) that binds to a peptide consisting of the amino acid sequence set forth in SEQ ID NO: 47 (e.g., a TCR that binds to a RVR[pS]PTRSP (SEQ ID NO: 47)-HLA-B*0702 complex), the TCR comprising an α chain and a β chain comprising the amino acid sequences set forth in SEQ ID NOs: 70 and 71, respectively. In certain embodiments, the instant disclosure provides a TCR (e.g., an isolated TCR) that binds to a peptide consisting of the amino acid sequence set forth in SEQ ID NO: 45 (e.g., a TCR that binds to a EPR[pS]PSHSM (SEQ ID NO: 45)-HLA-B*0702 complex), the TCR comprising an α chain and a β chain comprising the amino acid sequences set forth in SEQ ID NOs: 70 and 72, respectively. In certain embodiments, the α chain further comprises the amino acid sequence of GSGATNFSLLKQAGDVEENPG (SEQ ID NO: 93) at the C-terminus, or the β chain further comprises the amino acid sequence of GSGATNFSLLKQAGDVEENPG (SEQ ID NO: 93) at the C-terminus. In certain embodiments, the α chain further comprises the amino acid sequence of GS at the C-terminus, or the β chain further comprises the amino acid sequence of GS at the C-terminus. In certain embodiment, the α chain further comprises the amino acid sequence of GS at the C-terminus, and the β chain further comprises the amino acid sequence of GSGATNFSLLKQAGD-VEENPG (SEQ ID NO: 93) at the C-terminus.

In another aspect, provided herein are TCRs which bind to the same epitope (e.g., the same amino acid residues) of a peptide comprising the amino acid sequence set forth in SEQ ID NO: 45 or 47 as the TCRs described supra. In certain embodiments, the peptide is in complex with an MHC as described supra (e.g., HLA-B*0702). In certain embodiments, the TCR comprises sequences that do not naturally exist within the TCR germline repertoire of an animal or mammal (e.g., human) in vivo.

In one aspect, provided herein is a TCR that binds to one, two, three, or all four of: i) a peptide consisting of the amino acid sequence set forth in SEQ ID NO: 45, ii) a peptide consisting of the amino acid sequence set forth in SEQ ID NO: 51, iii) a peptide consisting of the amino acid sequence set forth in SEQ ID NO: 56, and iv) a peptide consisting of an amino acid sequence selected from the group consisting of SEQ ID NOs: 117, 128, 135, 192, and 233. In one embodiment, the TCR does not bind to, or does not substantially bind to: i) a peptide consisting of the amino acid sequence set forth in SEQ ID NO: 46, ii) a peptide consisting of the amino acid sequence set forth in SEQ ID NO: 49, 50, 52, 53, 54, 55, or 57, or iii) a peptide consisting of the amino acid sequence set forth in SEQ ID NO: 47, or iv) any combination thereof, e.g., as measured in a flow cytometry analysis or a Biacore analysis. In one embodiment, the TCR does not bind to, or does not substantially bind to, any of: i) a peptide consisting of the amino acid sequence set forth in SEQ ID NO: 46, ii) a peptide consisting of the amino acid sequence set forth in SEQ ID NO: 49, iii) a peptide consisting of the amino acid sequence set forth in SEQ ID NO: 50, iv) a peptide consisting of the amino acid sequence set forth in SEQ ID NO: 52, v) a peptide consisting of the amino acid sequence set forth in SEQ ID NO: 53, vi) a peptide consisting of the amino acid sequence set forth in SEQ ID NO: 54, vii) a peptide consisting of the amino acid sequence set forth in SEQ ID NO: 55, viii) a peptide consisting of the amino acid sequence set forth in SEQ ID NO: 57, and ix) a peptide consisting of the amino acid sequence set forth in SEQ ID NO: 47, e.g., as measured in a flow cytometry analysis or a Biacore analysis. In one embodiment, the binding between the TCR and a peptide consisting of the amino acid sequence set forth in SEQ ID NO: 46, 49, 50, 52, 53, 54, 55, 57, or 47 is substantially weakened (e.g., is weakened by at least 30%, 40%, 50%, 60%, 70%, 80%, or 90%) relative to the binding between the TCR and a peptide consisting of the amino acid sequence set forth in SEQ ID NO: 45, 51, 56, 117, 128, 135, 192, or 233, e.g., as measured in a flow cytometry analysis or a Biacore analysis.

In one aspect, provided herein is a TCR, wherein when the TCR is expressed on the surface of a T cell, the T cell is activated: i) when co-cultured with a second cell displaying a peptide consisting of the amino acid sequence set forth in SEQ ID NO: 45, ii) when co-cultured with a second cell displaying a peptide consisting of the amino acid sequence set forth in SEQ ID NO: 51; iii) when co-cultured with a second cell displaying a peptide consisting of the amino acid sequence set forth in SEQ ID NO: 56, or when co-cultured with a second cell displaying a peptide consisting of the amino acid sequence set forth in SEQ ID NOs: 117, 128, 135, 192, and 233, or v) any combination thereof, e.g., as measured by an assay described herein, e.g., as measured using an IL-2-(NFAT)$_3$-EGFP reporter construct. In one embodiment, when the TCR is expressed on the surface of a T cell, the T cell is not activated, or is not substantially activated: i) when co-cultured with a second cell displaying a peptide consisting of the amino acid sequence set forth in SEQ ID NO: 46, ii) when co-cultured with a second cell displaying a peptide consisting of the amino acid sequence set forth in SEQ ID NO: 49, 50, 52, 53, 54, 55, or 57, or iii) when co-cultured with a second cell displaying a peptide consisting of the amino acid sequence set forth in SEQ ID NO: 47, or iv) any combination thereof, e.g., as measured by an assay described herein, e.g., as measured using an IL-2-(NFAT)$_3$-EGFP reporter construct. In one embodiment, when the TCR is expressed on the surface of a T cell, the T cell is not activated, or is not substantially activated, when co-cultured with a second cell displaying any of the following peptides: i) a peptide consisting of the amino acid sequence set forth in SEQ ID NO: 46, ii) a peptide consisting of the amino acid sequence set forth in SEQ ID NO: 49, iii) a peptide consisting of the amino acid sequence set forth in SEQ ID NO: 50, iv) a peptide consisting of the amino acid sequence set forth in SEQ ID NO: 52, v) a peptide consisting of the amino acid sequence set forth in SEQ ID NO: 53, vi) a peptide consisting of the amino acid sequence set forth in SEQ ID NO: 54, vii) a peptide consisting of the amino acid sequence set forth in SEQ ID NO: 55, viii) a peptide consisting of the amino acid sequence set forth in SEQ ID NO: 57, and ix) a peptide consisting of the amino acid sequence set forth in SEQ ID NO: 47, e.g., as measured by an assay described herein, e.g., as measured using an IL-2-(NFAT)$_3$-EGFP reporter construct. In one embodiment, when the TCR is expressed on the surface of a T cell, the activation of the T cell is substantially weakened (e.g., is weakened by at least 30%, 40%, 50%, 60%, 70%, 80%, or 90%) when the T cell is co-cultured with a second cell displaying a peptide consisting of the amino acid sequence set forth in SEQ ID NO: 46, 49, 50, 52, 53, 54, 55, 57, or 47 relative to the activation of the T cell when the T cell is co-cultured with a third cell displaying a peptide consisting of the amino acid sequence set forth in SEQ ID NO: 45, 51, 56, 117, 128, 135, 192, or 233, e.g., as measured by an assay described herein, e.g., using an assay comprising the following steps: (a) expressing the test TCR in a T cell comprising an IL-2-(NFAT)$_3$-EGFP reporter construct; (b) pulsing a HLA-B*0702 positive T2 cell ("T2-B7 cell") with the first peptide or the second peptide; (c) co-culturing the TCR-expressing T cell with the peptide-pulsed T2-B7 target cell at a ratio of 1:2 for 16 hours at 37° C. and 10% $CO_2$; (d) analyzing the expression of TCR and EGFP using flow cytometry; (e) determining the percentage of TCR+ EGFP+ cells; and (0 determining the reduction of T cell activation when co-cultured with a T2-B7 target cell displaying the first peptide relative to when co-cultured with a T2-B7 target cell displaying the second peptide based on the respective percentages of TCR+EGFP+ cells.

Any TCR constant region from any species can be used in the TCRs disclosed herein. In certain embodiments, the TCR comprises a human α, β, γ, or δ TCR constant region. In certain embodiments, the TCR comprises a wild-type constant region. In certain embodiments, the TCR comprises an altered constant region, such as a chimeric constant region or constant region comprising one or more amino acid substitutions, insertions, or deletions relative to a wild-type constant region. In some embodiments, the TCR comprises an α chain comprising an α chain constant region of SEQ ID NO: 41. In some embodiments, the TCR comprises an α chain comprising an α chain constant region of SEQ ID NO: 42. In some embodiments, the TCR comprises a β chain comprising a β chain constant region of SEQ ID NO: 43 or 44. In certain embodiments, the TCR comprises a mouse TCR constant region. In certain embodiments, the TCR comprises a wild-type mouse constant region. In certain embodiments, the TCR comprises an altered mouse constant region, such as a chimeric constant region or constant region comprising one or more amino acid substitutions, insertions, or deletions relative to a wild-type mouse constant region. In some embodiments, the TCR comprises an α chain comprising an α chain constant region of SEQ ID NO: 247. In some embodiments, the TCR comprises a β chain comprising a β chain constant region of SEQ ID NO: 248.

The TCRs disclosed herein can be used in any TCR structural format. For example, in certain embodiments, the TCR is a full-length TCR comprising a full-length a chain and a full-length β chain. The transmembrane regions (and optionally also the cytoplasmic regions) can be removed from a full-length TCR to produce a soluble TCR. Accordingly, in certain embodiments, the TCR is a soluble TCR lacking transmembrane and/or cytoplasmic region(s). The methods of producing soluble TCRs are well-known in the art. In some embodiments, the soluble TCR comprises an engineered disulfide bond that facilitates dimerization, see, e.g., U.S. Pat. No. 7,329,731, which is incorporated by reference herein in its entirety. In some embodiments, the soluble TCR is generated by fusing the extracellular domain of a TCR described herein to other protein domains, e.g., maltose binding protein, thioredoxin, human constant kappa domain, or leucine zippers, see, e.g., Loset et al., Front Oncol. 2014; 4: 378, which is incorporated by reference herein in its entirety. A single-chain TCR (scTCR) comprising Vα and Vβ linked by a peptide linker can also be generated. Such scTCRs can comprise Vα and Vβ, each linked to a TCR constant region. Alternatively, the scTCRs can comprise Vα and Vβ, where either the Vα, the Vβ, or both the Vα and Vβ are not linked to a TCR constant region. Exemplary scTCRs are described in PCT Publication Nos. WO 2003/020763, WO 2004/033685, and WO 2011/044186, each of which is incorporated by reference herein in its entirety. Furthermore, the TCRs disclosed herein can comprise two polypeptide chains (e.g., an α chain and a β chain) in which the chains have been engineered to each have a cysteine residue that can form an interchain disulfide bond. Accordingly, in certain embodiments, the TCRs disclosed herein comprise two polypeptide chains linked by an engineered disulfide bond. Exemplary TCRs having an engineered disulfide bond are described in U.S. Pat. Nos. 8,361,794 and 8,906,383, each of which is incorporated by reference herein in its entirety.

In certain embodiments, the TCRs disclosed herein comprise one or more chains (e.g., an α chain and/or a β chain) having a transmembrane region. In certain embodiments, the TCRs disclosed herein comprise two chains (e.g., an α chain and a β chain) having a transmembrane region. The transmembrane region can be the endogenous transmembrane region of that TCR chain, a variant of the endogenous transmembrane region, or a heterologous transmembrane region. In certain embodiments, the TCRs disclosed herein comprise an α chain and a β chain having endogenous transmembrane regions.

In certain embodiments, the TCRs disclosed herein comprise one or more chains (e.g., an α chain and/or a β chain) having a cytoplasmic region. In certain embodiments, the TCRs disclosed herein comprise two chains (e.g., an α chain and a β chain) each having a cytoplasmic region. The cytoplasmic region can be the endogenous cytoplasmic region of that TCR chain, variant of the endogenous cytoplasmic region, or a heterologous cytoplasmic region. In certain embodiments, the TCRs disclosed herein comprise two chains (e.g., an α chain and a β chain) where both chains have transmembrane regions but one chain is lacking a cytoplasmic region. In certain embodiments, the TCRs disclosed herein comprise two chains (e.g., an α chain and a β chain) where both chains have endogenous transmembrane regions but lack an endogenous cytoplasmic region. In certain embodiments, the TCRs disclosed herein comprise an α chain and a β chain where both chains have endogenous transmembrane regions but lack an endogenous cytoplasmic region. In certain embodiments, the TCRs disclosed herein comprise a co-stimulatory signaling region from a co-stimulatory molecule; see, e.g., PCT Publication Nos.: WO 1996/018105, WO 1999/057268, and WO 2000/031239, and U.S. Pat. No. 7,052,906, all of which incorporated herein by reference in their entireties.

In certain embodiments, the TCRs described herein bind to a peptide-MHC complex comprising a peptide having the amino acid sequence set forth in SEQ ID NO: 45 or 47, wherein the MHC may be any MHC. In certain embodiments, the MHC is a human MHC. In certain embodiments, the MHC is an MHC class I molecule comprising an MHC class I heavy chain (e.g., an HLA-A, an HLA-B, or an HLA-C, including any subtypes in any polymorphic forms) and a β2-microglobulin light chain. In certain embodiments, the MHC is HLA-B*0702. In certain embodiments, the peptide-MHC complex is EPR[pS]PSHSM (SEQ ID NO: 45)-HLA-B*0702. In certain embodiments, the peptide-MHC complex is RVR[pS]PTRSP (SEQ ID NO: 47)-HLA-B*0702. In certain embodiments, the MHC is an MHC class II molecule comprising an MHC class II α chain (e.g., an α chain of an HLA-DR, an HLA-DQ, or an HLA-DP, including any subtypes in any polymorphic forms) and an MHC class II β chain (e.g., a β chain of an HLA-DR, an HLA-DQ, or an HLA-DP, including any subtypes in any polymorphic forms). In certain embodiments, the MHC class II α chain and the MHC class II β chain are derived from the same type (e.g., HLA-DR, HLA-DQ, or HLA-DP).

In certain embodiments, the instant disclosure provides a polypeptide comprising an α chain variable region (Vα) and a β chain variable region (Vβ) of a TCR fused together. For example, such polypeptide may comprise, in order, the Vα and Vβ, or the Vβ and the Vα, optionally with a linker (e.g., a peptide linker) between the two regions. For example, a Furin and/or a 2A cleavage site (e.g., one of the sequences in Table 7), or combinations thereof, may be used in the linker for the Vα/Vβ fusion polypeptide.

In certain embodiments, the instant disclosure provides a polypeptide comprising an α chain and a β chain of a TCR fused together. For example, such polypeptide may comprise, in order, an α chain and a β chain, or a β chain and an α chain, optionally with a linker (e.g., a peptide linker) between the two chains. For example, a Furin and/or a 2A cleavage site (e.g., one of the sequences in Table 7), or combinations thereof, may be used in the linker for the α/β fusion polypeptide. For example, a fusion polypeptide may comprise, from the N-terminus to the C-terminus: the α chain of a TCR, a furin cleavage site, a 2A cleavage site, and the β chain of the TCR. Exemplary α chain-Furin-P2A-β chain fusion TCR sequences for TCR0078 include SEQ ID NOs: 268 and 269. In certain embodiments, the polypeptide comprises, from the N-terminus to the C-terminus: the β chain of a TCR, a furin cleavage site, a 2A element, and the α chain of the TCR. Exemplary β chain-Furin-P2A-α chain fusion TCR sequences include SEQ ID NOs: 265 (for TCR0080), 266 (for TCR0078), and 267 (for TCR0078). In certain embodiments, the polypeptide comprises, from the N-terminus to the C-terminus: the α chain of a TCR, a 2A cleavage site, and the β chain of the TCR. Exemplary α chain-P2A-β chain fusion TCR sequences for TCR0078 include SEQ ID NOs: 270 and 271. In certain embodiments, the polypeptide comprises from the N-terminus to the C-terminus: the β chain of a TCR, a 2A element, and the α chain of the TCR. In certain embodiments, the polypeptide comprises, from the N-terminus to the C-terminus: the α chain of a TCR, a Furin cleavage site, and the β chain of the TCR. In certain embodiments, the polypeptide comprises from the N-terminus to the C-terminus: the β chain of a TCR, a Furin element, and the α chain of the TCR. Exemplary β chain-P2A-α chain fusion TCR sequences include SEQ ID NOs: 83 (for TCR0078), 91 (for TCR0080), and 92 (for TCR0086).

5.3 Cells Presenting T Cell Receptors

In another aspect, the instant disclosure provides a mammalian cell (e.g., an engineered mammalian cell) or a population thereof presenting a TCR disclosed herein on the cell surface. Any mammalian cell can be used to present a TCR disclosed herein. In certain embodiments, the mammalian cell expresses CD3 (e.g., a CD3γ chain, a CD3δ chain, and two CD3ε chains). In certain embodiments, the mammalian cell is a human cell. Effector cells of the cellular immune system are particularly useful for presenting a TCR disclosed herein because the cell surface TCR can target these effector cells to tumor cells expressing a MLL polypeptide (e.g., a MLL phosphopeptide, e.g., a peptide consisting of the amino acid sequence of SEQ ID NO: 45 or 47), thereby facilitating killing of the tumor cells. Accordingly, in certain embodiments, the mammalian cell is a lymphocyte (e.g., a human lymphocyte), such as a T cell or a natural killer (NK) cell. In certain embodiments, the lymphocyte is a T cell. Any T cell at any developmental stage can be used to present a TCR disclosed herein. For example, in certain embodiments, the T cell is selected from the group consisting of a CD8$^+$ cytotoxic T cell, a CD4$^+$ cytotoxic T cell, a CD4$^+$ helper T cell (e.g., a Th1 or a Th2 cell), a CD4/CD8 double positive T cell, a tumor infiltrating T cell, a thymocyte, a memory T cell, a naïve T cell, and a natural killer T cell, e.g., an invariant natural killer T cell. Precursor cells of the cellular immune system (e.g., precursors of T lymphocytes) are also useful for presenting a TCR disclosed herein because these cells may differentiate, develop, or mature into effector cells. Accordingly, in certain embodiments, the mammalian cell is a pluripotent stem cell (e.g., an embryonic stem cell, an induced pluripotent stem cell), a hematopoietic stem cell, or a lymphocyte progenitor cell. In certain embodiments, the hematopoietic stem cell or lymphocyte progenitor cell is isolated and/or enriched from, e.g., bone marrow, umbilical cord blood, or peripheral blood.

Cells can be obtained from numerous sources, including but not limited to, tumor, blood, bone marrow, lymph node, thymus, or another tissue or bodily fluid, or an apheresis product. In certain embodiments, cells are obtained from a patient directly following a treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, in certain embodiments, cells are collected from blood, bone marrow, lymph node, thymus, or another tissue or bodily fluid, or an apheresis product, during this recovery phase.

In certain embodiments, the mammalian cell is a population of cells presenting a TCR disclosed herein on the cell surface. The population of cells can be heterogeneous or homogenous. In certain embodiments, at least 50% (e.g., at least 60%, 70%, 80%, 90%, 95%, 99%, 99.5%, or 99.9%) of the population is a cell as described herein. In certain embodiments, the population is substantially pure, wherein at least 50% (e.g., at least 60%, 70%, 80%, 90%, 95%, 99%, 99.5%, or 99.9%) of the population is homogeneous. In certain embodiments, the population is heterogeneous and comprises a mixed population of cells (e.g., the cells have different cell types, developmental stages, origins, are isolated, purified, or enriched by different methods, are stimulated with different agents, and/or are engineered by different methods). In certain embodiments, the cells are a population of peripheral blood mononuclear cells (PBMC) (e.g., human PBMCs).

Populations of cells can be enriched or purified, as needed. In certain embodiments, regulatory T cells (e.g., CD25$^+$ T cells) are depleted from the population, e.g., by using an anti-CD25 antibody conjugated to a surface such as a bead, particle, or cell. In certain embodiments, an anti-CD25 antibody is conjugated to a fluorescent dye (e.g., for use in fluorescence-activated cell sorting). In certain embodiments, cells expressing checkpoint receptors (e.g., CTLA-4, PD-1, TIM-3, LAG-3, TIGIT, VISTA, BTLA, TIGIT, CD137, or CEACAM1) are depleted from the population, e.g., by using an antibody that binds specifically to a checkpoint receptor conjugated to a surface such as a bead, particle, or cell. In certain embodiments, a T cell population can be selected so that it expresses one or more of IFNγ, TNFα, IL-17A, IL-2, IL-3, IL-4, GM-CSF, IL-13, granzyme (e.g., granzyme B), and perforin, or other appropriate molecules, e.g., other cytokines. Methods for determining such expression are described, for example, in PCT Publication No.: WO 2013/126712, which is incorporated by reference herein in its entirety.

Cells can be stimulated ex vivo to increase viability, proliferation, and/or activity. In some embodiments, the induction does not include any defined antigen, thus providing a cell population which is polyclonal with respect to antigen reactivity. In certain embodiments, the cell is contacted with a first agent, which induces or activates a TCR/CD3 complex-associated signal (e.g., an anti-CD3 antibody). In certain embodiments, the cell is contacted with a second agent, which stimulates an accessory molecule on the T cell surface (e.g., a ligand of CD28 or an anti-CD28 antibody). In certain embodiments, the cell is contacted with a molecule or complex that interacts with both CD3 and CD28, wherein the molecule or complex may be presented on a surface (e.g., a bead, particle, or cell). In certain embodiments, the cell is contacted with a surface (e.g., a bead, particle, or cell) presenting an anti-CD3 antibody and an anti-CD28 antibody. In certain embodiments, the cell is contacted with one or more agents that bind to cell surface receptors to increase T cell viability, proliferation, and/or activity (e.g., IL-2 or IL-7). In certain embodiments, the cell is contacted with phytohemagglutinin. In certain embodiments, the cell is contacted with an agent that stimulates one or more intracellular signals such as $Ca^{2+}$ release (e.g., phorbol 12-myristate 13-acetate and/or ionomycin). Alternatively, the induction may include an antigen comprising a peptide (e.g., a MLL polypeptide (e.g., a MLL phosphopeptide, e.g., a peptide consisting of the amino acid sequence of SEQ ID NO: 45 or 47)) which binds to the TCR presented on the cell surface, thus providing a cell population which is enriched (e.g., monoclonal) with respect to antigen reactivity. The antigen may further comprise an MHC molecule (e.g., an HLA molecule) in complex with the peptide. The antigen may be presented as a soluble form, bound to a membrane, or presented on a surface. The agents as described above can be used in any combination, and may be contacted with the effector cell or precursor thereof either simultaneously or sequentially. The contact can be terminated while the cell may remain in a state of increased viability, proliferation, and/or activity. Sustained proliferation of T cells over an extended period of time can yield a multi-fold increase in the number of cells relative to the original T cell population. In some embodiments, activation may be performed to promote metabolic fitness through provision of bioenergetic fuel sources, which enables conditioning of T cells for optimal biological activity and survival.

In certain embodiments, the mammalian cell (e.g., lymphocyte) expresses a TCR disclosed herein from a transgene introduced into the cell and presents the TCR on the cell surface. The TCR may be displayed constitutively on the cell surface. Alternatively, the cell may be capable of conditional expression and/or display of the TCR. For example, the expression or display of the TCR may be induced by an exogenous stimulus or by cellular differentiation. In certain embodiments, the transgene encodes a TCR α chain and/or β chain, or a fragment thereof (e.g., Vα, CDR3α and/or CDR3β). In certain embodiments, the transgene is operably linked to an exogenous transcriptional and/or translational control sequence (e.g., a promoter, an enhancer, and/or a Kozak sequence). In certain embodiments, the transgene is operably linked to an endogenous transcriptional and/or translational control sequence (e.g., a promoter, an enhancer, and/or a Kozak sequence) not at its native genomic locus (e.g., introduced by a vector). In certain embodiments, the transgene is operably linked to an endogenous transcriptional and/or translational control sequence (e.g., a promoter, an enhancer, and/or a Kozak sequence) at its native genomic locus (e.g., by inserting the transgene into the native genomic locus).

In certain embodiments, the transgene is a DNA integrated into the host cell genome, wherein the integration occurs through site-specific integration (e.g., homologous recombination) or random insertion of the DNA. In certain embodiments, the transgene is a DNA not integrated into the host cell genome (e.g., maintained as a non-integrating viral genome or as an episomal DNA). In certain embodiments, the transgene is a polynucleotide (including but not limited to DNA, RNA, modified DNA, and modified RNA) that can be transcribed and/or translated to express the TCR disclosed herein. In certain embodiments, the transgene is an RNA having a cap on the 5' end and/or a poly(A) tail on the 3' end, wherein the cap and the poly(A) tail may modulate ribosome binding, initiation of translation and stability of the RNA in the cell.

In certain embodiments, the transgene comprises a first and a second sequence, the first sequence encoding a polypeptide comprising a TCR α chain or a fragment thereof (e.g., Vα or CDR3α), and the second sequence encoding a polypeptide comprising a TCR β chain or a fragment thereof (e.g., Vβ or CDR3β). In certain embodiments, the first and the second sequences are each operably linked to a transcriptional and/or translational control sequence (e.g., a promoter, an enhancer, and/or a Kozak sequence). In certain embodiments, the first and second sequences are in different polynucleotides (e.g., DNA, RNA, modified DNA, or modified RNA) molecules. In certain embodiments, the first and second sequences of the transgene are in the same polynucleotide (e.g., DNA, RNA, modified DNA, or modified RNA) molecule. In certain embodiments, the first and second sequences are operably linked by a linker sequence that promotes the production of two separate polypeptides (e.g., an internal ribosome entry site (IRES), a self-cleavage peptide (e.g., a 2A peptide), or a peptide sequence recognized by an intracellular or an extracellular protease). In certain embodiments, the first and second sequences can be transcribed and/or translated independently. In certain embodiments, the first and second sequences are each integrated into the host cell genome. In certain embodiments, the first and second sequences are each integrated into different regions of the host cell genome.

Alternatively, in certain embodiments, the cell does not express the TCR, but instead the TCR is attached to the outside surface of the cell by chemical means or by binding of the TCR to a cell surface antigen. Accordingly, in certain embodiments, the TCR is linked to a binding moiety that binds to a cell surface antigen. Any type of binding moiety can be linked (covalently or non-covalently) to a TCR disclosed herein. In certain embodiments, the TCR is fused (chemically or genetically) to an antibody or antigen binding fragment thereof that specifically binds to a cell surface antigen of the cell (e.g., lymphocyte).

In certain embodiments, the cell further comprises a polynucleotide encoding a polypeptide capable of inducing cell death. In certain embodiments, the polypeptide is a chimeric polypeptide comprising a multimerization (e.g., dimerization or oligomerization) region and a cell death-inducing region, wherein the cell death-inducing region is activated by multimerization. In certain embodiments, the cell death-inducing region comprises a sequence of a caspase (e.g., caspase-9) that has protease activity. In certain embodiments, the cell death-inducing region comprises the full-length human caspase-9 polypeptide. In certain embodiments, the cell death-inducing region comprises a truncated human caspase-9 polypeptide (e.g., wherein the CARD domain of caspase-9 is deleted).

In certain embodiments, the cell further comprises a polynucleotide encoding a polypeptide capable of inducing T cell activation. In certain embodiments, the polypeptide is an inducible chimeric stimulating molecule, for example, as described in PCT Publication No. WO 2015/123527, incorporated herein by reference in its entirety. In certain embodiments, the polypeptide comprises a multimerization (e.g., dimerization or oligomerization) region, wherein the polypeptide induces T cell activation upon multimerization.

A multimerization region present, for example, in a polypeptide capable of inducing cell death or a polypeptide capable of inducing T cell activation, can comprise a ligand-binding domain that will multimerize upon binding to a ligand (e.g., a synthetic ligand). The ligand may have two or more binding sites, each binding site capable of binding to a ligand-binding domain of the chimeric polypeptide. In certain embodiments, the ligand has two binding sites and is capable of inducing dimerization of the chimeric polypeptide. A variety of synthetic ligands and corresponding ligand-binding domains can be employed. For example, a multimeric (e.g., dimeric) FK506 can be used to multimerize an FK506 binding protein (FKBP; e.g., FKBP12 or a variant thereof); a multimeric (e.g., dimeric) cyclosporin A can be used to multimerize a cyclophilin receptor; a multimeric (e.g., dimeric) estrogen can be used to multimerize an estrogen receptor; a multimeric (e.g., dimeric) glucocorticoid can be used to multimerize a glucocorticoid receptor; a multimeric (e.g., dimeric) tetracycline can be used to multimerize a tetracycline receptor; a multimeric (e.g., dimeric) vitamin D can be used to multimerize a vitamin D receptor. The ligand-binding domain can be internal or external to the cellular membrane, depending upon the nature of the construct and the choice of ligand. Non-limiting examples of ligands and corresponding ligand-binding domains are described in U.S. Pat. No. 9,089,520; Kopytek, S. J., et al., Chemistry & Biology 7:313-321 (2000); Gestwicki, J. E., et al., Combinatorial Chem. & High Throughput Screening 10:667-675 (2007); Clackson T Chem Biol Drug Des 67:440-2 (2006); and Schreiber, et al., *Chemical Biology From Small Molecules to Systems Biology and Drug Design* (Wiley, 2007), the contents of which are incorporated by reference herein in their entireties.

In certain embodiments, the polypeptide capable of inducing cell death is a chimeric polypeptide comprising an FKBP12 polypeptide and a full-length or truncated caspase-9 (e.g., human caspase-9) polypeptide. In certain embodiments, the FKBP12 polypeptide comprises a valine at position 36. In certain embodiments, the FKBP12 polypeptide comprises the amino acid sequence set forth in SEQ ID NO: 94. In certain embodiments, the ligand capable of inducing FKBP12 multimerization is AP1903 (CAS Registry Number: 195514-63-7; Molecular Formula: C78H98N4O20; Molecular Weight: 1411.65). In certain embodiments, the ligand is AP20187 or an AP20187 analog (e.g., AP1510). In certain embodiments, the caspase-9 polypeptide comprises the amino acid sequence set forth in SEQ ID NO: 95.

TABLE 6

FKBP12 and caspase-9 sequences.

| SEQ ID NO: | Description | Amino acid Sequence |
|---|---|---|
| 94 | FKBP12 | GVQVETISPGDGRTFPKRGQTCVVHYTGML EDGKKVDSSRDRNKPFKFMLGKQEVIRGWE EGVAQMSVGQRAKLTISPDYAYGATGHPGI IPPHATLVFDVELLKLE |

TABLE 6-continued

FKBP12 and caspase-9 sequences.

| SEQ ID NO: | Description | Amino acid Sequence |
|---|---|---|
| 95 | caspase-9 | GFGDVGALESLRGNADLAYILSMEPCGHCL IINNVNFCRESGLRTRTGSNIDCEKLRRRF SSLHFMVEVKGDLTAKKMVLALLELAQQDH GALDCCVVVILSHGCQASHLQFPGAVYGTD GCPVSVEKIVNIFNGTSCPSLGGKPKLFFI QACGGEQKDHGFEVASTSPEDESPGSNPEP DATPFQEGLRTFDQLDAISSLPTPSDIFVS YSTFPGFVSWRDPKSGSWYVETLDDIFEQW AHSEDLQSLLLRVANAVSVKGIYKQMPGCF NFLRKKLFFKTS |

In certain embodiments, the polynucleotide encoding the polypeptide capable of inducing cell death is operably linked to a transcriptional and/or translational control sequence (e.g., a promoter, an enhancer, and/or a Kozak sequence). The polynucleotide may be integrated into the host cell genome. Alternatively, the polynucleotide may be maintained as a non-integrating viral genome or as an episomal DNA. In certain embodiments, the polynucleotide is operably linked to the first and/or second sequences encoding a TCR by a linker sequence that promotes the production of two separate polypeptides (e.g., an internal ribosome entry site (IRES), a self-cleavage peptide (e.g., a 2A peptide), or a peptide sequence recognized by an intracellular or an extracellular protease). In certain embodiments, the polynucleotide is transcribed and/or translated independently from the first and/or second sequences.

In certain embodiments, the cell is provided in a solution. In certain embodiments, the cell is cryopreserved at about or lower than −80° C. (e.g., in a liquid nitrogen storage tank). Methods of cryopreservation are well-known in the art, e.g., as described in U.S. Pat. Nos. 5,580,714 and 6,740,484, which are incorporated by reference herein in their entireties. The cryopreserved cell may be recovered by thawing, and any of the isolation, purification, enrichment, stimulation, and display of the TCR as described above may be conducted prior to the cryopreservation or after the recovery.

5.4 Methods of Use

In another aspect, the instant disclosure provides a method of treating a subject using the TCRs, polynucleotides, vectors, engineered cells (e.g., a cell comprising a heterologous and/or recombinant nucleic acid), or pharmaceutical compositions disclosed herein. Any disease or disorder in a subject that would benefit from the targeting of a TCR to a MLL peptide (e.g., a MLL phosphopeptide, e.g., a peptide consisting of the amino acid sequence of SEQ ID NO: 45 or 47) can be treated using the TCRs disclosed herein. The TCRs, polynucleotides, vectors, engineered cells, and pharmaceutical compositions disclosed herein are particularly useful for inducing immunity to tumors displaying a MLL peptide (e.g., a peptide-MHC complex comprising a MLL peptide, e.g., a peptide-MHC complex comprising a MLL phosphopeptide, e.g., EPR[pS]PSHSM (SEQ ID NO: 45)-HLA-B*0702 or RVR[pS]PTRSP (SEQ ID NO: 47)-HLA-B*0702), and accordingly can be used as an immunotherapy for subjects with MLL-positive cancer (e.g., MLL phosphopeptide-positive cancer). For example, in certain embodiments, the instant disclosure provides a method of inducing cell-mediated immunity in response to a MLL peptide (e.g., a MLL phosphopeptide, e.g., a peptide consisting of the amino acid sequence of SEQ ID NO: 45 or 47) in a subject, the method comprising administering to the subject an effective amount of a TCR, polynucleotide, vector, engineered cell, or pharmaceutical composition as described herein. In certain embodiments, the instant disclosure provides a method of treating cancer in a subject, the method comprising administering to the subject an effective amount of the TCR, polynucleotide, vector, engineered cell, or pharmaceutical composition, as disclosed herein.

In certain embodiments, the method comprises administering to the subject an effective amount of a cell or population thereof as disclosed herein. In certain embodiments, the cell is engineered to constitutively display a TCR as disclosed herein on the cell surface. In certain embodiments, the cell is engineered to conditionally display a TCR as disclosed herein on the cell surface in response to an induction event. This induction event can be either a stimulus by an exogenous agent administered prior to, simultaneously with, or after the administration of the cell. Additionally or alternatively, the induction event can be a stimulus by a cell, tissue, or lesion in the subject.

In certain embodiments, the cell further comprises a polynucleotide encoding a chimeric polypeptide comprising a ligand-binding multimerization (e.g., dimerization or oligomerization) region and a cell death-inducing region, and the method further comprises a step of administering a ligand of the multimerization region. In certain embodiments, the chimeric polypeptide comprises an FKBP12 polypeptide and a caspase-9 (e.g., human caspase-9) polypeptide, and the method further comprises a step of administering an FKBP12 ligand (e.g., AP1903). In certain embodiments, the FKBP12 ligand is administered after observing an indication of an improvement of a disease (e.g., shrinkage of a cancer, reduction of a cancer marker, and/or improvement of a cancer symptom) or after identifying an intolerable side effect (e.g., a high level of an inflammatory cytokine, and/or a rejection of the administered cell by the host).

As disclosed supra, cells administered to the subject can be autologous or allogeneic. In certain embodiments, autologous cells are obtained from a patient directly following a cancer treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, in certain embodiments, cells are collected from blood, bone marrow, lymph node, thymus, or another tissue or bodily fluid, or an apheresis product, during this recovery phase. Further, in certain aspects, mobilization and conditioning regimens can be used to create a condition in a subject wherein repopulation, recirculation, regeneration, and/or expansion of particular cell types is favored, especially during a defined window of time following therapy. The mobilization agent can be selected from the group consisting of CXCL12-interacting heparinoids, GM-CSF, G-CSF (e.g., unmodified, glycosylated, or PEGylated), IL-2 (e.g., unmodified, glycosylated, or PEGylated), CXCR4 antagonists (e.g., plerixafor), integrin α4β1 antagonists (e.g., BIO5192), cyclophosphamide, 5-fluorouracil, cisplatin, etoposide, ifosfamide, cytarabine, and a combination thereof.

The number of cells that are employed will depend upon a number of circumstances including, the lifetime of the cells, the protocol to be used (e.g., the number of administrations), the ability of the cells to multiply, the stability of the recombinant construct, and the like. In certain embodiments, the cells are applied as a dispersion, generally being injected at or near the site of interest. The cells may be administered in any physiologically acceptable medium.

Cancers that can be treated with the TCRs, polynucleotide, vector, engineered cells, or pharmaceutical compositions disclosed herein can be any tumor expressing MLL (e.g., any tumor displaying a MLL phosphopeptide/MHC complex on the cell surface). Examples of tumors expressing MLL (e.g., tumor displaying a MLL phosphopeptide/MHC complex on the cell surface) have been disclosed in, e.g., Cobbold et al., Sci Transl Med. 2013 Sep. 18; 5(203): 203ra125; Rao et al., Nat Rev Cancer. 2015 June; 15(6): 334-46; Li et al., Exp Hematol. 2014 December; 42(12): 995-1012; and Krivtsov et al., Nat Rev Cancer. 2007 November; 7(11):823-33, each of which is incorporated by reference herein in its entirety.

In certain embodiments, the cancer is leukemia (e.g., mixed lineage leukemia, acute lymphocytic leukemia, acute myeloid leukemia, chronic lymphocytic leukemia, or chronic myeloid leukemia), alveolar rhabdomyosarcoma, bone cancer, brain cancer (e.g., glioblastoma), breast cancer, cancer of the anus, anal canal, or anorectum, cancer of the eye, cancer of the intrahepatic bile duct (e.g., intrahepatic cholangiocellular cancer), cancer of the joints, cancer of the neck, gallbladder, or pleura, cancer of the nose, nasal cavity, or middle ear, cancer of the oral cavity, cancer of the vulva, myeloma (e.g., chronic myeloid cancer), colon cancer, esophageal cancer, cervical cancer, gastrointestinal carcinoid tumor. Hodgkin's lymphoma, hypopharynx cancer, kidney cancer, larynx cancer, liver cancer (e.g., hepatocellular carcinoma), lung cancer (e.g., non-small cell lung cancer), malignant mesothelioma, melanoma, multiple myeloma, nasopharynx cancer, non-Hodgkin's lymphoma, ovarian cancer, pancreatic cancer, peritoneum, omentum, and mesentery cancer, pharynx cancer, prostate cancer, rectal cancer, renal cancer (e.g., renal cell carcinoma (RCC)), gastric cancer, small intestine cancer, soft tissue cancer, stomach cancer, carcinoma, sarcoma (e.g., synovial sarcoma, rhabdomyosarcoma), testicular cancer, thyroid cancer, head and neck cancer, ureter cancer, and urinary bladder cancer. In certain embodiments, the cancer is melanoma, breast cancer, lung cancer, prostate cancer, thyroid cancer, ovarian cancer, or synovial sarcoma. In one embodiment, the cancer is synovial sarcoma or liposarcoma (e.g., myxoid/round cell liposarcoma).

In certain embodiments, these methods further comprise administering an additional therapeutic agent to the subject. In certain embodiments, the additional therapeutic agent is a chemotherapeutic, radiotherapeutic, or a checkpoint targeting agent. In certain embodiments, the chemotherapeutic agent is a hypomethylating agent (e.g., azacitidine). In certain embodiments, the checkpoint targeting agent is selected from the group consisting of an antagonist anti-CTLA-4 antibody, an antagonist anti-PD-L1 antibody, an antagonist anti-PD-L2 antibody, an antagonist anti-PD-1 antibody, an antagonist anti-TIM-3 antibody, an antagonist anti-LAG-3 antibody, an antagonist VISTA antibody, an antagonist CD96 antibody, an antagonist anti-CEACAM1 antibody, an antagonist anti-TIGIT antibody, an agonist anti-CD137 antibody, an agonist anti-GITR antibody, and an agonist anti-OX40 antibody.

In certain embodiments, an anti-PD-1 antibody is used in methods disclosed herein. In certain embodiments, the anti-PD-1 antibody is nivolumab, also known as BMS-936558 or MDX1106, developed by Bristol-Myers Squibb. In certain embodiments, the anti-PD-1 antibody is pembrolizumab, also known as lambrolizumab or MK-3475, developed by Merck & Co. In certain embodiments, the anti-PD-1 antibody is pidilizumab, also known as CT-011, developed by CureTech. In certain embodiments, the anti-PD-1 antibody is MEDI0680, also known as AMP-514, developed by Medimmune. In certain embodiments, the anti-PD-1 antibody is PDR001 developed by Novartis Pharmaceuticals. In certain embodiments, the anti-PD-1 antibody is REGN2810 developed by Regeneron Pharmaceuticals. In certain embodiments, the anti-PD-1 antibody is PF-06801591 developed by Pfizer. In certain embodiments, the anti-PD-1 antibody is BGB-A317 developed by BeiGene. In certain embodiments, the anti-PD-1 antibody is TSR-042 developed by AnaptysBio and Tesaro. In certain embodiments, the anti-PD-1 antibody is SHR-1210 developed by Hengrui.

Further non-limiting examples of anti-PD-1 antibodies that may be used in treatment methods disclosed herein are disclosed in the following patents and patent applications, which are incorporated herein by reference in their entireties for all purposes: U.S. Pat. Nos. 6,808,710; 7,332,582; 7,488,802; 8,008,449; 8,114,845; 8,168,757; 8,354,509; 8,686,119; 8,735,553; 8,747,847; 8,779,105; 8,927,697; 8,993,731; 9,102,727; 9,205,148; U.S. Publication No. US 2013/0202623 A1; U.S. Publication No. US 2013/0291136 A1; U.S. Publication No. US 2014/0044738 A1; U.S. Publication No. US 2014/0356363 A1; U.S. Publication No. US 2016/0075783 A1; and PCT Publication No. WO 2013/033091 A1; PCT Publication No. WO 2015/036394 A1; PCT Publication No. WO 2014/179664 A2; PCT Publication No. WO 2014/209804 A1; PCT Publication No. WO 2014/206107 A1; PCT Publication No. WO 2015/058573 A1; PCT Publication No. WO 2015/085847 A1; PCT Publication No. WO 2015/200119 A1; PCT Publication No. WO 2016/015685 A1; and PCT Publication No. WO 2016/020856 A1.

In certain embodiments, an anti-PD-L1 antibody is used in methods disclosed herein. In certain embodiments, the anti-PD-L1 antibody is atezolizumab developed by Genentech. In certain embodiments, the anti-PD-L1 antibody is durvalumab developed by AstraZeneca, Celgene and Medimmune. In certain embodiments, the anti-PD-L1 antibody is avelumab, also known as MSB0010718C, developed by Merck Serono and Pfizer. In certain embodiments, the anti-PD-L1 antibody is MDX-1105 developed by Bristol-Myers Squibb. In certain embodiments, the anti-PD-L1 antibody is AMP-224 developed by Amplimmune and GSK.

Non-limiting examples of anti-PD-L1 antibodies that may be used in treatment methods disclosed herein are disclosed in the following patents and patent applications, which are incorporated herein by reference in their entireties for all purposes: U.S. Pat. Nos. 7,943,743; 8,168,179; 8,217,149; 8,552,154; 8,779,108; 8,981,063; 9,175,082; U.S. Publication No. US 2010/0203056 A1; U.S. Publication No. US 2003/0232323 A1; U.S. Publication No. US 2013/0323249 A1; U.S. Publication No. US 2014/0341917 A1; U.S. Publication No. US 2014/0044738 A1; U.S. Publication No. US 2015/0203580 A1; U.S. Publication No. US 2015/0225483 A1; U.S. Publication No. US 2015/0346208 A1; U.S. Publication No. US 2015/0355184 A1; and PCT Publication No. WO 2014/100079 A1; PCT Publication No. WO 2014/022758 A1; PCT Publication No. WO 2014/055897 A2; PCT Publication No. WO 2015/061668 A1; PCT Publication No. WO 2015/109124 A1; PCT Publication No. WO 2015/195163 A1; PCT Publication No. WO 2016/000619 A1; and PCT Publication No. WO 2016/030350 A1.

In certain embodiments, a TCR, cell, or pharmaceutical composition disclosed herein is administered to a subject in combination with a compound that targets an immunomodulatory enzyme(s) such as IDO (indoleamine-(2,3)-dioxygenase) and/or TDO (tryptophan 2,3-dioxygenase). In certain embodiments, such compound is selected from the group consisting of epacadostat (Incyte Corp; see, e.g., PCT Publication No. WO 2010/005958 which is incorporated by reference herein in its entirety), F001287 (Flexus Biosciences/Bristol-Myers Squibb), indoximod (NewLink Genetics), and NLG919 (NewLink Genetics). In one embodiment, the compound is epacadostat. In another embodiment, the compound is F001287. In another embodiment, the compound is indoximod. In another embodiment, the compound is NLG919. In a specific embodiment, the TCR, cell, or pharmaceutical composition disclosed herein is administered to a subject in combination with an IDO inhibitor for treating cancer. The IDO inhibitor as described herein for use in treating cancer is present in a solid dosage form of a pharmaceutical composition such as a tablet, a pill or a capsule, wherein the pharmaceutical composition includes an IDO inhibitor and a pharmaceutically acceptable excipient. As such, the TCR, cell, or pharmaceutical composition as described herein and the IDO inhibitor as described herein can be administered separately, sequentially, or concurrently as separate dosage forms. In one embodiment, the cell, or pharmaceutical composition is administered parenterally, and the IDO inhibitor is administered orally. In particular embodiments, the inhibitor is selected from the group consisting of epacadostat (Incyte Corporation), F001287 (Flexus Biosciences/Bristol-Myers Squibb), indoximod (NewLink Genetics), and NLG919 (NewLink Genetics). Epacadostat has been described in PCT Publication No. WO 2010/005958, which is incorporated herein by reference in its entirety for all purposes. In one embodiment, the inhibitor is epacadostat. In another embodiment, the inhibitor is F001287. In another embodiment, the inhibitor is indoximod. In another embodiment, the inhibitor is NLG919.

In certain embodiments, a TCR, cell, or pharmaceutical composition disclosed herein is administered to a subject in combination with a vaccine. The vaccine can be, e.g., a peptide vaccine, a DNA vaccine, or an RNA vaccine. In certain embodiments, the vaccine is a heat shock protein based tumor vaccine or a heat shock protein based pathogen vaccine. In a specific embodiment, a TCR, cell, or pharmaceutical composition disclosed herein is administered to a subject in combination with a heat shock protein based tumor-vaccine. Heat shock proteins (HSPs) are a family of highly conserved proteins found ubiquitously across all species. Their expression can be powerfully induced to much higher levels as a result of heat shock or other forms of stress, including exposure to toxins, oxidative stress, or glucose deprivation. Five families have been classified according to molecular weight: HSP-110, -90, -70, -60 and -28. HSPs deliver immunogenic peptides through the cross-presentation pathway in antigen presenting cells (APCs) such as macrophages and dendritic cells (DCs), leading to T cell activation. HSPs function as chaperone carriers of tumor-associated antigenic peptides forming complexes able to induce tumor-specific immunity. Upon release from dying tumor cells, the HSP-antigen complexes are taken up by antigen-presenting cells (APCs) wherein the antigens are processed into peptides that bind MHC class I and class II molecules leading to the activation of anti-tumor CD8+ and CD4+ T cells. The immunity elicited by HSP complexes derived from tumor preparations is specifically directed against the unique antigenic peptide repertoire expressed by the cancer of each subject.

A heat shock protein peptide complex (HSPPC) is a protein peptide complex consisting of a heat shock protein non-covalently complexed with antigenic peptides. HSPPCs elicit both innate and adaptive immune responses. In a specific embodiment, the antigenic peptide(s) displays antigenicity for the cancer being treated. HSPPCs are efficiently seized by APCs via membrane receptors (mainly CD91) or by binding to Toll-like receptors. HSPPC internalization results in functional maturation of the APCs with chemokine and cytokine production leading to activation of natural killer cells (NK), monocytes, and Th1 and Th-2-mediated immune responses. In certain embodiments, HSPPCs used in methods disclosed herein comprise one or more heat shock proteins from the hsp60, hsp70, or hsp90 family of stress proteins complexed with antigenic peptides. In certain embodiments, HSPPCs comprise hsc70, hsp70, hsp90, hsp110, grp170, gp96, calreticulin, or combinations of two or more thereof.

In a specific embodiment, the heat shock protein peptide complex (HSPPC) comprises recombinant heat shock proteins (e.g., hsp70 or hsc70) or a peptide-binding domain thereof complexed with recombinant antigenic peptides. Recombinant heat shock proteins can be produced by recombinant DNA technology, for example, using human hsc70 sequence as described in Dworniczak and Mirault, Nucleic Acids Res. 15:5181-5197 (1987) and GenBank accession no. P11142 and/or Y00371, each of which is incorporated herein by reference in its entirety. In certain embodiments, Hsp70 sequences are as described in Hunt and Morimoto Proc. Natl. Acad. Sci. U.S.A. 82 (19), 6455-6459 (1985) and GenBank accession no. PODMV8 and/or M11717, each of which is incorporated herein by reference in its entirety. Antigenic peptides can also be prepared by recombinant DNA methods known in the art.

In certain embodiments, the antigenic peptides comprise a modified amino acid. In certain embodiments, the modified amino acid comprises a post-translational modification. In certain embodiments, the modified amino acid comprises a mimetic of a post-translational modification. In certain embodiments, the modified amino acid is a Tyr, Ser, Thr, Arg, Lys, or His that has been phosphorylated on a side chain hydroxyl or amine. In certain embodiments, the modified amino acid is a mimetic of a Tyr, Ser, Thr, Arg, Lys, or His amino acid that has been phosphorylated on a side chain hydroxyl or amine.

In a specific embodiment, a TCR, cell, or pharmaceutical composition disclosed herein is administered to a subject in combination with a heat shock protein peptide complex (HSPPC), e.g., heat shock protein peptide complex-96 (HSPPC-96), to treat cancer. HSPPC-96 comprises a 96 kDa heat shock protein (Hsp), gp96, complexed to antigenic peptides. HSPPC-96 is a cancer immunotherapy manufactured from a subject's tumor and contains the cancer's antigenic "fingerprint." In certain embodiments, this fingerprint contains unique antigens that are present only in that particular subject's specific cancer cells and injection of the vaccine is intended to stimulate the subject's immune system to recognize and attack any cells with the specific cancer fingerprint.

In certain embodiments, the HSPPC, e.g., HSPPC-96, is produced from the tumor tissue of a subject. In a specific embodiment, the HSPPC (e.g., HSPPC-96) is produced from a tumor of the type of cancer or metastasis thereof being treated. In another specific embodiment, the HSPPC (e.g., HSPPC-96) is autologous to the subject being treated. In certain embodiments, the tumor tissue is non-necrotic tumor tissue. In certain embodiments, at least 1 gram (e.g., at least 1, at least 2, at least 3, at least 4, at least 5, at least 6, at least 7, at least 8, at least 9, or at least 10 grams) of non-necrotic tumor tissue is used to produce a vaccine regimen. In certain embodiments, after surgical resection, non-necrotic tumor tissue is frozen prior to use in vaccine preparation. In some embodiments, the HSPPC, e.g., HSPPC-96, is isolated from the tumor tissue by purification techniques, filtered and prepared for an injectable vaccine. In certain embodiments, a subject is administered 6-12 doses of the HSPPC, e.g., HSPCC-96. In such embodiments, the HSPPC, e.g., HSPPC-96, doses may be administered weekly for the first 4 doses and then biweekly for the 2-8 additional doses.

Further examples of HSPPCs that may be used in accordance with the methods described herein are disclosed in the following patents and patent applications, which are incorporated herein by reference herein in their entireties, U.S. Pat. Nos. 6,391,306, 6,383,492, 6,403,095, 6,410,026, 6,436,404, 6,447,780, 6,447,781 and 6,610,659.

In certain embodiments, a TCR, cell, or pharmaceutical composition disclosed herein is administered to a subject in combination with an adjuvant. Various adjuvants can be used depending on the treatment context. Non-limiting examples of appropriate adjuvants include, but not limited to, Complete Freund's Adjuvant (CFA), Incomplete Freund's Adjuvant (IFA), montanide ISA (incomplete Seppic adjuvant), the Ribi adjuvant system (RAS), Titer Max, muramyl peptides, Syntex Adjuvant Formulation (SAF), alum (aluminum hydroxide and/or aluminum phosphate), aluminum salt adjuvants, Gerbu® adjuvants, nitrocellulose absorbed antigen, encapsulated or entrapped antigen, 3 De-O-acylated monophosphoryl lipid A (3 D-MPL), immunostimulatory oligonucleotides, toll-like receptor (TLR) ligands, mannan-binding lectin (MBL) ligands, STING agonists, immuno-stimulating complexes such as saponins, Quil A, QS-21, QS-7, ISCOMATRIX, and others. Other adjuvants include CpG oligonucleotides and double stranded RNA molecules, such as poly(A) and poly(U). Combinations of the above adjuvants may also be used. See, e.g., U.S. Pat. Nos. 6,645,495; 7,029,678; and 7,858,589, all of which are incorporated herein by reference in their entireties. In one embodiment, the adjuvant used herein is QS-21 STIMULON.

In certain embodiments, a TCR, polynucleotide, vector, engineered cell, or pharmaceutical composition disclosed herein is administered to a subject in combination with a tumor microenvironment (TME)-conditioning agent. In certain embodiments, the TME-conditioning agent is a cytokine (e.g., interleukin-2, interferon-α, interferon-β, interferon-γ, tumor necrosis factor superfamily member 14 (TNFSF14)). In certain embodiments, the cytokine is a chemokine (e.g., (C—C motif) ligand 21 (CCL21) and C—X—C motif chemokine 10 (CXCL10)). In certain embodiments, the TME-conditioning agent is an agonist of a pattern recognition receptor (PRR). In certain embodiments, the agonist is a synthetic agonist of TLR9 (e.g., CpG). In certain embodiments, the agonist is a synthetic agonist of STING (e.g., cGAMP).

The TCR, polynucleotide, vector, engineered cell, or pharmaceutical composition and the additional therapeutic agent (e.g., chemotherapeutic, radiotherapeutic, checkpoint targeting agent, IDO inhibitor, vaccine, adjuvant, and/or TME-conditioning agent) can be administered separately, sequentially or concurrently as separate dosage forms. In one embodiment, the TCR, polynucleotide, vector, engineered cell, or pharmaceutical composition is administered parenterally, and an IDO inhibitor is administered orally.

A TCR, polynucleotide, vector, engineered cell, or pharmaceutical composition described herein may be delivered to a subject by a variety of routes. These include, but are not limited to, parenteral, intranasal, intratracheal, oral, intradermal, topical, intramuscular, intraperitoneal, transdermal, intravenous, intratumoral, conjunctival, intrathecal, and subcutaneous routes. Pulmonary administration can also be employed, e.g., by use of an inhaler or nebulizer, and formulation with an aerosolizing agent for use as a spray. In certain embodiments, the TCR, polynucleotide, vector, engineered cell, or pharmaceutical composition described herein is delivered intravenously. In certain embodiments, the TCR, polynucleotide, vector, engineered cell, or pharmaceutical composition described herein is delivered subcutaneously. In certain embodiments, the TCR, polynucleotide, vector, engineered cell, or pharmaceutical composition described herein is delivered intratumorally. In certain embodiments, the TCR, polynucleotide, vector, engineered cell, or pharmaceutical composition described herein is delivered into a tumor draining lymph node.

The amount of the TCR, polynucleotide, vector, engineered cell, or pharmaceutical composition which will be effective in the treatment and/or prevention of a condition will depend on the nature of the disease, and can be determined by standard clinical techniques.

The precise dose to be employed in a composition will also depend on the route of administration, and the seriousness of the infection or disease caused by it, and should be decided according to the judgment of the practitioner and each subject's circumstances. For example, effective doses may also vary depending upon means of administration, target site, physiological state of the patient (including age, body weight, and health), whether the patient is a human or an animal, other medications administered, or whether treatment is prophylactic or therapeutic. Usually, the patient is a human but non-human mammals including transgenic mammals can also be treated. Treatment dosages are optimally titrated to optimize safety and efficacy.

A TCR described herein can also be used to assay the levels of a peptide-MHC complex comprising a MLL peptide (e.g., a MLL phosphopeptide, e.g., a peptide consisting of the amino acid sequence of SEQ ID NO: 45 or 47) and/or the numbers of cells displaying a peptide-MHC complex comprising a MLL peptide (e.g., a MLL phosphopeptide, e.g., a peptide consisting of the amino acid sequence of SEQ ID NO: 45 or 47) in a biological sample using classical immunohistological methods known to those of skill in the art, including immunoassays, such as the enzyme linked immunosorbent assay (ELISA), immunoprecipitation, or Western blotting. Suitable TCR assay labels are known in the art and include enzyme labels, such as, glucose oxidase; radioisotopes, such as iodine ($^{125}$I, $^{121}$I), carbon ($^{13}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin. Such labels can be used to label a TCR described herein. Alternatively, a molecule that recognizes a TCR described herein can be labeled and used in combination with a TCR described herein to detect a peptide-MHC complex comprising a MLL peptide (e.g., a MLL phosphopeptide, e.g., a peptide consisting of the amino acid sequence of SEQ ID NO: 45 or 47) and/or the numbers of cells displaying a peptide-MHC complex comprising a MLL peptide (e.g., a MLL phosphopeptide, e.g., a peptide consisting of the amino acid sequence of SEQ ID NO: 45 or 47) in a biological sample.

Assaying for the levels of a peptide-MHC complex comprising a MLL peptide (e.g., a MLL phosphopeptide, e.g., a peptide consisting of the amino acid sequence of SEQ ID NO: 45 or 47) is intended to include qualitatively or quantitatively measuring or estimating the level of a peptide-MHC complex comprising a MLL peptide (e.g., a MLL phosphopeptide, e.g., a peptide consisting of the amino acid sequence of SEQ ID NO: 45 or 47) in a first biological sample either directly (e.g., by determining or estimating absolute protein level) or relatively (e.g., by comparing to the disease associated protein level in a second biological sample). The level of a peptide-MHC complex comprising a MLL peptide (e.g., a MLL phosphopeptide, e.g., a peptide consisting of the amino acid sequence of SEQ ID NO: 45 or 47) in the first biological sample can be measured or estimated and compared to a standard level, the standard being taken from a second biological sample obtained from an individual not having the disease or being determined by averaging levels from a population of individuals not having the disease. As will be appreciated in the art, once the "standard" level is known, it can be used repeatedly as a standard for comparison.

As used herein, the term "biological sample" refers to any biological sample obtained from a subject, cell line, tissue, or other source of cells potentially displaying a peptide-MHC complex comprising a MLL peptide (e.g., a MLL phosphopeptide, e.g., a peptide consisting of the amino acid sequence of SEQ ID NO: 45 or 47). Methods for obtaining tissue biopsies and body fluids from animals (e.g., humans) are well-known in the art. Biological samples include peripheral mononuclear blood cells.

A TCR described herein can be used for prognostic, diagnostic, monitoring and screening applications, including in vitro and in vivo applications well-known and standard to the skilled artisan and based on the present description. Prognostic, diagnostic, monitoring and screening assays and kits for in vitro assessment and evaluation of immune system status and/or immune response may be utilized to predict, diagnose, and monitor to evaluate patient samples including those known to have or suspected of having a disorder associated with cells displaying a peptide-MHC complex comprising a MLL peptide (e.g., a MLL phosphopeptide, e.g., a peptide consisting of the amino acid sequence of SEQ ID NO: 45 or 47). In vivo applications include directed cell therapy and immune system modulation and radio imaging of a cell, tissue, or organ displaying a peptide-MHC complex comprising a MLL peptide (e.g., a MLL phosphopeptide, e.g., a peptide consisting of the amino acid sequence of SEQ ID NO: 45 or 47).

In one embodiment, a TCR described herein can be used for detecting a peptide-MHC complex comprising a MLL peptide (e.g., a MLL phosphopeptide, e.g., a peptide consisting of the amino acid sequence of SEQ ID NO: 45 or 47) and/or the numbers of cells displaying a peptide-MHC complex comprising a MLL peptide (e.g., a MLL phosphopeptide, e.g., a peptide consisting of the amino acid sequence of SEQ ID NO: 45 or 47) in immunohistochemistry of biopsy samples. A TCRs described herein may carry a detectable or functional label. When fluorescence labels are used, currently available microscopy and fluorescence-activated cell sorter analysis (FACS) or a combination of both methods known in the art may be utilized to identify and to quantitate the specific binding members. A TCR described herein may carry a fluorescence label. Exemplary fluorescence labels include, for example, reactive and conjugated probes, e.g., aminocoumarin, fluorescein and Texas red, Alexa Fluor dyes, Cy dyes, and DyLight dyes. A TCR described herein may carry a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{67}$Cu, $^{90}$Y, $^{99}$Tc, $^{111}$In, $^{117}$Lu, $^{121}$I, $^{124}$I, $^{125}$I, $^{131}$I, $^{198}$Au, $^{211}$At, $^{213}$Bi, $^{225}$Ac and $^{186}$Re. When radioactive labels are used, currently available counting procedures known in the art may be utilized to identify and quantitate the specific binding of the TCR to a peptide-MHC complex comprising a MLL polypeptide (e.g., a MLL phosphopeptide, e.g., a peptide consisting of the amino acid sequence of SEQ ID NO: 45 or 47). In the instance where the label is an enzyme, detection may be accomplished by any of the presently utilized colorimetric, spectrophotometric, fluorospectrophotometric, amperometric, or gasometric techniques as known in the art. This can be achieved by contacting a sample or a control sample with a TCR described herein under conditions that allow for the formation of a complex between the TCR and the peptide-MHC complex comprising a MLL peptide (e.g., a MLL phosphopeptide, e.g., a peptide consisting of the amino acid sequence of SEQ ID NO: 45 or 47). Any complexes formed between the TCR and the peptide-MHC complex are detected and compared in the sample and the control. In light of the specific binding of the TCRs described herein for a peptide-MHC complex comprising a MLL peptide (e.g., a MLL phosphopeptide, e.g., a peptide consisting of the amino acid sequence of SEQ ID NO: 45 or 47), the TCRs can be used to detect cells displaying a peptide-MHC complex comprising a MLL polypeptide (e.g., a MLL phosphopeptide, e.g., a peptide consisting of the amino acid sequence of SEQ ID NO: 45 or 47). The TCR described herein can also be used to purify such a complex or cell via immunoaffinity purification. Also included herein is an assay system which may be prepared in the form of a test kit for semi-quantitative or quantitative analysis of the extent of the presence of, for instance, a peptide-MHC complex comprising a MLL peptide (e.g., a MLL phosphopeptide, e.g., a peptide consisting of the amino acid sequence of SEQ ID NO: 45 or 47), or a complex comprising the peptide-MHC complex. The system or test kit may comprise a labeled component, e.g., a labeled TCR, and one or more additional immunochemical reagents.

5.5 Polynucleotides, Vectors and Methods of Producing TCRs

In another aspect, provided herein are polynucleotides comprising a nucleotide sequence encoding a TCR described herein (e.g., α chain, β chain, Vα domain, and/or Vβ domain) that binds to a MLL peptide (e.g., a MLL phosphopeptide, e.g., a peptide consisting of the amino acid sequence of SEQ ID NO: 45 or 47), and vectors, e.g., vectors comprising such polynucleotides for recombinant expression in host cells (e.g., E. coli and mammalian cells). Provided herein are polynucleotides comprising nucleotide sequences encoding an α chain and/or β chain of any of the TCRs provided herein, as well as vectors comprising such polynucleotide sequences, e.g., expression vectors for their efficient expression in host cells, e.g., mammalian cells.

In certain embodiments, a polynucleotide or nucleic acid molecule described herein is isolated or purified. In general, an isolated polynucleotide or nucleic acid molecule is one which is separated from other nucleic acid molecules which are present in the natural source (e.g., in a mouse or a human) of the nucleic acid molecule. Additionally or alternatively, an isolated polynucleotide or nucleic acid molecule (e.g., a cDNA molecule) is substantially free of other cellular material, or culture medium when produced by recombinant techniques, or substantially free of chemical precursors or other chemicals when chemically synthesized. For example, the language "substantially free" includes preparations of polynucleotides or nucleic acid molecules having less than about 15%, 10%, 5%, 2%, 1%, 0.5%, or 0.1% (in particular less than about 10%) of other material, e.g., cellular material, culture medium, other nucleic acid molecules, chemical precursors, and/or other chemicals.

In a particular aspect, provided herein are polynucleotides comprising nucleotide sequences encoding TCRs which bind to the same epitope of a peptide comprising the amino acid sequence set forth in SEQ ID NO: 45 or 47 as the TCRs described supra. In certain embodiments, the peptide is in complex with an MHC as described supra (e.g., HLA-B*0702). In certain embodiments, the TCR comprises sequences that do not naturally exist within the TCR germline repertoire of an animal or mammal (e.g., human) in vivo. In certain embodiments, the polynucleotide comprises sequences that do not naturally exist within the TCR-encoding DNA germline repertoire of an animal or mammal (e.g., human) in vivo.

In certain aspects, provided herein are polynucleotides comprising a nucleotide sequence encoding the α chain and/or β chain of a TCR described herein. The polynucleotides can comprise nucleotide sequences encoding an α chain comprising the α chain FRs and CDRs of TCRs described herein (see, e.g., Table 1) or nucleotide sequences encoding a β chain comprising the β chain FRs and CDRs of TCRs described herein (see, e.g., Table 1).

In certain embodiments, the polynucleotide encodes the α chain and β chain of a TCR described herein. In certain embodiments, the polynucleotide encodes a polypeptide comprising from the N-terminus to the C-terminus: the α chain of the TCR, a 2A cleavage site, and the β chain of the TCR. In certain embodiments, the polynucleotide encodes a polypeptide comprising from the N-terminus to the C-terminus: the β chain of the TCR, a 2A cleavage site, and the α chain of the TCR. In certain embodiments, the polynucleotide encodes a polypeptide comprising from the N-terminus to the C-terminus: the α chain of the TCR, a furin cleavage site, a 2A cleavage site, and the β chain of the TCR. In certain embodiments, the polynucleotide encodes a polypeptide comprising from the N-terminus to the C-terminus: the β chain of the TCR, a furin cleavage site, a 2A cleavage site, and the α chain of the TCR. The furin cleavage site generally has a consensus sequence of $RX_1X_2R$, wherein $X_1$ can be any amino acid, and $X_2$ is K or R (SEQ ID NO: 96). In certain embodiments, $X_1$ is K or R. In certain embodiments, the furin cleavage site has a sequence of RAKR (SEQ ID NO: 97). In certain embodiments, the furin cleavage site is cleaved after the second arginine residue. The 2A cleavage site generally comprises a consensus sequence of $X_1X_2EX_3NPGP$, wherein $X_1$ is D or G, $X_2$ is V or I, and $X_3$ is any amino acid (SEQ ID NO: 99). In certain embodiments, the 2A cleavage site is cleaved between the C-terminal proline residue and the preceding glycine residue. In certain embodiments, the 2A cleavage site comprises an amino acid sequence selected from SEQ ID NOs: 100-105 and 239-246 (Table 7). In certain embodiments, the 2A cleavage site is a porcine teschovirus-1 2A (P2A) cleavage site having the amino acid sequence set forth in SEQ ID NO: 100. In certain embodiments, the 2A cleavage site is a porcine teschovirus-1 2A (P2A) cleavage site having the amino acid sequence set forth in SEQ ID NO: 239. In certain embodiments, the polynucleotide comprises a nucleic acid sequence encoding SEQ ID NO: 90. In certain embodiments, the polynucleotide comprises a nucleic acid sequence encoding SEQ ID NO: 238.

50 fold, 60 fold, 70 fold, 80 fold, 90 fold, or 100 fold or more relative to the expression of a TCR encoded by polynucleotides that have not been optimized.

TABLE 7

Exemplary 2A cleavage sites

| SEQ ID NO: | Description | Amino acid Sequence |
|---|---|---|
| 100 | porcine teschovirus-1 2A (P2A) variant 1 | ATNFSLLKQAGDVEENPGP |
| 239 | porcine teschovirus-1 2A (P2A) variant 2 | GSGATNFSLLKQAGDVEENPGP |
| 101 | thosea-asigna virus 2A peptide (T2A) variant 1 | EGRGSLLTCGDVEENPGP |
| 240 | thosea-asigna virus 2A peptide (T2A) variant 2 | GSGEGRGSLLTCGDVEENPGP |
| 102 | equine rhinitis A virus 2A peptide (E2A) variant 1 | QCTNYALLKLAGDVESNPGP |
| 241 | equine rhinitis A virus 2A peptide (E2A) variant 2 | GSGQCTNYALLKLAGDVESNPGP |
| 103 | foot-and-mouth disease virus 2A peptide (F2A) variant 1 | VKQTLNFDLLKLAGDVESNPGP |
| 242 | foot-and-mouth disease virus 2A peptide (F2A) variant 2 | GSGVKQTLNFDLLKLAGDVESNPGP |
| 104 | cytoplasmic polyhedrosis virus 2A peptide (BmCPV 2A) variant 1 | DVFRSNYDLLKLCGDIESNGPG |
| 243 | cytoplasmic polyhedrosis virus 2A peptide (BmCPV 2A) variant 2 | GSGDVFRSNYDLLKLCGDIESNPGP |
| 105 | flacherie virus of *B. mori* 2A peptide (BmIFV 2A) variant 1 | TLTRAKIEDELIRAGIESNPGP |
| 244 | flacherie virus of *B. mori* 2A peptide (BmIFV 2A) variant 2 | GSGTLTRAKIEDELIRAGIESNPGP |
| 245 | Dual P2A-T2A peptide variant 1 | ATNFSLLKQAGDVEENPGPEGRGSLLTCGDVEENPGP |
| 246 | Dual P2A-T2A peptide variant 2 | GSGATNFSLLKQAGDVEENPGPEGRGSLLTCGDVEENPGP |

Also provided herein are polynucleotides encoding a TCR described herein that are optimized, e.g., by codon/RNA optimization, replacement with heterologous signal sequences, and elimination of mRNA instability elements. Methods to generate optimized nucleic acids encoding a TCR (e.g., α chain, β chain, Vα domain, and/or Vβ domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid. Such methods can increase expression of a TCR by at least 1 fold, 2 fold, 3 fold, 4 fold, 5 fold, 10 fold, 20 fold, 30 fold, 40 fold, In certain embodiments, an optimized polynucleotide sequence encoding a TCR described herein (e.g., α chain, β chain, Vα domain and/or Vβ domain) can hybridize to an antisense (e.g., complementary) polynucleotide of an unoptimized polynucleotide sequence encoding a TCR described herein (e.g., α chain, β chain, Vα domain, and/or Vβ domain). In specific embodiments, an optimized nucleotide sequence encoding a TCR described herein under high stringency conditions to antisense polynucleotide of an unoptimized polynucleotide sequence encoding a TCR described herein. In a specific embodiment, an optimized nucleotide sequence encoding a TCR described herein hybridizes under high stringency, intermediate or lower stringency hybridization conditions to an antisense polynucleotide of an unoptimized nucleotide sequence encoding a TCR described herein. Information regarding hybridization conditions has been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding TCRs described herein, e.g., TCRs described in Tables 1-4, and modified versions of these TCRs can be determined using methods well-known in the art, i.e., nucleotide codons known to encode particular amino acids are assembled in such a way to generate a nucleic acid that encodes the TCR. Such a polynucleotide encoding the TCR can be assembled from chemically synthesized oligonucleotides (e.g., as described in Kutmeier G et al., (1994), BioTechniques 17: 242-6), which, briefly, involves the synthesis of overlapping oligonucleotides containing portions of the sequence encoding the TCR, annealing and ligating of those oligonucleotides, and then amplification of the ligated oligonucleotides by PCR.

Alternatively, a polynucleotide encoding a TCR described herein can be generated from nucleic acid from a suitable source (e.g., a T lymphocyte) using methods well-known in the art (e.g., PCR and other molecular cloning methods). For example, PCR amplification using synthetic primers hybridizable to the 3' and 5' ends of a known sequence can be performed using genomic DNA obtained from T cells expressing the TCR of interest. Such PCR amplification methods can be used to obtain nucleic acids comprising the sequence encoding the α chain and/or β chain of a TCR. Such PCR amplification methods can be used to obtain nucleic acids comprising the sequence encoding the Vα domain and/or Vβ domain of a TCR. The amplified nucleic acids can be cloned into vectors for expression in host cells and for further cloning, for example, to generate chimeric and humanized TCRs.

If a clone containing a nucleic acid encoding a particular TCR is not available, but the sequence of the TCR molecule is known, a nucleic acid encoding the TCR can be chemically synthesized or obtained from a suitable source (e.g., a TCR cDNA library or a cDNA library generated from, or nucleic acid, e.g., poly A+ RNA, isolated from, any tissue or cells expressing the TCR, such as T lymphocytes selected to express a TCR described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes TCRs. Amplified nucleic acids generated by PCR can then be cloned into replicable cloning vectors using any method well-known in the art.

DNA encoding TCRs described herein can be readily isolated and sequenced using conventional procedures, e.g., by using oligonucleotide probes that are capable of binding specifically to genes encoding the α chain and/or β chain of the TCR. T lymphocytes can serve as a source of such DNA. Once isolated, the DNA can be placed into expression vectors, which are then transfected into host cells such as E. coli cells, simian COS cells, Chinese hamster ovary (CHO) cells (e.g., CHO cells from the CHO GS System™ (Lonza)), or myeloma cells that do not otherwise produce TCR protein, to obtain the synthesis of TCRs in the recombinant host cells.

To generate whole TCRs, PCR primers including Vα or Vβ nucleotide sequences, a restriction site, and a flanking sequence to protect the restriction site can be used to amplify the Vα or Vβ sequences into clones, e.g., clones of individual Vα or Vβ nucleotide sequences, or clones of single-chain TCRs containing variable regions of TCRs attached by a flexible linker. Utilizing cloning techniques known to those of skill in the art, the PCR amplified Vα domains can be cloned into vectors expressing an α chain constant region, and the PCR amplified Vβ domains can be cloned into vectors expressing a β chain constant region. In certain embodiments, the vectors for expressing the Vα or Vβ domains comprise an EF-1α promoter, a secretion signal, a cloning site for the variable region, constant domains, and a selection marker such as neomycin. The α chain and β chain vectors are then co-transfected into cell lines, either simultaneously or sequentially, to generate stable or transient cell lines that express whole TCRs using techniques known to those of skill in the art. The Vα or Vβ domains can also be cloned into one vector expressing the necessary constant regions. The vector is then transfected into cell lines to generate stable or transient cell lines that express whole TCRs using techniques known to those of skill in the art.

The DNA also can be modified, for example, by substituting the coding sequence for human α chain and β chain constant domains in place of the murine sequences, or by covalently joining to the TCR coding sequence all or part of the coding sequence for a non-TCR polypeptide.

Also provided are polynucleotides that hybridize under high, intermediate, or low stringency hybridization conditions to polynucleotides that encode a TCR described herein. In specific embodiments, polynucleotides described herein hybridize under high, intermediate, or low stringency hybridization conditions to polynucleotides encoding a Vα domain and/or Vβ domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) *Current Protocols in Molecular Biology*, Vol. I, Green Publishing Associates, Inc. and John Wiley & Sons, Inc., New York at pages 6.3.1-6.3.6 and 2.10.3.

In certain aspects, provided herein are cells (e.g., host cells) expressing (e.g., recombinantly) TCRs described herein which bind to a MLL polypeptide (e.g., a MLL phosphopeptide, e.g., a peptide consisting of the amino acid sequence of SEQ ID NO: 45 or 47), and related polynucleotides and expression vectors. Provided herein are vectors (e.g., expression vectors) comprising polynucleotides comprising nucleotide sequences encoding such TCRs for recombinant expression in host cells, e.g., in mammalian cells. Also provided herein are host cells comprising such vectors for recombinantly expressing TCRs described herein (e.g., human or humanized TCR). In a particular aspect, provided herein are methods for producing a TCR described herein, comprising expressing such TCR from a host cell.

In another aspect, provided herein are methods for producing an engineered cell (e.g., a cell comprising a heterologous and/or recombinant nucleic acid) as described herein. In certain embodiments, the method comprises contacting a cell with a vector as described herein under conditions that allow introduction of the vector into the cell. In certain embodiments, the condition allows transfection of the cell with the vector (e.g., by liposome or electroporation). In one embodiment, the condition allows transfection of the cell with an mRNA vector by electroporation. In certain embodiments, the vector is a viral vector, and the conditions allow transduction of the cell with the viral vector. In certain embodiments, the vector is introduced to the cell in vitro or ex vivo. In certain embodiments, the vector is introduced to the cell in vivo.

Recombinant expression of a TCR described herein (e.g., a full-length TCR, a chain and/or β chain of a TCR, or a single-chain TCR described herein) that binds to a MLL polypeptide (e.g., a MLL phosphopeptide, e.g., a peptide consisting of the amino acid sequence of SEQ ID NO: 45 or 47) involves construction of an expression vector containing a polynucleotide that encodes the TCR. Once a polynucleotide encoding a TCR described herein has been obtained, the vector for the production of the TCR molecule can be produced by recombinant DNA technology using techniques well-known in the art. Thus, methods for preparing a protein by expressing a polynucleotide containing a TCR encoding nucleotide sequence are described herein. Methods which are well-known to those skilled in the art can be used to construct expression vectors containing TCR encoding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding a TCR molecule described herein (e.g., a full-length TCR, α chain or β chain of a TCR, Vα or Vβ of a TCR, or an α or β chain CDR), operably linked to a promoter.

The vector can comprise any type of nucleotides (including but not limited to DNA and RNA) which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. In one embodiment, the non-naturally occurring or altered nucleotides or inter-nucleotide linkages do not hinder the transcription or replication of the vector. The expression vector can be a viral vector (e.g., a retroviral vector, an adenoviral vector, an adeno-associated viral vector, or a baculoviral vector). In certain embodiments, the retroviral vector is a lentiviral vector (e.g., a vector comprising genetic elements of the HIV-1 genome) or an equine infectious anemia viral vector. In certain embodiments, the vector is packaged with one or more viral capsid proteins to provide a viral particle.

An expression vector can be transferred to a cell (e.g., a host cell) by conventional techniques and the resulting cell can then be cultured by conventional techniques to produce a TCR described herein. Thus, provided herein are host cells containing a polynucleotide encoding a TCR molecule described herein (e.g., a full-length TCR, α chain or β chain of a TCR, Vα or Vβ of a TCR, or an α or β chain CDR) operably linked to a promoter for expression of such sequences in the host cell. In certain embodiments, for the expression of double-chained TCRs, vectors encoding both the α and β chains, individually, can be co-expressed in the host cell for expression of the entire TCR molecule, as detailed below. In certain embodiments, a host cell contains a vector comprising a polynucleotide encoding both the α chain and β chain of a TCR described herein. In specific embodiments, a host cell contains two different vectors, a first vector comprising a polynucleotide encoding an α chain or an α chain variable region of a TCR described herein, and a second vector comprising a polynucleotide encoding a β chain or a β chain variable region of a TCR described herein. In other embodiments, a first host cell comprises a first vector comprising a polynucleotide encoding an α chain or an α chain variable region of a TCR described herein, and a second host cell comprises a second vector comprising a polynucleotide encoding a β chain or a β chain variable region of a TCR described herein. In specific embodiments, an α chain or a chain variable region expressed by a first cell associated with a β chain or β chain variable region expressed by a second cell to form a TCR described herein. In certain embodiments, provided herein is a population of host cells comprising such first host cell and such second host cell.

In a particular embodiment, provided herein is a population of vectors comprising a first vector comprising a polynucleotide encoding an α chain or α chain variable region of a TCR described herein, and a second vector comprising a polynucleotide encoding a β chain or β chain variable region of a TCR described herein.

A variety of host-expression vector systems can be utilized to express TCR molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express a TCR molecule described herein in situ. These include but are not limited to microorganisms such as bacteria (e.g., *E. coli* and *B. subtilis*) transformed with recombinant bacteriophage DNA, plasmid DNA, or cosmid DNA expression vectors containing TCR coding sequences; yeast (e.g., *Saccharomyces Pichia*) transformed with recombinant yeast expression vectors containing TCR coding sequences; insect cell systems infected with recombinant virus expression vectors (e.g., baculovirus) containing TCR coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing TCR coding sequences; or mammalian cell systems (e.g., COS (e.g., COS1 or COS), CHO, BHK, MDCK, HEK 293, NS0, PER.C6, VERO, CRL7O3O, HsS78Bst, HeLa, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing TCRs described herein are CHO cells, for example CHO cells from the CHO GS System™ (Lonza). In a particular embodiment, cells for expressing TCRs described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant TCR molecule, are used for the expression of a recombinant TCR molecule. For example, mammalian cells such as Chinese hamster ovary (CHO) cells, in conjunction with a vector such as the major intermediate early gene promoter element from human cytomegalovirus, are an effective expression system for TCRs (Foecking M K & Hofstetter H (1986) Gene 45: 101-5; and Cockett M I et al., (1990) Biotechnology 8(7): 662-7). In certain embodiments, TCRs described herein are produced by CHO cells or NSO cells. In a specific embodiment, the expression of nucleotide sequences encoding TCRs described herein is regulated by a constitutive promoter, inducible promoter, or tissue specific promoter.

In certain embodiments, the mammalian host cell is a lymphocyte (e.g., a human lymphocyte), such as a T cell or a natural killer (NK) cell. In certain embodiments, the lymphocyte is a T cell. Any T cell at any developmental stage can be used to express a TCR disclosed herein. For example, in certain embodiments, the T cell is selected from the group consisting of a $CD8^+$ cytotoxic T cell, a $CD4^+$ cytotoxic T cell, a $CD4^+$ helper T cell (e.g., a Th1 or a Th2 cell), a CD4/CD8 double positive T cells, a tumor infiltrating T cell, a thymocyte, a memory T cell, a naïve T cell, and a natural killer T cell (e.g., an invariant natural killer T cell). Precursor cells of the cellular immune system (e.g., precursors of T lymphocytes) are also useful for presenting a TCR disclosed herein because these cells may differentiate, develop, or mature into effector cells. Accordingly, in certain embodiments, the mammalian host cell is a pluripotent stem cell (e.g., an embryonic stem cell, an induced pluripotent stem cell), lymphocyte progenitor cell, or a hematopoietic stem cell (e.g., isolated and/or enriched from bone marrow, umbilical cord blood, or peripheral blood).

Cells can be obtained from numerous sources, including but not limited to, tumor, blood, bone marrow, lymph node, thymus, or another tissue or bodily fluid, or an apheresis product. In certain embodiments, cells are obtained from a patient directly following a treatment that leaves the subject with functional T cells. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, in certain embodiments, cells are collected from blood, bone marrow, lymph node, thymus, or another tissue or bodily fluid, or an apheresis product, during this recovery phase.

In certain embodiments, the mammalian host cell is a population of cells presenting a TCR disclosed herein on the cell surface. The population of cells can be heterogeneous or homogenous. In certain embodiments, at least 50% (e.g., at least 60%, 70%, 80%, 90%, 95%, 99%, 99.5%, or 99.9%) of the population is a cell as described herein. In certain embodiments, the population is substantially pure, wherein at least 50% (e.g., at least 60%, 70%, 80%, 90%, 95%, 99%, 99.5%, or 99.9%) of the population is homogeneous. In certain embodiments, the population is heterogeneous and comprises a mixed population of cells (e.g., the cells have different cell types, developmental stages, origins, are isolated, purified, or enriched by different methods, are stimulated with different agents, and/or are engineered by different methods). In certain embodiments, the cells are a population of peripheral blood mononuclear cells (PBMC) (e.g., human PBMCs).

In bacterial systems, a number of expression vectors can be advantageously selected depending upon the use intended for the TCR molecule being expressed. For example, when a large quantity of such a TCR is to be produced, for the generation of pharmaceutical compositions of a TCR molecule, vectors which direct the expression of high levels of fusion protein products that are readily purified can be desirable. Such vectors include, but are not limited to, the *E. coli* expression vector pUR278 (Ruether U & Mueller-Hill B (1983) EMBO J 2: 1791-1794), in which the TCR coding sequence can be ligated individually into the vector in frame with the lac Z coding region so that a fusion protein is produced; pIN vectors (Inouye S & Inouye M (1985) Nuc Acids Res 13: 3101-3109; Van Heeke G & Schuster S M (1989) J Biol Chem 24: 5503-5509); and the like. For example, pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV), for example, can be used as a vector to express foreign genes. The virus grows in *Spodoptera frugiperda* cells. The TCR coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the TCR encoding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the TCR molecule in infected hosts (e.g., see Logan J & Shenk T (1984) PNAS 81(12): 3655-9). Specific initiation signals can also be required for efficient translation of inserted TCR coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bitter G et al., (1987) Methods Enzymol. 153: 516-544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, MDCK, HEK 293, NIH 3T3, W138, BT483, Hs578T, HTB2, BT2O and T47D, NS0 (a murine myeloma cell line that does not endogenously produce any immunoglobulin chains), CRL7O3O, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. In certain embodiments, TCR molecules described herein are produced in mammalian cells, such as CHO cells.

For long-term expression of the recombinant TCRs, stable expression cells can be generated. For example, cell lines which stably express a TCR described herein can be engineered. In specific embodiments, a cell provided herein stably expresses an α chain or α chain variable region and a β chain or β chain variable region which associate to form a TCR described herein.

In certain aspects, host cells can be transformed with DNA controlled by appropriate expression control elements (e.g., promoter, enhancer, sequences, transcription terminators, polyadenylation sites, etc.), and a selectable marker. Following the introduction of the foreign DNA/polynucleotide, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express a TCR described herein. Such engineered cell lines can be particularly useful in screening and evaluation of compositions that interact directly or indirectly with the TCR molecule.

A number of selection systems can be used, including but not limited to, the herpes simplex virus thymidine kinase (Wigler M et al., (1977) Cell 11(1): 223-32), hypoxanthine-guanine phosphoribosyltransferase (Szybalska E H & Szybalski W (1962) PNAS 48(12): 2026-2034), and adenine phosphoribosyltransferase (Lowy I et al., (1980) Cell 22(3): 817-23) genes in tk-, hgprt- or aprt-cells, respectively, each of which is incorporated by reference herein in its entirety. Also, antimetabolite resistance can be used as the basis of selection for the following genes: dhfr, which confers resistance to methotrexate (Wigler M et al., (1980) PNAS 77(6): 3567-70; O'Hare K et al., (1981) PNAS 78: 1527-31); gpt, which confers resistance to mycophenolic acid (Mulligan R C & Berg P (1981) PNAS 78(4): 2072-6); neo, which confers resistance to the aminoglycoside G-418 (Wu G Y & Wu C H (1991) Biotherapy 3: 87-95; Tolstoshev P (1993) Ann Rev Pharmacol Toxicol 32: 573-596; Mulligan R C (1993) Science 260: 926-932; and Morgan R A & Anderson W F (1993) Ann Rev Biochem 62: 191-217; Nabel G J & Felgner P L (1993) Trends Biotechnol 11(5): 211-5); and hygro, which confers resistance to hygromycin (Santerre R F et al., (1984) Gene 30(1-3): 147-56), each of which is incorporated by reference herein in its entirety. Methods commonly known in the art of recombinant DNA technology can be routinely applied to select the desired recombinant clone and such methods are described, for example, in Ausubel F M et al., (eds.), *Current Protocols in Molecular Biology*, John Wiley & Sons, NY (1993); Kriegler M, *Gene Transfer and Expression*, A Laboratory Manual, Stockton Press, NY (1990); and in Chapters 12 and 13, Dracopoli N C et al., (eds.), *Current Protocols in Human Genetics*, John Wiley & Sons, NY (1994); Colbère-Garapin F et al., (1981) J Mol Biol 150: 1-14, which are incorporated by reference herein in their entireties.

The expression levels of a TCR molecule can be increased by vector amplification (for a review, see Bebbington C R & Hentschel C C G, The use of vectors based on gene amplification for the expression of cloned genes in mammalian cells in DNA cloning, Vol. 3 (Academic Press, New York, 1987), which is incorporated by reference herein in its entirety). When a marker in the vector system expressing TCR is amplifiable, increase in the level of inhibitor present in culture of host cells will result in selection of host cells with increased numbers of copies of the marker gene. Since the amplified region is associated with the TCR gene, production of the TCR will also increase (Crouse G F et al., (1983) Mol Cell Biol 3: 257-66, which is incorporated by reference herein in its entirety).

In other aspects, the host cell can be transduced with a viral vector (e.g., a retroviral vector, an adenoviral vector, an adeno-associated viral vector, or a baculoviral vector) comprising a sequence encoding a TCR as described herein. In certain embodiments, the retroviral vector is a lentiviral vector (e.g., a vector comprising genetic elements of the HIV-1 genome) or an equine infectious anemia viral vector. In certain embodiments, the vector is packaged with one or more viral capsid proteins to provide a viral particle.

In certain embodiments, the vector further comprises a transcriptional and/or translational control sequence (e.g., a promoter, an enhancer, and/or a Kozak sequence) operably linked to the sequence encoding a TCR as described herein. Alternatively, the sequence encoding the TCR may not be operably linked to a transcriptional and/or translational control sequence (e.g., a promoter, an enhancer, and/or a Kozak sequence), but is flanked by sequences homologous to the sequences flanking a locus of the host cell genome, wherein the integration of the TCR-coding sequence allows expression of the encoded TCR from the transcriptional and/or translational control sequence at or near the genomic locus.

The host cell can be co-transferred (e.g., co-transfected or co-transduced) with two or more expression vectors described herein, the first vector encoding an α chain derived polypeptide and the second vector encoding a β chain derived polypeptide. The two vectors can contain identical selectable markers which enable equal expression of α chain and β chain polypeptides. The host cells can be co-transferred with different amounts of the two or more expression vectors. For example, host cells can be co-transferred with any one of the following ratios of a first expression vector and a second expression vector: 1:1, 1:2, 1:3, 1:4, 1:5, 1:6, 1:7, 1:8, 1:9, 1:10, 1:12, 1:15, 1:20, 1:25, 1:30, 1:35, 1:40, 1:45, or 1:50. In some embodiments, the coding sequences for the α and β chains are DNA. In some embodiments, the coding sequences for the α and β chains are RNA.

Alternatively, a single vector can be used which encodes, and is capable of expressing, both α and β chain polypeptides. The coding sequences for the α and β chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., β chain of a TCR described herein), and a second gene (e.g., α chain of a TCR described herein). In such an expression vector, the transcription of both genes can be driven by the promoter, whereas the translation of the mRNA from the first gene can be initiated by a cap-dependent scanning mechanism and the translation of the mRNA from the second gene can be by a cap-independent mechanism, e.g., by an IRES. Alternatively, the two genes can be operably linked by a self-cleavage peptide (e.g., a 2A peptide) or a peptide sequence recognized by an intracellular or an extracellular protease.

Once a TCR molecule described herein has been produced by recombinant expression, it can be purified by any method known in the art for purification of an immunoglobulin molecule, for example, by chromatography (e.g., ion exchange, affinity, and sizing column chromatography), centrifugation, differential solubility, or by any other standard technique for the purification of proteins. Further, the TCR described herein can be fused to heterologous polypeptide sequences described herein or otherwise known in the art to facilitate purification.

In specific embodiments, a TCR described herein is isolated or purified. Generally, an isolated TCR is one that is substantially free of other TCRs with different antigenic specificities than the isolated TCRs. For example, in a particular embodiment, a preparation of a TCR described herein is substantially free of cellular material and/or chemical precursors. The language "substantially free of cellular material" includes preparations of a TCR in which the TCR is separated from cellular components of the cells from which it is isolated or recombinantly produced. Thus, a TCR that is substantially free of cellular material includes preparations of the TCR having less than about 30%, 20%, 10%, 5%, 2%, 1%, 0.5%, or 0.1% (by dry weight) of heterologous protein (also referred to herein as a "contaminating protein") and/or variants of the TCR, for example, different post-translational modified forms of the TCR or other different versions of the TCR (e.g., fragments thereof). When the TCR is recombinantly produced, it is also generally substantially free of culture medium, i.e., culture medium represents less than about 20%, 10%, 2%, 1%, 0.5%, or 0.1% of the volume of the protein preparation. When the TCR is produced by chemical synthesis, it is generally substantially free of chemical precursors or other chemicals, i.e., it is separated from chemical precursors or other chemicals which are involved in the synthesis of the TCR. Accordingly, such preparations of the TCR have less than about 30%, 20%, 10%, or 5% (by dry weight) of chemical precursors or compounds other than the TCR of interest. In a specific embodiment, TCRs described herein are isolated or purified.

TCRs that bind to a MLL polypeptide (e.g., a MLL phosphopeptide, e.g., a peptide consisting of the amino acid sequence of SEQ ID NO: 45 or 47) can be produced by any method known in the art for the synthesis of TCRs, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described, for example, in the references cited herein and are fully explained in the literature. See, e.g., Maniatis T et al., (1982) *Molecular Cloning: A Laboratory Manual*, Cold Spring Harbor Laboratory Press; Sambrook J et al., (1989), *Molecular Cloning: A Laboratory Manual*, Second Edition, Cold Spring Harbor Laboratory Press; Sambrook J et al., (2001) *Molecular Cloning: A Laboratory Manual*, Cold Spring Harbor Laboratory Press, Cold Spring Harbor, N.Y.; Ausubel F M et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren B et al., (eds.) (1999) *Genome Analysis: A Laboratory Manual*, Cold Spring Harbor Laboratory Press, each of which is incorporated by reference herein in its entirety.

In a specific embodiment, a TCR described herein is a TCR (e.g., recombinant TCR) prepared, expressed, created, or isolated by any means that involves creation, e.g., via synthesis, genetic engineering of DNA sequences. In certain embodiments, such TCR comprises sequences (e.g., DNA sequences, RNA sequences, or amino acid sequences) that do not naturally exist within the TCR germline repertoire of an animal or mammal (e.g., human) in vivo.

In one aspect, provided herein is a method of making a TCR that binds to a MLL polypeptide (e.g., a MLL phosphopeptide, e.g., a peptide consisting of the amino acid sequence of SEQ ID NO: 45 or 47), the method comprising culturing a cell or host cell described herein. In a certain aspect, provided herein is a method of making a TCR which binds to a MLL polypeptide (e.g., a MLL phosphopeptide, e.g., a peptide consisting of the amino acid sequence of SEQ ID NO: 45 or 47), the method comprising expressing (e.g., recombinantly expressing) the TCR using a cell or host cell described herein (e.g., a cell or a host cell comprising polynucleotides encoding a TCR described herein). In a particular embodiment, the cell is an isolated cell. In a particular embodiment, the exogenous polynucleotides have been introduced into the cell. In a particular embodiment, the method further comprises the step of purifying the TCR obtained from the cell or host cell.

The TCRs described herein can be generated using various phage display methods known in the art. In phage display methods, functional TCR domains are displayed on the surface of phage particles which carry the polynucleotide sequences encoding them. In particular, DNA sequences encoding Vα and Vβ domains are amplified from animal cDNA libraries (e.g., human or murine cDNA libraries of affected tissues). The DNA encoding the Vα and Vβ domains are connected with a peptide linker by PCR and cloned into a phagemid vector. The vector is electroporated in *E. coli* and the *E. coli* is infected with helper phage. Phage used in these methods are typically filamentous phage including fd and M13, and the Vα and Vβ domains are usually recombinantly fused to either the phage gene III or gene VIII. Phage expressing an antigen binding domain that binds to a particular antigen can be selected or identified with a peptide or a peptide-MHC complex, e.g., using such a complex displayed on the surface of a cell or captured to a solid surface or bead. Examples of phage display methods that can be used to make the TCRs described herein include those disclosed in Zhao Y et al., (2007) J Immunol 179: 5845-54, which is incorporated by reference herein in its entirety.

As described in the above references, after phage selection, the TCR coding regions from the phage can be isolated and used to generate whole TCRs, including human TCRs, and expressed in any desired host, including mammalian cells, insect cells, plant cells, yeast, and bacteria, e.g., as described below.

In certain embodiments, to generate whole TCRs, PCR primers including Vα or Vβ nucleotide sequences, a restriction site, and a flanking sequence to protect the restriction site can be used to amplify the Vα or Vβ sequences from a template, e.g., clones of single-chain TCRs containing variable regions of TCRs connected by a peptide linker. Utilizing cloning techniques known to those of skill in the art, the PCR amplified Vα domains can be cloned into vectors expressing a Vα constant region, and the PCR amplified Vβ domains can be cloned into vectors expressing a Vβ constant region. The α chain and β chain vectors are then co-transfected into cell lines, either simultaneously or sequentially, to generate stable or transient cell lines that express whole TCRs using techniques known to those of skill in the art. The Vα or Vβ domains can also be cloned into one vector expressing the necessary constant regions. The vector is then transfected into cell lines to generate stable or transient cell lines that express whole TCRs using techniques known to those of skill in the art.

In certain embodiments, to generate whole TCRs from a polynucleotide encoding the α chain and β chain of a TCR as described herein, or from a vector comprising thereof, a polypeptide comprising the α chain and β chain of the TCR is expressed from the polynucleotide or vector. The polypeptide is optionally isolated and/or purified. The polypeptide is contacted with a Furin enzyme. In certain embodiments, where the Furin cleavage site has the amino acid sequence of $RX_1X_2R$, wherein $X_1$ is K or R, and $X_2$ is K or R (SEQ ID NO: 98), the polypeptide is further contacted with a carboxypeptidases either simultaneously or subsequently, wherein the carboxypeptidase removes the basic amino acids, K or R, from the C-terminus of a polypeptide.

A chimeric TCR is a molecule in which different portions of the TCR are derived from different TCR molecules, e.g., TCRs from different species.

In particular embodiments, a TCR described herein, which binds to the same epitope of a peptide comprising the amino acid sequence set forth in SEQ ID NO: 45 or 47 as a TCR described herein, is a human TCR. Human TCRs can be produced using any method known in the art. For example, transgenic mice which are incapable of expressing functional endogenous TCRs, but which can express human TCR genes, can be used. In particular, the human α and β chain TCR genes can be introduced randomly or by homologous recombination into mouse embryonic stem cells. The mouse α and β chain TCR genes can be rendered nonfunctional separately or simultaneously with the introduction of human TCR loci by homologous recombination. In particular, homozygous deletion of the JH region prevents endogenous TCR production. The modified embryonic stem cells are expanded and microinjected into blastocysts to produce chimeric mice. The chimeric mice are then bred to produce homozygous offspring which express human TCRs. The transgenic mice are immunized in the normal fashion with a selected antigen, e.g., all or a portion of an antigen (e.g., a MLL peptide, e.g., a MLL phosphopeptide). T lymphocytes comprising TCRs directed against the antigen can be obtained from the immunized, transgenic mice. The human TCR transgenes harbored by the transgenic mice rearrange during T cell differentiation. Thus, using such a technique, it is possible to produce therapeutically useful TCRs arising from in vivo immunization.

Human TCRs which bind to a MLL peptide (e.g., a MLL phosphopeptide, e.g., a peptide consisting of the amino acid sequence of SEQ ID NO: 45 or 47) can be made by a variety of methods known in the art including phage display methods or mammalian display using TCR libraries derived from human TCR sequences.

5.6 Kits

Also provided are kits comprising one or more TCRs described herein, pharmaceutical compositions or conjugates thereof, polynucleotides (e.g., expression vectors) encoding one or more TCRs described herein, or cells expressing one or more TCRs described herein. In a specific embodiment, provided herein is a pharmaceutical pack or kit comprising one or more containers filled with one or more of the ingredients of the pharmaceutical compositions described herein, such as one or more TCRs, polynucleotides, or cells provided herein. In some embodiments, the kits contain a pharmaceutical composition described herein and any prophylactic or therapeutic agent, such as those described herein. In certain embodiments, the kits may contain a T cell mitogen, such as, e.g., phytohaemagglutinin (PHA) and/or phorbol 12-myristate 13-acetate (PMA), or a TCR complex stimulating antibody, such as an anti-CD3 antibody and anti-CD28 antibody. Optionally associated with such container(s) can be a notice in the form prescribed by a governmental agency regulating the manufacture, use or sale of pharmaceuticals or biological products, which notice reflects approval by the agency of manufacture, use or sale for human administration.

Also provided, are kits that can be used in the above methods. In one embodiment, a kit comprises a TCR described herein, e.g., a purified TCR, in one or more containers. In a specific embodiment, kits described herein contain a substantially isolated peptide-MHC complex comprising a MLL peptide (e.g., a MLL phosphopeptide, e.g., a peptide consisting of the amino acid sequence of SEQ ID NO: 45 or 47) as a control antigen. In another specific embodiment, the kits described herein further comprise a control TCR which does not react with a peptide-MHC complex comprising a MLL peptide (e.g., a MLL phosphopeptide, e.g., a peptide consisting of the amino acid sequence of SEQ ID NO: 45 or 47). In another specific embodiment, kits described herein contain one or more elements for detecting the binding of a TCR to a peptide-MHC complex comprising a MLL peptide (e.g., a MLL phosphopeptide, e.g., a peptide consisting of the amino acid sequence of SEQ ID NO: 45 or 47) (e.g., the TCR can be conjugated to a detectable substrate such as a fluorescent compound, an enzymatic substrate, a radioactive compound or a luminescent compound, or a binding molecule which recognizes the TCR can be conjugated to a detectable substrate). In specific embodiments, a kit provided herein can include a recombinantly produced or chemically synthesized peptide-MHC complex comprising a MLL peptide (e.g., a MLL phosphopeptide, e.g., a peptide consisting of the amino acid sequence of SEQ ID NO: 45 or 47). The peptide-MHC complex comprising a MLL peptide (e.g., a MLL phosphopeptide, e.g., a peptide consisting of the amino acid sequence of SEQ ID NO: 45 or 47) provided in the kit can be attached to a solid support (e.g., a solid surface or a bead) or be integrated into a lipid membrane (e.g., a liposome, or a fixed cell). In a more specific embodiment, the detecting means of the above described kit includes a solid support to which a peptide-MHC complex comprising a MLL peptide (e.g., a MLL phosphopeptide, e.g., a peptide consisting of the amino acid sequence of SEQ ID NO: 45 or 47) is attached. Such a kit can also include a non-attached reporter-labeled binding molecule which recognizes the TCR. In this embodiment, binding of the TCR to the peptide-MHC complex can be detected by binding of the said reporter-labeled binding molecule.

6. EXAMPLES

The examples in this Section (i.e., Section 6) are offered by way of illustration, and not by way of limitation.

6.1 Example 1: Discovery of Novel MLL TCRs

Novel TCRs that bind to MLL phosphopeptides were identified using two proprietary platforms. The first platform is a primary T cell expansion platform in which phosphopeptide-specific cognate TCRα β pairs were identified by functional screening and NGS-based sequencing. The second platform is a TCR display platform in which a and 13 chain libraries were generated from donor PBMCs, optionally without previous target-specific stimulation, followed by rounds of TCR enrichment for target-specific phosphopeptide binding.

6.1.1 Preparation of Cells

Human dendritic cells (DCs) and CD8+ T cells were isolated from healthy donor HLA-B*0702+ PBMCs (Cellular Technologies Ltd., Shaker Heights, Ohio).

Briefly, CD14+ monocytes were isolated from the PBMCs by positive selection via magnetic separation using anti-CD14 microbeads according to the manufacturer's instructions (Miltenyi Biotech, Bergisch Gladbach, Germany, Cat. No.: 130-050-201) and cultivated in growth medium composed of CellGro® DC-medium (Cell Genix, Cat. No.: 20801-05500) supplemented with 5% human serum (Sigma, Cat. No.: H3667-100mL), 1% Penicillin/Streptomycin (Amimed Direct, London, UK, Cat. No.: 4-01F00-H), 800 U/mL of GM-CSF (Miltenyi Biotech, Cat. No.: 130-095-372), and 10 ng/mL of IL-4 (Miltenyi Biotech, Cat. No.: 130-093-917) for three days to induce differentiation to DCs. Following full differentiation after an additional 16-hour incubation in growth medium supplemented with 10 ng/mL of *Escherichia coli* LPS (Sigma-Aldrich, St. Louis, Mo., #L4391-1MG), 100 U/mL of IFNγ (Peprotech, Rocky Hill, N.J., Cat. No.: 300-02), and 20 µg/mL of the MLL-pM peptide (EPR[pS]PSHSM; SEQ ID NO: 45) or FLU and CMV control peptides, DCs were incubated in the presence of 50 µg/mL of Mitomycin (Sigma, Cat. No.: M05053-2MG) for 60 min to inhibit dendritic cell proliferation. DCs incubated in the absence of antigen peptide were prepared as control samples.

CD8+ T cells were isolated from CD14+ monocyte depleted PBMCs via negative selection using a magnetic bead human CD8+ T cell isolation kit according to the manufacturer's instructions (Miltenyi Biotech, Cat. No.: 130-096-495). CD8+ T cells were separated into CD45RO+/CD57− memory T cell and CD45RA+/CCR7+/CD62L+ naïve T cell populations after surface staining with a cocktail of anti-CD8-PerCP (eBioscience, Thermo Fisher, Waltham, Mass., Cat. No.: 9043-0087-120), anti-CD45RA-PE-Cy7 (eBiosciences, Cat. No.: 25-0458-42), anti-CD45RO-FITC (eBioscience, Cat. No.: 11-0457-42), anti-CD57-PE (Biolegend, San Diego, Calif., Cat. No.: 322312), anti-CCR7-BV421 (BD horizon, Cat. No.: 562555), and anti-CD62L-APC (eBioscience, Cat. No.: 17-0629-42) reagents using a FACSArialII (Becton Dickinson, Franklin Lakes, N.J.) cell sorter.

6.1.2 Phosphopeptide-Specific Stimulation and Staining of Human CD8+ T Cells

Memory and naïve CD8+ T cell subsets ($1.0 \times 10^6$ cells/mL) treated with 5 µg/mL of IL-7 (Miltenyi Biotech, Cat. No.: 130-093-937) for 16 hours were co-incubated with peptide-pulsed or non-pulsed DCs ($2.5 \times 10^5$ cells/mL) at a T cell:DC ratio of 4:1 in growth medium supplemented with 30 ng/mL of IL-21 (Peprotech, Cat. No.: 200-21) for 10 days. After days 3, 6, 8, and 10, fresh growth medium supplemented with 5 ng/mL (10 ng/mL at day 10) of IL-15 (BioLegend, Cat. No.: 570302) and IL-7 was added to the co-cultures.

$1.0 \times 10^6$ cells from the co-cultures were treated with 1 µM of Dasatinib (Cell Signaling Technology, Cat. No.: 9052S) before 10 µL of HLA-B*0702 pentamers loaded with the MLL-pM peptide EPR[pS]PSHSM (SEQ ID NO: 45), the Flu control peptide QPEWFRNVL (SEQ ID NO: 84), or the CMV control peptide TPRVTGGGAM (SEQ ID NO: 85) were added. Following addition of an anti-CD8-Per-CP reagent, pentamer-binding of CD8+ T cells was assessed by flow cytometry using a FACScantoII cytometer. Subsequently, up to $1.0 \times 10^6$ cells of the co-cultures containing memory or naïve CD8+ T cells that bind to the MLL-pM peptide were treated with Monensin (1:1000) (eBioscience, Cat. No.: 00-4505-51) and Brefeldin A (1:1000) (eBioscience, Cat. No.: 004506-61) and stained with pMHC pentamers as described above. Cocktails comprising anti-CD8-FITC, anti-KLGR1-PerCP-eFluor710 (eBioscience, Cat. No.: 46-9488-49), anti-4-1BB-BV421, anti-CD69-PE-Cy7 (eBioscience, Cat. No.: 25-069942), anti-IFNγ-APC (eBioscience, Cat. No.: 17-7319-82) or anti-IFNγ-PE (eBioscience, Cat. No.: 12-7319-82), and anti-TNFα-BV510 (BioLegend, Cat. No.: 502950) were used to detect surface and intracellular expression of T cell activation markers. Cells were permeabilized using Cytofix/Cytoperm (BD, Cat. No.: 51-2090KZ) and PermWash Buffer (BD, Cat. No.: 51-20911 (Z) according to the manufacturer's instructions. Peptide pentamer-binding was re-assessed using a FACSCantoII cytometer and memory and naïve CD8+ T cell subsets that bind to the MLL-pM peptide and/or respond to the MLL-pM stimulation were then acquired using a FACSArialI cytometer.

6.1.3 Exemplary Data from the Screening Process

In a first study, PBMCs from 17 HLA-B*0702 healthy donors were stimulated for 7 days with the MLL-pM peptide (EPR[pS]PSHSM; SEQ ID NO: 45) or the MLL-pP peptide (RVR[pS]PTRSP; SEQ ID NO: 47), followed by intracellular cytokine staining (ICS) for IFNγ and TNFα. A pool of 32 peptides selected from viral T cell epitopes was used as a positive control. Shown in FIG. 1 are representative data from three donors with increased TNFα production over the no peptide negative control.

In a second study, memory CD8+ T cell subsets were co-cultured with peptide-pulsed or non-pulsed DCs for 10 days. Cells from the co-cultures were stained with HLA-B*0702 pentamers loaded with the MLL-pM peptide EPR [pS]PSHSM (SEQ ID NO: 45) and an anti-CD8 antibody, followed by binding assessment by flow cytometry. As shown in FIG. 2, a CD8+ pentamer+ population of cells was detected after co-culturing with DCs pulsed with the MLL-pM peptide.

6.1.4 TCR Sublibrary Generation and Retroviral Transduction

Separate libraries were generated for TCR α and β chains. RNA was isolated from healthy donor HLA-B*0702+ PBMC-derived CD8+ T cells or CD8+ T cells enriched by stimulation with MLL-pM-pulsed DCs using the RNeasy®Midi kit (Qiagen, Cat. No.: 75142) or the AllPrep™ DNA/RNA Micro kit (Qiagen, Cat. No.: 80204). The isolated RNA was analyzed in a RNA6000 Pico assay (Agilent, Cat. No.: 5067-1513) using a 2100 Bioanalyzer (Agilent, Cat. No.: DE13701147) according to the manufacturer's instructions. RNA was transcribed into cDNA using the SMARTer® RACE 5'/3' kit (Clontech Laboratories, Cat. No.: 634860) and variable TCR α (TRAV and TRAJ genes) and β chains (TRBV and TRBJ genes) were separately amplified by multiplex PCR.

The resulting variable chain TCRα and TCRβ gene libraries were separately cloned into retroviral expression vectors (derived from MIGR1, Addgene, Cat. No.: 27490) containing murine non-variable α or β regions including transmembrane and intracellular domains to enable interactions with murine CD3 and signal transduction in murine T cells. The α and β chain expression vectors also comprise the expression markers CD6 and CD7, respectively. Diversity of the resulting plasmid library was assessed by next generation sequencing (NGS). To obtain a stable cellular TCRαβ library, TCRα and TCRβ library plasmids were consecutively introduced to a murine cell line AK-D10R3. AK-D10R3 is a murine thymoma-derived mouse TCR-negative, mouse CD8-negative cell line that expresses chimeric CD8 (human CD8α and β extracellular regions fused to the corresponding mouse CD8α and β transmembrane and intracellular regions) and a T cell activation reporter construct comprising a minimal IL-2 promoter, which includes three NFAT binding sites, operably linked to EGFP (the "IL-2-(NFAT)$_3$-EGFP" reporter construct). Expression of α and β chains was confirmed by flow cytometry after staining with anti-human CD6-bio (Antibodies Online, Cat. No.: ABIN609887) (1:1000) and anti-mouse-TCRβ-PE (BD Bioscience, Cat. No.: 553172) (1:1000) reagents and the final chain distribution and diversity determined via NGS.

6.2 Example 2: Characterization of Novel MLL TCRs in Murine Cells

Five novel TCRs that bind to MLL phosphopeptides were developed using a proprietary mammalian cell TCR display platform. Four of these TCRs, TCR0077, TCR0079, TCR0081, and TCR0083, bind to EPR[pS]PSHSM (SEQ ID NO: 45)-HLA-B*0702. One of these TCRs, TCR0085, binds to RVR[pS]PTRSP (SEQ ID NO: 47)-HLA-B*0702. The two phosphopeptides EPR[pS]PSHSM (SEQ ID NO: 45) and RVR[pS]PTRSP (SEQ ID NO: 47) were referred to as MLL-pM and MLL-pP peptides, respectively. The α chain variable region (Vα) and β chain variable region (Vβ) sequences of these five TCRs are provided in Table 4. These TCRs were expressed as chimeric proteins, with human variable regions fused to murine constant regions, on the surface of the murine cell line AK-D10R3 described above. The murine constant regions ensure proper anchoring and interaction with murine CD3 and proper triggering of murine signaling pathways.

6.2.1 Binding of TCR-Expressing AK-D10R3 Cells to Peptide-MHC Pentamers

AK-D10R3 cells were transduced to express the chimeric TCRs TCR0077, TCR0079, TCR0081, TCR0083, or TCR0085 and were expanded for three days at 37° C. and 10% CO$_2$ using SF-IMDM media (BioConcept, Cat. No.: 1-28S07-1). TCR-negative AK-D10R3 cells were included as a negative control. $1.0 \times 10^5$ AK-D10R3 cells were plated per well of a 96-well assay plate, centrifuged at 300×g and 4° C. for 5 min, washed twice using 200 µL assay buffer (1×PBS supplemented with 2% FCS), and resuspended in assay buffer at a concentration of $1.0 \times 10^5$ cells/100 µL. For staining, 20 µL of stock solutions of anti-mouse TCR β-chain-APC antibody (BD, Cat. No.: 553174, clone H57-597) (1:500) and PE-labeled HLA-B*0702 pentamers (Proimmune) loaded with the MLL-pM peptide EPR[pS]PSHSM (SEQ ID NO: 45) (5 µL/well or 0.5 µL/well), the MLL-pP peptide RVR[pS]PTRSP (SEQ ID NO: 47) (5 µL/well), or the non-phosphorylated control peptide MLL-M EPRSPSHSM (SEQ ID NO: 46) (5 µL/well) were added per well. Following 30 min incubation at room temperature, cells were washed twice and analyzed by flow cytometry using a BD FACSCanto II cytometer. Cells were analyzed for TCR expression (APC+) versus pMHC-binding (PE+). Using the FlowJo software, dot plots were generated and the percentage (%) of TCR+ pMHC+ cells was determined.

As shown in FIG. 3, the chimeric TCRs TCR0077, TCR0079, TCR0081, and TCR0083 all bind to the MLL-pM/HLA-B*0702 pentamers whereas the chimeric TCR TCR0085 binds to the MLL-pP/HLA-B*0702 pentamers. None of the five TCRs binds to HLA-B*0702 pentamers loaded with the non-phosphorylated control peptide MLL-M.

6.2.2 Activation of TCR-Expressing AK-D10R3 Cells by Peptide-Pulsed HLA-B*0702 T2 Cells AK-D10R3 cells expressing an IL-2-(NFAT)$_3$-EGFP reporter construct and the chimeric TCRs TCR0077, TCR0079, TCR0081, TCR0083, or TCR0085 were cultivated in SF-IMDM media as described above. In parallel, HLA-B*0702 positive T2 target cells ("T2-B7 cells") were pulsed with MLL peptides. Briefly, T2-B7 cells were centrifuged at 300×g and 4° C. for 5 min, washed using 1×PBS and resuspended in 1×PBS supplemented with 50 µg/mL or 5 µg/mL of the MLL-pM peptide EPR[pS]PSHSM (SEQ ID NO: 45), 50 µg/mL of the MLL-pP peptide RVR[pS]PTRSP (SEQ ID NO: 47), or 50 µg/mL of the non-phosphorylated control peptide MLL-M EPRSPSHSM (SEQ ID NO: 46) at a final concentration of $1.0 \times 10^6$ cells/250 µL. Cells were incubated for 3 hours at 37° C., washed twice using 1×PBS, and resuspended at a final concentration of $5.0 \times 10^6$ cells/20 mL using SF-IMDM media. 200 µL ($5.0 \times 10^4$ cells) of the TCR-expressing AK-D10R3 cells were added per well of a 96-well assay plate and centrifuged at 300×g for 5 min, and the supernatant was discarded. Next, 100 µL ($2.5 \times 10^4$ cells) of the T2-B7 target cell suspension was added to each well and co-incubated for 16 hours at 37° C. and 10% CO$_2$.

For staining, cell suspensions were centrifuged at 300×g for 10 min, washed twice using assay buffer, resuspended using 20 µL/well of staining solution (1×PBS supplemented with 1:500 APC-labeled anti-mouse TCR β-chain antibody) and incubated for 30 min at room temperature. Subsequently, cells were washed twice using assay buffer, resuspended in 80 µL assay buffer and analyzed by flow cytometry using a BD FACSCanto II cytometer. Cells were gated for TCR expression (APC+) versus T cell activation (EGFP+). Using FlowJo software, dot plots were generated and the percentage (%) of APC+ EGFP+ cells was determined. AK-D10R3 cultivated in the absence of T2-B7 target cells or co-cultures of TCR-expressing AK-D10R3 cells with non-pulsed T2-B7 cells served as negative controls.

AK-D10R3 cells expressing the chimeric TCRs TCR0077, TCR0079, TCR0081, or TCR0083 showed activation of the IL-2-NFAT reporter construct after being co-cultured with T2-B7 cells pulsed with the phosphopeptide MLL-pM, but not the non-phosphorylated control peptide MLL-M (FIG. 4A). The chimeric TCR TCR0085 mediated the activation of the IL-2-NFAT reporter construct after being co-cultured with T2-B7 cells pulsed with the phosphopeptide MLL-pP (FIG. 4A). The activation of AK-D10R3 cells was dependent on the interaction between the MLL TCRs and their cognate peptide-MHC complexes, since such activation was not observed when AK-D10R3 cells were tested on their own, or when TCR-expressing AK-D10R3 cells were incubated with T2-B7 cells that were not pulsed with any peptide (FIG. 4B).

6.2.3 Cytotoxicity Assays

Next, in a similar co-culture study, TCR-expressing AK-D10R3 cells were assessed for their potential to induce apoptosis in peptide-pulsed T2-B7 target cells. Briefly, T2-B7 target cells were pulsed with 5 µg/mL or 50 µg/mL of the MLL-pM peptide EPR[pS]PSHSM (SEQ ID NO: 45), 50 µg/mL of the MLL-pP peptide RVR[pS]PTRSP (SEQ ID NO: 47), or 50 µg/mL of the non-phosphorylated control peptide MLL-M EPRSPSHSM (SEQ ID NO: 46). AK-D10R3 cells expressing the chimeric TCRs TCR0077, TCR0079, TCR0081, TCR0083, or TCR0085 were co-cultured with peptide-pulsed T2-B7 target cells for 16 hours at 37° C. and 10% CO$_2$ in SF-IMDM medium (Amimed #1-28507-I) supplemented with 500 ng/mL anti-FAS reagent (Biolegend #305702, clone E059.1) and 10 µM Campothecin (Sigma #C9911) as described above. The cells were then stained with anti-mouse TCRβ-APC and anti-caspase3-PE (BD Biosciences #550821) and assessed by flow cytometry using a FACSCantoII cytometer. Co-cultures containing non-pulsed T2-B7 cells or T2-B7 cells in the absence of AK-D10R3 cells served as controls.

As shown in FIG. 5, AK-D10R3 cells expressing the chimeric TCRs TCR0077, TCR0079, TCR0081, or TCR0083 increased caspase 3 expression levels in T2-B7 target cells pulsed with the MLL-pM phosphopeptide, but not T2-B7 cells pulsed with the non-phosphorylated control peptide MLL-M. AK-D10R3 cells expressing the chimeric TCR TCR0085 increased caspase 3 expression levels in T2-B7 cells pulsed with the MLL-pP phosphopeptide (FIG. 5). Caspase 3 expression was minimal in co-cultures containing non-pulsed T2-B7 cells or T2-B7 cells in the absence of TCR-expressing AK-D10R3 cells (FIG. 5).

6.2.4 Characterization of TCR Specificity Using Alanine Scanning

To assess antigen recognition of the MLL-pM peptide EPR[pS]PSHSM (SEQ ID NO: 45), AK-D10R3 cells expressing an IL-2-(NFAT)$_3$-EGFP reporter construct and the chimeric TCR TCR0077 or TCR0085, or TCR negative AK-D10R3 cells were co-cultured with T2-B7 target cells pulsed with the MLL-pM peptide or its alanine modified variants: MLL-pM-A1 APR[pS]PSHSM (SEQ ID NO: 49), MLL-pM-A2 EAR[pS]PSHSM (SEQ ID NO: 50), MLL-pM-A3 EPA[pS]PSHSM (SEQ ID NO: 51), MLL-pM-A4 EPRAPSHSM (SEQ ID NO: 52), MLL-pM-AS EPR[pS]ASHSM (SEQ ID NO: 53), MLL-pM-A6 EPR[pS]PAHSM (SEQ ID NO: 54), MLL-pM-A7 EPR[pS]PSASM (SEQ ID NO: 55), MLL-pM-A8 EPR[pS]PSHAM (SEQ ID NO: 56), or MLL-pM-A9 EPR[pS]PSHSA (SEQ ID NO: 57) at a target:effector ratio of 2:1 for 16 hours at 37° C. and 10% $CO_2$. After staining with anti-mouse TCRβ-APC antibody, expression of the IL-2-(NFAT)$_3$-EGFP reporter was assessed by flow cytometry. Cells were gated for TCR expression versus T cell activation (EGFP+). Using the FlowJo software, dot plots were generated and the percentage (%) of APC+ EGFP+ cells was determined. Data were copied into Microsoft Excel for background correction by subtraction of activation values determined for co-cultures containing T2-B7 cells not pulsed with peptides for graph generation.

As shown in FIG. 6A, AK-D10R3 cells expressing the chimeric TCR TCR0077 showed activation of the IL-2-NFAT reporter construct after being co-cultured with T2-B7 cells pulsed with the MLL-pM peptide, the MLL-pM-A3 peptide, or the MLL-pM-A8 peptide. Minimal activation was detected when TCR0077-expressing AK-D10R3 cells were incubated with T2-B7 cells pulsed with the other alanine modified variants of MLL-pM, the MLL-M control peptide, or the MLL-pP control peptide (FIG. 6A). As a control, AK-D10R3 cells expressing the chimeric TCR TCR0085 were tested under the same conditions and these cells showed increased EGFP expression only in the presence of MLL-pP-pulsed T2-B7 cells, but not T2-B7 cells pulsed with the MLL-M peptide, the MLL-pM peptide, or any alanine modified variants of the MLL-pM peptide (FIG. 6B).

6.2.5 Characterization of TCR Specificity Using X-Scan

Target specificity of TCR0077 and TCR0081 was assessed by "x-scan" assays using a library of variants of the peptide EPR[pS]PSHSM (SEQ ID NO: 45), as described below.

A set of variants of the peptide EPR[pS]PSHSM (SEQ ID NO: 45) was prepared, in which each amino acid position in each peptide, except for the anchor positions P2 (P) and P9 (M), of SEQ ID NO: 45 was individually substituted with each of the 19 other possible naturally occurring amino acids, with position P4 ([pS]) being additionally substituted with non-phosphorylated serine. The resulting 134 variant peptides are listed in Table 8. The specificity profiles of TCR0077 and TCR0081 were evaluated by measuring activation of TCR-expressing AK-D10R3 effector cells after co-culturing with T2-B7 target cells loaded with one of the 134 variant peptides or the parental peptide EPR[pS]PSHSM (SEQ ID NO: 45).

AK-D10R3 cells were stably transduced with chimeric TCRs TCR0077 or

TCR0081, a chimeric mouse/human CD8, and an EGFP-reporter construct linked to a minimal IL-2 promoter comprising three NFAT-binding sites (3xNFAT). Cells were cultured in SF-IMDM (Amimed Direct, London, UK) supplemented with 3% Fetal Calf Serum (FCS; Amimed Direct), 1% Penicillin/Streptomycin (SIGMA-ALDRICH, St. Louis, Mo.), and 50 μM β-mercaptoethanol (Gibco, Fisher Scientific, UK) at 37° C. and 10% $CO_2$. Antigen presenting Tap-deficient T2 (174xCEM.T2) cells from ATCC (CRL-1992™) were maintained in RPMI 1640 (SIGMA-ALDRICH) supplemented with 10% FCS and 1% penicillin/streptomycin at 37° C. and 5% $CO_2$.

Peptides (purchased from Peptides and Elephants, Germany, or produced in-house) were suspended in DMSO and the concentration was adjusted to 4 mg/ml.

T2-B7 cells were washed in PBS (Gibco) and incubated with 20 μg each of the 134 altered peptides per 1×10$^6$ cells for 3 hours at 37° C. and 5% $CO_2$. After incubation, T2-B7 cells were washed in PBS/2% FCS and then resuspended in SF-IMDM media. Effector cells expressing the TCR of interest were co-cultured with peptide-pulsed T2-B7 cells in a 1:2 ratio (total 150,000 cells per well of a 96-well plate) for 16 hours in SF-IMDM media at 37° C. and 10% $CO_2$. Cells were washed twice in 2% FCS/PBS and stained with an anti-mouse TCR-β chain antibody (clone H57-597; BD Pharmingen, San Jose, Calif.) at a 1:500 dilution for 30 min at room temperature. Cells were washed twice, followed by FACS-analysis using a BD FACSCanto™ II flow cytometer (Becton Dickinson).

Data analysis was performed using FlowJo V10 Software. TCR activation was calculated as the proportion of EGFP-expressing cells in the AK-D10R3 population (AK-D10R3 cells were identified based on TCR expression). Background activation (where T2-B7 cells in the assay were not loaded with peptide) was subtracted from all peptide-loaded samples (altered and native sequences). The mean and standard error of the mean (SEM) of background-subtracted values were calculated from all replicates (at least 3 replicates for each TCR) and values were normalized to those of the peptide EPR[pS]PSHSM (SEQ ID NO: 45), with normalized values cropped to a minimum of 0.0 (heat maps only) and to a maximum of 1.0 (heat maps only) for display purposes. Normalized values are shown in heat map format in FIGS. 7A (TCR0077) and 7B (TCR0081) and in bar chart format in FIGS. 8A (TCR0077) and 8B (TCR0081).

The heat maps and bar charts reveal the distinct specificity profiles of each TCR tested. In general, a larger percentage of white (low normalized values) indicates lower tolerance for mutations in the MLL-pM cognate peptide and a higher degree of specificity for the MLL-pM cognate peptide in the context of the above-described assay. As shown in FIGS. 7A and 7B, TCR0077 and TCR0081 both exhibited variable degrees of specificity for each residue position of the MLL-pM cognate peptide.

TABLE 8

Altered peptides used to generate specificity profiles of chimeric TCRs.

| SEQ ID NO | Target Peptide Sequence | SEQ ID NO | Target Peptide Sequence | SEQ ID NO | Target Peptide Sequence |
|---|---|---|---|---|---|
| 49 | APR[pS]PSHSM | 126 | WPR[pS]PSHSM | 142 | EPT[pS]PSHSM |
| 110 | CPR[pS]PSHSM | 127 | YPR[pS]PSHSM | 143 | EPV[pS]PSHSM |
| 111 | DPR[pS]PSHSM | 51 | EPA[pS]PSHSM | 144 | EPW[pS]PSHSM |
| 112 | FPR[pS]PSHSM | 128 | EPC[pS]PSHSM | 145 | EPY[pS]PSHSM |
| 113 | GPR[pS]PSHSM | 129 | EPD[pS]PSHSM | 52 | EPRAPSHSM |
| 114 | HPR[pS]PSHSM | 130 | EPE[pS]PSHSM | 146 | EPRCPSHSM |
| 115 | IPR[pS]PSHSM | 131 | EPF[pS]PSHSM | 147 | EPRDPSHSM |
| 116 | KPR[pS]PSHSM | 132 | EPG[pS]PSHSM | 148 | EPREPSHSM |
| 117 | LPR[pS]PSHSM | 133 | EPH[pS]PSHSM | 149 | EPRFPSHSM |
| 118 | MPR[pS]PSHSM | 134 | EPI[pS]PSHSM | 150 | EPRGPSHSM |
| 119 | NPR[pS]PSHSM | 135 | EPK[pS]PSHSM | 151 | EPRHPSHSM |
| 120 | PPR[pS]PSHSM | 136 | EPL[pS]PSHSM | 152 | EPRIPSHSM |
| 121 | QPR[pS]PSHSM | 137 | EPM[pS]PSHSM | 153 | EPRKPSHSM |
| 122 | RPR[pS]PSHSM | 138 | EPN[pS]PSHSM | 154 | EPRLPSHSM |
| 123 | SPR[pS]PSHSM | 139 | EPP[pS]PSHSM | 155 | EPRMPSHSM |
| 124 | TPR[pS]PSHSM | 140 | EPQ[pS]PSHSM | 156 | EPRNPSHSM |
| 125 | VPR[pS]PSHSM | 141 | EPS[pS]PSHSM | 157 | EPRPPSHSM |
| 158 | EPRQPSHSM | 186 | EPR[pS]PGHSM | 216 | EPR[pS]PSWSM |
| 159 | EPRRPSHSM | 187 | EPR[pS]PHHSM | 217 | EPR[pS]PSYSM |
| 46 | EPRSPSHSM | 188 | EPR[pS]PIHSM | 56 | EPR[pS]PSHAM |
| 160 | EPRTPSHSM | 189 | EPR[pS]PKHSM | 218 | EPR[pS]PSHCM |
| 161 | EPRVPSHSM | 190 | EPR[pS]PLHSM | 219 | EPR[pS]PSHDM |
| 162 | EPRWPSHSM | 191 | EPR[pS]PMHSM | 220 | EPR[pS]PSHEM |
| 163 | EPRYPSHSM | 192 | EPR[pS]PNHSM | 221 | EPR[pS]PSHFM |
| 53 | EPR[pS]ASHSM | 193 | EPR[pS]PPHSM | 222 | EPR[pS]PSHGM |
| 164 | EPR[pS]CSHSM | 194 | EPR[pS]PQHSM | 223 | EPR[pS]PSHHM |
| 165 | EPR[pS]DSHSM | 195 | EPR[pS]PRHSM | 224 | EPR[pS]PSHIM |
| 166 | EPR[pS]ESHSM | 196 | EPR[pS]PTHSM | 225 | EPR[pS]PSHKM |
| 167 | EPR[pS]FSHSM | 197 | EPR[pS]PVHSM | 226 | EPR[pS]PSHLM |
| 168 | EPR[pS]GSHSM | 198 | EPR[pS]PWHSM | 227 | EPR[pS]PSHMM |
| 169 | EPR[pS]HSHSM | 199 | EPR[pS]PYHSM | 228 | EPR[pS]PSHNM |
| 170 | EPR[pS]ISHSM | 55 | EPR[pS]PSASM | 229 | EPR[pS]PSHPM |
| 171 | EPR[pS]KSHSM | 200 | EPR[pS]PSCSM | 230 | EPR[pS]PSHQM |
| 172 | EPR[pS]LSHSM | 201 | EPR[pS]PSDSM | 231 | EPR[pS]PSHRM |
| 173 | EPR[pS]MSHSM | 202 | EPR[pS]PSESM | 232 | EPR[pS]PSHTM |
| 174 | EPR[pS]NSHSM | 203 | EPR[pS]PSFSM | 233 | EPR[pS]PSHVM |
| 175 | EPR[pS]QSHSM | 204 | EPR[pS]PSGSM | 234 | EPR[pS]PSHWM |

TABLE 8-continued

Altered peptides used to generate specificity profiles of chimeric TCRs.

| SEQ ID NO | Target Peptide Sequence | SEQ ID NO | Target Peptide Sequence | SEQ ID NO | Target Peptide Sequence |
|---|---|---|---|---|---|
| 176 | EPR[pS]RSHSM | 205 | EPR[pS]PSISM | 235 | EPR[pS]PSHYM |
| 177 | EPR[pS]SSHSM | 206 | EPR[pS]PSKSM | 45 | EPR[pS]PSHSM (MLL-pM peptide) |
| 178 | EPR[pS]TSHSM | 207 | EPR[pS]PSLSM | | |
| 179 | EPR[pS]VSHSM | 208 | EPR[pS]PSMSM | | |
| 180 | EPR[pS]WSHSM | 209 | EPR[pS]PSNSM | | |
| 181 | EPR[pS]YSHSM | 210 | EPR[pS]PSPSM | | |
| 54 | EPR[pS]PAHSM | 211 | EPR[pS]PSQSM | | |
| 182 | EPR[pS]PCHSM | 212 | EPR[pS]PSRSM | | |
| 183 | EPR[pS]PDHSM | 213 | EPR[pS]PSSSM | | |
| 184 | EPR[pS]PEHSM | 214 | EPR[pS]PSTSM | | |
| 185 | EPR[pS]PFHSM | 215 | EPR[pS]PSVSM | | |

6.3 Example 3: Characterization of Novel MLL TCRs in Primary Human T Cells

In this example, the chimeric TCRs TCR0077 and TCR0085 described above were expressed as fully human TCRs, designated TCR0078 and TCR0086, respectively. TCR0078 shares variable region sequences with TCR0077 except for a small number of mutations in framework 4 of the variable regions and contains human constant regions. Specifically, TCR0078 comprises an α chain and a β chain comprising the amino acid sequences set forth in SEQ ID NOs: 58 and 59, respectively. TCR0086 shares variable region sequences with TCR0085 and contains human constant regions. TCR0086 comprises an α chain and a β chain comprising the amino acid sequences set forth in SEQ ID NOs: 70 and 71, respectively. An exemplary expression construct for TCR0078 or TCR0086, as described in this Example, encodes a fusion protein encoding, in order, the TCR β chain, a P2A self-cleavage site, and the TCR α chain. As listed in Table 1, an exemplary immature TCR0078 or TCR0086 fusion protein (containing signal peptides for both α and β chains) has the amino acid sequence set forth in SEQ ID NO: 83 or 92, respectively. After expression, the fusion protein is cleaved at the P2A site to produce mature α and β chains of TCR0078 (SEQ ID NOs: 236 and 237, respectively) or TCR0086. As shown in SEQ ID NO: 236, the exemplary mature α chain of TCR0078 comprises a GS amino acid residue extension to the C-terminus of its core sequence (SEQ ID NO: 58), resulting from a cloning scar on the fusion protein. As shown in SEQ ID NO: 237, the exemplary mature β chain of TCR0078 comprises a short peptide extension (GSGATNFSLLKQAGDVEENPG, SEQ ID NO: 93) to the C-terminus of its core sequence (SEQ ID NO: 59), resulting from the P2A cleavage of the fusion protein. Additional exemplary immature TCR0078 fusion proteins (containing signal peptides for both α and β chains) have the amino acid sequences set forth in SEQ ID NOs: 266-271, as shown in Table 1.

6.3.1 Expression of TCR0078 on the Surface of Transduced T Cells

Primary T cells were stimulated by co-incubation with CD3/CD28 Dynabeads® (Thermo Fisher, Waltham, Mass.) at a concentration of $1\times10^6$ cells/ml and a T cells:beads ratio of 1:1 at 37° C. for 48 hours. The T cells were then transduced with a lentivirus encoding, in order, the β chain, a P2A cleavage site, and the α chain of TCR0078 (SEQ ID NO: 83), manufactured by Lentigen (Gaithersburg, Md.). For transduction, the T cells/beads were resuspended at $1\times10^6$ cells/ml in fresh T cell medium containing 8 μg/ml polybrene (EMD, Millipore). The cell suspension was mixed with the lentivirus (MOI 10:1) and then centrifuged for 90 minutes at 1200 g, 32° C. to facilitate transduction. The cell/bead suspension was incubated at 37° C. for 4 hours, after which time 1 volume of T cell medium was added and the cells/beads were further incubated at 37° C. overnight. The following day, cells were washed and resuspended at $1\times10^6$ cells/ml in T cell medium, followed by further incubation at 37° C. At Day 3 post-transduction, beads were removed from the cell culture using DynaMag magnet (Thermo Fisher). At Day 5 post-transduction, TCR0078 expression was evaluated by flow cytometry. Specifically, cells were first stained with Zombie NIR™ (Biolegend) to discriminate live from dead cells, according to the manufacturer's instructions. Cells were then washed and stained with PE-conjugated HLA-B*0702 pentamer loaded with the MLL-pM peptide EPR[pS]PSHSM (SEQ ID NO:45; Pro-Immune, Inc, Oxford, UK), and an antibody cocktail comprising anti-CD3-FITC, anti-CD4-PerCp/Cy5.5 and anti-CD8-PE/Cy7 antibodies (Biolegend) for 30 minutes at room temperature protected from light. Untransduced T cells were used as a negative control. The stained T cells were washed and analyzed by flow cytometry using a BD FACSCanto™ II cytometer.

TCR0078 was efficiently expressed in intact, live, singlet T cells. As shown in FIG. 9A, for control cells, 62.8% of the detected cells were intact (left panel). Of these intact cells, 99.2% were living cells (middle panel). Of these living cells, 81.3% were singlets (right panel). The same flow cytometry gates were used for cells transduced with TCR0078 and obtained similar data (data not shown). Intact, live, singlet cells were selected for use in the remainder of the experiment. For control T cells, only 1.11% were positive for both CD3 and pentamer staining (FIG. 9B, left panel). In cells transduced with TCR0078, 58.1% were both CD3 and pentamer positive (FIG. 9B, right panel). The high level of pentamer staining in the TCR0078-transduced cells was indicative of positive expression of TCR0078 in stimulated T cells.

Both control and TCR0078 expressing stimulated T cells were predominantly in one of two populations: a CD8+/CD4− cell population and a CD8−/CD4+ cell population. Control T cells were 44.6% CD8+/CD4− and 49.1% CD8−/CD4+ (FIG. 9C, left panel). Similar results were obtained for the whole population of TCR0078-transduced cells (FIG. 9C, middle panel) and TCR0078 expressing cells determined by pentamer staining (FIG. 9C, right panel). CD8+ or CD4+ populations were also identifiable in the flow cytometry data presented to show the level of pentamer staining (FIG. 9D, both panels).

6.3.2 Characterization of Human T Cells Expressing MLL TCRs Co-Cultured with KG1a Target Cells Primary human T cells were mixed with mRNA encoding TCR0078 or TCR0086 and electroporated on Day 0. The two TCRs were expressed from vectors encoding, in order, the TCR β chain, a P2A cleavage site, and the TCR α chain. On Day 1, target TCR expression was evaluated by flow cytometry following staining with HLA-B*0702 pentamers loaded with the MLL-pM peptide EPR[pS]PSHSM (SEQ ID NO: 45) or the MLL-pP peptide RVR[pS]PTRSP (SEQ ID NO: 47). T cells were then labeled using the Celltrace Violet cell proliferation kit (Life Technologies, Cat. No.: C34557). In parallel, KG1a cells (a myelogenous leukemia cell line endogenously expressing MLL and overexpressing HLA-B*0702 ("KG1a-B7 cells") or HLA-A*0201 ("KG1a-A2 cells") were labeled with carboxyfluorescein succinimidyl ester (CFSE) (Biolegend, Cat. No.: 423801). The Celltrace Violet-labeled T cells were co-cultured with the CFSE-labeled KG1a-B2 cells or KG1a-A2 cells at an effector:target ratio ranging from 4:1 to 0.25:1. T cells that were incubated with anti-CD3 and anti-CD28 antibodies were used as positive controls. On Day 2, the cells were evaluated for CD25 expression, CD107a expression, T cell proliferation, and specific killing of target cells using flow cytometry. Primary human T cells electroporated with mock mRNA (mRNA encoding a control TCR) were used as a negative control.

A representative experiment with an effector:target ratio of 2:1 is shown in FIG. 10. T cells expressing the MLL TCR TCR0078 or TCR0086 were only activated by KG1a cells expressing HLA-B*0702, but not KG1a cells expressing HLA-A*0201, as measured by CD25 expression, CD107a expression, and T cell proliferation. The activation of T cells was dependent on the expression of the MLL TCRs since T cells electroporated with mock mRNA were not activated under the same conditions (FIG. 10).

T cells expressing the MLL TCR TCR0078 or TCR0086 were able to specifically kill KG1-B7 target cells even at low effector:target ratios, while T cells electroporated with mock mRNA did not kill the target cells (FIG. 11).

6.3.3 Characterization of TCR0078 Using an IL-2-NFAT Luciferase Reporter-Expressing T Cell Line This study assesses the specificity of activation of T cells expressing TCR0078 upon co-culturing with various tumor cell lines, using an IL-2-NFAT luciferase reporter T cell line. Specifically, Jurkat cell line J.RT3-T3.5 (ATCC® Cat. No.: TIB-153™), stably expressing a luciferase reporter under the control of an IL-2-NFAT response element and a short CMV minimal promoter, was transduced with the same lentivirus as described in Section 6.3.1. Briefly, control (not transduced) or TCR0078-transduced Jurkat cells were co-cultured with KG1a cells stably expressing HLA-B*0702, K562 cells (a myelogenous leukemia cell line endogenously expressing MLL) stably expressing HLA-B*0702, Loucy cells (alymphoblastic leukemia cell line endogenously expressing MLL and HLA-B*0702), or Namalwa cells (a Burkitt's Lymphoma cell line endogenously expressing MLL and HLA-B*0702) at various Jurkat:tumor (effector:target) cell ratios (ranging from 0.1:1 to 2:1) for 24 hours at 37° C. Cells were then washed, lysed, and mixed with Nano-Glo® Luciferase Assay reagent (Promega, Madison, Wis.), according to the manufacturer's instructions. The luminescence from the expressed IL-2-NFAT-lucifearase reporter, representing the degree of Jurkat cell activation, was recorded. As a positive control for activation of the IL-2-NFAT reporter, phorbol 12-myristate 13-acetate (PMA) and Ionomycin (Biolegend) were used to induce maximum NFAT-luciferase expression in the control and TCR0078-transduced Jurkat effector cells, according to the manufacturer's instructions.

As shown in FIG. 12A, Jurkat cells expressing TCR0078 were significantly activated when co-cultured, at various ratios, with KG1a cells or K562 cells stably expressing HLA-B*0702. Namalwa cells activated TCR0078-expressing Jurkat cells at all effector:target ratios tested. Loucy cells activated TCR0078-expressing Jurkat cells at higher effector:target ratios, compared to the control Jurkat cell activation levels shown in FIG. 12B. As expected, PMA/Ionomycin induced maximal reporter activation in the Jurkat cells (FIG. 12C).

The foregoing reporter activation assays were also performed with other tumor target cells. H929 cells and U266B1 cells (which both endogenously express HLA-B*0702), as well as THP-1 cells (HLA-B*0702 negative) overexpressing HLA-B*0702, all activated the Jurkat effector cells (FIGS. 13A and 13C). Raji cells (ATCC® CCL-86™, an HLA-B*0702 negative cell line) and LCL 721.221 cells (an MHC-I-negative human cell line), when both were overexpressing HLA-B*0702, significantly activated the Jurkat effector cells, more potently than KG1a-HLA-B*0702 cells (FIGS. 13B and 13C). By contrast, YT-Indy cells (HLA-B*0702 negative), J.RT3-T3.5 cells (HLA-B*0702 negative), Raji cells, THP-1 cells, and LCL 721.221 cells did not activate Jurkat effector cells (FIGS. 13A-13C).

6.3.4 Impact of Peptide Dose Titration on T Cell Activation and Target Cell Killing Next, a study was conducted to assess sensitivity of MLL-specific TCRs. Briefly, on Day 0, primary human T cells were electroporated with mock mRNA (mRNA encoding a control TCR) or TCR0078 mRNA as described above. On Day 1, T2 cells expressing HLA-B*0702 ("T2-B7 cells") were labeled using the Celltrace Violet cell proliferation kit (Life Technologies, Cat. No.: C34557) and pulsed with a dose titration of the MLL-pM peptide EPR[pS]PSHSM (SEQ ID NO: 45) or the non-phosphorylated MLL-M control peptide EPRSPSHSM (SEQ ID NO: 46). The T2-B7 target cells were then co-cultured with electroporated T cells that had been labeled with CFSE (Biolegend, Cat. No.: 423801) at an effector:target ratio of 1:1. T cells that were incubated with anti-CD3 and anti-CD28 antibodies were used as positive controls. On Day 2, the cells were evaluated for CD25 expression, CD107a expression, and specific killing of target cells using flow cytometry.

As shown in FIG. 14, T cells expressing the MLL TCR TCR0078 were activated by T2-B7 target cells pulsed with the phosphopeptide MLL-pM, even at low doses of the peptide. The activation of T cells was dependent on the presence of the phosphoseryl moiety as the non-phosphorylated MLL-M control peptide did not activate the T cells (FIG. 14, upper right and lower right panels). T cells electroporated with mock mRNA were not activated by target cells (FIG. 14).

Consistent with the observations of T cell activation, T cells expressing the MLL TCR TCR0078 killed the T2-B7 target cells pulsed with the MLL-pM peptide effectively, but not the T2-B7 target cells pulsed with the non-phosphorylated MLL-M control peptide (FIG. 15). T cells electroporated with mock mRNA did not kill the target cells (FIG. 15).

A similar study assessing TCR sensitivity to the MLL phosphopeptide EPR[pS]PSHSM (SEQ ID NO: 45) was conducted using primary T cells stably expressing TCR0078. Briefly, primary T cells were transduced with lentivirus encoding TCR0078 (SEQ ID NO: 83), as described in Section 6.3.1. After 13 days, the transduced T cells were tested for their activation and cytotoxic activity toward target cells in presence of the MLL phosphopeptide. T2 cells expressing HLA-B*0702 ("T2-B7 cells") were labeled with carboxyfluorescein succinimidyl ester (CFSE) (Biolegend, Cat. No.: 423801) and then pulsed for 2.5 hours with a dose titration of either EPR[pS]PSHSM (SEQ ID NO: 45) phosphopeptide or EPRSPSHSM (SEQ ID NO: 46) peptide. The pulsed T2-B7 cells (Target) were then co-cultured with the primary T cells expressing TCR0078 (Effector), previously labeled using the Cell Trace™ Violet cell proliferation kit (Life Technologies, Carlsbad, Calif., Cat. No.: C34557), at an effector:target ratio of 1:1 for 20 hours at 37° C. Cytotoxic activity (measured by killing of T2-B7 cells) and CD25 and IFN-γ expression of the effector primary T cells were assessed the following day by flow cytometry. The numbers of living T2-B7 cells, detected by Cell Trace™ Violet staining, were counted. The percentage of dead T2-B7 cells (calculated by subtracting the living T2-B7 cell number after co-culturing from the total T2-B7 cell number without co-culturing with the effector primary T cells, then divided by the total T2-B7 cell number without co-culturing) represents the cytotoxic activity of the effector primary T cells. For detection of CD25, cells were first stained with Zombie NIR™ (Biolegend) to discriminate living cells and then stained with an anti-CD25-PE/Cy7 antibody (Biolegend), according to the manufacturer's instructions. For detection of IFN-γ expression, cells were incubated with Brefeldin A and Monensin (Biolegend) for 5 hours before staining. Following cell viability staining and surface staining for CD25-PE/Cy7, CD4-PerCP/Cy5.5, and CD8/PE, as previously described, cells were fixed and permeabilized (Biolegned), according to the manufacturer's instructions, and then stained with an anti-IFN-γ-FITC antibody (Biolegend). The measured fluorescence indicated CD25 and IFN-γ expression levels.

As shown in FIGS. 16A-16C, an increase of cytotoxic activity, CD25 expression and IFN-γ expression was observed in the effector primary T cells in a dose dependent manner with increasing phosphopeptide EPR[pS]PSHSM (SEQ ID NO: 45) concentrations. In contrast, the unmodified MLL-M peptide did not increase the cytotoxic activity, CD25 expression, or IFN-γ expression of the T cells (FIGS. 16A-16C). These results indicate that TCR0078 is specific for the phosphopeptide EPR[pS]PSHSM (SEQ ID NO: 45).

To further characterize TCR0078 specificity for HLA-B*0702 and phosphopeptide EPR[pS]PSHSM (SEQ ID NO: 45), primary T cells transduced with TCR0078 were co-cultured with peptide-pulsed T2 cells expressing either HLA-B*0702 or HLA-A*02.01. Cells were then stained, and CD25 and IFN-γ T cell expression was analyzed by flow cytometry, using the same methods described above.

As shown in FIGS. 17A and 17B, primary T cells were activated when co-cultured with T2-HLA-B*0702 pulsed with the phosphopeptide EPR[pS]PSHSM (SEQ ID NO: 45). By contrast, primary T cells were not activated when co-cultured with T2-HLA-A*02.02 pulsed with either the phosphopeptide or unmodified peptide.

6.4 Example 4: Characterization of TCR0078 as a Cancer Therapy 6.4.1 Characterization of TCR0078 Using Tumor Cells as Target Cells To assess the efficacy of TCR0078 against tumor cell lines, primary T cells, not transduced or transduced with TCR0078, were co-cultured for 20 hours with KG1a cells (endogenously expressing MLL and overexpressing HLA-B*0702 or HLA-A*02.02), at various effector:target ratios, as described in Example 3. Cells were stained (e.g., with Zombie NIR™, anti-CD25 antibody, and anti-IFN-γ antibody) and cytotoxic activity and activation of the effector primary T cells were analyzed by flow cytometry, as described in Example 3.

Activation of TCR0078-expressing primary T cells by KG1a cells stably expressing-HLA-B*0702, but not KG1a cells expressing HLA-A*02.01, at various effector:target ratios, was confirmed by increased killing of the target KG1a cells (FIG. 18A) and increased CD25 (FIG. 18B) and IFN-γ (FIG. 18C) expression in the effector primary T cells. In contrast, untransduced primary T cells (negative control) were not activated by either of the foregoing KG1a cell lines.

Similar assays were performed using primary T cells (with or without TCR0078 transduction) co-cultured with various tumor cells (KG1a cell, K562 cells, SK-MEL-5 cells, U266B1 cells, and Namalwa cells) expressing endogenous or recombinant HLA-B*0702, at various effector:target ratios. The activation of the primary T cells was measured by killing of the target tumor cells, using the same protocol and flow cytometry methods as described in Example 3. As shown in FIG. 19, TCR0078-expressing primary T cells, but not control T cells not expressing TCR0078, significantly promoted killing, at various effector:target ratios, of target KG1a (FIG. 19A) and K562 (FIG. 19B) cells, stably expressing recombinant HLA-B*0702, as well as SK-MEL-5 cells (FIG. 19C) and U266B1 cells (FIG. 19D). The cytotoxic activity of the effector primary T cells was less potent but still statistically significant toward target Namalwa cells (FIG. 19E).

6.4.2 In Vivo Anti-Cancer Activities of TCR0078

To assess efficacy of TCR0078-expressing primary T cells in vivo, a T cell adoptive transfer experiment in immuno-suppressed NOG mice (Jackson Laboratory, Bar Harbor, Me.) bearing a KG1a-HLA-B*0702 tumor was conducted.

Prior to the adoptive transfer, TCR0078-transduced primary T cells were tested in vitro to confirm their activation and cytotoxic activity toward KG1a-HLA-B*0702 tumor cells. As previously described, control and TCR0078-transduced T cells were co-cultured with tumor cells at various effector:target ratios. Killing efficiency and T cells activation were analyzed by flow cytometry, as described in Example 3.

As shown in FIG. 20A, the T cells expressing TCR0078, but not control T cells, significantly promoted killing, at various effector:target ratios, of target KG1a cells expressing HLA-B*0702. CD25 expression in the primary T cells expressing TCR0078 was also significantly increased, compared to the CD25 levels in control T cells (FIG. 20B). Thus, the TCR0078-expressing primary T cells were activated by and had cytotoxic activity toward KG1a-HLA-B*0702 cells in vitro.

For the adoptive transfer, at Day 0, one million of KG1a-HLA-B*0702 tumors cells were injected subcutaneously to each of twenty mice. At Day 1, $5 \times 10^6$ primary T cells, transduced with TCR0078 fifteen days prior, were injected intravenously into ten of the mice. The other ten mice remained un-injected as control. Two of the ten injected mice were sacrificed at Day 7, after measuring the length and width of their tumors and calculating the volume of tumors (by multiplying the measured length and width and then 0.52), to confirm T cells injection and homing. The volume of tumors on other injected and control mice was calculated by the same method at Day 7 and then every 3-5 days, until Day 42. All mice were then sacrificed at Day 42 post tumor implantation and their spleens were collected, processed and stained with Zombie NIR™ reagent, anti-CD3 antibody, and anti-CD45 antibody (Biolegend) to detect T cells and tumor cells.

As shown in FIG. 21A, mice injected with TCR0078-expressing T cells showed significantly slower tumor growth on average, compared to un-injected mice. Among all eight injected mice alive for the 42-day period, only two showed significant tumor growth (white circles in FIG. 21B, comparable to tumor volumes in un-injected mice in FIG. 21A), while the other six had minimal tumor growth (black circles in FIG. 21B), indicating significant tumor inhibition. As detected by flow cytometry, one mouse with significant tumor growth in FIG. 21B had 0.027% of spleen cells as injected human T cells (CD45+/CD3+) and 0.25% of spleen cells as metastatic tumoral cells (CD45+/CD3−) (FIG. 21C, left panel). In contrast, one mouse with minimal tumor growth in FIG. 21B had a larger percentage of spleen cells as CD45+/CD3+ T cells (72.5%) and a smaller percentage of spleen cells as metastatic CD45+/CD3− tumor cells (0.037%) (FIG. 21C, right panel), indicating that the injection of TCR0078-expressing T cells inhibited metastasis as well as tumor volume.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entireties and for all purposes to the same extent as if each individual reference (e.g., publication or patent or patent application) was specifically and individually indicated to be incorporated by reference in its entirety for all purposes.

Other embodiments are within the following claims.

What is claimed:

1. An isolated T cell receptor (TCR) comprising:
   (a) a CDR1α comprising the amino acid sequence of SEQ ID NO: 11, a CDR2α comprising the amino acid sequence of SEQ ID NO: 16, a CDR3α comprising the amino acid sequence of SEQ ID NO: 21, a CDR1β comprising the amino acid sequence of SEQ ID NO: 26, a CDR2β comprising the amino acid sequence of SEQ ID NO: 31, and a CDR3β comprising the amino acid sequence of SEQ ID NO: 36;
   (b) a CDR1α comprising the amino acid sequence of SEQ ID NO: 12, a CDR2α comprising the amino acid sequence of SEQ ID NO: 17, a CDR3α comprising the amino acid sequence of SEQ ID NO: 22, a CDR1β comprising the amino acid sequence of SEQ ID NO: 27, a CDR2β comprising the amino acid sequence of SEQ ID NO: 32, and a CDR3β comprising the amino acid sequence of SEQ ID NO: 37;
   (c) a CDR1α comprising the amino acid sequence of SEQ ID NO: 13, a CDR2α comprising the amino acid sequence of SEQ ID NO: 18, a CDR3α comprising the amino acid sequence of SEQ ID NO: 23, a CDR1β comprising the amino acid sequence of SEQ ID NO: 28, a CDR2β comprising the amino acid sequence of SEQ ID NO: 33, and a CDR3β comprising the amino acid sequence of SEQ ID NO: 38;
   (d) a CDR1α comprising the amino acid sequence of SEQ ID NO: 13, a CDR2α comprising the amino acid sequence of SEQ ID NO: 109, a CDR3α comprising the amino acid sequence of SEQ ID NO: 23, a CDR1β comprising the amino acid sequence of SEQ ID NO: 28, a CDR2β comprising the amino acid sequence of SEQ ID NO: 33, and a CDR3β comprising the amino acid sequence of SEQ ID NO: 38; or
   (e) a CDR1α comprising the amino acid sequence of SEQ ID NO: 14, a CDR2α comprising the amino acid sequence of SEQ ID NO: 19, a CDR3α comprising the amino acid sequence of SEQ ID NO: 24, a CDR1β comprising the amino acid sequence of SEQ ID NO: 29, a CDR2β comprising the amino acid sequence of SEQ ID NO: 34, and a CDR3β comprising the amino acid sequence of SEQ ID NO: 39.

2. The isolated TCR of claim 1, wherein the TCR is a human TCR.

3. An engineered cell presenting the TCR of claim 1 on the cell surface.

4. The engineered cell of claim 3, wherein the cell is a T cell, a CD8+ T cell, a CD4+ T cell, a natural killer T (NKT) cell, or a natural killer (NK) cell.

5. The engineered cell of claim 3, wherein the cell is an invariant natural killer T (iNKT) cell, or a mucosal-associated invariant T (MAiT) cell.

6. A pharmaceutical composition comprising the TCR of claim 1, and a pharmaceutically acceptable carrier.

7. The isolated TCR of claim 1, wherein the TCR comprises:
   (a) an α chain variable region (Vα) comprising the amino acid sequence of SEQ ID NO: 1, and a β chain variable region (Vβ) comprising the amino acid sequence of SEQ ID NO: 2;
   (b) an α chain variable region (Vα) comprising the amino acid sequence of SEQ ID NO: 86, and a β chain variable region (Vβ) comprising the amino acid sequence of SEQ ID NO: 87;
   (c) an α chain variable region (Vα) comprising the amino acid sequence of SEQ ID NO: 3, and a β chain variable region (Vβ) comprising the amino acid sequence of SEQ ID NO: 4;
   (d) an α chain variable region (Vα) comprising the amino acid sequence of SEQ ID NO: 88, and a β chain variable region (Vβ) comprising the amino acid sequence of SEQ ID NO: 89;

(e) an α chain variable region (Vα) comprising the amino acid sequence of SEQ ID NO: 5, and a β chain variable region (Vβ) comprising the amino acid sequence of SEQ ID NO: 6;
(f) an α chain variable region (Vα) comprising the amino acid sequence of SEQ ID NO: 106, and a β chain variable region (Vβ) comprising the amino acid sequence of SEQ ID NO: 107;
(g) an α chain variable region (Vα) comprising the amino acid sequence of SEQ ID NO: 7, and a β chain variable region (Vβ) comprising the amino acid sequence of SEQ ID NO: 8; or
(h) an α chain variable region (Vα) comprising the amino acid sequence of SEQ ID NO: 7, and a β chain variable region (Vβ) comprising the amino acid sequence of SEQ ID NO: 108.

8. The isolated TCR of claim 1, wherein the TCR comprises:
(a) an α chain comprising the amino acid sequence of SEQ ID NO: 249, and a β chain comprising the amino acid sequence of SEQ ID NO: 250;
(b) an α chain comprising the amino acid sequence of any one of SEQ ID NOs: 58, 236, 259, 260, 272, 261, or 249, and a β chain comprising the amino acid sequence of any one of SEQ ID NOs: 59, 237, 262, 263, 264, 273, 60, and 250;
(c) an α chain comprising the amino acid sequence of SEQ ID NO: 251, and a β chain comprising the amino acid sequence of SEQ ID NO: 252;
(d) an α chain comprising the amino acid sequence of SEQ ID NO: 61, and a β chain comprising the amino acid sequence of SEQ ID NOs: 62 or 63;
(e) an α chain comprising the amino acid sequence of SEQ ID NO: 64, and a β chain comprising the amino acid sequence of SEQ ID NOs: 65 or 66;
(f) an α chain comprising the amino acid sequence of SEQ ID NO: 255, and a β chain comprising the amino acid sequence of SEQ ID NO: 256; or
(g) an α chain comprising the amino acid sequence of SEQ ID NO: 67, and a β chain comprising the amino acid sequence of SEQ ID NOs: 68 or 69.

9. The isolated TCR of claim 1, wherein the TCR comprises a CDR1α comprising the amino acid sequence of SEQ ID NO: 11, a CDR2α comprising the amino acid sequence of SEQ ID NO: 16, a CDR3α comprising the amino acid sequence of SEQ ID NO: 21, a CDR1β comprising the amino acid sequence of SEQ ID NO: 26, a CDR2β comprising the amino acid sequence of SEQ ID NO: 31, and a CDR3β comprising the amino acid sequence of SEQ ID NO: 36.

10. The isolated TCR of claim 1, wherein the TCR comprises an α chain variable region (Vα) comprising the amino acid sequence of SEQ ID NO: 86, and a β chain variable region (Vβ) comprising the amino acid sequence of SEQ ID NO: 87.

11. The isolated TCR of claim 1, wherein the TCR comprises an α chain comprising the amino acid sequence of SEQ ID NO: 58, and a β chain comprising the amino acid sequence of SEQ ID NO: 58.

12. The isolated TCR of claim 1, wherein the TCR is a full-length TCR, a soluble TCR, or a single-chain TCR.

13. An isolated T cell receptor (TCR) comprising: a complementarity determining region (CDR)1α comprising the amino acid sequence of SEQ ID NO: 15, a CDR2α comprising the amino acid sequence of SEQ ID NO: 20, a CDR3α comprising the amino acid sequence of SEQ ID NO: 25, a CDR1β comprising the amino acid sequence of SEQ ID NO: 30, a CDR2β comprising the amino acid sequence of SEQ ID NO: 35, and a CDR3β comprising the amino acid sequence of SEQ ID NO: 40.

14. The isolated TCR of claim 13, wherein the TCR comprises an α chain variable region (Vα) comprising the amino acid sequence of SEQ ID NO: 9, and a β chain variable region (Vβ) comprising the amino acid sequence of SEQ ID NO: 10.

15. The isolated TCR of claim 13, wherein the TCR comprises:
(a) an α chain comprising the amino acid sequence of SEQ ID NO: 257, and a β chain comprising the amino acid sequence of SEQ ID NO: 258; or
(b) an α chain comprising the amino acid sequence of SEQ ID NO: 70, and a β chain comprising the amino acid sequence of SEQ ID NOs: 71 or 72.

16. The isolated TCR of claim 13, wherein the TCR is a human TCR.

17. The isolated TCR of claim 13, wherein the TCR is a full-length TCR, a soluble TCR, or a single-chain TCR.

18. An engineered cell presenting the TCR of claim 13 on the cell surface.

19. The engineered cell of claim 13, wherein the cell is a T cell, a CD8+ T cell, a CD4+ T cell, a natural killer T (NKT) cell, or a natural killer (NK) cell.

20. The engineered cell of claim 13, wherein the cell is an invariant natural killer T (iNKT) cell, or a mucosal-associated invariant T (MAiT) cell.

21. A pharmaceutical composition comprising the TCR of claim 13, and a pharmaceutically acceptable carrier.

* * * * *